(12) United States Patent
Wahhab et al.

(10) Patent No.: US 8,338,437 B2
(45) Date of Patent: Dec. 25, 2012

(54) AMINES AS SMALL MOLECULE INHIBITORS

(75) Inventors: Amal Wahhab, Laval (CA); Eric Therrien, Laval (CA); Martin Allan, Montreal (CA); Sukhdev Manku, Pincourt (CA)

(73) Assignee: MethylGene Inc., Montreal (CA)

( * ) Notice: Subject to any disclaimer, the term of this patent is extended or adjusted under 35 U.S.C. 154(b) by 757 days.

(21) Appl. No.: 12/039,141

(22) Filed: Feb. 28, 2008

(65) Prior Publication Data

US 2008/0280925 A1    Nov. 13, 2008

Related U.S. Application Data

(60) Provisional application No. 60/892,056, filed on Feb. 28, 2007.

(51) Int. Cl.
*A61K 31/4162* (2006.01)
*C07D 487/04* (2006.01)

(52) U.S. Cl. .................................. 514/262.1; 544/256

(58) Field of Classification Search ............... 514/262.1; 544/256
See application file for complete search history.

(56) References Cited

FOREIGN PATENT DOCUMENTS

| WO | WO2006/069155 | 6/2006 |
| WO | WO2006/113458 | 10/2006 |

OTHER PUBLICATIONS

Vippagunta, et al. Advanced Drug Delivery Reviews 48 (2001) 3-26.*
Purandare, et al. Bioorg. Med. Chem. Lett. 18 (2008) 4438-4441.*
Chevillard-Briet et al., "Control of CBP co-activiating activity by arginine methylation"; The EMBO Journal 21:20 5457-5466 (2002).
Lee et al., "PRMT8, a new membrane-bound tissue-specific member of the protein arginine methyltransferase family"; The Journal of Biological Chemistry 280(38):32890-32896 (2005).
Xu et al. "A transcriptional switch mediated by cofactor methylation"; Science 294:2507-2511 (2001).
Naeem et al. "The activity and stability of the transcriptional coactivator p/CIP/SRC-3 are regulated by CARM1-dependent Methylation"; Molecular and Cellular Biology 120-134 (2007).
Lee and Bedford, "PABP1 identified as an arginine methyltransferase substrate using high-density protein arrays"; The EMBO Reports 3(3):268-273 (2002).
Li et al. "Involvement of histone methylation and phosphorylation in regulation of transcription by thyroid hormone receptor"; Molecular and Cellular Biology 22(16):5688-5697 (2002).
Espego et al. "A protein-domain microarray identified novel protein-protein interactions" Biochem J., 367:697-702 (2002).
Cheng et al. "The Arginine Methyltransferase CARM1 Regulates the Coupling of Transcription and mRNA Processing"; Molecular Cell 25:71-83 (2007).
Chen et al., "Regulation of Transcription by a Protein Methyltransferase"; Science 284:2174-2177 (1999).
Wang et al., "The Methylation of Histone H4 at Arginine 3 Facilitating Transcriptional Activation by Nucleoar Hormone Receptor"; Science 293:853-857 (2001).
El Messaoudi et al., "Coactivator-associated arginine methyltransferase 1 (CARM1) is a positive regulator of the Cyclin E1 gene" PNAS; 103(36):13351-13356 (2006).
Covic et al. "Arginine Methyltransferase CARM1 is a promoter-specific regulator of NF-kB-dependent gene expression", The EMBO Journal 24:85-96 (2005).
Teferedegne et al. "Mechanism of Action of a Distal NF-kB-Dependent Enhancer"; Molecular and Cellular Biology 26(15):5759-5770 (2006).
Uemura and Chatani, "Copper Salt Catalyzed Addition of Arylboronic Acids to Azodicarboxylates"; J. Org. Chem. 70:8631-8634 (2005).
Jeong et al., "Coactivator-Associated Arginine Methyltransferase 1 Enhances Transcriptional Activity of the Human T-Cell Lymphotropic Virus Type 1 Long Terminal Repeat through Direct Interaction with Tax"; Journal of Virology 80(20):10036-10044 (2006).
Koh et al., "Synergistic Enhancement of Nuclear Receptor Function by p160 Coactivators and Two Coactivators with Protein Methyltransferase Activities*"; The Journal of Biological Chemistry 276(2):1089-1098 (2001).

\* cited by examiner

*Primary Examiner* — Shawquia Young
(74) *Attorney, Agent, or Firm* — McDonnell Boehnen Hulbert & Berghoff LLP

(57) ABSTRACT

The present invention relates to compounds that are useful as inhibitors of protein arginine methyltransferase that have a formula selected from Formula (I), Formula (II) and Formula (III), as well as racemic mixtures, diastereomers, enantiomers and tautomers thereof and N-oxides, hydrates, solvates, pharmaceutically acceptable salts, prodrugs and complexes thereof as defined herein. The compound are useful as inhibitors of PRMTs and/or CARM-I. The invention further relates to compositions comprising such compounds and methods for their use.

25 Claims, No Drawings

AMINES AS SMALL MOLECULE INHIBITORS

This application claims the benefit of U.S. Provisional Application Ser. No. 60/892,056, filed Feb. 28, 2007.

BACKGROUND OF THE INVENTION (a) Field of the Invention

The present invention relates to novel compounds which are inhibitors of Protein ARginine Methyl Transferases (PRMTs), to methods of using such compounds for inhibiting protein methyltransferases, to methods of using such compounds in the treatment of hyperproliferative, inflammatory, infectious, and immunoregulatory disorders and diseases, and to pharmaceutical compositions containing such compounds.

The compounds and pharmaceutical compositions of the invention are particularly well suited as inhibitors of protein methyltransferases and, consequently, can be advantageously used as therapeutic agents for the treatment of certain diseases and/or conditions, including cancer, asthma, COPD, allergic diseases; rheumatoid arthritis, spinal muscular atrophy, atherosclerosis, and psoriasis; viral infections; solid organ transplant rejection, osteoarthritis, and inflammatory bowel syndrome. This invention also relates to methods of using the compounds of this invention alone or in combination with other pharmaceutically active agents.

(b) Summary of the Related Art

PRMTs are enzymes that catalyze the transfer of methyl groups from S-Adenosyl-L-Methionine (SAM) to specific arginine residues of proteins. Arginine methylation of proteins has been implicated to play roles in pre-mRNA splicing, nucleo-cytoplasmic RNA transport, signal transduction and transcriptional activation.

To date, eight family members have been identified (PRMTs 1-8) in mammalian cells and each appear to have distinct substrate preferences and biological functions. Co-activator Associated Arginine Methyltransferase-1 (CARM-1; also called PRMT4) has been shown to methylate histone H3 both in vitro and in vivo, and it is speculated that this modification positively affects chromatin remodeling and thus transcriptional activation. CARM-1 also methylates non-histone proteins, such as CREB-binding protein (CBP)/p300 (Chevillard-Briet et al., 2002; Lee et al., 2005; Xu et al., 2001), steroid receptor co-activator (SRC)-3 (Naeem et al., 2006), poly-A binding protein (PABP) (Lee and Bedford, 2002), members of the Hu family of proteins HuD and HuR (Li et al., 2002), and splicing factors CA150, SAP49, SmB, and U1C (Espego et al., 2002; Cheng et al., 2007).

CARM-1 has oncogenic potential, through its ability to modulate chromatin organization, regulate transcription and increase the half-life of specific mRNAs involved in cancer. CARM-1 plays a co-activator role in androgen- and estrogen-induced gene expression mediated by the nuclear hormone receptor family of transcription factors (Chen et al., 1999). Mutations of critical residues in the catalytic domain compromise the co-activator function of CARM-1 and the arginine-specific histone methylation of the promoter regions of nuclear receptor-responsive genes, suggesting that the integrity of its methyltransferase domain is indispensable for its co-activator function (Chen et al., 1999; Koh et al., 2001; Wang et al., 2001). CARM-1 is also involved in the activation of cyclin E1 gene expression (El Messaoudi et al., 2006). CARM-1 levels are significantly higher in prostatic intraepithelial neoplasia and prostatic adenocarcinoma compared to benign prostate tissue, and higher in patients with androgen-independent prostatic adenocarcinoma compared to patients without previous hormonal treatment. From these findings, it is an attractive chemotherapeutic option to inhibit the enzymatic function of CARM-1 using a small molecule inhibitor.

CARM-1 may also play a role in inflammation and viral gene expression. Studies of cells derived from CARM-1-null mice and knockdown experiments reveal that CARM-1 acts as a co-activator for NF-kappaB in the regulation of inflammatory gene expression (Covic et al., 2004; Teferedegne et al., 2006), and cooperates with CBP and CIITA in the expression of the major histocompatibility class II gene in response to interferon-gamma. CARM-1 is also implicated in the transactivation of the human T-cell lymphotropic virus type 1 long terminal repeat through direct interaction with Tax (Jeong et al., 2006). These findings suggest that inhibition of CARM-1 may also be effective against viral infection and inflammatory disorders.

It would be highly desirable to be provided with novel compounds which are inhibitors of protein arginine methyl transferase. It would also be highly desirable to be provided with novel compounds which are inhibitors of CARM-1.

BRIEF SUMMARY OF THE INVENTION

The present invention provides compounds which are inhibitors of protein arginine methyl transferases (PRMTs).

Another aim of the present invention is to provide compounds which are inhibitors of CARM-1.

In a first aspect, the present invention provides compounds that are useful as inhibitors of protein arginine methyltransferase having the formula of Formula (I), Formula (II), or Formula (III):

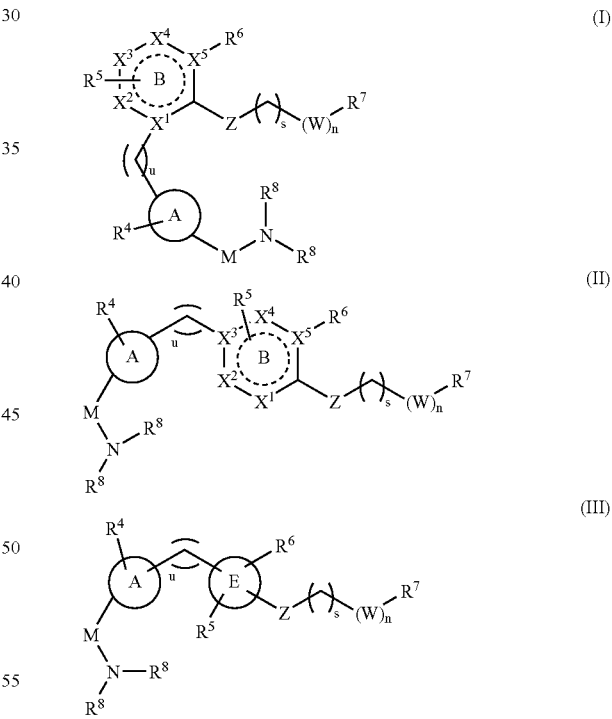

as well as N-oxides, hydrates, solvates, pharmaceutically acceptable salts, prodrugs and complexes thereof and racemic mixtures, diastereomers, enantiomers and tautomers thereof, wherein groups E, A, B, M, n, $R^1$, $R^2$, $R^3$, $R^4$, $R^5$, $R^6$, $R^7$, $R^8$, s, u, W, $X^1$, $X^2$, $X^3$, $X^4$, $X^5$, Y and Z are as defined herein. Said compounds are useful as inhibitors of PRMTs and/or CARM-1.

In a second aspect, the invention provides a composition comprising a compound according to the first aspect and a pharmaceutically acceptable carrier.

In a third aspect, the invention provides a method of inhibiting protein arginine methyltransferase, the method comprising contacting the protein arginine methyltransferase or a cell containing protein arginine methyltransferase, with an protein arginine methyltransferase inhibiting amount of a compound according to the first aspect or a composition according to second aspect.

The present invention provides novel compounds for use in therapy. In some preferred embodiments the therapy is a method of treating cancer, preferably breast cancer, lung cancer, ovarian cancer, prostate cancer, leukemia, lymphoma, glioblastoma, brain cancer, melanoma and/or colon cancer.

The present invention provides a method for treating a proliferative disease via modulation of CARM-I (PRMT-4) by administering to a patient in need of such treatment an effective amount of a compound according to the present invention or a composition according to the second aspect. In some preferred embodiments the patient is administered an effective amount of a compound according to the present invention, or a composition according to the second aspect, in combination (simultaneously or sequentially) with at least one other anti-cancer agent. In a preferred embodiment, the proliferative disease is cancer.

The present invention provides novel compounds for use in the manufacture of a medicament for the treatment of an oncological, immunological or viral infection disease.

The present invention also relates to methods of using a compound according to the first aspect, or a composition according to the second aspect, in the treatment of hyperproliferative, inflammatory, infectious, and immunoregulatory disorders and diseases.

The foregoing merely summarizes various aspects of the invention and is not intended to be limiting in nature. These aspects and other aspects and embodiments are described more fully below. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

DETAILED DESCRIPTION OF THE PREFERRED EMBODIMENTS

The present invention provides compounds which are inhibitors of protein arginine methyl transferase (PRMT). The present invention provides compounds which are inhibitors of CARM-1.

In a first aspect aspect, the invention provides a compound of Formula (I), Formula (II) or Formula (III)

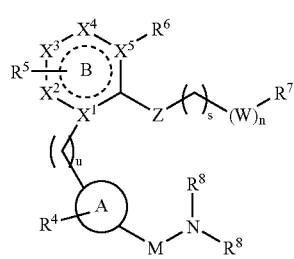

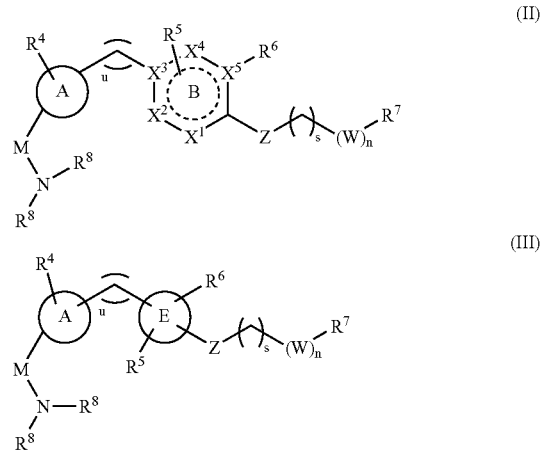

as well as N-oxides, hydrates, solvates, pharmaceutically acceptable salts, prodrugs and complexes thereof, and racemic mixtures, diastereomers, enantiomers and tautomers thereof, wherein groups E, A, B, M, n, $R^1$, $R^2$, $R^3$, $R^4$, $R^5$, $R^6$, $R^7$, $R^8$, s, u, W, $X^1$, $X^2$, $X^3$, $X^4$, $X^5$, Y and Z are as defined herein. Said compound are useful as inhibitors of PRMTs and/or CARM-I.

In a second aspect, the invention provides a composition comprising a compound according to the first aspect or a preferred embodiment thereof and a pharmaceutically acceptable carrier.

In a third aspect, the invention provides a method of inhibiting protein arginine methyltransferase. In one embodiment, the method comprises contacting the protein arginine methyltransferase with a protein arginine methyltransferase inhibiting amount of a compound according to the first aspect or a preferred embodiment thereof. In a further embodiment of the third aspect, the method comprises contacting the protein arginine methyltransferase with a protein arginine methyltransferase inhibiting amount of a composition according to the second aspect. In yet another embodiment, the method comprises inhibiting protein arginine methyltransferase in a cell, comprising contacting the cell with a protein arginine methyltransferase inhibiting amount of a compound according to the first aspect or a preferred embodiment thereof. In still another embodiment, the method comprises inhibiting protein arginine methyltransferase in a cell comprising contacting the cell with a protein arginine methyltransferase inhibiting amount of a composition according to the second aspect. According to this aspect, the compounds and compositions according to the invention are useful as tools for exploring the role of protein arginine methyltransferases in various disease conditions.

In another aspect, the present invention provides compounds and methods for modulating apoptosis.

In another aspect, the present invention provides a method of treating a disease or condition such as cancer, including breast cancer, lung cancer, ovarian cancer, prostate cancer, leukemia, lymphoma, glioblastoma, brain cancer, melanoma and/or colon cancer, comprising administering to an individual in need of treatment a therapeutically effective amount of a compound according to the present invention, or a composition thereof.

In certain preferred embodiments, the disease is selected from the group consisting of hyperproliferative, inflammatory, infectious, and immunoregulatory disorders and diseases.

In a preferred method of the present invention, the cell in which inhibition of protein arginine methyltransferase is desired is a mammalian cell, preferably a primate cell, more preferably a human cell. In another preferred method of the present invention, the cell in which inhibition of protein arginine methyltransferase is desired is in a mammal, preferably a primate, more preferably a human.

The present invention provides a method for treating a proliferative disease via modulation of CARM-I (PRMT-4) by administering to a patient in need of such treatment an effective amount of a compound according to the first aspect, or a composition according to the second aspect. In a preferred embodiment, the proliferative disease is cancer. In some preferred embodiments the patient is administered an effective amount of a compound according to the first aspect, or a composition according to the second aspect, in combination (simultaneously or sequentially) with at least one other anti-cancer agent. The term "anti-cancer agent" includes any agent that is useful for the treatment of cancer.

The compounds of the present invention may be employed alone or in combination with each other and/or other suitable anti-cancer agents useful in the treatment of cancer, such as PTK inhibitors, antiinflammatories, antiproliferatives, chemotherapeutic agents, immunosuppressants, anticancer agents, HDAC inhibitors, demethylating agents, and cytotoxic agents. The compounds of the invention may also be used in conjunction with radiation therapy, or surgery. The compounds of the invention may also be used in conjunction with other PRMT and/or CARM-1 inhibitors.

Reference to "a compound of the formula (I)" (or equivalently, "a compound according to the first aspect", or "a compound of the present invention", and the like), herein is understood to include reference to racemic mixtures, diastereomers, enantiomers and tautomers thereof and N-oxides, hydrates, solvates, pharmaceutically acceptable salts, prodrugs and complexes thereof, unless otherwise indicated.

For purposes of the present invention, the following definitions will be used (unless expressly stated otherwise).

The terms "treating", "treatment", or the like, as used herein covers the treatment of a disease-state in an organism, and includes at least one of: (i) preventing the disease-state from occurring, in particular, when such animal is predisposed to the disease-state but has not yet been diagnosed as having it; (ii) inhibiting the disease-state, i.e., partially or completely arresting its development; (iii) relieving the disease-state, i.e., causing regression of symptoms of the disease-state, or ameliorating a symptom of the disease; and (iv) reversal or regression of the disease-state, preferably eliminating or curing of the disease. In a preferred embodiment of the present invention the organism is an animal, preferably a mammal, preferably a primate, more preferably a human. As is known in the art, adjustments for systemic versus localized delivery, age, body weight, general health, sex, diet, time of administration, drug interaction, the severity of the condition, etc., may be necessary, and will be ascertainable with routine experimentation by one of ordinary skill in the art. In a preferred embodiment, the terms "treating", "treatment", or the like, as used herein covers the treatment of a disease-state in an organism and includes at least one of (ii), (iii) and (iv) above.

As used herein, the terms "protein arginine methyltransferase" and "PRMT" are intended to refer to any one of a family of enzymes that catalyze the transfer of methyl groups from S-adenosyl-L-methionine (SAM) to specific arginine residues of proteins. Preferred protein arginine methyltransferases include Type I and Type II enzymes. The type I enzymes have been described to catalyze the formation of ω—$N^G$-Monomethylarginine and asymmetric ω—$N^G$, ω—$N^G$-dimethylarginine, whereas the type II enzymes have been described to catalyze the formation of ω—$N^G$-monomethylarginine and symmetric ω—$N^G$, ω—$N^G$-dimethylarginine. A family of at least eight mammalian protein arginine methyltransferases have been described. Preferably the arginine methyltransferase is a mammalian PRMT, including, but not limited to, PRMT1, PRMT2, PRMT3, PRMT4 (also called CARM-I), PRMT5, PRMT6, PRMT7 and PRMT8. In some other preferred embodiments, the protein arginine methyltransferase is derived from a fungal source.

The terms "protein arginine methyltransferase inhibitor" and "inhibitor of protein arginine methyltransferase" are intended to mean a compound having a structure as defined herein, which is capable of inhibiting enzymatic activity of a protein arginine methyltransferase.

The term "inhibiting protein arginine methyltransferase enzymatic activity", and the like, is intended to mean reducing the ability of a protein arginine methyltransferase to transfer a methyl group to an arginine residue of a protein. The concentration of inhibitor which reduces the activity of a protein arginine methyltransferase to 50% of that of the uninhibited enzyme is determined as the $IC_{50}$ value. In some preferred embodiments, such reduction of protein arginine methyltransferase activity is at least 50%, more preferably at least about 75%, and still more preferably at least about 90%. In other preferred embodiments, protein arginine methyltransferase activity is reduced by at least 95% and more preferably by at least 99%.

Preferably, such inhibition is specific, i.e., the protein arginine methyltransferase inhibitor reduces the ability of a protein arginine methyltransferase to transfer a methyl group to an arginine residue of a protein at a concentration that is lower than the concentration of the inhibitor that is required to produce another, unrelated biological effect. Preferably, the concentration of the inhibitor required for protein arginine methyltransferase inhibitory activity is at least 2-fold lower, more preferably at least 5-fold lower, even more preferably at least 10-fold lower, and most preferably at least 20-fold lower than the concentration required to produce an unrelated biological effect.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$-B-, wherein a is 0 or 1. In such instances, when a is 0 the moiety is B- and when a is 1 the moiety is A-B-.

For simplicity, reference to a "$C_n$-$C_m$" heterocyclyl or "$C_n$-$C_m$" heteroaryl means a heterocyclyl or heteroaryl having from "n" to "m" annular atoms, where "n" and "m" are integers. Thus, for example, a $C_5$-$C_6$ heterocyclyl is a 5- or 6-membered ring having at least one heteroatom, and includes pyrrolidinyl ($C_5$) and piperidinyl ($C_6$); $C_6$heteroaryl includes, for example, pyridyl and pyrimidyl.

The term "hydrocarbyl" refers to a straight, branched, or cyclic alkyl, alkenyl, or alkynyl, each as defined herein. A "$C_0$" hydrocarbyl is used to refer to a covalent bond. Thus, "$C_0$-$C_3$ hydrocarbyl" includes a covalent bond, methyl, ethyl, ethenyl, ethynyl, propyl, propenyl, propynyl, and cyclopropyl.

The term "alkyl" is intended to mean a straight chain or branched aliphatic group having from 1 to 12 carbon atoms, preferably 1-8 carbon atoms, and more preferably 1-6 carbon atoms. Other preferred alkyl groups have from 2 to 12 carbon atoms, preferably 2-8 carbon atoms and more preferably 2-6 carbon atoms. Preferred alkyl groups include, without limitation, methyl, ethyl, propyl, isopropyl, butyl, isobutyl, sec-butyl, tert-butyl, pentyl, hexyl and the like. A "$C_0$" alkyl (as in "$C_0$-$C_3$alkyl") is a covalent bond.

The term "alkenyl" is intended to mean an unsaturated straight chain or branched aliphatic group with one or more carbon-carbon double bonds, having from 2 to 12 carbon atoms, preferably 2-8 carbon atoms, and more preferably 2-6 carbon atoms. Preferred alkenyl groups include, without limitation, ethenyl, propenyl, butenyl, pentenyl, and hexenyl.

The term "alkynyl" is intended to mean an unsaturated straight chain or branched aliphatic group with one or more carbon-carbon triple bonds, having from 2 to 12 carbon atoms, preferably 2-8 carbon atoms, and more preferably 2-6 carbon atoms. Preferred alkynyl groups include, without limitation, ethynyl, propynyl, butynyl, pentynyl, and hexynyl.

The terms "alkylene," "alkenylene," or "alkynylene" as used herein are intended to mean an alkyl, alkenyl, or alkynyl group, respectively, as defined hereinabove, that is positioned between and serves to connect two other chemical groups. Preferred alkylene groups include, without limitation, methylene, ethylene, propylene, and butylene. Preferred alkenylene groups include, without limitation, ethenylene, propenylene, and butenylene. Preferred alkynylene groups include, without limitation, ethynylene, propynylene, and butynylene.

The term "cycloalkyl" is intended to mean a saturated or unsaturated mono-, bi-, tri- or poly-cyclic hydrocarbon group having about 3 to 15 carbons, preferably having 3 to 12 carbons, preferably 3 to 8 carbons, and more preferably 3 to 6 carbons. In certain preferred embodiments, the cycloalkyl group is fused to an aryl, heteroaryl or heterocyclic group. Preferred cycloalkyl groups include, without limitation, cyclopenten-2-enone, cyclopenten-2-enol, cyclohex-2-enone, cyclohex-2-enol, cyclopropyl, cyclobutyl, cyclobutenyl, cyclopentyl, cyclopentenyl, cyclohexyl, cyclohexenyl, cycloheptyl, cyclooctyl, etc.

The term "heteroalkyl" is intended to mean a saturated or unsaturated, straight chain or branched aliphatic group, wherein one or more carbon atoms in the group are independently replaced by a heteroatom selected from the group consisting of O, S, and N.

The term "aryl" is intended to mean a mono-, bi-, tri- or polycyclic aromatic moiety, preferably a $C_6$-$C_{14}$aromatic moiety, preferably comprising one to three aromatic rings. Preferably, the aryl group is a $C_6$-$C_{10}$aryl group, more preferably a $C_6$aryl group. Preferred aryl groups include, without limitation, phenyl, naphthyl, anthracenyl, and fluorenyl.

The terms "aralkyl" or "arylalkyl" is intended to mean a group comprising an aryl group covalently linked to an alkyl group. If an aralkyl group is described as "optionally substituted", it is intended that either or both of the aryl and alkyl moieties may independently be optionally substituted or unsubstituted. Preferably, the aralkyl group is ($C_1$-$C_6$)alk($C_6$-$C_{10}$)aryl, including, without limitation, benzyl, phenethyl, and naphthylmethyl. For simplicity, when written as "aralkyl" this term, and terms related thereto, is intended to indicate the order of groups in a compound as "aryl-alkyl". Similarly, "alkyl-aryl" is intended to indicate the order of the groups in a compound as "alkyl-aryl".

The terms "heterocyclyl", "heterocyclic" or "heterocycle" are intended to mean a group which is a mono-, bi-, or polycyclic structure having from about 3 to about 14 atoms, wherein one or more atoms are independently selected from the group consisting of N, O, and S. The ring structure may be saturated, unsaturated or partially unsaturated. In certain preferred embodiments, the heterocyclic group is non-aromatic. In a bicyclic or polycyclic structure, one or more rings may be aromatic; for example one ring of a bicyclic heterocycle or one or two rings of a tricyclic heterocycle may be aromatic, as in indan and 9,10-dihydro anthracene. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds where an annular O or S atom is adjacent to another O or S atom.

In certain preferred embodiments, the heterocyclic group is a heteroaryl group. As used herein, the term "heteroaryl" is intended to mean a mono-, bi-, tri- or polycyclic group having 5 to 14 ring atoms, preferably 5, 6, 9, or 10 ring atoms; having 6, 10, or 14 pi electrons shared in a cyclic array; and having, in addition to carbon atoms, between one or more heteroatoms independently selected from the group consisting of N, O, and S. For example, a heteroaryl group may be pyrimidinyl, pyridinyl, benzimidazolyl, thienyl, benzothiazolyl, benzofuranyl and indolinyl. Preferred heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl.

The terms "arylene," "heteroarylene," or "heterocyclylene" are intended to mean an aryl, heteroaryl, or heterocyclyl group, respectively, as defined hereinabove, that is positioned between and serves to connect two other chemical groups.

Preferred heterocyclyls and heteroaryls include, but are not limited to, azepinyl, azetidinyl, acridinyl, azocinyl, benzidolyl, benzimidazolyl, benzofuranyl, benzofurazanyl, benzofuryl, benzothiofuranyl, benzothiophenyl, benzoxazolyl, benzothiazolyl, benzothienyl, benztriazolyl, benztetrazolyl, benzisoxazolyl, benzisothiazolyl, benzimidazolinyl, benzoxazolyl, benzoxadiazolyl, benzopyranyl, carbazolyl, 4aH-carbazolyl, carbolinyl, chromanyl, chromenyl, cinnolinyl, coumarinyl, decahydroquinolinyl, 1,3-dioxolane, 2H,6H-1,5,2-dithiazinyl, dihydrofuro[2,3-b]tetrahydrofuran, dihydroisoindolyl, dihydroquinazolinyl (such as 3,4-dihydro-4-oxo-quinazolinyl), furanyl, furopyridinyl (such as fuor[2,3-c]pyridinyl, furo[3,2-b]pyridinyl or furo[2,3-b]pyridinyl), furyl, furazanyl, hexahydrodiazepinyl, imidazolidinyl, imidazolinyl, imidazolyl, indazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolidinyl, isothiazolyl, isoxazolinyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxetanyl, 2-oxoazepinyl, 2-oxopiperazinyl, 2-oxopiperidinyl, 2-oxopyrrolodinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolopyridyl, 2H-pyrrolyl, pyrrolyl, quinazolinyl, quinolinyl, 4H-quinolizinyl, quinoxalinyl, quinuclidinyl, tetrahydro-1,1-dioxothienyl, tetrahydrofuranyl, tetrahydrofuryl, tetrahydroisoquinolinyl, tetrahydroquinolinyl, tetrahydropyranyl, tetrazolyl, thiazolidinyl, 6H-1,2,5-thiadiazinyl, thiadiazolyl (e.g., 1,2,3-thiadiazolyl, 1,2,4-thiadiazolyl, 1,2,5-thiadiazolyl, 1,3,4-thiadiazolyl), thiamorpholinyl, thiamorpholinyl sulfoxide, thiamorpholuiyl sulfone, thianthrenyl, thiazolyl, thienyl, thienothiazolyl, thienooxazolyl, thienoimidazolyl, thiophenyl, triazinyl, triazinylazepinyl, triazolyl (e.g., 1,2,3-triazolyl, 1,2,4-triazolyl, 1,2,5-triazolyl, 1,3,4-triazolyl), and xanthenyl.

As employed herein, and unless stated otherwise, when a moiety (e.g., alkyl, heteroalkyl, cycloalkyl, aryl, heteroaryl, heterocyclyl, etc.) is described as "optionally substituted" it is meant that the group optionally has from one to four, preferably from one to three, more preferably one or two, independently selected non-hydrogen substituents. Suitable substituents include, without limitation, halo, hydroxy, oxo (e.g., an annular —CH— substituted with oxo is —C(O)—) nitro, halohydrocarbyl, hydrocarbyl, alkyl, cycloalkyl, heterocyclyl, aryl, heteroaryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, (b) $C_1$-$C_5$alkyl or alkenyl or arylalkyl imino, carbamoyl, azido, carboxamido, mercapto, hydroxy, hydroxyalkyl, alkylaryl, arylalkyl, $C_1$-$C_8$alkyl, $C_1$-$C_8$alkenyl, $C_1$-$C_8$alkoxy, $C_1$-$C_8$alkoxycarbonyl, aryloxycarbonyl, $C_2$-$C_8$acyl, $C_2$-$C_8$acylamino, $C_1$-$C_8$alkylthio, arylalkylthio, arylthio, $C_1$-$C_8$alkylsulfinyl, arylalkylsulfinyl, arylsulfinyl, $C_1$-$C_8$alkylsulfonyl, arylalkylsulfonyl, arylsulfonyl, $C_0$-$C_6$N-alkyl carbamoyl, $C_2$-$C_{15}$N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, $C_5$-$C_{15}$ heteroaryl or any of these rings fused or spiro-fused to a cycloalkyl, heterocyclyl, or aryl, wherein each of the foregoing is further optionally substituted with one more moieties listed in (a), above; and (c) —$(CR^{32}R^{33})_s$—$NR^{30}R^{31}$, wherein s is from 0 (in which case the nitrogen is directly bonded to the moiety that is substituted) to 6, $R^{32}$ and $R^{33}$ are each independently hydrogen, halo, hydroxyl or $C_1$-$C_4$alkyl, and $R^{30}$ and $R^{31}$ are each independently hydrogen, cyano, oxo, hydroxyl, $C_1$-$C_8$alkyl, $C_1$-$C_8$ heteroalkyl, $C_1$-$C_8$alkenyl, carboxamido, $C_1$-$C_3$alkyl-carboxamido, carboxamido-$C_1$-$C_3$alkyl, amidino, $C_2$-$C_8$ hydroxyalkyl, $C_1$-$C_3$alkylaryl, aryl-$C_1$-$C_3$alkyl, $C_1$-$C_3$alkylheteroaryl, heteroaryl-$C_1$-$C_3$alkyl, $C_1$-$C_3$alkylheterocyclyl, heterocyclyl-$C_1$-$C_3$alkyl $C_1$-$C_3$alkylcycloalkyl, cycloalkyl-$C_1$-$C_3$alkyl, $C_2$-$C_8$alkoxy, $C_2$-$C_8$alkoxy-$C_1$-$C_4$alkyl, $C_1$-$C_8$alkoxycarbonyl, aryloxycarbonyl, aryl-$C_1$-$C_3$alkoxycarbonyl, heteroaryloxycarbonyl, heteroaryl-$C_1$-$C_3$alkoxycarbonyl, $C_1$-$C_8$acyl, $C_0$-$C_8$alkyl-carbonyl, aryl-$C_0$-$C_8$alkyl-carbonyl, heteroaryl-$C_0$-$C_8$alkyl-carbonyl, cycloalkyl-$C_0$-$C_8$alkyl-carbonyl, $C_0$-$C_8$alkyl-NH-carbonyl, aryl-$C_0$-$C_8$alkyl-NH-carbonyl, heteroaryl-$C_0$-$C_8$alkyl-NH-carbonyl, cycloalkyl-$C_0$-$C_8$alkyl-NH-carbonyl, $C_0$-$C_8$alkyl-O-carbonyl, aryl-$C_0$-$C_8$alkyl-O-carbonyl, heteroaryl-$C_0$-$C_8$alkyl-O-carbonyl, cycloalkyl-$C_0$-$C_8$alkyl-O-carbonyl, $C_1$-$C_8$alkylsulfonyl, arylalkylsulfonyl, arylsulfonyl, heteroarylalkylsulfonyl, heteroarylsulfonyl, $C_1$-$C_8$alkyl-NH-sulfonyl, arylalkyl-NH-sulfonyl, aryl-NH-sulfonyl, heteroarylalkyl-NH-sulfonyl, heteroaryl-NH-sulfonyl aroyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, or protecting group, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents selected from the group consisting of (a) above, a protecting group, and ($X^{30}$-$Y^{31}$-), wherein said heterocyclyl may also be bridged (forming a bicyclic moiety with a methylene, ethylene or propylene bridge); wherein $X^{30}$ is selected from the group consisting of $C_1$-$C_8$alkyl, $C_2$-$C_8$alkenyl-, $C_2$-$C_8$alkynyl-, —$C_0$-$C_3$alkyl-$C_2$-$C_8$alkenyl-$C_0$-$C_3$alkyl, $C_0$-$C_3$alkyl-$C_2$-$C_8$alkynyl-$C_0$-$C_3$alkyl, $C_0$-$C_3$alkyl-O—$C_0$-$C_3$alkyl-, HO—$C_0$-$C_3$alkyl-, $C_0$-$C_4$alkyl-N($R^{30}$)—$C_0$-$C_3$alkyl-, N($R^{30}$)($R^{31}$)—$C_0$-$C_3$alkyl-, N($R^{30}$)($R^{31}$)—$C_0$-$C_3$alkenyl-, N($R^{30}$)($R^{31}$)—$C_0$-$C_3$alkynyl-, (N($R^{30}$)($R^{31}$))$_2$—C=N—, $C_0$-$C_3$alkyl-S(O)$_{0-2}$-$C_0$-$C_3$alkyl-, $CF_3$—$C_0$-$C_3$alkyl-, $C_1$-$C_8$ heteroalkyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, N($R^{30}$)($R^{31}$)-heterocyclyl-$C_1$-$C_3$alkyl-, wherein the aryl, cycloalkyl, heteroaryl and heterocycyl are optionally substituted with from 1 to 3 substituents from (a); and $Y^{31}$ is selected from the group consisting of a direct bond, —O—, —N($R^{30}$)—, —C(O)—, —O—C(O)—, —C(O)—O—, —N($R^{30}$)—C(O)—, —C(O)—N($R^{30}$)—, —N($R^{30}$)—C(S)—, —C(S)—N($R^{30}$)—, —N($R^{30}$)—C(O)—N($R^{31}$)—, —N($R^{30}$)—C(N$R^{30}$)—N($R^{31}$)—, —N($R^{30}$)—C(N$R^{31}$), —C(N$R^{31}$)—N($R^{30}$)—, —N($R^{30}$)C(S)—N($R^{31}$)—, —N($R^{30}$)—C(O)—O—, —O—C(O)—N($R^{31}$)—, —N($R^{30}$)—C(S)—O—, —O—C(S)—N($R^{31}$)—, —S(O)$_{0-2}$—, —SO$_2$N($R^{31}$)—, —N($R^{31}$)—SO$_2$— and —N($R^{30}$)—SO$_2$N($R^{31}$)—.

As a non-limiting example, substituted phenyls include 2-flurophenyl, 3,4-dichlorophenyl, 3-chloro-4-fluoro-phenyl, 2-fluoro-3-propylphenyl. As another non-limiting example, substituted n-octyls include 2,4-dimethyl-5-ethyloctyl and 3-cyclopentyl-octyl. Included within this definition are methylenes (—CH$_2$—) substituted with oxygen to form carbonyl —CO—.

When there are two optional substituents bonded to adjacent atoms of a ring structure, such as for example a phenyl, thiophenyl, or pyridinyl, the substituents, together with the atoms to which they are bonded, optionally form a 5- or 6-membered cycloalkyl or heterocycle having 1, 2, or 3 annular heteroatoms.

In a preferred embodiment, a hydrocarbyl, heteroalkyl, heterocyclic and/or aryl group is unsubstituted.

In other preferred embodiments, a hydrocarbyl, heteroalkyl, heterocyclic and/or aryl group is substituted with from 1 to 3 independently selected substituents.

Preferred substituents on alkyl groups include, but are not limited to, hydroxyl, halogen (e.g., a single halogen substituent or multiple halo substituents; in the latter case, groups such as $CF_3$ or an alkyl group bearing $Cl_3$), cyano, nitro, alkyl, cycloalkyl, alkenyl, cycloalkenyl, alkynyl, heterocycle, aryl, —$OR^a$, —$SR^a$, —$S(\!=\!O)R^e$, —$S(\!=\!O)_2R^e$, —$P(\!=\!O)_2R^e$, —$S(\!=\!O)_2OR^e$, —$P(\!=\!O)_2OR^e$, —$NR^bR^c$, —$NR^bS(\!=\!O)_2R^e$, —$NR^bP(\!=\!O)_2R^e$, —$S(\!=\!O)_2NR^bR^c$, —$P(\!=\!O)_2NR^bR^c$, —$C(\!=\!O)OR^e$, —$C(\!=\!O)R^a$, —$C(\!=\!O)NR^bR^c$, —$OC(\!=\!O)R^a$, —$OC(\!=\!O)NR^bR^c$, —$NR^bC(\!=\!O)OR^e$, —$NR^dC(\!=\!O)NR^bR^c$, —$NR^dS(\!=\!O)_2NR^bR^c$, —$NR^dP(\!=\!O)_2NR^bR^c$, —$NR^bC(\!=\!O)R^a$ or —$NR^bP(\!=\!O)_2R^e$, wherein $R^a$ is hydrogen, alkyl, cycloalkyl, alkenyl, cycloalkenyl, alkynyl, heterocycle or aryl; $R^b$, $R^c$ and $R^d$ are independently hydrogen, alkyl, cycloalkyl, heterocycle or aryl, or said $R^b$ and $R^c$ together with the N to which they are bonded optionally form a heterocycle; and $R^e$ is alkyl, cycloalkyl, alkenyl, cycloalkenyl, alkynyl, heterocycle or aryl. In the aforementioned exemplary substituents, groups such as alkyl, cycloalkyl, alkenyl, alkynyl, cycloalkenyl, heterocycle and aryl can themselves be optionally substituted.

Preferred substituents on alkenyl and alkynyl groups include, but are not limited to, alkyl or substituted alkyl, as well as those groups recited as preferred alkyl substituents.

Preferred substituents on cycloalkyl groups include, but are not limited to, nitro, cyano, alkyl or substituted alkyl, as well as those groups recited about as preferred alkyl substituents. Other preferred substituents include, but are not limited to, spiro-attached or fused cyclic substituents, preferably spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Preferred substituents on cycloalkenyl groups include, but are not limited to, nitro, cyano, alkyl or substituted alkyl, as well as those groups recited as preferred alkyl substituents. Other preferred substituents include, but are not limited to, spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Preferred substituents on aryl groups include, but are not limited to, nitro, cycloalkyl or substituted cycloalkyl, cycloalkenyl or substituted cycloalkenyl, cyano, alkyl or substituted alkyl, as well as those groups recited above as preferred alkyl substituents. Other preferred substituents include, but are not limited to, fused cyclic groups, especially fused cycloalkyl, fused cycloalkenyl, fused heterocycle, or fused aryl, where the aforementioned cycloalky, cylcoalkenyl, heterocycle and aryl substituents can themselves be optionally substituted. Still other preferred substituents on aryl groups (phenyl, as a non-limiting example) include, but are not limited to, haloalkyl and those groups recited as preferred alkyl substituents.

Preferred substituents on heterocylic groups include, but are not limited to, cycloalkyl, substituted cycloalkyl, cycloalkenyl, substituted cycloalkenyl, nitro, oxo (i.e., =O), cyano, alkyl, substituted alkyl, as well as those groups recited as preferred alkyl substituents. Other preferred substituents on heterocyclic groups include, but are not limited to, spiro-attached or fused cylic substituents at any available point or points of attachement, more preferably spiro-attached cycloalkyl, spiro-attached cycloalkenyl, spiro-attached heterocycle (excluding heteroaryl), fused cycloalkyl, fused cycloakenyl, fused heterocycle and fused aryl, where the aforementioned cycloalkyl, cycloalkenyl, heterocycle and aryl substituents can themselves be optionally substituted.

In certain preferred embodiments, a heterocyclic group is substituted on carbon, nitrogen and/or sulfur at one or more positions. Preferred substituents on nitrogen include, but are not limited to alkyl, aryl, aralkyl, alkylcarbonyl, alkylsulfonyl, arylcarbonyl, arylsulfonyl, alkoxycarbonyl, or aralkoxycarbonyl. Preferred substituents on sulfur include, but are not limited to, oxo and $C_{1-6}$alkyl. In certain preferred embodiments, nitrogen and sulfur heteroatoms may independently be optionally oxidized and nitrogen heteroatoms may independently be optionally quaternized.

Especially preferred substituents on ring groups, such as aryl, heteroaryl, cycloalkyl and heterocyclyl, include halogen, alkoxy and alkyl.

The term "halogen" or "halo" is intended to mean chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is additionally optionally substituted. The term "sulfonamido" refers to a sulfonamide substituent attached by either the sulfur or the nitrogen atom. The term "amino" is meant to include $NH_2$, alkylamino, arylamino, cyclic amino, and the like groups. The term "ureido" as employed herein refers to a substituted or unsubstituted urea moiety.

The term "radical" is intended to mean a chemical moiety comprising one or more unpaired electrons.

Where optional substituents are chosen from "one or more" groups it is to be understood that this definition includes all substituents being chosen from one of the specified groups or the substituents being chosen from two or more of the specified groups.

In addition, substituents on cyclic moieties (i.e., cycloalkyl, heterocyclyl, aryl, heteroaryl) include 5- to 6-membered mono- and 9- to 14-membered bi-cyclic moieties fused to the parent cyclic moiety to form a bi- or tri-cyclic fused ring system. Substituents on cyclic moieties also include 5- to 6-membered mono- and 9- to 14-membered bi-cyclic moieties attached to the parent cyclic moiety by a covalent bond to form a bi- or tri-cyclic bi-ring system. For example, an optionally substituted phenyl includes, but is not limited to, the following:

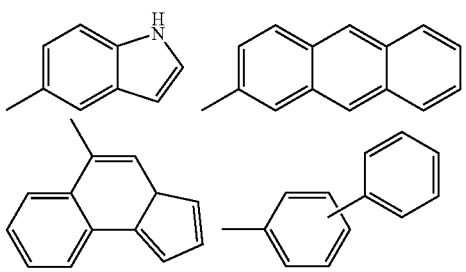

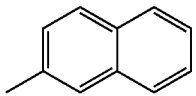

The term "protecting group" is intended to mean a group used in synthesis to temporarily mask the characteristic chemistry of a functional group because it interferes with another reaction. A good protecting group should be easy to put on, easy to remove and in high yielding reactions, and inert to the conditions of the reaction required. A protecting group or protective group is introduced into a molecule by chemical modification of a functional group in order to obtain chemoselectivity in a subsequent chemical reaction. One skilled in the art will recognize that during any of the processes for preparation of the compounds in the present invention, it may be necessary and/or desirable to protect sensitive or reactive groups on any of the molecules concerned. This may be achieved by means of conventional protecting groups, such as but not limited to Bn- (or —CH$_2$Ph), -CHPh$_2$, alloc (or CH$_2$=CH—CH$_2$—O—C(O)—), BOC-, -Cbz (or Z-), -Fmoc, —C(O)—CF$_3$, N-Phthalimide, 1-Adoc-, TBDMS-, TBDPS-, TMS-, TIPS-, IPDMS-, —SiR$_3$, SEM-, t-Bu-, Tr-, THP- and Allyl-, and those described in standard textbooks, such as Greene, T. W. et al., *Protective Groups in Organic Synthesis*, Wiley, N.Y. (1999). These protecting groups may be removed at a convenient stage using methods known from the art.

When a functional group is termed "protected", this means that the group is in modified form to mitigate, especially preclude, undesired side reactions at the protected site.

The term "therapeutically effective amount" as that term is used herein refers to an amount which elicits the desired therapeutic effect. The therapeutic effect is dependent upon the disease being treated and the results desired. As such, the therapeutic effect can be a decrease in the severity of symptoms associated with the disease and/or inhibition (partial or complete) of progression of the disease, or reversal or regression of the disease-state, preferably eliminating or curing of the disease. In other embodiments, the therapeutic effect can be preventing the disease-state from occurring, in particular, when an animal is predisposed to the disease-state but has not yet been diagnosed as having it. Further, the therapeutic effect can be inhibition of PRMT and/or CARM-I. The amount needed to elicit the therapeutic effect can be determined based on the age, health, size and sex of the patient. Optimal amounts can also be determined based on monitoring of the patient's response to treatment.

The compounds of the present invention form salts which are also within the scope of this invention. Reference to a compound of the formula (I) herein is understood to include reference to salts thereof, unless otherwise indicated.

The term "salt(s)", as employed herein, denotes acidic and/or basic salts formed with inorganic and/or organic acids and bases. In addition, when a compound of formula (I) contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic (exhibiting minimal or no undesired toxicological effects), physiologically acceptable) salts are preferred, although other salts are also useful, e.g., in isolation or purification steps which may be employed during preparation. Salts of the compounds of the invention may be formed, for example, by reacting a compound of the present invention with an amount of acid or base, such as an equivalent amount, in a medium such as one in which the salts precipitates or in an aqueous medium followed by lyophilization.

The compounds of the present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfanotes (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of the present invention which contain an acidic moiety, such as but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl) ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl and butyl chlorides, bromides and iodides), dialkyl sulfates (e.g. dimethyl, diethyl, dibuty and diamyl sulfates), long chain halides (e.g. decyl, lauryl, myristyl and stearyl chlorides, bromides and iodides), aralkyl halides (e.g. benzyl and phenethyl bromides), and others.

As used herein, the term "pharmaceutically acceptable salts" is intended to mean salts that retain the desired biological activity of the above-identified compounds and exhibit minimal or no undesired toxicological effects.

Some compounds of the invention may have one or more chiral centers and/or geometric isomeric centers (E- and Z-isomers), and it is to be understood that the invention encompasses all such optical, diastereoisomers and geometric isomers. The invention also comprises all tautomeric forms of the compounds disclosed herein.

Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration. The racemic forms can be resolved by physical methods, such as, for example, fractional crystallization, separation or crystallization of diastereomeric derivates or separation by chiral column chromatography. The individual optical isomers can be obtained from the racemates by any suitable method, including without limitation, conventional methods, such as, for example, salt formation with an optically active acid followed by crystallization.

The present invention also includes prodrugs of compounds of the invention. The term "prodrug" is intended to represent a compound with a covalently bonded carrier, which is capable of releasing the active ingredient when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of the invention include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I)), amides (e.g., trifluoroacetylamino, acetylamino, and the like), and the like.

The compounds of the invention may be administered as is or as a prodrug, for example in the form of an in vivo hydrolyzable ester or in vivo hydrolyzable amide. An in vivo hydrolyzable ester of a compound of the invention containing carboxy or hydroxy group is, for example, a pharmaceutically acceptable ester which is hydrolyzed in the human or animal body to produce the parent acid or alcohol. Suitable pharmaceutically acceptable esters for carboxy include $C_1$-$C_6$alkoxymethyl esters (e.g., methoxymethyl), $C_1$-$C_6$alkanoyloxymethyl esters (e.g., for example pivaloyloxymethyl), phthalidyl esters, $C_3$-$C_8$cycloalkoxycarbonyloxy-$C_1$-$C_6$alkyl esters (e.g., 1-cyclohexylcarbonyloxyethyl); 1,3-dioxolen-2-onylmethyl esters (e.g., 5-methyl-1,3-dioxolen-2-onylmethyl; and $C_1$-$C_6$alkoxycarbonyloxyethyl esters (e.g., 1-methoxycarbonyloxyethyl) and may be formed at any appropriate carboxy group in the compounds of this invention.

An in vivo hydrolyzable ester of a compound of the invention containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolyzable ester forming groups for hydroxy include alkanoyl, benzoyl, phenylacetyl and substituted benzoyl and phenylacetyl, alkoxycarbonyl (to give alkyl carbonate esters), dialkylcarbamoyl and N—(N,N-dialkylaminoethyl)-N-alkylcarbamoyl (to give carbamates), N,N-dialkylaminoacetyl and carboxyacetyl. Examples of substituents on benzoyl include morpholino and piperazino linked from a ring nitrogen atom via a methylene group to the 3- or 4-position of the benzoyl ring. A suitable value for an in vivo hydrolyzable amide of a compound of the invention containing a carboxy group is, for example, a N—$C_1$-$C_6$alkyl or N,N-di-$C_1$-$C_6$alkyl amide such as N-methyl, N-ethyl, N-propyl, N,N-dimethyl, N-ethyl-N-methyl or N,N-diethyl amide.

Upon administration to a subject, the prodrug undergoes chemical conversion by metabolic or chemical processes to yield a compound of the present invention, or a salt and/or solvate thereof. Solvates of the compounds of the present invention include, for example, hydrates.

The foregoing merely summarizes some aspects and preferred embodiments thereof and is not intended to be limiting in nature. These aspects and preferred embodiments thereof are described more fully below.

Compounds

In a first aspect, the invention provides novel inhibitors of protein arginine methyl transferase (PRMT). In an embodiment, the novel inhibitors of PRMT are represented by a formula selected from Formula (I) Formula (II) and Formula (III):

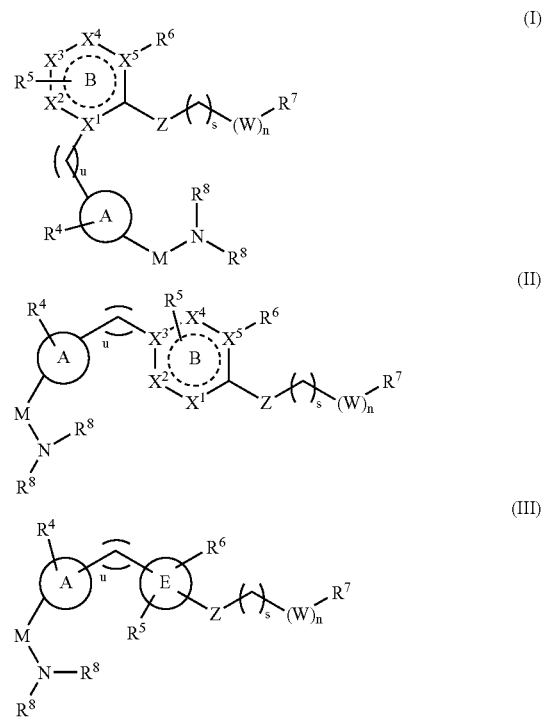

and N-oxides, hydrates, solvates, pharmaceutically acceptable salts, prodrugs and complexes thereof and racemic mixtures, diastereomers, enantiomers and tautomers thereof, wherein A is a cycloalkyl ring, a heterocyclic ring, a heteroaryl ring, or an aryl ring;

B is selected from the group consisting of phenyl, and a 5- or 6-membered heteroaryl, wherein when B is a 5-membered heteroaryl, $X^4$ is a bond, and $X^1$, $X^2$, $X^3$ and $X^5$ are each independently selected from the group consisting of C, N, O and S, provided that at least one of $X^1$, $X^2$, $X^3$ and $X^5$ is N, O or S, and provided that for Formula (I), $X^1$ is not O or S, and for Formula (II), $X^3$ is not O or S; and when B is a 6-membered heteroaryl, each of $X^1$, $X^2$, $X^3$, $X^4$ and $X^5$ are independently C or N, provided that at least one of $X^1$, $X^2$, $X^3$, $X^4$ and $X^5$ are N;

E is a 5 to 10-membered heterocycle, preferably a 9-membered heterocycle;

M is selected from the group consisting of

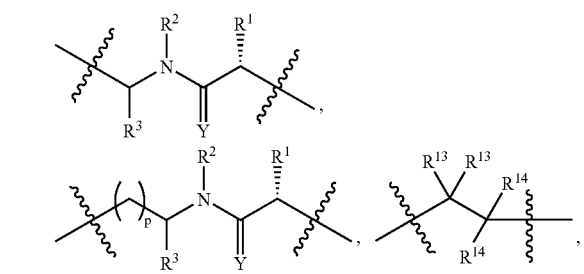

-continued

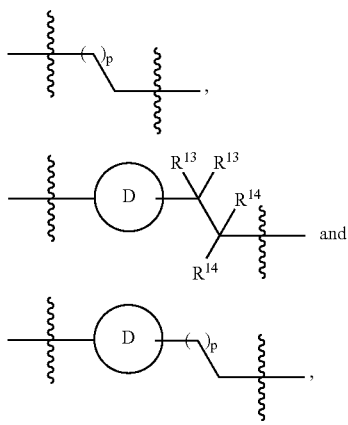

or
M is selected from the group consisting of

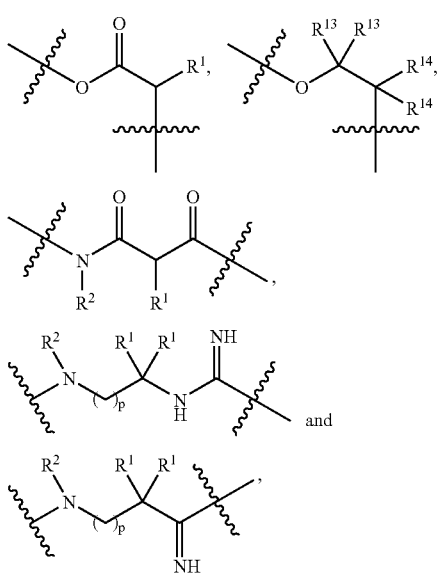

or
M is selected from the group consisting of

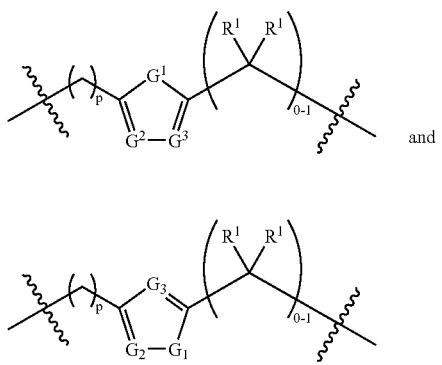

or
M is selected from the group consisting of

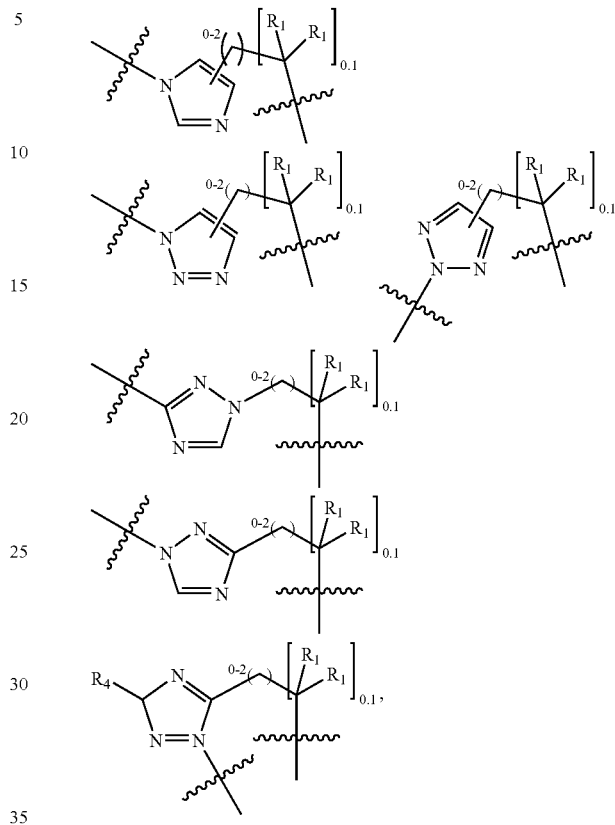

wherein p is 1, 2 or 3;
each $R^{13}$ is independently selected from the group consisting of H and $C_1$-$C_4$alkyl;
each $R^{14}$ is independently selected from the group consisting of H and $C_1$-$C_4$alkyl; or alternatively,
$R^8$ and $R^{14}$ may join to form a 4-, 5- or 6-membered saturated ring containing one N atom; and
ring D is a heterocycle, preferably selected from the group consisting of

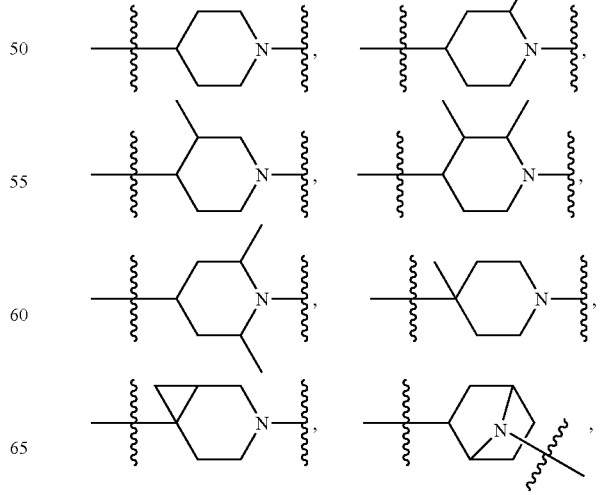

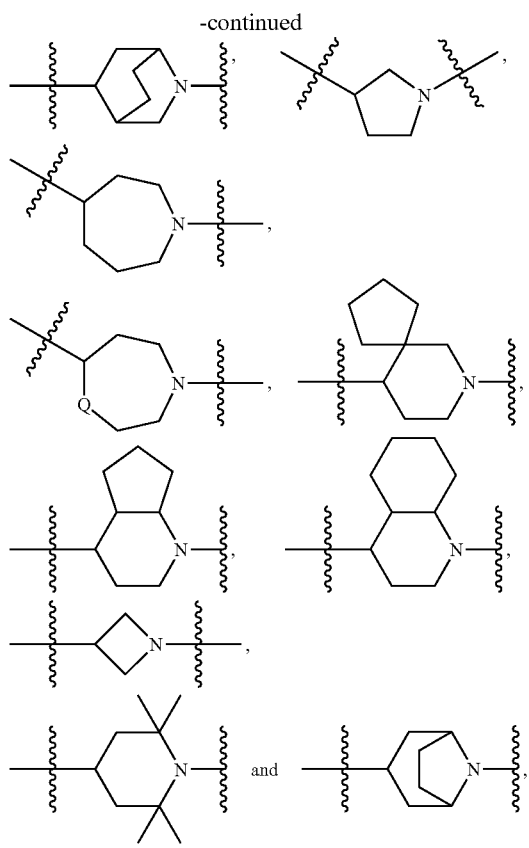

wherein the left side of ring D as shown is attached to ring A; and wherein Q is selected from the group consisting of —N(R$^{15}$)—, O and S; and R$^{15}$ is C$_1$-C$_6$alkyl; and each R$^1$ is independently selected from the group consisting of H, —OH, —CF$_3$, —CHF$_2$, —CH$_2$F, halo, —CN, alkyl, alkenyl, alkynyl, aryl, heteroaryl, alkoxy, cycloalkyl, heterocyclyl, —O-alkyl, —S(O)$_{0-1}$-alkyl, —O-cycloalkyl, —S(O)$_{0-1}$-cycloalkyl, —O-heterocyclyl, —S(O)$_{0-1}$-heterocyclyl, —O-aryl, —S(O)$_{0-1}$aryl, —O-heteroaryl, —S(O)$_{0-1}$-heteroaryl, -alkyl-cycloalkyl, -alkyl-heterocyclyl, -alkyl-aryl, -alkyl-heteroaryl and =O (R$^1$ is preferably H, Me, Et, propyl, iso-propyl, —CF$_3$, CH$_2$Ph, OH or OPh;

R$^2$ is selected from the group consisting of H, alkyl, aryl, heteroaryl, cycloalkyl, heterocyclyl, -alkyl-aryl, -alkyl-heteroaryl, -alkyl-cycloalkyl and -alkyl-heterocycle, each of which is optionally substituted (preferably R$^2$ is H, Me or Et); or R$^1$ and R$^2$ together form a 5-, 6- or 7-membered heterocycle, each of which is optionally substituted; or R$^2$ optionally bonds with Ring A to form a 5 or 6 membered heterocycle fused to ring A;

R$^3$ is selected from the group consisting of H, —OH, —CF$_3$, —CHF$_2$, —CH$_2$F, halo, —CN, alkyl, alkenyl, alkynyl, aryl, heteroaryl, alkoxy, cycloalkyl, heterocyclyl, —O-alkyl, —S(O)$_{0-1}$-alkyl, —O-cycloalkyl, —S(O)$_{0-1}$-cycloalkyl, —O-heterocyclyl, —S(O)$_{0-1}$-heterocyclyl, —O-aryl, —S(O)$_{0-1}$-aryl, —O-heteroaryl, —S(O)$_{0-1}$-heteroaryl, -alkyl-cycloalkyl, -alkyl-heterocyclyl, -alkyl-aryl, -alkyl-heteroaryl and =O (preferably R$^3$ is H or C$_1$-C$_4$ alky); or R$^2$ together with R$^3$ optionally form a 4-, 5-, 6- or 7-membered heterocycle, each of which is optionally substituted;

R$^4$ is selected from the group consisting of H, —OH, halo, —CN, alkyl, alkenyl, alkynyl, aryl, heteroaryl, alkoxy, cycloalkyl, heterocyclyl, —O-alkyl, —S(O)$_{0-1}$-alkyl, —O-cycloalkyl, —S(O)$_{0-1}$-cycloalkyl, —O-heterocyclyl, —S(O)$_{0-1}$-heterocyclyl, —O-aryl, —S(O)$_{0-1}$aryl, —O-heteroaryl, —S(O)$_{0-1}$-heteroaryl, -alkyl-cycloalkyl, -alkyl-heterocyclyl, -alkyl-aryl, -alkyl-heteroaryl and =O, each of which is optionally substituted, (preferably R$^4$ is selected from the group consisting of H, halogen, CN, alkyl, substituted alkyl, —O—(C$_1$-C$_4$alkyl), —S—(C$_1$-C$_4$alkyl) and —S(O)$_2$—(C$_1$-C$_4$alkyl));

R$^5$ is selected from the group consisting of H, —NO$_2$, halo, —CN, —CF$_3$, —CHF$_2$, —CH$_2$F, —OH, —SH, C$_1$-C$_6$alkyl, C$_2$-C$_6$alkenyl, C$_2$-C$_6$alkynyl, alkoxy, cycloalkyl, heterocyclyl, aryl, heteroaryl, —O-alkyl, —S(O)$_{0-1}$-alkyl, —O-cycloalkyl, —S(O)$_{0-1}$-cycloalkyl, —O-heterocyclyl, —S(O)$_{0-1}$-heterocyclyl, =O, —O-aryl, —S(O)$_{0-1}$-aryl, —O-heteroaryl, —S(O)$_{0-1}$-heteroaryl, —O—C(O)—N(R$^2$)$_2$, —N(R$^2$)—C(O)—O—R$^2$, —C(O)—NH2, —C(O)—O—R$^2$, —C(O)—N(R$^2$)$_2$, (preferably R$^5$ is selected from the group consisting of H, Me, Et, propyl, iso-propyl, OMe, OEt, SMe, SO$_2$Me, CF$_3$ and OCF$_3$);

R$^6$ is selected from the group consisting of H, —CN, alkyl, alkenyl, alkynyl, halo, —OH, —SH, =O, —CF$_3$, —CHF$_2$, —CHF$_2$, alkoxy, aryl, heteroaryl, cycloalkyl, heterocyclyl, —O-alkyl, —S(O)$_{0-1}$-alkyl, —O-cycloalkyl, —S(O)$_{0-1}$-cycloalkyl, —O-heterocyclyl, —S(O)$_{0-1}$-heterocyclyl, —O-aryl, —S(O)$_{0-1}$-aryl, —O-heteroaryl and —S(O)$_{0-1}$-heteroaryl, (preferably R$^6$ is selected from the group consisting of H, Me, Et, —NH$_2$, —CF$_3$ and —NO$_2$);

R$^7$ is selected from the group consisting of cycloalkyl, substituted cycloalkyl, heterocycle, substituted heterocycle, aryl, substituted aryl, heteroaryl and substituted heteroaryl, alkyl, optionally substituted alkyl;

each R$^8$ is independently selected from the group consisting of H and C$_1$-C$_4$alkyl;

Y is nil (i.e., =Y is —H), O, S or —N(R$^8$);

G$^1$ is O, S or NR$^8$;

G$^2$ is N or CH; and

G$^3$ is N or CH; and

Z is a moiety selected from the group consisting of a bond, —O—, —N(R$^9$)—, —S—, —C(O)—, optionally substituted aryl, optionally substituted heteroaryl, optionally substituted -aryl-N(R$^2$)—, optionally substituted -heteroaryl-N(R$^2$)—,

| —C(=O)N(R$^{10}$)—, | —N(R$^{10}$)C(=O)—, | —N(R$^{10}$)C(=O)N(R$^{10}$)—, | —N(R$^{10}$)C(=O)O—, |
| —C(=S)N(R$^{10}$)—, | —N(R$^{10}$)C(=S)—, | —N(R$^{10}$)C(=S)N(R$^{10}$)—, | —N(R$^{10}$)C(=S)O—, |
| —N(R$^{10}$)—S(O)$_2$—, | —S(O)$_2$—N(R$^{10}$)—, | —O—C(O)—N(R$^{10}$)— and | —N(R$^{10}$)—C(O)—O—; | wherein

R$^{10}$ is selected from the group consisting of H, alkyl, aryl, heteroaryl, cycloalkyl, heterocyclyl, -alkyl-aryl, -alkylheteroaryl, -alkyl-cycloalkyl and -alkyl-heterocycle, each of which is optionally substituted (preferably $R^{10}$ is H, or Me);

W is selected from the group consisting of a bond, an optionally substituted $C_1$-$C_4$alkyl, —O—, —S(O)$_{0-2}$—, —N($R^{10}$)—, —O—C(O)—N($R^{10}$)—, —N($R^{10}$)—C(O)—O—, —O—C(S)—N($R^{10}$)—, —N($R^{10}$)—C(S)—O—, —N($R^{10}$)—S(O)$_2$—, —S(O)$_2$—N($R^{10}$)—, —C(O)—, —C(S)—, —O—C(O)— and —C(O)—O—; or $R^6$ together with W optionally form a 5- or 6-membered heterocycle; or W together with $R^7$ optionally form a 5- or 6-membered heterocycle, wherein the heterocycle is optionally substituted;

or $R^6$ together with Z form an optionally substituted heteroaryl;

u is 0 or 1;

s is 0, 1, 2 or 3; and n is 0 or 1;

or

—Z—(CH$_2$)$_s$—(W)$_n$—$R^7$ is an optionally substituted —C(O)-heterocycle or an optionally substituted 5- to 10-membered heteroaryl, preferably selected from the group consisting of.

wherein t is 1, 3 or 4; and $R^{12}$ is selected from the group consisting of hydrogen, halogen, haloalkyl, cyano, nitro, alkyl, cycloalkyl, alkenyl, cycloalkenyl, alkynyl, heterocycle, aryl, heteroaryl, —OR, —SR, —S(=O)R, —S(=O)$_2$R, —P(=O)$_2$R, —S(=O)$_2$OR, —P(=O)$_2$OR, —N(R)(R), —N(R)S(=O)$_2$R, —S(=O)$_2$N(R)(R), —N(R)P(=O)$_2$R, —P(=O)$_2$N(R)(R), —C(=O)OR, —C(=O)R, —C(=O)N(R)(R), —C(=S)N(R)(R), —OC(=O)R, —OC(=O)N(R)(R), —OC(=S)N(R)(R), —N(R)C(=O)OR, —N(R)C(=S)OR, —N(R)C(=O)N(R)(R), —N(R)C(=S)N(R)(R), —N(R)S(=O)$_2$N(R)(R), —N(R)P(=O)$_2$N(R)(R), —N(R)C(=O)R, —N(R)C(=S)R and —N(R)P(=O)$_2$R, wherein each R is independently selected from the group consisting of hydrogen, alkyl, cycloalkyl, alkenyl, cycloalkenyl, alkynyl, heterocycle, aryl and heteroaryl;

provided that —Z—(CH$_2$)$_s$—(W)$_n$— is not —O—O— or —O—CH$_2$—O—; and provided that Formula (I) excludes those compounds wherein (1) M is $R^8$ are both H;

Y is O;

$R^3$ is H or $C_1$-$C_4$alkyl;

A is phenyl;

u is 0;

Z is a moiety selected from the group consisting of

—C(=O)N($R^9$)—, —N($R^{10}$)C(=O)—,

—N($R^{10}$)C(=O)N($R^9$)—, and and

W is O;

or (2) M is $R^8$ are both H;

Y is O;

$R^3$ is H or $C_1$-$C_4$alkyl;

A is phenyl;

u is 0; and

—Z—(CH$_2$)$_m$—(W)$_n$—$R^7$ is selected from the group consisting of

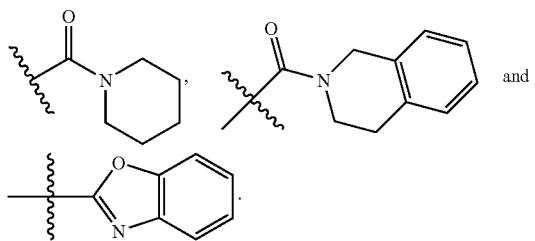

In a preferred embodiment, of the compounds according to the present invention, ring A is a 5 or 6 membered heterocyclic ring, or a fused heterocyclic ring, preferably a bicyclic ring.

In a preferred embodiment ring A is a heterocyclic ring, preferably selected from the group consisting of

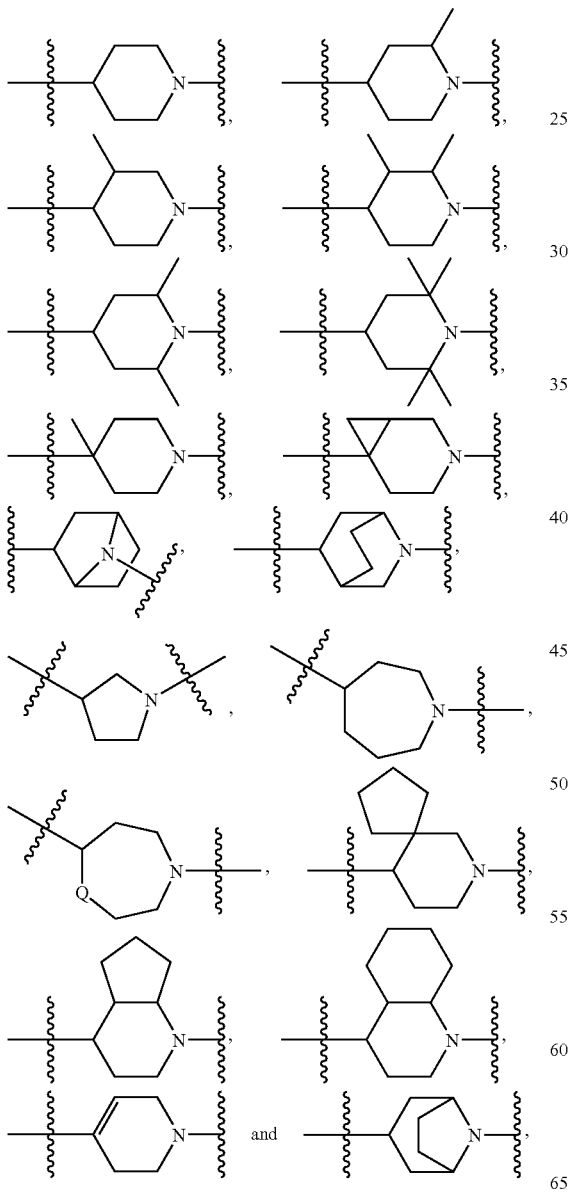

wherein group M is attached via the N atom of ring A;

O is selected from the group consisting of —N(R$^{15}$)—, O and S; and

R$^{15}$ is $C_1$-$C_6$alkyl;

In another preferred embodiment of the compounds according to the present invention, ring A is selected from the group consisting of

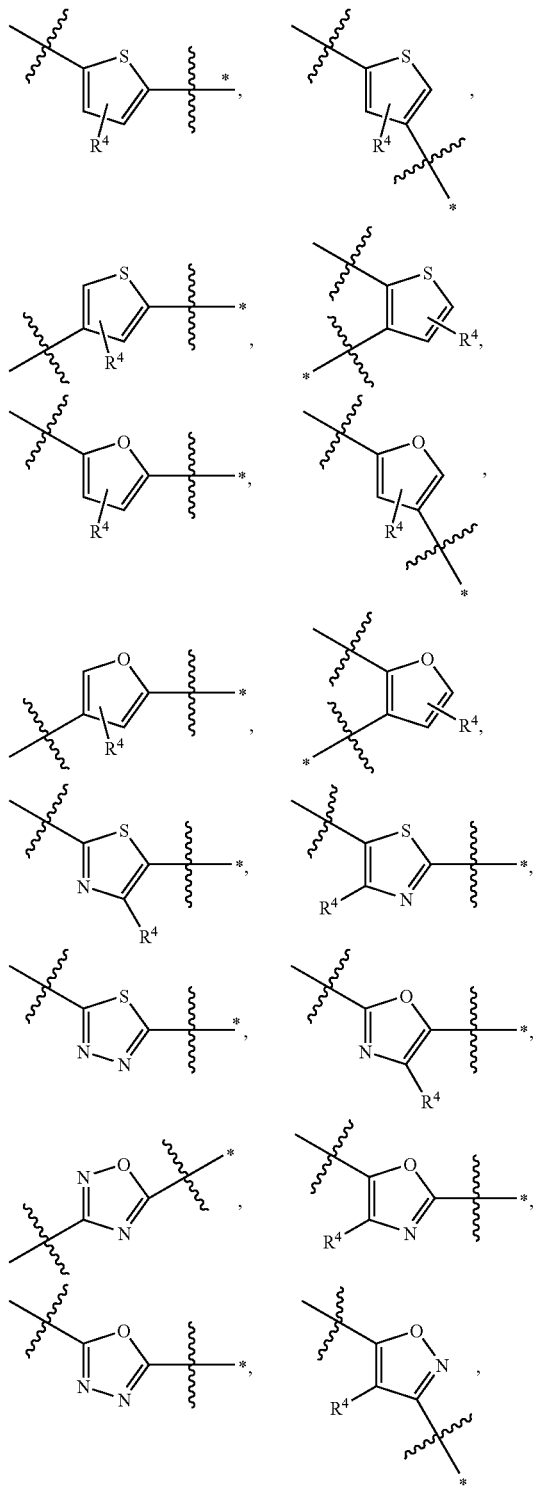

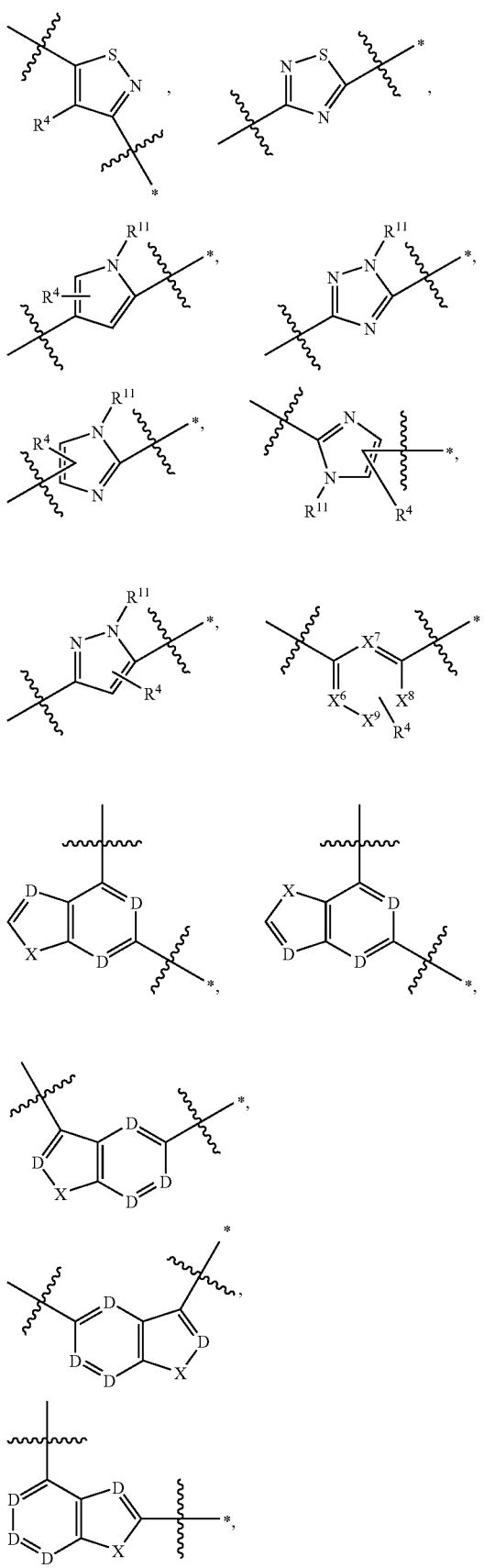

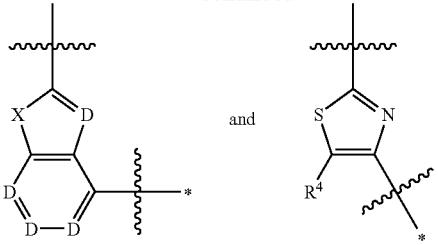

wherein
* represents the point of attachment to group M;
D is CH or N;
X is selected from the group consisting of O, S, NH and N(Me); and
$X^6$, $X^7$, $X^8$ and $X^9$ are independently CH or N;

In another preferred embodiment of the compounds according to the present invention, ring A is phenyl.

In another preferred embodiment of the compounds according to the present invention, ring A is pyridine, thiophene or thiazolyl, more preferably thiophene.

In another preferred embodiment of the compounds according to the present invention, ring A is selected from the group consisting of

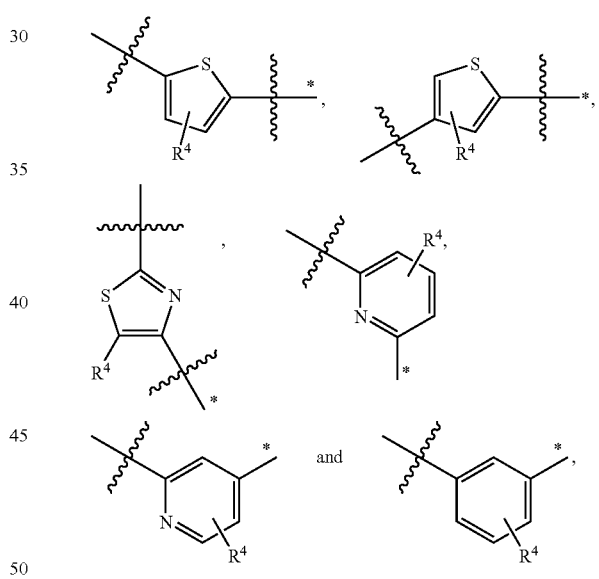

wherein * represents the point of attachment to group M. In another preferred embodiment of the compound according to the present invention, ring A is selected from the group consisting of

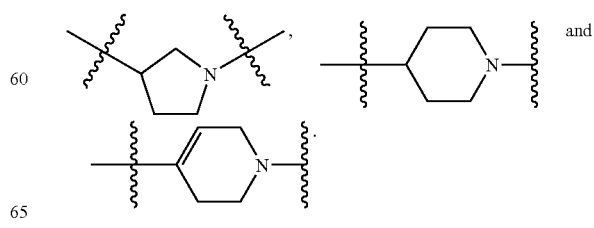

wherein group M is attached via the N atom of ring A.

In another preferred embodiment of the compounds according to the present invention, ring B is phenyl or a 5 membered heteroaryl, in which $X^4$ is a bond, $X^1$, $X^2$, $X^3$ and $X^5$ are each independently C, N, O, or S, and at least one of $X^1$, $X^2$, $X^3$ and $X^5$ is a heteroatom selected from N, O and S; or a 6-membered heteroaryl, in which $X^1$, $X^2$, $X^3$, $X^4$ and $X^5$ are each independently C, or N, and at least one of $X^1$, $X^2$, $X^3$, $X^4$ and $X^5$ is N.

In another preferred embodiment, of the compounds according to the present invention, ring B is phenyl or a 5 membered heteroaryl, in which $X^4$ is a bond, $X^1$, $X^2$, $X^3$ and $X^5$ are each independently C, N, O, or S, and at least one of $X^1$, $X^2$, $X^3$ and $X^5$ is a heteroatom selected from N, O and S.

In another preferred embodiment, of the compounds according to the present invention, $X^4$ is a bond, $X^1$ and $X^2$, are each independently N; $X^3$ and $X^5$ are each independently C. Preferably, $X^3$ is C substituted with $CF_3$.

In another preferred embodiment of the compounds according to the present invention, ring B is

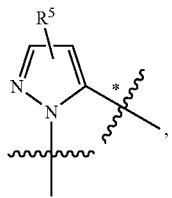

wherein * represents the point of attachment towards group Z.

In another preferred embodiment of the compounds according to the present invention, ring B is phenyl.

In another preferred embodiment of the compounds according to the present invention, $R^7$ is aryl, heteroaryl, substituted aryl or substituted heteroaryl.

In another preferred embodiment of the compounds according to the present invention, $R^7$ is selected from the group consisting of phenyl, pyridine, napthylene and cyclohexyl, each of is optionally substituted, preferably $R^7$ isoptionally substituted phenyl.

In another preferred embodiment of the compounds according to the present invention, $R^7$ is an optionally substituted heterocycle.

In another preferred embodiment of the compounds according to the present invention, $R^7$ is selected from the group consisting of

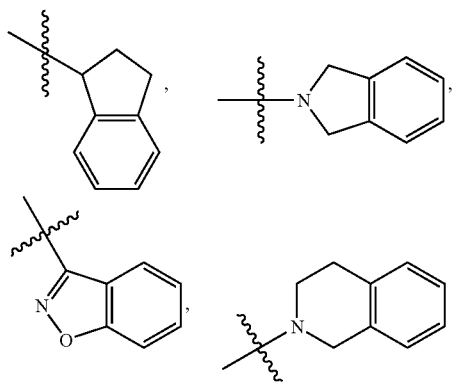

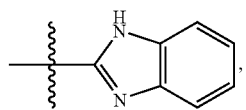

each of which is optionally substituted.

In another preferred embodiment of the compounds according to the present invention, Z is selected from the group consisting of

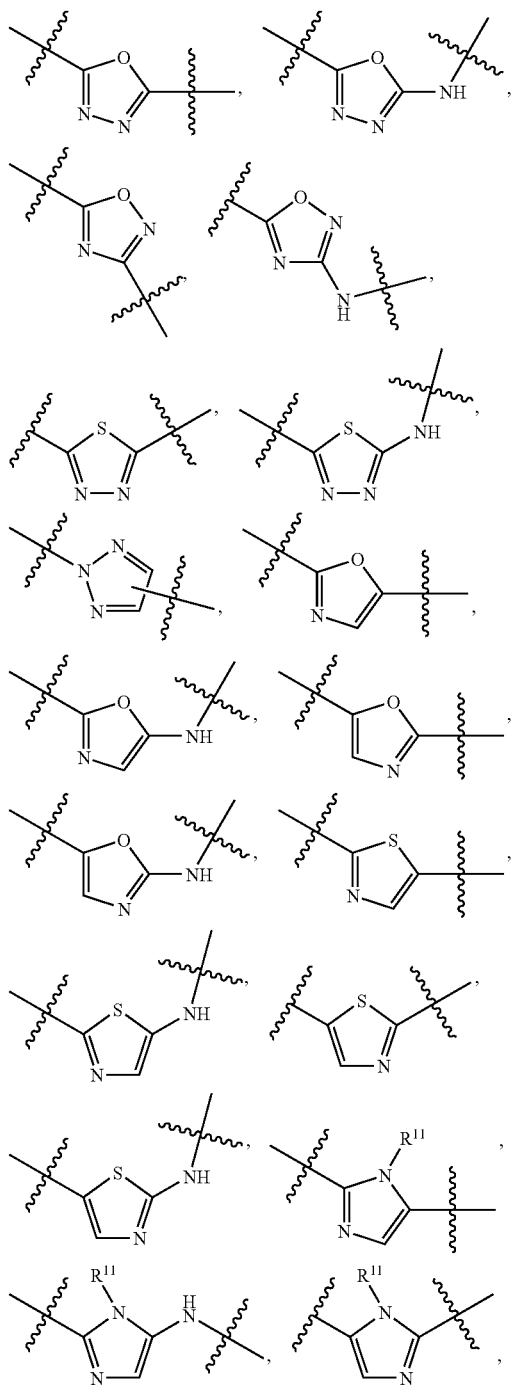

-continued

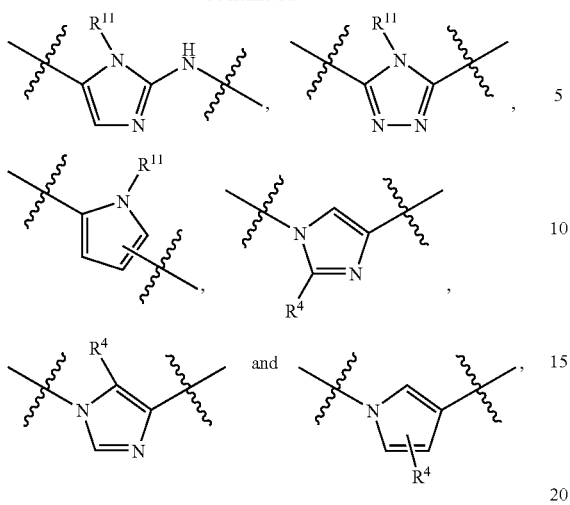

wherein

R[4] is selected from the group consisting of H, —OH, halo, —CN, alkyl, alkenyl, alkynyl, aryl, heteroaryl, alkoxy, cycloalkyl, heterocyclyl, —O-alkyl, —S(O)$_{0-1}$-alkyl, —O-cycloalkyl, —S(O)$_{0-1}$-cycloalkyl, —O-heterocyclyl, —S(O)$_{0-1}$-heterocyclyl, —O-aryl, —S(O)$_{0-1}$-aryl, —O-heteroaryl, —S(O)$_{0-1}$-heteroaryl, -alkyl-cycloalkyl, -alkyl-heterocyclyl, -alkyl-aryl, -alkyl-heteroaryl and =O, each of which is optionally substituted, (preferably R[4] is selected from the group consisting of H, halogen, CN, alkyl, substituted alkyl, —O—(C$_1$-C$_4$alkyl), —S—(C$_1$-C$_4$alkyl) and —S(O)$_2$—(C$_1$-C$_4$alkyl)); and R[11] is H or C$_1$-C$_4$alkyl, preferably Me.

In another preferred embodiment of the compounds according to the present invention, Z is selected from the group consisting of —C(=O)N(R[9])—, —N(R[9])—C(O)—, —N(R[9])— and

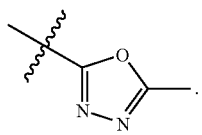

In another preferred embodiment of the compounds according to the present invention, Z is

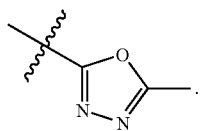

In another preferred embodiment of the compounds according to the present invention, Z is —C(=O)N(R9)-.

In another preferred embodiment of the compounds according to the present invention, Z is —N(R9)-C(O)—.

In another preferred embodiment of the compounds according to the present invention, —Z—(CH$_2$)$_s$—(W)$_n$—R[7] is selected from the group consisting of

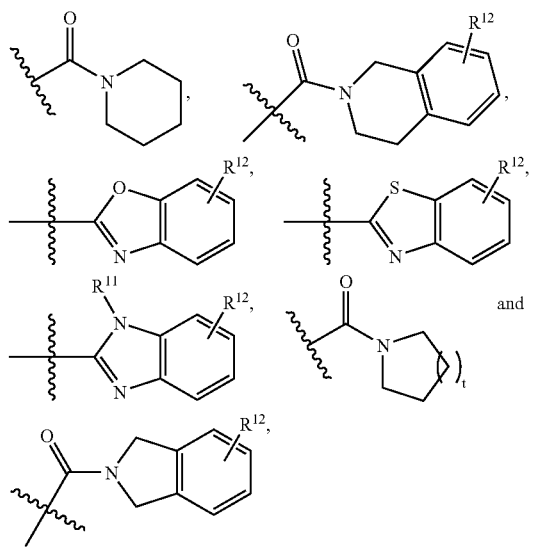

wherein t is 1, 3 or 4; and

R[12] is selected from the group consisting of hydrogen, halogen, haloalkyl, cyano, nitro, alkyl, cycloalkyl, alkenyl, cycloalkenyl, alkynyl, heterocycle, aryl, heteroaryl, —OR, —SR, —S(=O)R, —S(=O)$_2$R, —P(=O)$_2$R, —S(=O)$_2$OR, —P(=O)$_2$OR, —N(R)(R), —N(R)S(=O)$_2$R, —S(=O)$_2$N(R)(R), —N(R)P(=O)$_2$R, —P(=O)$_2$N(R)(R), —C(=O)OR, —C(=O)R, —C(=O)N(R)(R), —C(=S)N(R)(R), —OC(=O)R, —OC(=O)N(R)(R), —OC(=S)N(R)(R), —N(R)C(=O)OR, —N(R)C(=S)OR, —N(R)C(=O)N(R)(R), —N(R)C(=S)N(R)(R), —N(R)S(=O)$_2$N(R)(R), —N(R)P(=O)$_2$N(R)(R), —N(R)C(=O)R, —N(R)C(=S)R and —N(R)P(=O)$_2$R, wherein each R is independently selected from the group consisting of hydrogen, alkyl, cycloalkyl, alkenyl, cycloalkenyl, alkynyl, heterocycle, aryl and heteroaryl.

In a preferred embodiment of the compounds according to the present invention, M is selected from the group consisting of

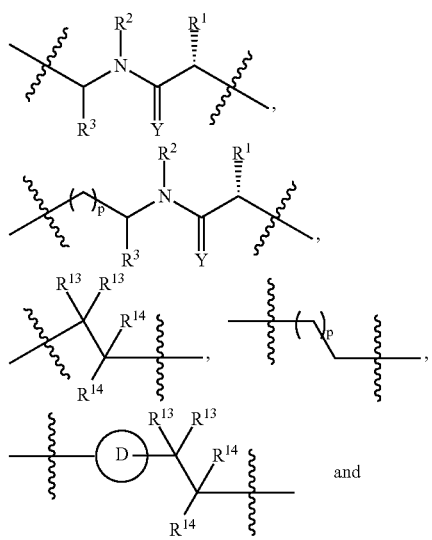

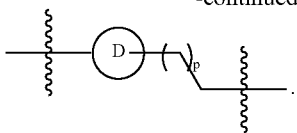

In another preferred embodiment of the compounds according to the present invention M is selected from the group consisting of

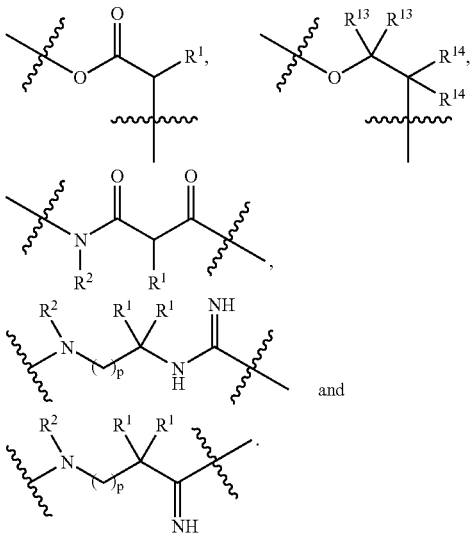

and

In another preferred embodiment of the compounds according to the present invention, M is selected from the group consisting of

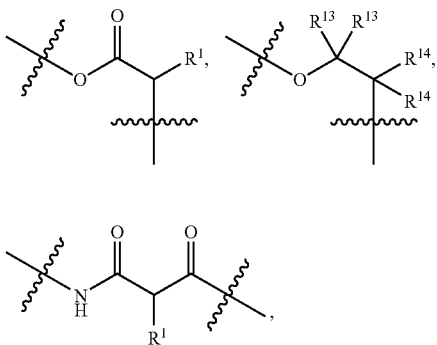

and

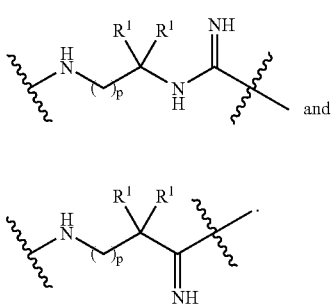

In another preferred embodiment of the compounds according to the present invention, M is

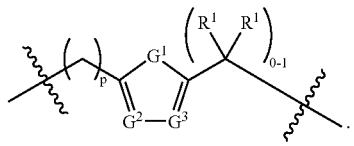

In another preferred embodiment of the compounds according to the present invention, M is

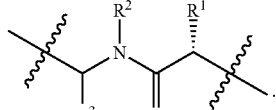

In another preferred embodiment of the compounds according to the present invention, M is

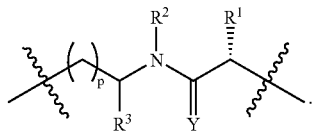

In another preferred embodiment of the compounds according to the present invention, M is

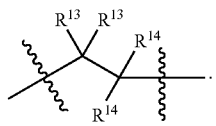

In another preferred embodiment of the compounds according to the present invention, M is

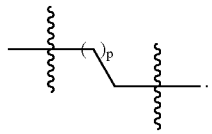

In another preferred embodiment of the compounds according to the present invention, M is

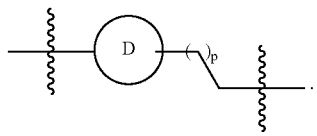

In another preferred embodiment of the compounds according to the present invention, $R^2$ is H, $R^3$ is H, and $R^1$ is Me, Et, OH, or Ph.

In another preferred embodiment of the compounds according to the present invention, $R^1$ is H, Me or —$CF_3$, preferably Me.

In another preferred embodiment of the compounds according to the present invention, $R^1$ is (S—) Me.

In another preferred embodiment of the compounds according to the present invention, $R^2$ is H or methyl.

In another preferred embodiment of the compounds according to the present invention, $R^3$ is H or methyl.

In another preferred embodiment of the compounds according to the present invention, W is —O—.

In another preferred embodiment of the compounds according to the present invention, n is 0.

In another preferred embodiment of the compounds according to the present invention, s is 0, 1 or 2, preferably 1.

In another preferred embodiment of the compounds according to the present invention, u is 0 or 1, preferably 0.

In another preferred embodiment of the compounds according to the present invention, $R^4$ is halo or alkyl, more preferably Cl, F or Me.

In another preferred embodiment of the compounds according to the present invention, $X^4$ is a bond, $X^1$ and $X^2$, are each independently N; $X^3$ and $X^5$ are each independently C, wherein $X^3$ is C substituted with $R^5$, wherein $R^5$ is preferably —$CF_3$.

In another preferred embodiment of the compounds according to the present invention, $R^5$ is —$CF_3$.

In another preferred embodiment of the compounds according to the present invention, $R^6$ is selected from the group consisting of Me, —$CF_3$, —$NH_2$ and —$NO_2$.

In another preferred embodiment of the compounds according to the present invention, $R^7$ is substituted with a substituent selected from the group consisting of alkoxy (preferably methoxy), alkyl (preferably methyl or ethyl, more preferably methyl), halo (preferably F, Cl or Br), —$CO_2$alkyl (preferably $CO_2$Me), $CF_3$, —C(O)—O-alkyl, fused heterocycle, —O—$CF_3$, —O—$CHF_2$, —$NH_2$, —NH-alkyl, —N(alkyl)$_2$ and —O-phenyl In another preferred embodiment of the compounds according to the present invention, $R^7$ is substituted with methoxy.

In another preferred embodiment of the compounds according to the present invention, each $R^8$ is independently selected from the group consisting of H, methyl, ethyl and isopropyl, more preferably each $R^8$ is independently H or methyl, more preferably still, each $R^8$ is H.

In another preferred embodiment of the compounds according to the present invention, $R^9$ is H.

In another preferred embodiment of the compounds according to the present invention, Y is nil.

In another preferred embodiment of the compounds according to the present invention, Y is O.

In another preferred embodiment of the compounds according to the present invention, D is

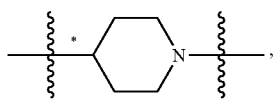

wherein * represents the point of attachment to ring A.

In another preferred embodiment of the compounds according to the present invention, $R^6$ and Z together form an optionally substituted heterocycle.

In another preferred embodiment of the compounds according to the present invention, the optionally substituted structure of ring B, $R^6$ and Z, wherein $R^6$ and Z together form a ring, is selected from the group consisting of

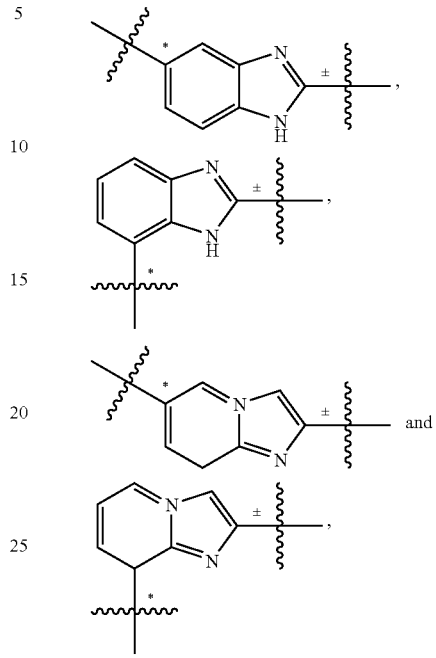

wherein * represents the point of attachment towards ring A and ± represents the point of attachment towards group Z. In a preferred embodiment, such structure is unsubstituted or substituted with methyl or —$CF_3$.

In another preferred embodiment of the compounds according to the present invention, the optionally substituted structure of ring B, $R^6$ and Z, wherein $R^6$ and Z together form a ring, is

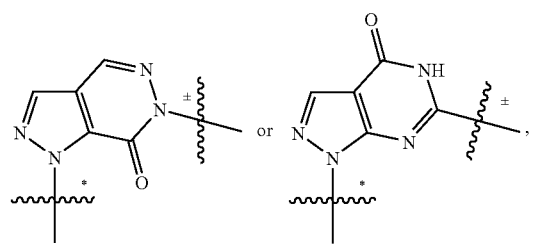

wherein * represents the point of attachment towards ring A and ± represents the point of attachment towards group Z. In a preferred embodiment, such structure is unsubstituted or substituted with methyl and/or —$CF_3$.

In a preferred embodiment of the present invention E is selected from the group consisting of

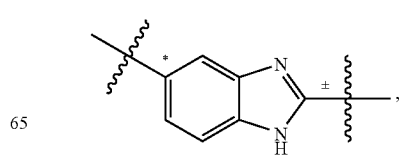

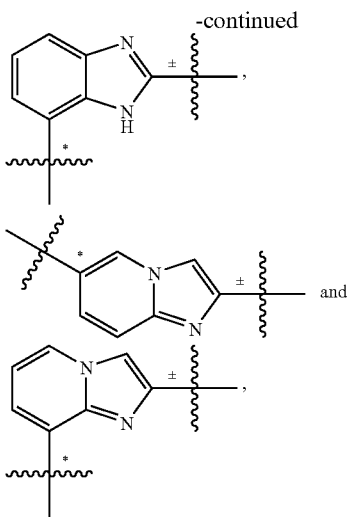

wherein * represents the point of attachment towards ring A and ± represents the point of attachment to group Z.

In another preferred embodiment of the compounds according to the present invention, M and ring B are in a meta or para position on ring A.

In another preferred embodiment of the compounds according to the present invention, the compound is a compound according to Formula (I).

In another preferred embodiment of the compounds according to the present invention, the compound is a compound according to Formula (II).

In another preferred embodiment of the compounds according to the present invention, the compound is a compound according to Formula (III).

In a preferred embodiment of Formula (I) of the compounds according to the present invention,
A is a 5 membered heteroaryl;
B is a 5 membered heteroaryl;
u is 0;
M is —(CH$_2$)—NH—C(O)—CH(CH$_3$)—
each R$^8$ is H;
R$^4$ is preferably H;
R$^5$ is preferably —CF$_3$;
R$^6$ is preferably H;
Z is —C(O)—NH—;
s is 1;
n is 0; and
R$^7$ is optionally substituted phenyl.

In another preferred embodiment of Formula (I) of the compounds according to the present invention,
A is

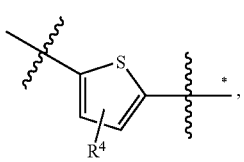

wherein * represents the point of attachment to M;
B is

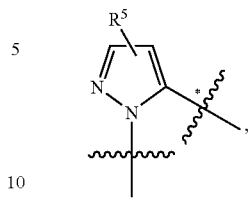

wherein * represents the point of attachment to group Z;
u is 0;
M is —(CH$_2$)—NH—C(O)—CH(CH$_3$)—
each R$^8$ is H;
R$^4$ is H;
R$^5$ is —CF$_3$;
R$^6$ is H;
Z is —C(O)—NH—;
s is 1;
n is 0; and
R$^7$ is optionally substituted phenyl.

In another preferred embodiment of Formula (I) of the compounds according to the present invention,
A is

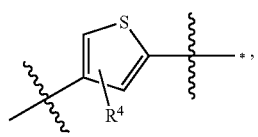

wherein * represents the point of attachment to M;
B is

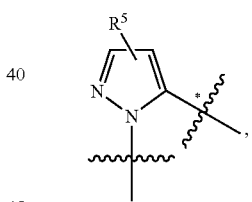

wherein * represents the point of attachment to group Z;
u is 0;
M is —(CH$_2$)—NH—C(O)—CH(CH$_3$)—
each R$^8$ is H;
R$^4$ is H;
R$^5$ is —CF$_3$;
R$^6$ is H;
Z is —C(O)—NH—;
s is 1;
n is 0; and
R$^7$ is optionally substituted phenyl.

In another preferred embodiment of Formula (I) of the compounds according to the present invention,
A is a 5 membered heteroaryl;
B is a 5 membered heteroaryl;
u is 0;
M is —(CH$_2$)—NH—C(O)—CH(CH$_3$)— or —(CH$_2$)—NH—(CH$_2$)$_2$—;
each R$^8$ is H or Me;
R$^4$ is preferably H;
R$^5$ is preferably —CF$_3$;
R$^6$ is preferably H;

Z is

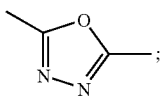

s is 0;
n is 0; and
R⁷ is optionally substituted phenyl.

In another preferred embodiment of Formula (I) of the compounds according to the present invention,
A is

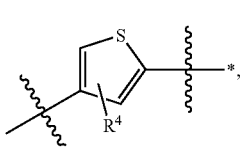

wherein * represents the point of attachment to M;
B is

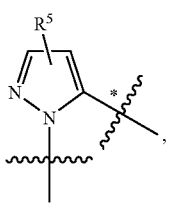

wherein * represents the point of attachment to group Z;
u is 0;
M is —(CH₂)—NH—C(O)—CH(CH₃)— or —(CH₂)—NH—(CH₂)₂—;
each R⁸ is H or Me;
R⁴ is H;
R⁵ is —CF₃;
R⁶ is H;
Z is

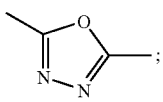

s is 0;
n is 0; and
R⁷ is optionally substituted phenyl.

In another preferred embodiment of Formula (I) of the compounds according to the present invention,
A is phenyl;
B is 5 membered heteroaryl;
u is 0;
M is

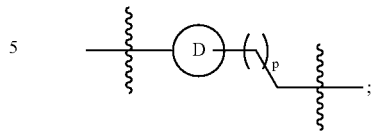

each R⁸ is H or Me;
R⁴ is preferably H;
R⁵ is preferably —CF₃;
R⁶ is preferably H;
Z is —C(O)—NH— or

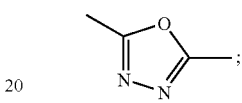

s is 1;
n is 0; and
R⁷ is optionally substituted phenyl.

In another preferred embodiment of Formula (I) of the compounds according to the present invention,
A is phenyl;
B is

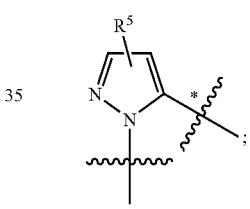

u is 0;
M is

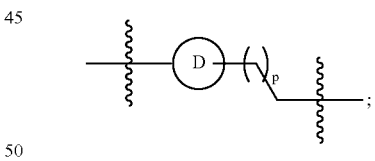

each R⁸ is H or Me;
R⁴ is H;
R⁵ is —CF₃;
R⁶ is H;
Z is —C(O)—NH— or

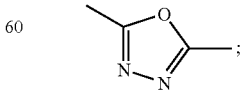

s is 1;
n is 0; and
R⁷ is optionally substituted phenyl.

In another preferred embodiment of Formula (I) of the compounds according to the present invention,
A is phenyl;
B is

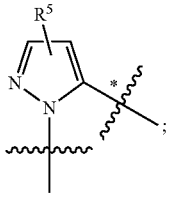

u is 0;
M is

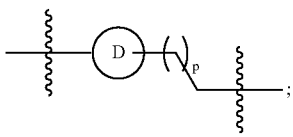

D is

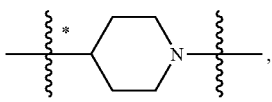

wherein * represents the point of attachment to ring A; each R$^8$ is H or Me;
R$^4$ is H;
R$^5$ is —CF$_3$;
R$^6$ is H;
Z is —C(O)—NH— or

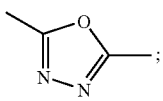

s is 1;
n is 0; and
R$^7$ is optionally substituted phenyl.

In another preferred embodiment of Formula (I) of the compounds according to the present invention,
A is phenyl;
B is a 5 membered heteroaryl;
u is 0;
M is —CH$_2$—NH—(CH$_2$)$_2$—, or —CH$_2$—N(CH$_3$)—(CH$_2$)$_2$—, preferably —CH$_2$—NH—(CH$_2$)$_2$—, each R$^8$ is H or Me, preferably one R$^8$ is H and the other R$^8$ is Me;
R$^4$ is H, halo (preferably F) or alkyl, preferably H;
R$^5$ is preferably —CF$_3$;
R$^6$ is preferably H;
Z is —C(O)—NH—;
s is 1;
n is 0; and
R$^7$ is optionally substituted phenyl.

In another preferred embodiment of Formula (I) of the compounds according to the present invention,
A is phenyl;
B is

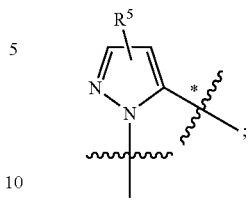

u is 0;
M is —CH$_2$—NH—(CH$_2$)$_2$—, or —CH$_2$—N(CH$_3$)—(CH$_2$)$_2$—, preferably —CH$_2$—NH—(CH$_2$)$_2$—, each R$^8$ is H or Me, preferably one R$^3$ is H and the other R$^3$ is Me;
R$^4$ is H, halo (preferably F) or alkyl, preferably H;
R$^5$ is —CF$_3$;
R$^6$ is H;
Z is —C(O)—NH—;
s is 1;
n is 0; and
R$^7$ is optionally substituted phenyl.

In another preferred embodiment of Formula (I) of the compounds according to the present invention,
A is phenyl;
B is a 5 membered heteroaryl;
u is 0;
M is —CH$_2$—NH—(CH$_2$)$_2$—, or —CH$_2$—N(CH$_3$)—(CH$_2$)$_2$—, preferably —CH$_2$—NH—(CH$_2$)$_2$—, each R$^3$ is H or Me, preferably one R$^3$ is H and the other R$^3$ is Me;
R$^4$ is H, halo (preferably F) or alkyl, preferably H;
R$^5$ is preferably —CF$_3$;
R$^6$ is preferably H;
Z is

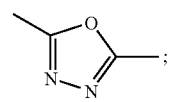

s is 0;
n is 0; and
R$^7$ is optionally substituted phenyl.

In another preferred embodiment of Formula (I) of the compounds according to the present invention,
A is phenyl;
B is

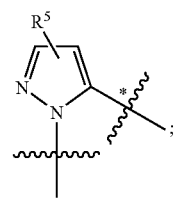

u is 0;
M is —CH$_2$—NH—(CH$_2$)$_2$—, or —CH$_2$—N(CH$_3$)—(CH$_2$)$_2$—, preferably —CH$_2$—NH—(CH$_2$)$_2$—, each R$^8$ is H or Me, preferably one R$^8$ is H and the other R$^8$ is Me;
R$^4$ is H, halo (preferably F) or alkyl, preferably H;
R$^5$ is —CF$_3$;
R$^6$ is H;

Z is

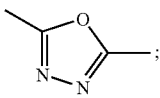

s is 0;
n is 0; and
R$^7$ is optionally substituted phenyl.

In another preferred embodiment of Formula (I) of the compounds according to the present invention,
A is phenyl;
B is a 5-membered heteroaryl;
u is 0;
M is —CH$_2$—NH—(CH$_2$)$_2$—, or —CH$_2$—N(CH$_3$)—(CH$_2$)$_2$—, preferably —CH$_2$—NH—(CH$_2$)$_2$—, each R$^8$ is H or Me, preferably one R$^8$ is H and the other R$^8$ is Me;
R$^4$ is H, halo (preferably F) or alkyl, preferably H;
R$^5$ is preferably —CF$_3$;
R$^6$ is preferably H;
Z is —O—;
s is 2;
n is 0; and
R$^7$ is optionally substituted phenyl.

In another preferred embodiment of Formula (I) of the compounds according to the present invention,
A is phenyl;
B is

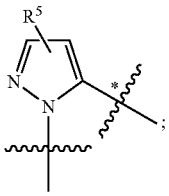

u is 0;
M is —CH$_2$—NH—(CH$_2$)$_2$—, or —CH$_2$—N(CH$_3$)—(CH$_2$)$_2$—, preferably —CH$_2$—NH—(CH$_2$)$_2$—, each R$^8$ is H or Me, preferably one R$^8$ is H and the other R$^8$ is Me;
R$^4$ is H, halo (preferably F) or alkyl, preferably H;
R$^5$ is preferably —CF$_3$;
R$^6$ is preferably H;
Z is —O—;
s is 2;
n is 0; and
R$^7$ is optionally substituted phenyl.

In another preferred embodiment of Formula (I) of the compounds according to the present invention,
A is a 5- or 6-membered heterocyclyl;
B is a 5 membered heteroaryl;
u is 0;
M is —(CH$_2$)$_2$— each R$^8$ is H or Me, preferably one R$^8$ is H and the other R$^8$ is Me;
R$^4$ is preferably H;
R$^5$ is preferably —CF$_3$;
R$^6$ is preferably H;
Z is —C(O)—NH—;
s is 1;
n is 0; and
R$^7$ is optionally substituted phenyl.

In another preferred embodiment of Formula (I) of the compounds according to the present invention,
A is a 5- or 6-membered heterocyclyl;
B is

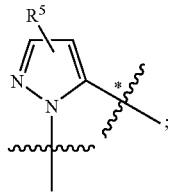

u is 0;
M is —(CH$_2$)$_2$—;
each R$^8$ is H or Me, preferably one R$^8$ is H and the other R$^8$ is Me;
R$^4$ is H;
R$^5$ is —CF$_3$;
R$^6$ is H;
Z is —C(O)—NH—;
s is 1;
n is 0; and
R$^7$ is optionally substituted phenyl.

In another preferred embodiment of Formula (I) of the compounds according to the present invention,
A is

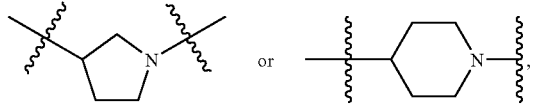

preferably

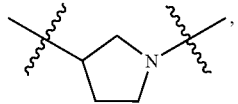

wherein group M is attached via the N atom of ring A;
B is

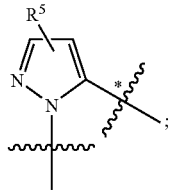

u is 0;
M is —(CH$_2$)$_2$—;
each R$^8$ is H or Me, preferably one R$^8$ is H and the other R$^8$ is Me;
R$^4$ is H;
R$^5$ is —CF$_3$;
R$^6$ is H;
Z is —C(O)—NH—;
s is 1;

n is 0; and

R⁷ is optionally substituted phenyl.

In another preferred embodiment of Formula (I) of the compounds according to the present invention, A is a 5- or 6-membered heterocyclyl;

B is a 5 membered heteroaryl;

u is 0;

M is —(CH$_2$)$_2$—;

each R$^8$ is H or Me, preferably one R$^8$ is H and the other R$^8$ is Me;

R$^4$ is preferably H;

R$^5$ is preferably —CF$_3$;

R$^6$ is preferably H;

Z is

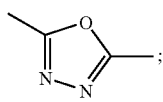

s is 1;

n is 0; and

R$^7$ is optionally substituted phenyl.

In another preferred embodiment of Formula (I) of the compounds according to the present invention, A is a 5- or 6-membered heterocyclyl;

B is

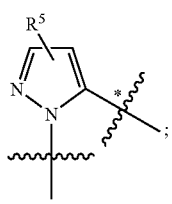

u is 0;

M is —(CH$_2$)$_2$—;

each R$^8$ is H or Me, preferably one R$^8$ is H and the other R$^8$ is Me;

R$^4$ is H;

R$^5$ is —CF$_3$;

R$^6$ is H;

Z is

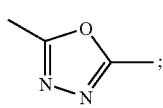

s is 1;

n is 0; and

R$^7$ is optionally substituted phenyl.

In another preferred embodiment of Formula (I) of the compounds according to the present invention, A is

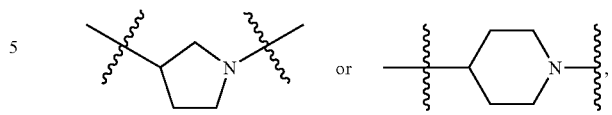

preferably

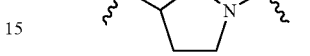

wherein group M is attached via the N atom of ring A;

B is

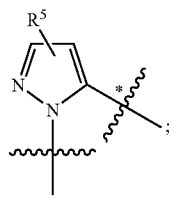

u is 0;

M is —(CH$_2$)$_2$—;

each R$^8$ is H or Me, preferably one R$^8$ is H and the other R$^8$ is Me;

R$^4$ is H;

R$^5$ is —CF$_3$;

R$^6$ is H;

Z is

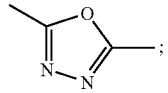

s is 1;

n is 0; and

R$^7$ is optionally substituted phenyl.

In a preferred embodiment of Formula (II) of the compounds according to the present invention, A is a 5- or 6-membered heterocyclyl;

B is phenyl;

u is 0;

M is —(CH$_2$)$_2$—;

each R$^8$ is H or Me, preferably one R$^8$ is H and the other R$^8$ is Me;

R$^4$ is preferably H;

R$^5$ is preferably H;

R$^6$ is H, Me, —NO$_2$, —NH$_2$ or —CF$_3$;

Z is —NH—C(O)—;

s is 0;

n is 0; and

R$^7$ is optionally substituted phenyl.

In another preferred embodiment of Formula (II) of the compounds according to the present invention, A is

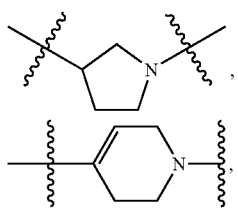 , 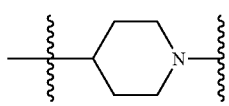 or

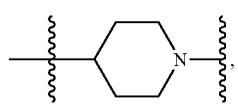, preferably

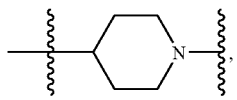, wherein group M is attached via the N atom of ring A;
B is phenyl;
u is 0;
M is —(CH$_2$)$_2$—;
each R$^8$ is H or Me, preferably one R$^8$ is H and the other R$^8$ is Me;
R$^4$ is H;
R$^5$ is H;
R$^6$ is H, Me, —NO$_2$, —NH$_2$ or —CF$_3$;
Z is —NH—C(O)—;
s is 0;
n is 0; and
R$^7$ is optionally substituted phenyl.

In a preferred embodiment of Formula (III),
E is selected from the group consisting of

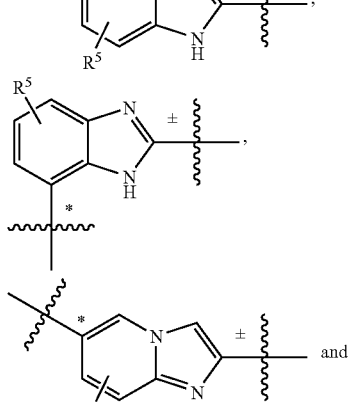

wherein * represents the point of attachment towards ring A and ± represents the point of attachment to group Z;

A is phenyl or a 5- or 6-membered heterocycle (preferably the 6-membered heterocycle is

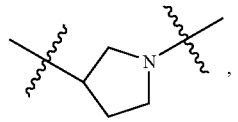, and the 5-membered heterocycle is

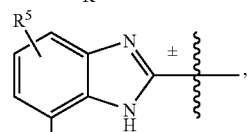, wherein group M is attached via the N atom of

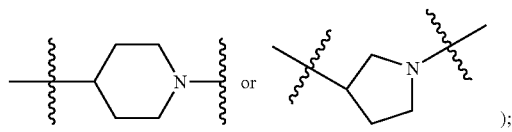 );

u is 0;
M is —(CH$_2$)—NH—(CH$_2$)$_2$—;
each R$^8$ is H or Me, preferably one R$^8$ is H and the other R$^8$ is Me;
R$^4$ is H;
R$^5$ is H, Me or —CF$_3$, preferably —CF$_3$;
Z is a bond;
s is 0;
n is 0; and
R$^7$ is optionally substituted phenyl.

In a preferred embodiment of Formula (III),
E is selected from the group consisting of

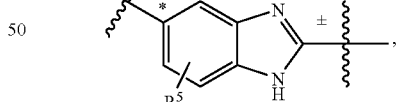

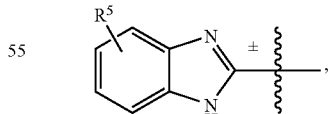

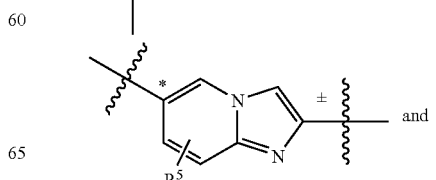

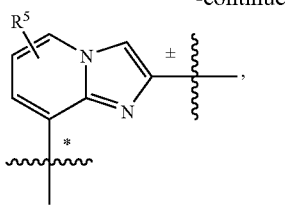

wherein * represents the point of attachment towards ring A and ± represents the point of attachment to group Z;
A is phenyl or

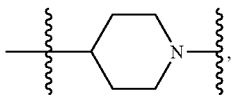

wherein group M is attached via the N atom of

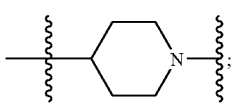

u is 0;
M is —(CH$_2$)—NH—(CH$_2$)$_2$—;
each R$^8$ is H or Me, preferably one R$^8$ is H and the other R$^8$ is Me;
R$^4$ is H;
R$^5$ is H, Me or —CF$_3$, preferably —CF$_3$;
Z is a bond;
s is 0;
n is 0; and
R$^7$ is optionally substituted phenyl.

Throughout the specification, preferred embodiments of one or more chemical groups are identified. Also preferred are combinations of preferred embodiments. It is understood that any and all embodiments of the present invention may be taken in conjunction with any other embodiment to describe additional even more preferred embodiments of the present invention. For example, the invention describes preferred embodiments of ring B in the compounds and describes preferred embodiments of group Z. Thus, as an example, also contemplated as within the scope of the invention are compounds in which preferred examples of ring B are as described and in which preferred examples of group Z are as described. The invention may be embodied in other specific forms without departing from the spirit or essential attributes thereof. Furthermore, any elements of an embodiment are meant to be combined with any and all other elements from any of the embodiments to describe additional embodiments.

Some examples of the compounds according to the first aspect of the invention are given below. These examples merely serve to exemplify some of the compounds of the first aspect of the invention and do not limit the scope of the invention.

Synthetic Schemes and Experimental Procedures

The compounds of the invention can be prepared according to the reaction schemes for the examples illustrated below utilizing methods known to one of ordinary skill in the art. These schemes serve to exemplify some procedures that can be used to make the compounds of the invention. One skilled in the art will recognize that other general synthetic procedures may be used. The compounds of the invention can be prepared from starting components that are commercially available. Any kind of substitutions can be made to the starting components to obtain the compounds of the invention according to procedures that are well known to those skilled in the art.

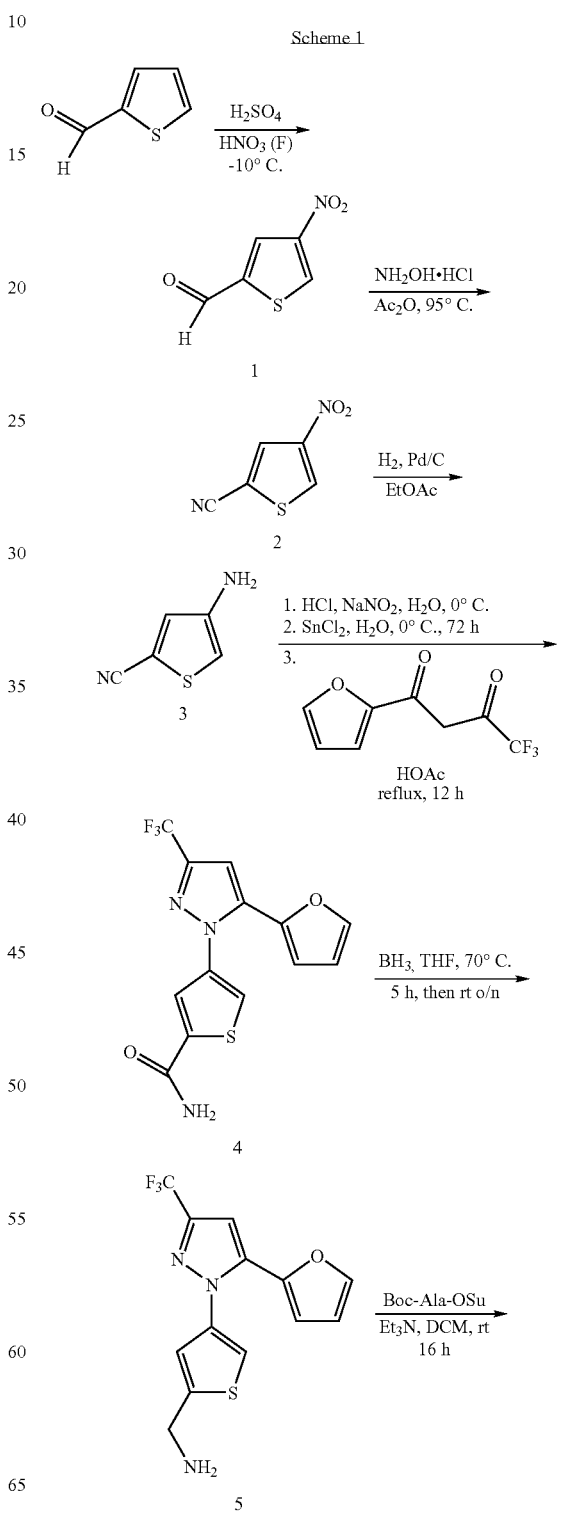

Scheme 1

-continued

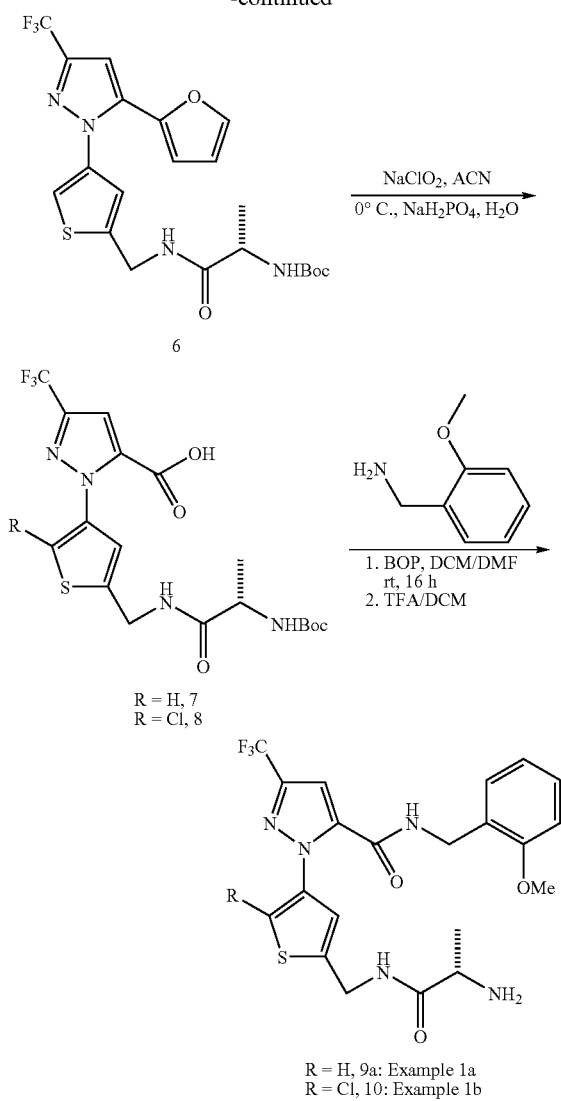

R = H, 7
R = Cl, 8

R = H, 9a: Example 1a
R = Cl, 10: Example 1b

Example 1a (S)-1-(5-((2-aminopropanamido)methyl)thiophen-3-yl)-N-(2-methoxybenzyl)-3-(trifluoromethyl)-1H-pyrazole-5-carboxamide (9a)

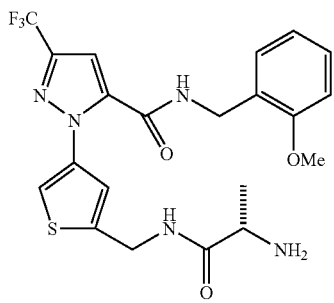

Step 1: 4-nitrothiophene-2-carbaldehyde (1)

A mixture of fuming $HNO_3$ (4.0 mL) in conc. $H_2SO_4$ (3.1 mL) was added to a solution of thiophene-2-carbaldehyde (2.0 g, 17.8 mmol) in conc. $H_2SO_4$ (4.7 mL) cooled in an ice-salt bath according to the procedure of Pierre Fournari and Jean Paul Chane (Bull. Soc. Chim. Fr., 1963, 479-484). After completion of addition the mixture was stirred for 5 min, then ice was added, and the mixture was extracted with ether. The ether extracts were washed with satd $NaHCO_3$, then with brine, dried over $MgSO_4$, filtered and concentrated giving brown oil. Proton NMR of the crude showed a mixture of the two regioisomers in a ratio of almost 40:60 for 4-nitrothiophene-2-carbaldehyde and 5-nitrothiophene-2-carbaldehyde respectively. The mixture was separated by column chromatography eluting with 30-50% DCM/hexanes. 4-Nitrothiophene-2-carbaldehyde was obtained in 40% yield as a light yellow solid.

$^1$H NMR (CDCl$_3$) δ(ppm): 9.95 (s, 1H); 8.63 (s, 1H), 8.27 (s, 1H).

Step 2: 4-nitrothiophene-2-carbonitrile (2)

Acetic anhydride (1.2 mL) was added to a mixture of aldehyde 1 (314.3 mg, 2.00 mmol) and hydroxylamine hydrochloride (277.6 mg, 4.00 mmol) in pyridine (1.5 mL) preheated at 95° C. according to the procedure of M. Bobosikova et al. (J. Chem. Soc., Perkin Trans. I, 2001, 680-689). After 2 h at 95° C. the mixture was cooled and poured over ice and the precipitate was filtered out and allowed to air dry. Nitrile 2 was obtained in 68% yield as beige solid $^1$H NMR (CDCl$_3$) δ(ppm): 8.51 (s, 1H), 8.14 (s, 1H).

Step 3: 4-aminothiophene-2-carbonitrile (3)

Nitrile 2 (100 mg, 0.65 mmol) in EtOAc (4 mL) and dioxane (0.2 mL) and 5% Pd/C (77 mg) were placed under hydrogen atmosphere. After 16 hours 10% Pd/C Degussa wet catalyst (30 mg) was added and the mixture was stirred under 1 atm of hydrogen for another 24 h. The catalyst was filtered over celite and the filtrate was concentrated under vacuum and purified by column chromatography eluting with 20-30% EtOAc/hexanes giving amine 3 in 41%. LRMS (ESI): calc. 124.2; found 125.1 (MH)$^+$.

Step 4: 4-(5-(furan-2-yl)-3-(trifluoromethyl)-1H-pyrazol-1-yl)thiophene-2-carboxamide (4)

Ice cold solution of $NaNO_2$ (99.3 mg, 1.44 mmol) in $H_2O$ (0.43 mL) was added drop-wise to ice cold solution of amine 3 (0.177 g, 1.43 mmol) in conc. HCl (1.43 mL) the mixture was stirred at 0° C. for 40 minutes according to the procedure of M. L. Quan et al. (JMC, 2005, 48, 1729-1744). Ice cold solution of $SnCl_2$ (1.007 g, 4.464 mmol) in conc. HCl (0.58 mL) was added dropwise, and the mixture was left at 0° C. for 16 h. The precipitate that formed was filtered and washed with ice-cold brine (4.5 mL) then with 2:1 Hex: ether (4.5 mL) and was air dried leaving 0.398 g of a beige solid. The material was refluxed with 4,4,4-trifluoro-1-(furan-2-yl)butane-1,3-dione (0.24 g, 1.16 mmol) in acetic acid (4.6 mL) for 16 h. The solvent was evaporated, EtOAc and 1N HCl solution were added and organic layer was separated and washed with brine, dried over $MgSO_4$, filtered and concentrated. The crude material was purified by column chromatography eluting with 20-100% EtOAc:hexanes to give compound 4 as a light yellow solid in 30.6% yield. LRMS (ESI): calc. 327.3; found 328.0 (MH)$^+$.

Step 5: (4-(5-(furan-2-yl)-3-(trifluoromethyl)-1H-pyrazol-1-yl)thiophen-2-yl)methanamine (5)

A one molar solution of BH$_3$ in THF (1.2 mL, 1.2 mmol) was added to amide 4 (128 mg, 0.39 mmol) in THF (1.5 mL) and the mixture was heated in a sealed tube at 70° C. for 5 h, then it was stirred at room temperature for 16 h. The mixture was cooled in ice and few drops of conc HCl were added, then most of the solvent was removed and H$_2$O was added and the mixture was heated to reflux for 20 min. EtOAc was added and the PH adjusted to 8 with saturated NaHCO$_3$ and extracted with EtOAc (2×). The organic extracts were dried over MgSO$_4$, filtered and concentrated leaving crude 5 (110 mg) as a clear oil. LRMS (ESI): calc. 313.3; found 314.0 (MH)$^+$. The material was used as is for the next step.

Step 6: (S)-tert-butyl 1-((4-(5-(furan-2-yl)-3-(trifluoromethyl)-1H-pyrazol-1-yl)thiophen-2-yl)methylamino)-1-oxopropan-2-ylcarbamate (6)

(S)-2,5-Dioxopyrrolidin-1-yl 2-(tert-butoxycarbonylamino)propanoate (130 mg, 0.45 mmol) was added to amine 5 (110 mg, 0.35 mmol) and Et$_3$N (94.4 mg, 130 μL, 0.93 mmol) in DCM (2 mL) and DMF (0.2 mL) and the mixture was stirred at room temperature for 36 h. DCM was added followed by 1N HCl and the organic layer was separated and washed with H$_2$O, then with saturated NaHCO$_3$, dried over MgSO$_4$, filtered and concentrated. The crude material was purified by chromatography (Biotage, 25+S column) eluting with 0-50% EtOAc/hexanes. Compound 6 was obtained in 49% yield as a white solid. LRMS (ESI): calc. 484.5; found 507.1 (MNa)$^+$.

Step 7: (S)-1-(5-((2-(tert-butoxycarbonylamino)propanamido)methyl)thiophen-3-yl)-3-(trifluoromethyl)-1H-pyrazole-5-carboxylic acid (7) and (S)-1-(5-((2-(tert-butoxycarbonylamino)propanamido)methyl)-2-chlorothiophen-3-yl)-3-(trifluoromethyl)-1H-pyrazole-5-carboxylic acid (8)

A solution of sodium chlorite (153.7 mg, 1.7 mmol) in H$_2$O (0.7 mL) was added dropwise to an ice cold mixture of compound 6 (83 mg, 0.17 mmol) in acetonitrile (0.5 mL) and NaH$_2$PO$_4$ (102 mg, 0.85 mmol) in H$_2$O (0.2 mL). The reaction was stirred at room temperature for 1 h. A solution of 1N NaOH was added till basic and the reaction was extracted with DCM, and the DCM extracts were washed with 1N NaOH solution. The combined basic extracts were acidified with conc. HCl and extracted with EtOAc. The EtOAc extracts were concentrated leaving a light yellow semi-solid (70 mg). LRMS (ESI): 462.4 (calc); 461.1 (obs M-1) and 495.1, 497.1 (M+Cl-1). HPLC is a mixture of ~8:2 of 7:8. LRMS (ESI): calc. 462.1 for 7; found 461.1 (M-H)— and calc. 496.9 for 8; found 495.1/497.1 (M-H). The material was used as is for the next step.

Step 8: (S)-1-(5-((2-aminopropanamido)methyl)thiophen-3-yl)-N-(2-methoxybenzyl)-3-(trifluoromethyl)-1H-pyrazole-5-carboxamide 9a and (S)-1-(5-((2-aminopropanamido)methyl)-2-chlorothiophen-3-yl)-N-(2-methoxybenzyl)-3-(trifluoromethyl)-1H-pyrazole-5-carboxamide 10

To the mixture of acids 7 and 8 (70 mg, 0.15 mmol) in DCM (2 mL) and Et$_3$N (47 μL, 0.34 mmol) was added BOP (73.6 mg, 0.17 mmol) followed by p-methoxybenzylamine (50 μL, 0.38 mmol) and the reaction mixture was stirred at room temperature for 36 h. EtOAc and 1N HCl were added and the organic layer was washed with 1N HCl, then H$_2$O, saturated NaHCO$_3$ (2×), dried over MgSO$_4$, filtered and then concentrated. The crude material was purified by chromatography (Biotage 25+S column) eluting with a gradient of 0-100% EtOAc/hexanes. HPLC showed the material to be 50:40 mixture of two very close peaks. LRMS (ESI): calc. 581.2 for 9a. found 482.2 (MH-Boc)$^+$, 604 (MNa)$^+$, calc. 615.2 for 10; found 638.2/640.2 (MNa)$^+$ This mixture in DCM (4 mL) was treated with TFA (1 mL) and after 1 h the material was taken to dryness and was purified by Prep-HPLC (Phenominix, Luna C18 column, 5-95% MeOH/H2O formic acid, 60 min)

9a:

H-NMR (MeOD-d$_4$) δ(ppm): 8.46 (s, 1H), 7.43 (d, J=1.4 Hz, 1H), 7.27 (dt, J=1.8, 6.9 Hz, 1H), 7.22 (dd, J=1.6, 7.6 Hz, 1H), 7.15 (d, J=0.8 Hz, 1H), 6.97 (d, J=8.2 Hz, 1H), 6.91 (t, J=7.4 Hz, 1H), 4.54 (d, J=3.5 Hz, 2H), 4.48 (s, 2H), 3.89 (quartet, J=7 Hz, 1H), 3.84 (s, 3H), 1.49 (d, J=7 Hz, 3H). LRMS (ESI): calc. 481.5; found 482.2 (MH)$^+$.

10:

H-NMR (MeOD-d$_4$) δ(ppm): 7.25 (dt, J=1.8, 7.2 Hz, 1H), 7.25 (s, 1H), 7.21 (d, J=7.6 Hz, 1H), 7.06 (s, 1H), 6.96 (d, J=8.2 Hz, 1H), 6.89 (t, J=7.4 Hz, 1H), 4.53 (s, 2H), 4.46 (s, 2H), 3.88 (quartet, J=7 Hz, 1H), 3.84 (s, 3H), 1.49 (d, J=6.8 Hz, 3H). LRMS (ESI): calc. 515.1/516.1; found 516.2/518.2 (MH)$^+$.

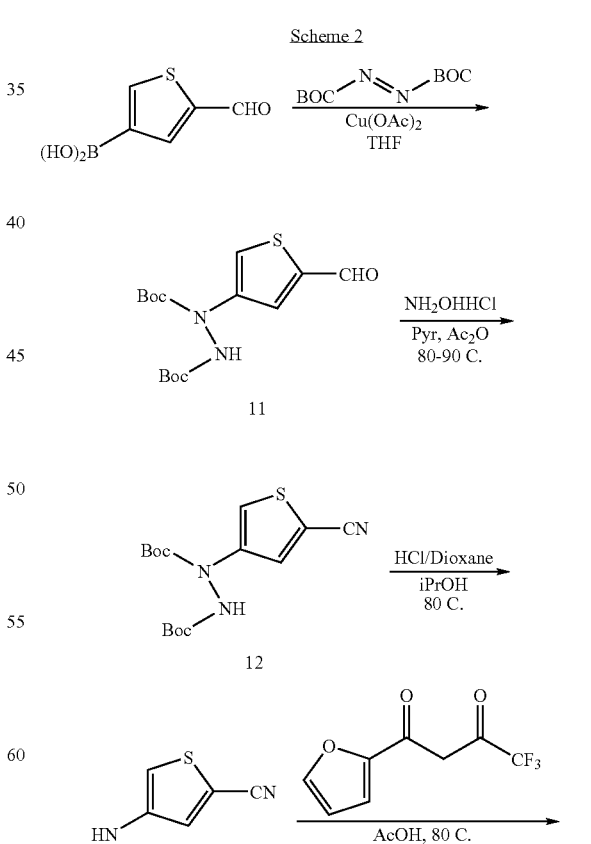

Scheme 2

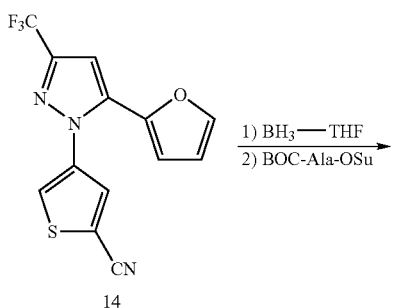

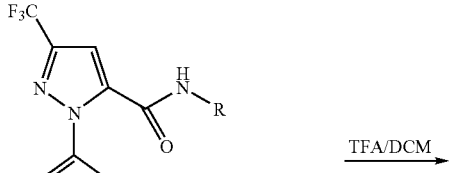

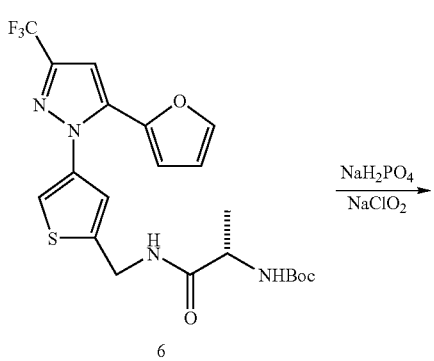

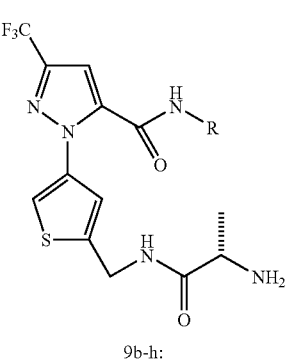

Example 1c (S)-1-(5-((2-aminopropanamido)methyl)thiophen-3-yl)-N-(2-methylbenzyl)-3-(trifluoromethyl)-1H-pyrazole-5-carboxamide (9b)

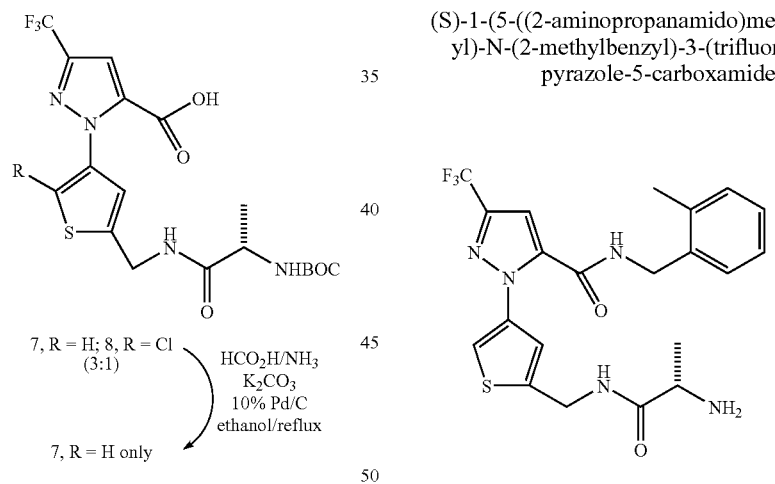

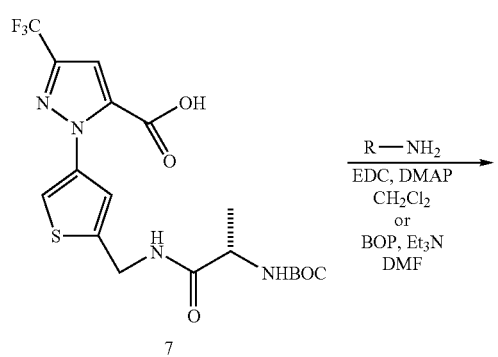

Step 1: Di-tert-butyl 1-(5-formylthiophen-3-yl)hydrazine-1,2-dicarboxylate (11)

To a solution of 5-formylthiophen-3-ylboronic acid (2 g, 12.82 mmol) and di-tert-butyl azodicarboxylate (1.476 g, 6.41 mmol) in THF (12 mL) under nitrogen was added copper (II) acetate (0.116 g, 0.641 mmol) in one portion according to the procedure of T. Uemura and N. Chatani (*J. Org. Chem.* 2005, 70, 8631-8634). The suspension was then stirred for 18.5 hours at room temperature. The resulting brown solution was then concentrated and the residue was dissolved in DCM and methanol and loaded on silica and applied to a 40M Biotage column. Elution with a gradient of 10 to 20% ethyl acetate in hexanes gave compound 11 (1.888 g, 86%) as a yellow crust. LRMS (ESI): calc. 342.12; found 365.2 $(MNa)^+$.

Step 2: Di-tert-butyl 1-(5-cyanothiophen-3-yl)hydrazine-1,2-dicarboxylate (12)

Hydroxylamine hydrochloride (0.766 g, 11.03 mmol) was added to a solution of compound 11 (1.888 g, 5.51 mmol) in pyridine (5.5 mL). The solution was heated to 90 degrees for 10 minutes and then cooled to room temperature. Acetic anhydride (3.23 mL, 34.2 mmol) was then added to the solution. It was then stirred at room temperature for 30 minutes and then at 80 degrees for 1 hour. The reaction was concentrated to half the volume under reduced pressure and then diluted with 300 mL of water, extracted into ethyl acetate (3×), washed with brine, dried over $Na_2SO_4$, filtered and then concentrated. The resulting yellow oil was then purified by silica gel chromatography through a 40M Biotage column with gradient of 12-24% ethyl acetate in hexanes to give compound 12 (1.39 g, 74%) as a white crusty solid. LRMS (ESI): calc. 339.13; found 338.1 (M-H)⁻.

Step 3: 4-hydrazinylthiophene-2-carbonitrile hydrochloride (13)

To a stirring solution of compound 12 (1.38 g, 4.07 mmol) in 2-propanol (10 mL) was added 4M HCl in dioxane (10 mL, 40.0 mmol). The reaction heated to 80 degrees for 1 hour turning into a dark brown solution. The mixture was evaporated to dryness and the resulting the brown solid suspended and sonicated in diethyl ether. The suspension was filtered to afford compound 13 (0.701 g, 97%) as a brown solid. LRMS (ESI): calc. 139.0; found 140.1 (MH)⁺.

Step 4: 4-(5-(furan-2-yl)-3-(trifluoromethyl)-1H-pyrazol-1-yl)thiophene-2-carbonitrile (14)

To a solution of compound 13 (0.701 g, 3.99 mmol) in AcOH (10 mL) was added 4,4,4-trifluoro-1-(2-furyl)-1,3-butanedione (0.591 mL, 3.99 mmol). The solution was stirred at 80 degrees for a total of 22 minutes. After the addition of toluene to the brown solution it was concentrated under reduced pressure to a brown-green sludge. The sludge was dry loaded onto a 40M Biotage column and then eluted with a gradient of 5 to 20% ethyl acetate in hexanes to furnish compound 14 (0.909 g, 74%) as a light brown oil which solidified upon standing. LRMS (ESI): calc. 309.2; found 310.1 (MH)⁺.

Step 5: (S)-tert-butyl 1-((4-(5-(furan-2-yl)-3-(trifluoromethyl)-1H-pyrazol-1-yl)thiophen-2-yl)methylamino)-1-oxopropan-2-ylcarbamate (6)

To a solution of compound 14 (0.907 g, 2.93 mmol) at 0 degrees in THF (3 mL) and under nitrogen was slowly added 1M borane tetrahydrofuran complex (11.73 mL, 11.73 mmol). The yellow solution was then stirred for 50 minutes at room temperature. It was cooled to 0 degrees and then slowly quenched with methanol (approx. 4 mL). After 10 minutes of stirring at room temperature the reaction solution was concentrated under reduced pressure to a yellow, gummy solid and dried under a high vacuum pump. The crude amine 5 was then dissolved in DCM (15 mL) at zero degrees and to this was added BOC-Ala-OSu (0.839 g, 2.93 mmol) followed by triethylamine (0.898 mL, 6.45 mmol). The reaction was stirred at zero degrees for 1 hour and at room temperature for 16 hours. The solvent was then removed under reduced pressure and the residue partitioned between ethyl acetate and saturated $NH_4Cl$. The layers were separated and the ethyl acetate phase washed further with saturated $NH_4Cl$ and then brine, dried over $Na_2SO_4$, filtered and concentrated. The residue was absorbed onto silica gel and then purified by silica gel chromatography using a 40M Biotage column with a gradient of 20 to 60% ethyl acetate and hexanes to give compound 6 (0.718 g, 51%) as a white crusty solid. LRMS (ESI): calc. 484.1; found 385.1 (MH-Boc)⁺, 507.2 (MNa)⁺.

Step 6: (S)-1-(5-((2-(tert-butoxycarbonylamino)propanamido)methyl)thiophen-3-yl)-3-(trifluoromethyl)-1H-pyrazole-5-carboxylic acid (7) and (S)-1-(5-((2-(tert-butoxycarbonylamino)propanamido)methyl)-2-chlorothiophen-3-yl)-3-(trifluoromethyl)-1H-pyrazole-5-carboxylic acid (8)

To a solution of compound 6 (1.20 g, 2.48 mmol) in acetonitrile (7.3 mL) at zero degrees was added sodium dihydrogen phosphate (1.486 g, 12.38 mmol) in water (3 mL). Sodium chlorite (2.240 g, 24.77 mmol) in water (10 mL) was then added slowly to the reaction. It was then stirred quickly at room temperature for 2 hours. The yellow colored biphasic reaction was then quenched with 15% NaOH (100 mL) and washed with dichloromethane. The combined dichloromethane layers were extracted with 15% NaOH. The aqueous phases were combined and then acidified with concentrated HCl (aq.) (50 mL) to give a cloudy yellow suspension. The suspension was extracted into ethyl acetate (3×), dried over $Na_2SO_4$, filtered and concentrated to give a yellow crusty solid. It was then purified by silica gel chromatography using a 40M Biotage column and a gradient of 5 to 10% methanol in DCM (1% AcOH) to give a inseparable mixture of compounds 7 and 8 in a ratio of 3:1 by proton NMR (0.689 g combined, approximately 60% yield) as a yellow crust. LRMS (ESI): calc. 462.1 for 7; found 461.1 (M-H)⁻, and calc. 496.9 for 8; found 495.1 (M-H)⁻.

Step 7: (S)-1-(5-((2-(tert-butoxycarbonylamino)propanamido)methyl)thiophen-3-yl)-3-(trifluoromethyl)-1H-pyrazole-5-carboxylic acid (7)

The mixture of compounds 7 and 8 (560 mg, 1.127 mmol), potassium carbonate (498 mg, 3.61 mmol), ammonium formate (1.102 g, 17.47 mmol) and 10% palladium on carbon (120 mg) in ethanol (8 mL) was heated to reflux for 19 hours. Another portion of ammonium formate (450 mg, 7.14 mmol) and Pd/C (60 mg) was added. The heating was then continued for another 7.5 hours before another portion of ammonium formate (250 mg, 3.96 mmol) and Pd/C (60 mg) was added. The reaction was then left for another 16 hours. The suspension was then filtered through celite and the filtrated concentrated under reduced pressure. The residue was dissolved in water and acidified with 1N HCl. The milky white suspension was then extracted into ethyl acetate, washed with brine, dried over $Na_2SO_4$, filtered and evaporated to give only compound 7 a yellow crust (518.4 mg, 99%). LRMS (ESI): calc. 462.1; found 461.1 (M-H)⁻

Step 8: (S)-tert-butyl 1-((4-(5-(2-methylbenzylcarbamoyl)-3-(trifluoromethyl)-1H-pyrazol-1-yl)thiophen-2-yl)methylamino)-1-oxopropan-2-ylcarbamate (15a)

To a solution of 2-methylbenzylamine (0.037 mL, 0.295 mmol) and compound 7 (0.091 g, 0.197 mmol) in dichloromethane (2 mL) under nitrogen was added EDC (0.075 g, 0.394 mmol) followed by DMAP (9.62 mg, 0.079 mmol). The reaction was left to stir for 16 hours at room temperature. The solvent was then removed on the rotary evaporator and the brown material was purified by silica gel chromatography with a 12M Biotage column and a gradient of 0-5% methanol in dichloromethane to give 61.3 mg of a yellow crust. The sample was further purified by preparative HPLC (C18 Aquasil 20×250 mm; 40-85% methanol in water in 45 minutes at 10 mL/min) to afford compound 15a (34.4 mg, 31%) as a white crust. LRMS (ESI): calc. 565.2; found 466.1 (MH-Boc)$^+$, 588.2 (MNa)$^+$.

Step 9: (S)-1-(5-((2-aminopropanamido)methyl)thiophen-3-yl)-N-(2-methylbenzyl)-3-(trifluoromethyl)-1H-pyrazole-5-carboxamide (9b)

Compound 15a (34.4 mg, 0.061 mmol) was shaken in a solution of 30% TFA in dichloromethane (1 mL) at room temperature for 1 hour. It was then diluted with dichloromethane and methanol and concentrated on the rotary evaporator. More dichloromethane was added to the residue and again it was concentrated. It was then dissolved in water and lyophilized to give an off-white fluffy solid as the TFA salt of compound 9b (33 mg, 94%). $^1$H NMR: (CD$_3$OD) δ(ppm): 9.16 (t, 1H), 8.90 (t, 1H), 7.46 (s, 1H), 7.25-7.23 (m, 1H), 7.17-7.15 (m, 4H), 7.11 (s, 1H), 4.56 (m, 2H), 4.50-4.49 (m, 2H), 3.90 (t, J=7.2 Hz, 1H), 2.32 (s, 3H), 1.50 (d, J=7.2 Hz, 3H). LRMS (ESI): calc. 465.1; found 466.1 (MH)$^+$.

Examples 1d-h were prepared as using the procedure described for compound 9b in Example 1c. Characterization data are presented in Table 1.

TABLE 1

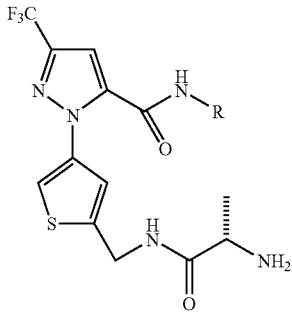

| Ex | Cpd | R | Name | Characterization | Scheme |
|---|---|---|---|---|---|
| 1d | 9c | OMe (2-methoxyphenyl) | (S)-1-(5-((2-aminopropanamido)methyl)thiophen-3-yl)-N-(2-methoxyphenyl)-3-(trifluoromethyl)-1H-pyrazole-5-carboxamide | $^1$H NMR (DMSO-d6) δ (ppm): 9.97 (s, 1 H), 8.92 (s, 1 H), 7.68-7.67 (m, 2 H), 7.50 (s, 1 H), 7.21-7.17 (m, 2 H), 7.08 (d, J = 8.0 Hz, 1 H), 6.94 (t, J = 7.6 Hz, 1 H), 4.49 (m, 2 H), 3.80 (s, 3 H), 3.72 (br s, 1 H), 1.29 (br s, 3 H). LRMS (ESI): calc 467.2; found 468.2 (MH)$^+$. | 2 |
| 1e | 9d | pyridin-2-ylmethyl | (S)-1-(5-((2-aminopropanamido)methyl)thiophen-3-yl)-N-(pyridin-2-ylmethyl)-3-(trifluoromethyl)-1H-pyrazole-5-carboxamide | $^1$H NMR (DMSO-d6) δ (ppm): 9.49 (t, J = 5.6 Hz, 1 H), 9.05 (t, J = 6.0 Hz, 1 H), 8.55-8.53 (m, 1 H), 8.09 (br, s, 3 H), 7.82 (dt, J = 1.6, 7.6 Hz, 1 H), 7.69 (s, 1 H), 7.44 (s, 1 H), 7.37 (d, J = 8.0 Hz, 1 H), 7.35-7.32 (m, 1 H), 7.21 (s, 1 H), 4.55-4.54 (m, 2 H), 4.50-4.49 (m, 2 H), 3.87-3.82 (m, 1 H), 1.35 (d, J = 6.8 Hz, 3 H). LRMS (ESI): calc 452.2; found 453.2 (MH)$^+$. | 2 |

TABLE 1-continued

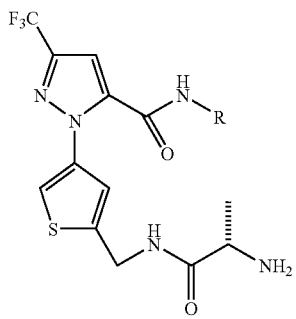

| Ex | Cpd | R | Name | Characterization | Scheme |
|---|---|---|---|---|---|
| 1f | 9e | (2-F-benzyl) | (S)-1-(5-((2-aminopropanamido)methyl)thiophen-3-yl)-N-(2-fluorobenzyl)-3-(trifluoromethyl)-1H-pyrazole-5-carboxamide | $^1$H NMR (DMSO-d6) δ (ppm): 9.39 (t, J = 5.6 Hz, 1 H), 9.05 (t, J = 6.0 Hz, 1 H), 8.09 (br, s, 3 H), 7.61 (s, 1 H), 7.41 (s, 1 H), 7.39-7.31 (m, 2 H), 7.22-7.17 (m, 3 H), 4.50 (dd, J = 1.2, 5.6 Hz, 2 H), 4.45 (d, J = 6.0 Hz, 2 H), 3.87-3.84 (m, 1 H), 1.36 (d, J = 7.2 Hz, 3 H). LRMS (ESI): calc 469.1; found 470.5 (MH)$^+$. | 2 |
| 1g | 9f | (3-OMe-benzyl) | (S)-1-(5-((2-aminopropanamido)methyl)thiophen-3-yl)-N-(3-methoxybenzyl)-3-(trifluoromethyl)-1H-pyrazole-5-carboxamide | $^1$H NMR (CD$_3$OD) δ (ppm): 9.38 (t, 1 H), 8.89 (t, 1 H), 7.45 (d, J = 1.6 Hz, 1 H), 7.25 (t, J = 8.4 Hz, 1 H), 7.17 (s, 1 H), 7.11 (s, 1 H), 6.89-6.83 (m, 3 H), 4.56 (m, 2 H), 4.46-4.45 (m, 2 H), 3.90 (q, J = 7.6 Hz, 1 H), 3.78 (s, 3 H), 1.50 (d, J = 6.8 Hz, 3 H). LRMS (ESI): calc 481.1; found 504.1 (MNa)$^+$. | 2 |
| 1h | 9g | (benzyl) | (S)-1-(5-((2-aminopropanamido)methyl)thiophen-3-yl)-N-benzyl-3-(trifluoromethyl)-1H-pyrazole-5-carboxamide | $^1$H NMR (CD$_3$OD) δ (ppm): 7.45 (d, J = 1.6 Hz, 1 H), 7.35-7.26 (m, 5 H), 7.16 (s, 1 H), 7.11 (s, 1 H), 4.60-4.52 (m, 2 H), 4.48 (s, 2 H), 3.90 (q, J = 7.2 Hz, 1 H), 1.50 (d, J = 7.2 Hz, 3 H). LRMS (ESI): calc 451.1; found 452.1 (MH)$^+$. | 2 |

Example 1i (S)-methyl 2-((1-(5-((2-aminopropanamido)methyl)thiophen-3-yl)-3-(trifluoromethyl)-1H-pyrazole-5-carboxamido)methyl)benzoate (9h)

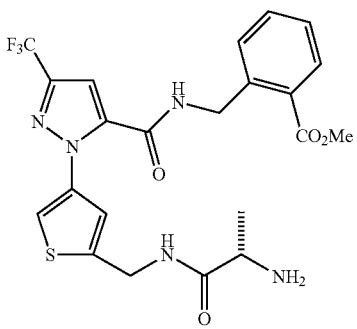

Scheme 3

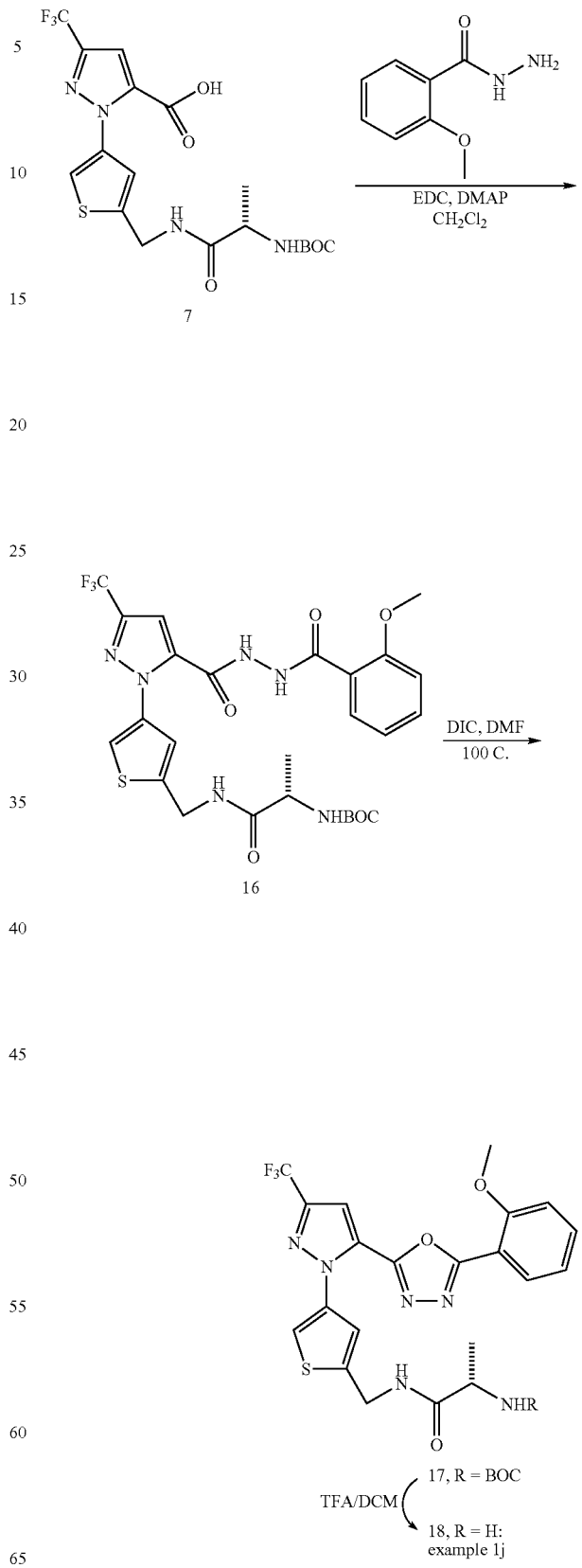

Example 1i describes the preparation of compound 9 h using the same procedures as described for compound 9b in Example 1c, Scheme 2, except using BOP/Et$_3$N in Step 8.

Step 8: (S)-methyl 2-((1-(5-((2-(tert-butoxycarbonylamino)propanamido)methyl)thiophen-3-yl)-3-(trifluoromethyl)-1H-pyrazole-5-carboxamido)methyl)benzoate (15f)

A solution of acid 7 (preparation described in scheme 2, example 1c, step 7) (140 mg, 0.303 mmol), methyl 2-(aminomethyl)benzoate hydrochloride (61.0 mg, 0.303 mmol), BOP (134 mg, 0.303 mmol) and triethylamine (0.127 mL, 0.908 mmol) in DMF (2 mL) was shaken for 16 hours at room temperature. It was then diluted with water (~30 mL) and extracted into ethyl acetate (3×). The ethyl acetate was combined and washed with saturated NaHCO$_3$, brine, dried over Na$_2$SO$_4$, filtered and concentrated. The crude was purified by silica gel chromatography using a 25S Biotage column with a gradient of 40-65% ethyl acetate in hexanes to give compound 15f (112.7 mg, 61.1% yield) as a white crusty solid. LRMS (ESI): calc. 609.2; found 632.1 (MNa)$^+$ Step 9: (S)-methyl 2-((1-(5-((2-aminopropanamido)methyl)thiophen-3-yl)-3-(trifluoromethyl)-1H-pyrazole-5-carboxamido)methyl)benzoate (9 h)

Compound 15f (108 mg, 0.177 mmol) was shaken in a solution of DCM (0.7 mL) and TFA (0.3 mL) for 1 hour. The reaction was then diluted with DCM and concentrated under reduced pressure. More DCM was added to the residue and then removed again by reduced pressure. The residue was then dissolved in ethyl acetate and washed with saturated NaHCO$_3$ (3×). The aqueous phases were combined and extracted with ethyl acetate. The organic phases were combined, washed with brine, dried over Na$_2$SO$_4$, filtered and concentrated to give the compound 9 h (89.3 mg, 99% yield) as a white crust. $^1$H NMR (CD$_3$OD) δ(ppm): 7.97 (d, J=8.0 Hz, 1H), 7.56 (t, J=7.2 Hz, 1H), 7.46-7.44 (m, 2H), 7.41 (t, J=7.6 Hz, 1H), 7.12 (s, 1H), 7.09 (s, 1H), 4.82 (s, 2H), 4.51 (d, J=15.6 Hz, 1H), 4.98 (d, J=15.6 Hz, 1H), 3.89 (s, 3H), 3.42 (q, 1H), 1.27 (d, J=6.8 Hz, 3H). LRMS (ESI): calc 509.1; found 510.1 (MH)$^+$.

Example 1j (S)-2-amino-N-((4-(5-(5-(2-methoxyphenyl)-1,3,4-oxadiazol-2-yl)-3-(trifluoromethyl)-1H-pyrazol-1-yl)thiophen-2-yl)methyl)propanamide (18)

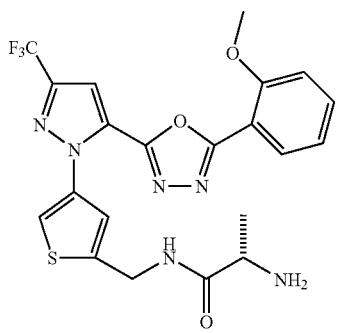

Step 1: (S)-tert-butyl 1-((4-(5-(2-(2-methoxybenzoyl)hydrazinecarbonyl)-3-(trifluoromethyl)-1H-pyrazol-1-yl)thiophen-2-yl)methylamino)-1-oxopropan-2-ylcarbamate (16)

To a solution of 2-methoxybenzhydrazide (0.040 g, 0.238 mmol) and compound 7 (preparation described in scheme 2 example 1c, step 7) (0.11 g, 0.238 mmol) in dichloromethane (2 mL) under nitrogen was added EDC (0.046 g, 0.238 mmol) followed by DMAP (5.81 mg, 0.048 mmol). The reaction was left to stir for 16 hours at room temperature. Another portion of EDC (20 mg, 0.104 mmol) was added and the reaction continued for 4 hours. The solvent was then removed on the rotary evaporator and the crude purified by silica gel column chromatography with a Biotage 12M column and a gradient of 0-5% methanol in dichloromethane to give compound 16 as a yellow crust (73.7 mg, 51%). LRMS (ESI): calc. 610.2; found 511.2 (MH-Boc)$^+$, 633.3 (MNa)$^+$.

Step 2: (S)-tert-butyl 1-((4-(5-(5-(2-methoxyphenyl)-1,3,4-oxadiazol-2-yl)-3-(trifluoromethyl)-1H-pyrazol-1-yl)thiophen-2-yl)methylamino)-1-oxopropan-2-ylcarbamate (17)

A solution of compound 16 (73 mg, 0.120 mmol) in DMF (1.0 mL) and DIC (0.1 mL, 0.642 mmol) was heated to 100 degrees for 13 hours. The reaction was concentrated down to a brown gum and then applied onto a 12M Biotage column and eluted with 0-5% methanol and dichloromethane to give 72 mg of a semi-purified compound. This material was further purified by preparative HPLC (C18 Aquasil 20×250 mm; 40-85% methanol in water in 45 minutes at 10 mL/min) to give compound 17 (20.3 mg, 29%) as a white crust. LRMS (ESI): calc. 592.2; found 493.2 (MH-Boc)$^+$, 593.3 (MH)$^+$.

Step 3: (S)-2-amino-N-((4-(5-(5-(2-methoxyphenyl)-1,3,4-oxadiazol-2-yl)-3-(trifluoromethyl)-1H-pyrazol-1-yl)thiophen-2-yl)methyl)propanamide (18)

The titled compound was obtained as light yellow crust (21 mg, 100%) using the procedure described for compound 9b (scheme 2, example 1c, step 9). $^1$H NMR (CD$_3$OD) δ(ppm): 8.98 (t, J=5.6 Hz, 1H), 7.82 (dd, J=2.0, 8.0 Hz, 1H), 7.77 (d, J=1.6 Hz, 1H), 7.61 (dt, J=2.0, 7.6 Hz, 1H), 7.54 (s, 1H), 7.30 (d, J=1.2 Hz, 1H), 7.12 (t, J=7.6 Hz, 1H), 4.64-4.24 (m, 2H), 3.95 (s, 3H), 3.95-3.91 (m, 1H), 1.50 (d, J=7.2 Hz, 3H). LRMS (ESI): calc. 492.2; found 493.2 (MH)$^+$.

Scheme 4

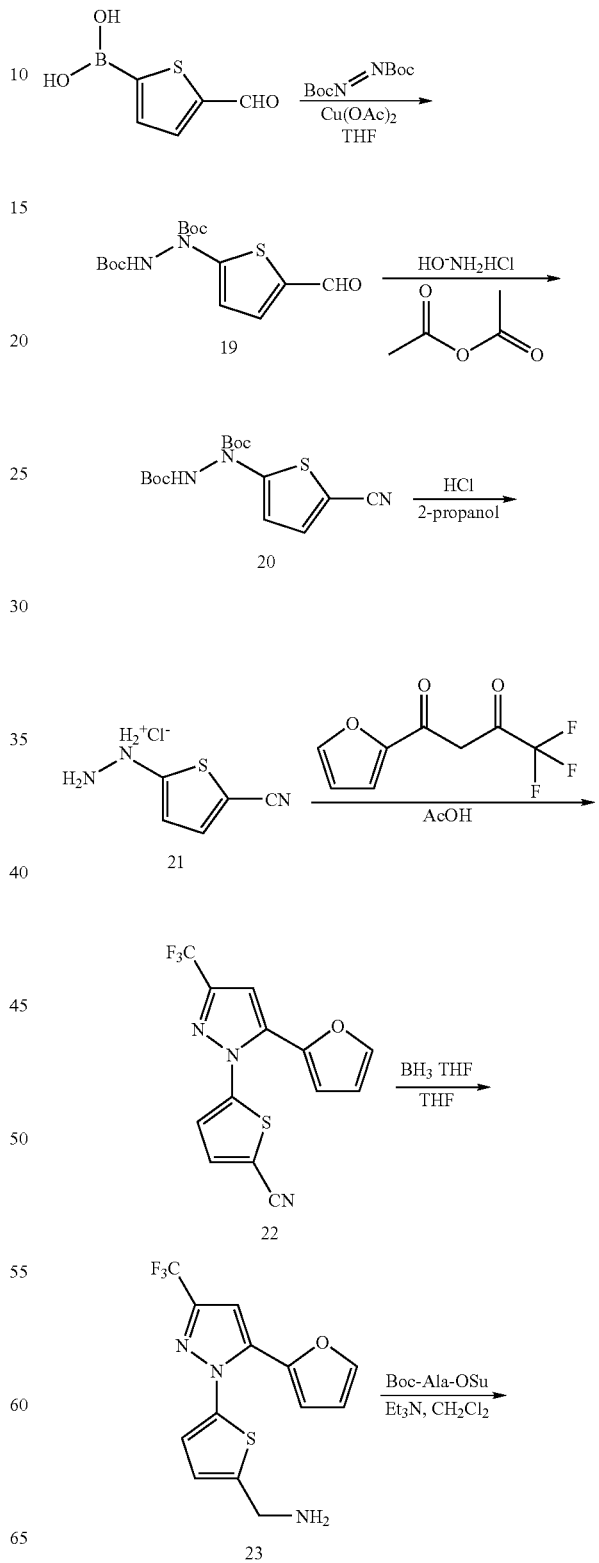

65
-continued

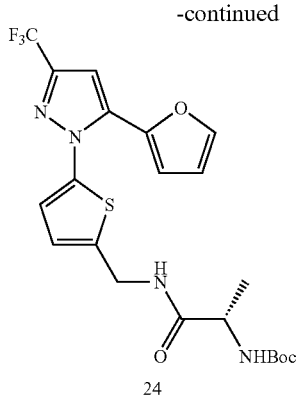

66

Example 2a (S)-1-(5-((2-aminopropanamido)methyl)thiophen-2-yl)-N-benzyl-3-(trifluoromethyl)-1H-pyrazole-5-carboxamide (27a)

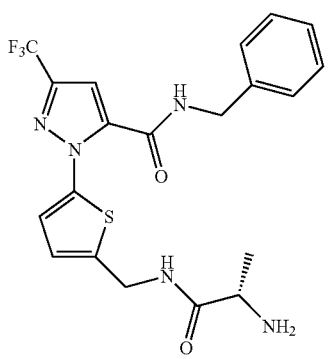

Step 1: Di-tert-butyl 1-(5-formylthiophen-2-yl)hydrazine-1,2-dicarboxylate (19)

Following the same procedure as described for compound 11 (step 1, scheme 2, example 1c) except using 5-formyl-2-thiopheneboronic acid (1.80 g, 11.5 mmol) instead of 5-formylthiophen-3-ylboronic acid to afford 19 (935 mg, 47%) as an orange solid. LRMS (ESI): calc. 342.1; found 343.2 (MH)$^+$.

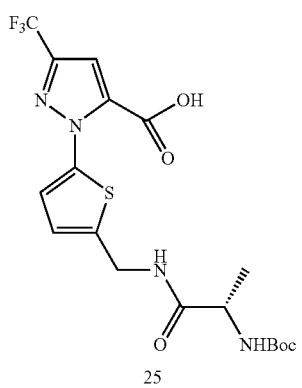

Step 2: Di-tert-butyl 1-(5-cyanothiophen-2-yl)hydrazine-1,2-dicarboxylate (20)

Following the same procedure as described for compound 12 (step 2, scheme 2, example 1c) except using 19 (935 mg, 2.73 mmol) instead of 11 to provide compound 20 (692 mg, 75%) as a yellow solid. LRMS (ESI): calc. 339.1; found 340.2 (MH)$^+$.

Step 3: 1-(5-cyanothiophen-2-yl)hydrazinium chloride (21)

Following the same procedure as described for compound 13 (step 3, scheme 2, example 1c) except using 20 (692 mg, 2.04 mmol) instead of 12 to afford 21 (278 mg, 78%) as a brown solid. LRMS (ESI): calc. 139.0; found 140.1 (MH)$^+$.

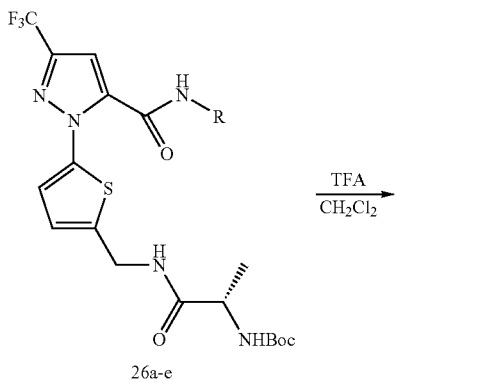

Step 4: 5-(5-(furan-2-yl)-3-(trifluoromethyl)-1H-pyrazol-1-yl)thiophene-2-carbonitrile (22)

Following the same procedure as described for compound 14 (step 4, scheme 2, example 1c) except using 21 (278 mg, 1.58 mmol) instead of 13 to afford 22 (182 mg, 37%) as a beige solid. LRMS (ESI): calc. 309.1; found 310.1 (MH)$^+$.

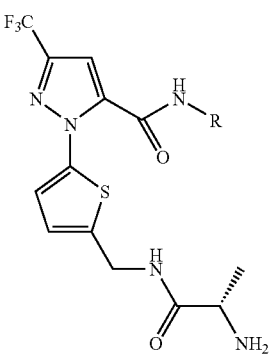

27a-e: Example 2a-e

Step 5: (5-(5-(furan-2-yl)-3-(trifluoromethyl)-1H-pyrazol-1-yl)thiophen-2-yl)methanamine (23)

To a stirred solution of 22 (182 mg, 0.588 mmol) in THF (0.6 mL) at 0 C was added a solution of BH$_3$.THF (1M in THF) (2.4 mL, 2.4 mmol). The resulting solution was allowed to stir for 30 min at 21° C. The mixture was quenched with methanol and then solvent was evaporated to afford 3 as a yellow oil. LRMS (ESI): calc. 313.1; found 314.1 (MH)$^+$.

Step 6: (S)-tert-butyl 1-((5-(5-(furan-2-yl)-3-(trifluoromethyl)-1H-pyrazol-1-yl)thiophen-2-yl)methylamino)-1-oxopropan-2-ylcarbamate (24)

To a stirred solution of 23 (crude) (0.588 mmol) in CH$_2$Cl$_2$ (2.9 mL) at 0 degrees were added Boc-Ala-OSu (185 mg, 0.647 mmol) and triethylamine (0.18 mL, 1.3 mmol). The mixture was allowed to reach 21° C. slowly, stirring for 16 h at room temperature. The solvent was then evaporated. The mixture was quenched with a saturated ammonium chloride solution and extracted with ethyl acetate, washed with brine, dried (MgSO$_4$) filtered and concentrated. The residue was purified by silica gel column chromatography with gradient of EtOAc (20-60%) in hexanes to afford 24 (140 mg, 49%) as a white solid. LRMS (ESI): calc. 484.1; found 507.2 (MNa)$^+$.

Step 7: (S)-1-(5-((2-(tert-butoxycarbonylamino)propanamido)methyl)thiophen-2-yl)-3-(trifluoromethyl)-1H-pyrazole-5-carboxylic acid (25)

To a stirred solution of 24 (70 mg, 0.144 mmol) in acetonitrile (0.42 mL) at 0° C. was added a solution of sodium dihydrogen phosphate (87 mg, 0.722 mmol) in water (0.17 mL). Then a solution of sodium chlorite (131 mg, 1.44 mmol) in water (0.59 mL) was added drop wise. The mixture was allowed to reach 21° C., stirring for 3 h at 21° C. The mixture was quenched with 1N NaOH, washed with CH$_2$Cl$_2$ (2×), and the combined organic phase was extracted with 1N NaOH. The combined aqueous phase was acidified to pH 1 with 1N HCl, extracted with AcOEt, dried (MgSO$_4$) filtered and concentrated to afford 25 (59 mg, 88%) as a yellow solid. LRMS (ESI): calc. 462.1; found 485.2 (MNa)$^+$.

Step 8: (S)-tert-butyl 1-((5-(5-(benzylcarbamoyl)-3-(trifluoromethyl)-1H-pyrazol-1-yl)thiophen-2-yl)methylamino)-1-oxopropan-2-ylcarbamate (26a)

To a stirred solution of 25 (45 mg, 0.097 mmol) in CH$_2$Cl$_2$ (0.65 mL) were added benzylamine (0.016 mL, 0.146 mmol), EDC (37.3 mg, 0.195 mmol) followed by DMAP (4.76 mg, 0.039 mmol). The mixture was stirred for 16 h at room temperature. The mixture was quenched with a saturated sodium carbonate solution and extracted with ethyl acetate, washed with brine, dried (MgSO$_4$) filtered and concentrated. The residue was purified by silica gel column chromatography with gradient of EtOAc (20-60%) in hexanes to afford 26a (24 mg, 45%) as a white solid. LRMS (ESI): calc. 551.2; found 574.6 (MNa)$^+$.

Step 9: (S)-1-(5-((2-aminopropanamido)methyl)thiophen-2-yl)-N-benzyl-3-(trifluoromethyl)-1H-pyrazole-5-carboxamide (27a)

To a stirred solution of 26a (24 mg, 0.044 mmol) in CH$_2$Cl$_2$ (0.44 mL) was added trifluoroacetic acid (44 μL, 0.571 mmol). The mixture was stirred for 2 h at room temperature. The solvent was then evaporated and the residue was purified by silica gel column chromatography with gradient of MeOH (5-20%) in CH$_2$Cl$_2$. The residue was purified by prep-HPLC using an Aquasil C18 column with gradient of MeOH (5-95%) in water to afford 27a (7.7 mg, 39%) as a white solid. $^1$H NMR (DMSO-d6) δ(ppm): 9.41 (t, J=5.7 Hz, 1H), 8.69 (m, 1H), 8.28 (s, 1H), 7.41 (s, 1H), 7.33 (d, J=6.8 Hz, 2H), 7.28-7.24 (m, 3H), 7.05 (d, J=3.3 Hz, 1H), 6.86 (d, J=3.9 Hz, 1H), 4.44 (m, 2H), 4.40 (d, J=5.9 Hz, 2H), 3.44 (q, J=6.8 Hz, 1H), 1.20 (d, J=6.8 Hz, 3H). LRMS: calc 451.1; found 452.5 (MH)$^+$.

Examples 2b-d

Examples 2b-d describe the preparation of compounds 27b-d using the same procedures as described for compound 27a in Example 2a. Characterization data are presented in Table 2.

TABLE 2

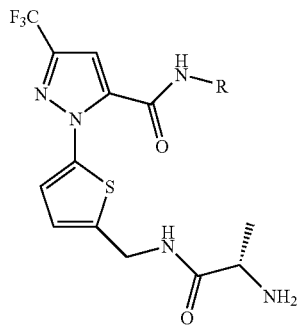

| Ex | Cpd | R | Name | Characterization | Scheme |
|----|-----|---|------|------------------|--------|
| 2b | 27b | (2-fluorobenzyl) | (S)-1-(5-((2-aminopropanamido)methyl)thiophen-2-yl)-N-(2-fluorobenzyl)-3-(trifluoromethyl)-1H-pyrazole-5-carboxamide | (DMSO-d6) δ (ppm): 9.41 (t, J = 5.7 Hz, 1 H), 8.68 (m, 1 H), 8.26 (s, 1 H), 7.41 (s, 1 H), 7.36-7.31 (m, 2 H), 7.21-7.16 (m, 2 H), 7.05 (d, J = 3.9 Hz, 1 H), 6.86 (d, J = 4.1 Hz, 1 H), 4.45-4.43 (m, 4 H), 3.43 (q, J = 6.8 Hz, 1 H), 1.19 (d, J = 7.0 Hz, 3 H). LRMS: (calc.) 469.1 (found) 470.5 (MH)+ | 4 |

TABLE 2-continued

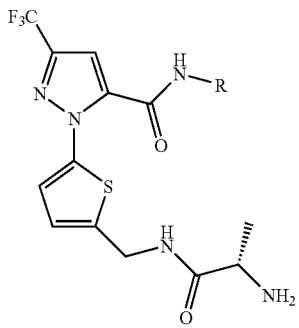

| Ex | Cpd | R | Name | Characterization | Scheme |
|---|---|---|---|---|---|
| 2c | 27c | (2-trifluoromethylbenzyl) | (S)-1-(5-((2-aminopropanamido)methyl)thiophen-2-yl)-3-(trifluoromethyl)-N-(2-(trifluoromethyl)benzyl)-1H-pyrazole-5-carboxamide | (DMSO-d6) d (ppm): 9.50 (t, J = 5.7 Hz, 1 H), 8.72 (bs, 1 H), 8.24 (s, 1 H), 7.72 (d, J = 7.8 Hz, 1 H), 7.65 (t, J = 7.4 Hz, 1 H), 7.50-7.46 (m, 3 H), 7.08 (d, J = 3.7 Hz, 1 H), 6.86 (d, J = 3.9 Hz, 1 H), 4.56 (d, J = 5.9 Hz, 2 H), 4.43 (bs, 2 H), 3.45 (q, J = 6.8 Hz, 1 H), 1.18 (d, J = 6.8 Hz, 3 H). LRMS: (calc.) 519.1 (found) 520.1 (MH)+ | 4 |
| 2d | 27d | (2-isopropoxybenzyl) | (S)-1-(5-((2-aminopropanamido)methyl)thiophen-2-yl)-N-(2-isopropoxybenzyl)-3-(trifluoromethyl)-1H-pyrazole-5-carboxamide | (DMSO-d6) d (ppm): 9.17 (t, J = 5.5 Hz, 1 H), 8.65 (m, 1 H), 8.22 (s, 1 H), 7.37 (s, 1 H), 7.20 (td, J = 9.8, 1.6 Hz, 1 H), 7.13 (d, J = 7.6 Hz, 1 H), 6.98 (d, J = 7.8 Hz, 1 H), 6.88-6.84 (m, 1 H), 4.60 (q, J = 5.9 Hz, 1 H), 4.42 (bs, 2 H), 4.33 (d, J = 5.9 Hz, 2 H), 3.39 (m, 1 H), 1.24 (d, J = 6.1 Hz, 6H), 1.16 (d, J = 6.8 Hz, 3 H). LRMS: (calc.) 509.2 (found) 510.2 (MH)+ | 4 |

Example 2e (S)-1-(5-((2-aminopropanamido)methyl)thiophen-2-yl)-N-(2-methoxybenzyl)-3-(trifluoromethyl)-1H-pyrazole-5-carboxamide (27e)

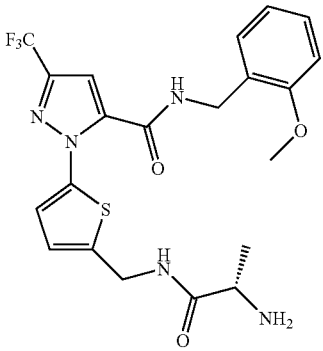

Example 2e describes the preparation of compound 27e using the same procedures as described for compound 27a in Example 2a, Scheme 4, except using POCl$_3$/Pyridine in place of BOP/Et$_3$N in Step 8.

Step 8: (S)-tert-butyl 1-((5-(5-(2-methoxybenzylcarbamoyl)-3-(trifluoromethyl)-1H-pyrazol-1-yl)thiophen-2-yl)methylamino)-1-oxopropan-2-ylcarbamate (26e)

To a stirred solution of 25 (0.059 g, 0.128 mmol) in pyridine (0.851 mL) at 0° C. was added 2-methoxybenzylamine (0.020 mL, 0.153 mmol) and followed by dropwise addition of POCl$_3$ (0.013 mL, 0.140 mmol). The mixture was stirred for 30 min at 0° C., then for 1 h from 0° C. to 21° C., then for 16 h at room temperature. The mixture was quenched with water and extracted with ethyl acetate, washed with brine, dried (MgSO$_4$) filtered and concentrated. The residue was purified by silica gel column chromatography with gradient of EtOAc (20-60%) in hexanes to afford 26e (18 mg, 24%) as a white solid. LRMS (ESI): calc. 581.2; found 604.3 (MNa)+.

Step 9: (S)-1-(5-((2-aminopropanamido)methyl)thiophen-2-yl)-N-(2-methoxybenzyl)-3-(trifluoromethyl)-1H-pyrazole-5-carboxamide (27e)
Compound 27e was obtained using the procedure described in step 9, example 2a except using 26e as the starting material. $^1$H NMR (DMSO-d6) δ(ppm): 9.20 (t, J=5.7 Hz, 1H), 8.53 (s, 1H), 7.37 (d, J=0.4 Hz, 1H), 7.24 (td, J=8.2, 1.8 Hz, 1H), 7.15 (dd, J=7.6, 1.8 Hz, 1H), 7.02 (1H, J=3.9 Hz, 1H), 6.97 (dd, J=8.2, 0.8 Hz, 1H), 6.89 (td, J=7.4, 1.0 Hz, 1H), 6.83 (d, J=3.7 Hz, 1H), 4.40 (bs, 2H), 4.35 (d, J=5.7 Hz, 2H), 3.78 (s, 3H), 3.28 (q, J=7.0 Hz, 1H), 1.13 (d, J=7.0 Hz, 3H). LRMS: calc. 481.1 found 482.2 (MH)$^+$
Scheme 5
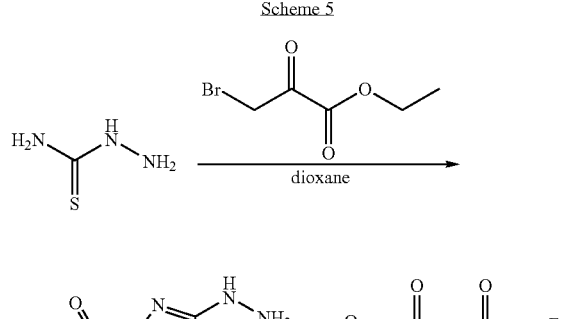
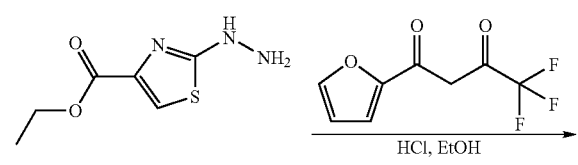
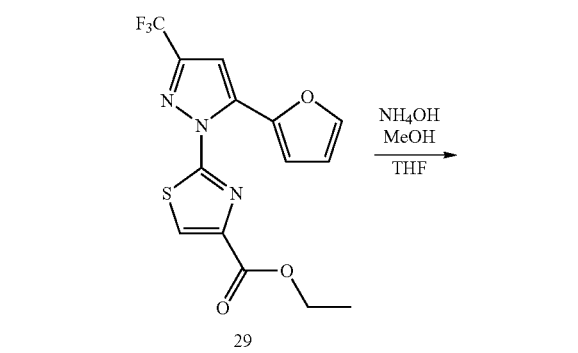
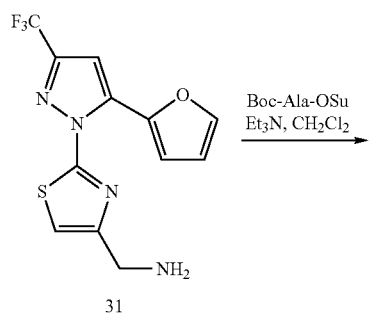
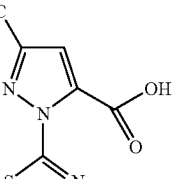
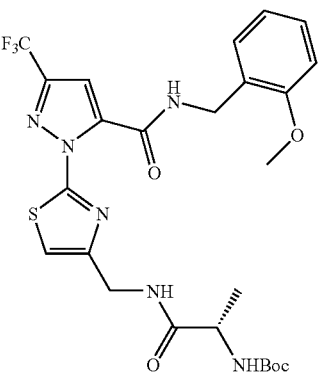

-continued

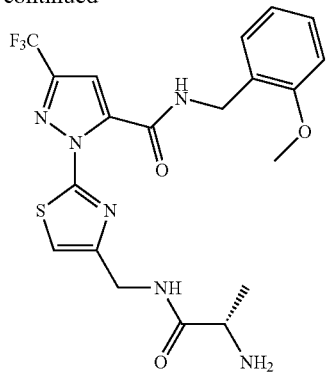

35: Example 3

Example 3

(S)-1-(4-((2-aminopropanamido)methyl)thiazol-2-yl)-N-(2-methoxybenzyl)-3-(trifluoromethyl)-1H-pyrazole-5-carboxamide (35)

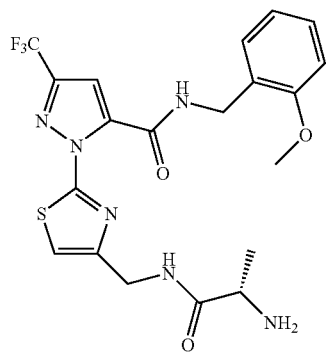

Step 1: ethyl 2-hydrazinylthiazole-4-carboxylate (28)

To a stirred solution of thiosemicarbazide (911 mg, 10 mmol) in dioxane (10 mL) was added ethyl bromopyruvate (1258 μl, 10.00 mmol). The resulting solution was allowed to stir for 16 h at room temperature, then for 2 h at 60° C. Solvent was evaporated and the residue was purified by silica gel column chromatography with gradient of methanol (0-10%) in $CH_2Cl_2$ to afford 28 (500 mg, 27%) as an orange solid. LRMS (ESI): calc. 187.1; found 188.1 $(MH)^+$.

Step 2: ethyl 2-(5-(furan-2-yl)-3-(trifluoromethyl)-1H-pyrazol-1-yl)thiazole-4-carboxylate (29)

To 28 (268 mg, 1.431 mmol) was added 4N HCl in dioxane (3.6 mL, 14.3 mmol) and 4,4,4-trifluoro-1-(2-furyl)-1,3-butanedione (0.23 mL, 1.6 mmol). The resulting suspension was allowed to stir for 16 h at 100° C. Ethanol (1.4 mL) was added, and the mixture was stirred for 4 h at 100° C. Solvent was evaporated and the residue was purified by silica gel column chromatography with gradient of EtOAc (10-20%) in hexanes to afford 29 (203 mg, 20%) as an orange solid. LRMS (ESI): calc. 357.0; found 358.1 $(MH)^+$.

Step 3: 2-(5-(furan-2-yl)-3-(trifluoromethyl)-1H-pyrazol-1-yl)thiazole-4-carboxamide (30)

To a stirred suspension of 29 (345 mg, 0.966 mmol) in methanol (1.5 mL) at room temperature was added ammonium hydroxide (1.5 mL, 38.5 mmol). The resulting solution was allowed to stir for 1 h at 50° C. THF (1 mL) was then added and the mixture was stirred for 16 h at 50° C. Solvent was evaporated, and the crude product 30 was isolated. LRMS (ESI): calc. 328.0; found 329.0 $(MH)^+$.

Step 4: (2-(5-(furan-2-yl)-3-(trifluoromethyl)-1H-pyrazol-1-yl)thiazol-4-yl)methanamine (31)

To a stirred suspension of 30 (317 mg, 0.966 mmol) in THF (966 μl) at 0° C. was added a solution of $BH_3$.THF (1M in THF) (3.9 mL, 3.9 mmol). The resulting solution was allowed to stir for 4 h at room temperature. Then more borane.THF (1M in THF) (1 mL) was added. Stirring was continued for 16 h at room temperature. The mixture was quenched with methanol, and then solvent was evaporated to afford 31 (297 mg, 98%) as a yellow solid. LRMS (ESI): calc. 314.0; found 315.1 $(MH)^+$.

Step 5: (S)-tert-butyl 1-((2-(5-(furan-2-yl)-3-(trifluoromethyl)-1H-pyrazol-1-yl)thiazol-4-yl)methylamino)-1-oxopropan-2-ylcarbamate (32)

Title compound 32 (95 mg, 21%) was obtained as a white solid by following the procedure described above for the synthesis of compound 24 (scheme 4, example 2a, step 6), except using 31 (297 mg, 0.945 mmol) in place of 23. LRMS (ESI): calc. 485.1; found 508.2 $(MNa)^+$.

Step 6: (S)-1-(4-((2-(tert-butoxycarbonylamino)propanamido)methyl)thiazol-2-yl)-3-(trifluoromethyl)-1H-pyrazole-5-carboxylic acid (33)

Title compound 33 (82 mg, 90%) was obtained by following the procedure described above for the synthesis of compound 25 (scheme 4, example 2a, step 7), except using 32 (95 mg, 0.196 mmol) in place of 24. LRMS (ESI): calc. 463.1; found 486.2 $(MNa)^+$.

Step 7: (S)-tert-butyl 1-((2-(5-(2-methoxybenzylcarbamoyl)-3-(trifluoromethyl)-1H-pyrazol-1-yl)thiazol-4-yl)methylamino)-1-oxopropan-2-ylcarbamate (34)

Title compound 34 (12 mg, 12%) was obtained as a white solid by following the procedure described above for the synthesis of compound 26e (scheme 4, example 2e, step 8), except using 33 (0.082 g, 0.177 mmol) in place of 25. LRMS (ESI): calc. 582.1; found 605.3 $(MNa)^+$.

Step 8: (S)-1-(4-((2-aminopropanamido)methyl)thiazol-2-yl)-N-(2-methoxybenzyl)-3-(trifluoromethyl)-1H-pyrazole-5-carboxamide (35)

Title compound 35 (6 mg, 60%) was obtained as a white solid by following the procedure described above for the synthesis of compound 27a (scheme 4, example 2a, step 9), except using 34 (12 mg, 0.021 mmol) in place of 26a. $^1H$ NMR (DMSO-d6) δ(ppm): 9.34 (t, J=5.7 Hz, 1H), 8.37 (m, 1H), 7.46 (s, 1H), 7.42 (s, 1H), 7.33 (d, J=7.2 Hz, 1H), 7.27 (t, J=8.2 Hz, 1H), 6.99 (d, J=8.2 Hz, 1H), 6.94 (t, J=7.6 Hz, 1H), 4.40 (d, J=6.1 Hz, 2H), 4.29 (bs, 2H), 3.81 (s, 3H), 3.32 (q, J=6.7 Hz, 1H), 1.17 (d, J=6.8 Hz, 3H). LRMS: calc. 482.1; found 483.2 (MH)+.
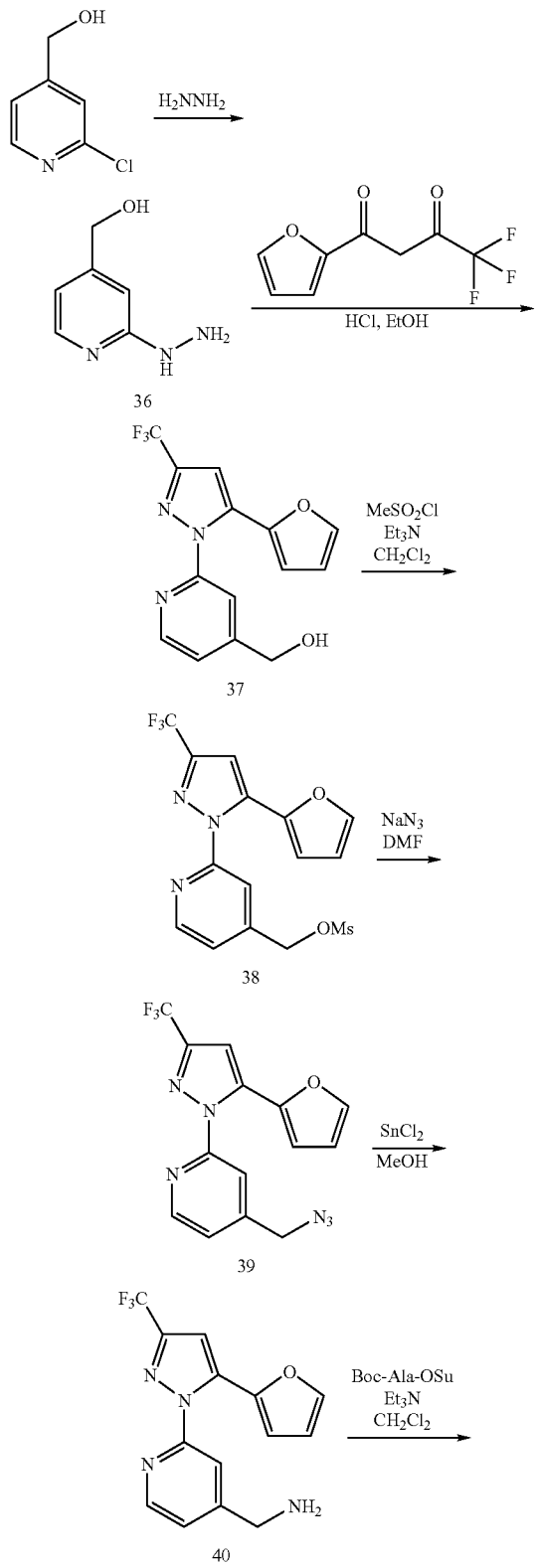
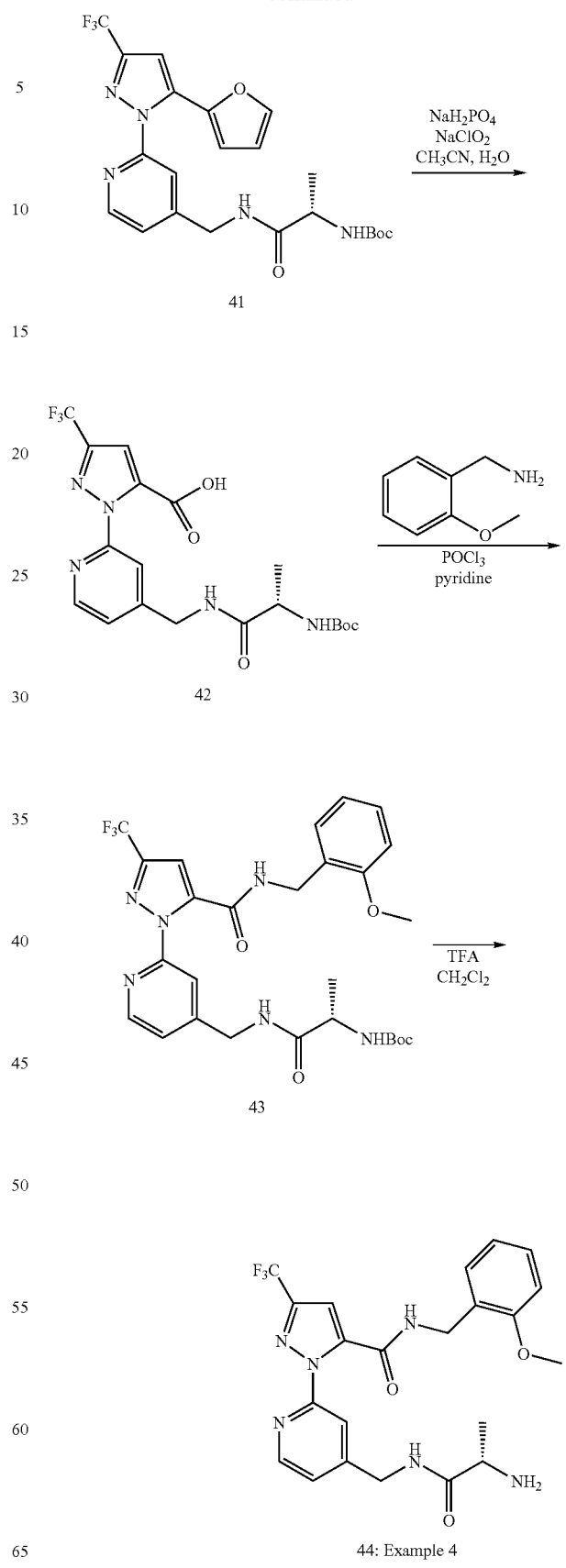

Example 4

(S)-1-(4-((2-aminopropanamido)methyl)pyridin-2-yl)-N-(2-methoxybenzyl)-3-(trifluoromethyl)-1H-pyrazole-5-carboxamide (44)

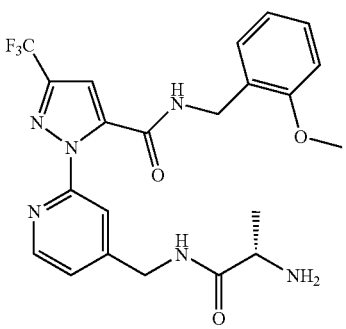

Step 1: (2-hydrazinylpyridin-4-yl)methanol (36)

To a stirred suspension of (2-chloro-4-pyridinyl) methanol (0.885 g, 6.16 mmol) in 2-propanol (9 mL) was added hydrazine monohydrate (6.0 mL, 124 mmol). The resulting suspension was allowed to stir for 24 h at 100° C. Solvent was evaporated. The residue was purified by silica gel column chromatography with gradient of MeOH (5-20%) in $CH_2Cl_2$ to afford 36 (223 mg, 26%) as a white solid. LRMS: calc 139.1; found 140.2 $(MH)^+$.

Step 2: (2-(5-(furan-2-yl)-3-(trifluoromethyl)-1H-pyrazol-1-yl)pyridin-4-yl)methanol (37)

Title compound 37 (175 mg, 51%) was obtained as a yellow solid by following the procedure described above for the synthesis of compound 29 (scheme 5, example 3, step 2), except using 36 (154 mg, 1.107 mmol) in place of 28. LRMS (ESI): calc. 309.1; found 310.1 $(MH)^+$.

Step 3: (2-(5-(furan-2-yl)-3-(trifluoromethyl)-1H-pyrazol-1-yl)pyridin-4-yl)methyl methanesulfonate (38)

To a stirred suspension of 37 (215 mg, 0.695 mmol) in dichloromethane (6.95 mL) at 0° C. was added triethylamine (0.388 mL, 2.78 mmol) followed by methanesulfonyl chloride (0.163 mL, 2.092 mmol). The resulting solution was allowed to stir at room temperature for 1 h. The solvent was evaporated. The mixture was quenched with a saturated sodium carbonate solution and extracted with ethyl acetate, washed with brine, dried ($MgSO_4$) filtered and concentrated. Compound 38 was isolated as an orange solid and used as is for the next step. LRMS (ESI): calc. 387.1; found 388.1 $(MH)^+$.

Step 4: 4-(azidomethyl)-2-(5-(furan-2-yl)-3-(trifluoromethyl)-1H-pyrazol-1-yl)pyridine (39)

To a stirred solution of 38 (0.695 mmol) in DMF (4.6 mL) at room temperature was added sodium azide (136 mg, 2.085 mmol) drop wise. The resulting solution was allowed to stir for 1 h at 60° C. The mixture was quenched with water and extracted with ethyl acetate, washed with brine (two times), dried ($MgSO_4$) filtered and concentrated. Compound 39 (205 mg, 88%) was isolated as a brown oil and used as is for the next step. LRMS (ESI): calc. 334.1; found 335.1 $(MH)^+$.

Step 5: (2-(5-(furan-2-yl)-3-(trifluoromethyl)-1H-pyrazol-1-yl)pyridin-4-yl)methanamine (40)

To a stirred solution of 39 (205 mg, 0.613 mmol) in MeOH (3.1 mL) at room temperature was added tin(II) chloride dihydrate (415 mg, 1.840 mmol) drop wise. The resulting solution was allowed to stir for 2 h at room temperature. The solvent was evaporated. The mixture was quenched with a saturated sodium carbonate solution and extracted with ethyl acetate, washed with brine, dried ($MgSO_4$) filtered and concentrated. Compound 40 (175 mg, 93%) was isolated and used as is for the next step. LRMS (ESI): calc. 308.1; found 309.1 $(MH)^+$.

Step 6: (S)-tert-butyl 1-((2-(5-(furan-2-yl)-3-(trifluoromethyl)-1H-pyrazol-1-yl)pyridin-4-yl)methylamino)-1-oxopropan-2-ylcarbamate (41)

Title compound 41 (147 mg, 54%) was obtained as a white solid by following the procedure described above for the synthesis of compound 24 (scheme 4, example 2a, step 6), except using 40 (175 mg, 0.568 mmol) in place of 23. LRMS (ESI): calc. 479.2; found 502.2 $(MNa)^+$.

Step 7: (S)-1-(4-((2-(tert-butoxycarbonylamino)propanamido)methyl)pyridin-2-yl)-3-(trifluoromethyl)-1H-pyrazole-5-carboxylic acid (42)

Title compound 42 (108 mg, 77%) was obtained as a yellow solid by following the procedure described above for the synthesis of compound 25 (scheme 4, example 2a, step 7), except using 41 (147 mg, 0.307 mmol) in place of 24. LRMS (ESI): calc. 457.2; found 458.2 $(MH)^+$.

Step 8: (S)-tert-butyl 1-((2-(5-(2-methoxybenzylcarbamoyl)-3-(trifluoromethyl)-1H-pyrazol-1-yl)pyridin-4-yl)methylamino)-1-oxopropan-2-ylcarbamate (43)

Title compound 43 (33 mg, 24%) was obtained as a white solid by following the procedure described above for the synthesis of compound 26e (scheme 4, example 2e, step 8), except using 42 (0.108 g, 0.236 mmol) in place of 25. LRMS (ESI): calc. 576.2; found 577.3 $(MH)^+$.

Step 9: (S)-1-(4-((2-aminopropanamido)methyl)pyridin-2-yl)-N-(2-methoxybenzyl)-3-(trifluoromethyl)-1H-pyrazole-5-carboxamide (44)

Title compound 44 (27 mg, 80%) was obtained as a white solid by following the procedure described above for the synthesis of compound 27a (scheme 4, example 2a, step 9), except using 43 (33 mg, 0.057 mmol) in place of 26a. $^1H$ NMR (DMSO-d6) δ(ppm): 9.22 (t, J=5.9 Hz, 1H), 8.76 (m, 1H), 8.36 (d, J=5.1 Hz, 1H), 7.66 (s, 1H), 7.41-7.35 (m, 3H), 7.26 (t, J=7.8 Hz, 1H), 6.99-6.95 (m, 2H), 4.45 (bd, J=4.7 Hz, 2H), 4.36 (d, J=5.9 Hz, 2H), 3.79 (s, 3H), 3.57 (q, J=6.8 Hz, 1H), 1.26 (d, J=6.8 Hz, 3H). LRMS: calc. 476.2; found 477.2 $(MH)^+$.

Scheme 7

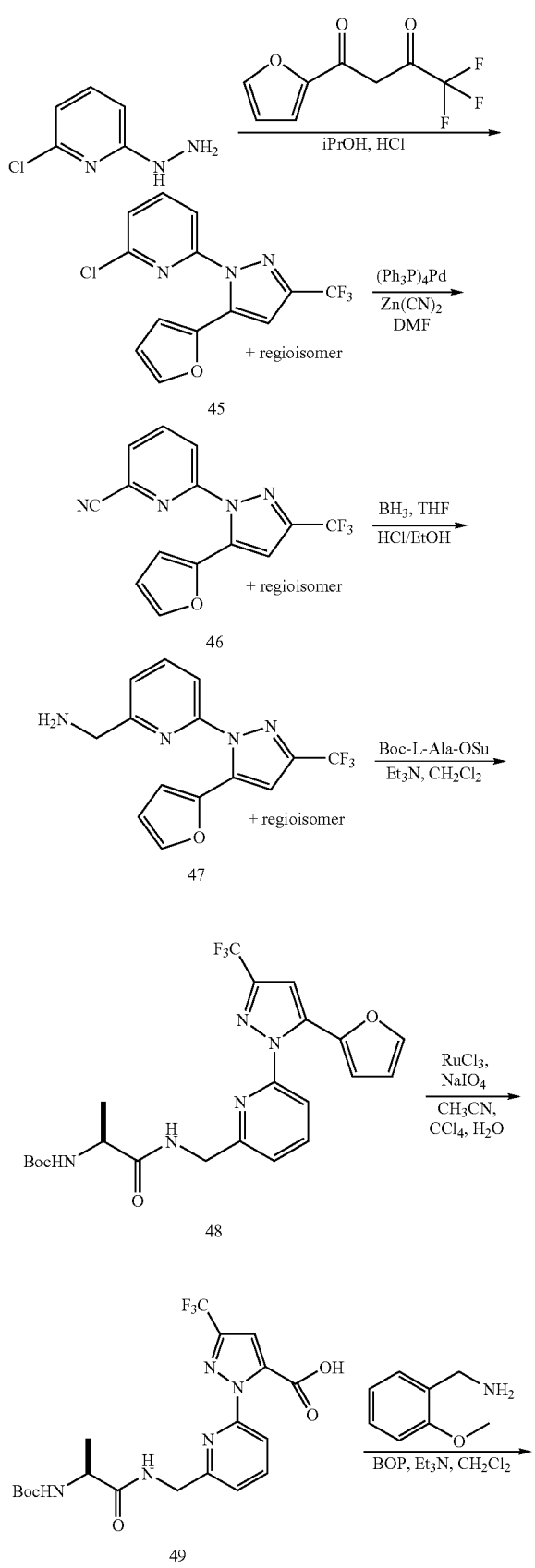

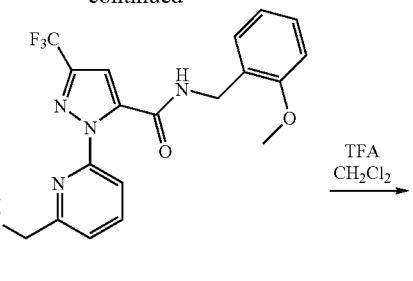

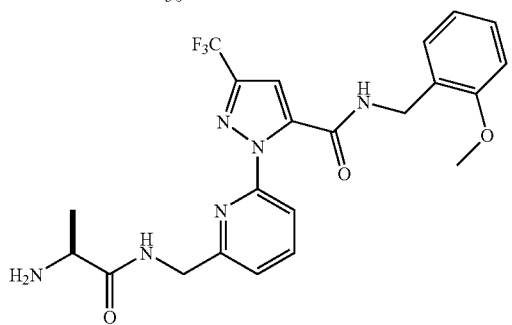

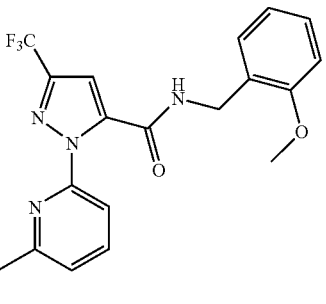

Example 5

(S)-1-(6-((2-aminopropanamido)methyl)pyridin-2-yl)-N-(2-methoxybenzyl)-3-(trifluoromethyl)-1H-pyrazole-5-carboxamide (51)

Step 1: 2-chloro-6-(5-(furan-2-yl)-3-(trifluoromethyl)-1H-pyrazol-1-yl)pyridine (45)

To a stirred solution of 2-chloro-6-hydrazinopyridine (300 mg, 2.09 mmol) in 2-propanol (10.4 mL), was added 4,4,4-trifluoro-1-(2-furyl)-1,3-butanedione (0.310 mL, 2.090 mmol) followed by 2 drops of conc HCl. The resulting mixture was heated to reflux overnight and then evaporated to dryness. A 2:1 mixture of regioisomeric products 45 (588 mg, 90% yield) were isolated as a pale yellow oil. LRMS (ESI): calc. 313.6; found 313.6 (M)$^+$.

Step 2: 6-(5-(furan-2-yl)-3-(trifluoromethyl)-1H-pyrazol-1-yl)picolinonitrile (46)

To a stirred solution of 45 (588 mg, 1.88 mmol) in DMF (12.5 mL) was added zinc cyanide (0.238 mL, 3.75 mmol)

followed by Pd(PPh₃)₄ (217 mg, 0.187 mmol). The resulting suspension was allowed to stir at 95° C. overnight. The residue was purified via ISCO flash chromatography (5% to 35% EtOAc/Hexane; 40G column). The title product 46 (68 mg, 11.9% yield) was isolated as a colorless oil. LRMS (ESI): calc. 304.2; found 305.3 (MH)⁺.

Step 3: (6-(5-(furan-2-yl)-3-(trifluoromethyl)-1H-pyrazol-1-yl)pyridin-2-yl)methanamine (47)

To a stirred solution of 46 (65 mg, 0.214 mmol) in THF (1.068 mL) was added 1M BH₃ in THF (1.1 mL, 1.1 mmol). The resulting solution was allowed to stir at 21°C. for 3 hours. The excess BH₃-THF was destroyed by the careful addition of MeOH. The solvent was evaporated, the residue dissolved in HCl/EtOH and the mixture was heated to reflux for 2 hours and then evaporated to dryness. The title product 47 (81 mg, 99% yield) was isolated as a pale yellow oil. LRMS (ESI): calc. 308.3; found 309.2 (MH)⁺.

Step 4: (S)-tert-butyl 1-((6-(5-(furan-2-yl)-3-(trifluoromethyl)-1H-pyrazol-1-yl)pyridin-2-yl)methylamino)-1-oxopropan-2-ylcarbamate (48)

To a stirred solution of 47 (81 mg, 0.212 mmol) in CH₂Cl₂ (1.1 mL) was added triethylamine (0.095 mL, 0.680 mmol) followed by N-tert-butoxycarbonyl-L-alanine-N-hydroxysuccinimide ester (66.9 mg, 0.234 mmol). The resulting solution was allowed to stir at 21° C. for 3 h. A saturated NaHCO₃ aqueous solution was then added. The mixture was extracted with CH₂Cl₂, dried over Na₂SO₄ and then evaporated to dryness. The residue was purified via ISCO flash chromatography (25% to 85% EtOAc/hexanes; 12G column). Only one isomer of 48 was isolated (41 mg, 40% yield) as colorless oil. LRMS (ESI): calc. 479.5; found 480.5 (MH)⁺.

Step 5: (S)-1-(6-((2-(tert-butoxycarbonylamino)propanamido)methyl)pyridin-2-yl)-3-(trifluoromethyl)-1H-pyrazole-5-carboxylic acid (49)

To a stirred solution of 48 (40 mg, 0.083 mmol) in acetonitrile (0.24 mL) at 23° C. was added carbon tetrachloride (0.238 mL) followed by ruthenium chloride (1.9 mg, 8.3 pmol). A solution of sodium periodate (80 mg, 0.375 mmol) in water (0.36 mL) was added and the resulting suspension was allowed to stir for 18 h. Isopropanol was added and after 10 min, the suspension was filtered through celite. A 1N HCl solution and saturated sodium thiosulfate aqueous solution were added and the mixture extracted with EtOAc, dried over Na₂SO₄ and then evaporated to dryness. The crude was used without any further purification. The title product 49 (38.2 mg, 100% yield) was isolated as a brown oil. LRMS (ESI): calc. 457.4; found 458.5 (MH)⁺.

Step 6: (S)-tert-butyl 1-((6-(5-(2-methoxybenzylcarbamoyl)-3-(trifluoromethyl)-1H-pyrazol-1-yl)pyridin-2-yl)methylamino)-1-oxopropan-2-ylcarbamate (50)

To a stirred solution of 49 (38 mg, 0.083 mmol) in CH₂Cl₂ (0.83 mL) were added triethylamine (0.025 mL, 0.183 mmol) and BOP (44.1 mg, 0.100 mmol) followed by 2-methoxybenzylamine (0.013 mL, 0.100 mmol). The resulting solution was allowed to stir at 21° C. overnight and evaporated to dryness. The residue was purified via ISCO flash chromatography (40% to 100% EtOAc/hexanes; 12G column). The title product 50 (28 mg, 59% yield) was isolated as a pale yellow oil. LRMS (ESI): calc. 576.6; found 577.6 (MH)⁺.

Step 7. (S)-1-(6-((2-aminopropanamido)methyl)pyridin-2-yl)-N-(2-methoxybenzyl)-3-(trifluoromethyl)-1H-pyrazole-5-carboxamide (51)

To a stirred solution of 50 (28 mg, 0.049 mmol) in CH₂Cl₂ (1 mL) was added trifluoroacetic acid (0.056 mL, 0.728 mmol). The resulting solution was allowed to stir at 21° C. for 2 h and evaporated to dryness. Water was added and the precipitate was removed by filtration. The aqueous phase was then lyophilized. The title product 51 (16.1 mg, 56.1% yield) was isolated as a white solid. ¹H NMR: (CD₃OD) o(ppm): 7.99 (t, 1H, J=8.0 Hz), 7.73 (d, 1H, J=8.0 Hz), 7.38 (d, 1H, J=7.6 Hz), 7.26 (d, 2H, J=7.6 Hz), 7.09 (s, 1H), 6.96 (d, 1H, J=7.6 Hz), 6.91 (t, 1H, J=7.6 Hz), 4.51 (dd, 2H, J=15.2, 23.6 Hz), 4.32 (dd, 2H, J=16, 54.4 Hz), 3.95 (q, 1H, J=7.2 Hz), 3.80 (s, 3H), 1.51 (d, 3H, J=6.8 Hz). LRMS (ESI): calc. 476.5; found 477.5 (MH)⁺.

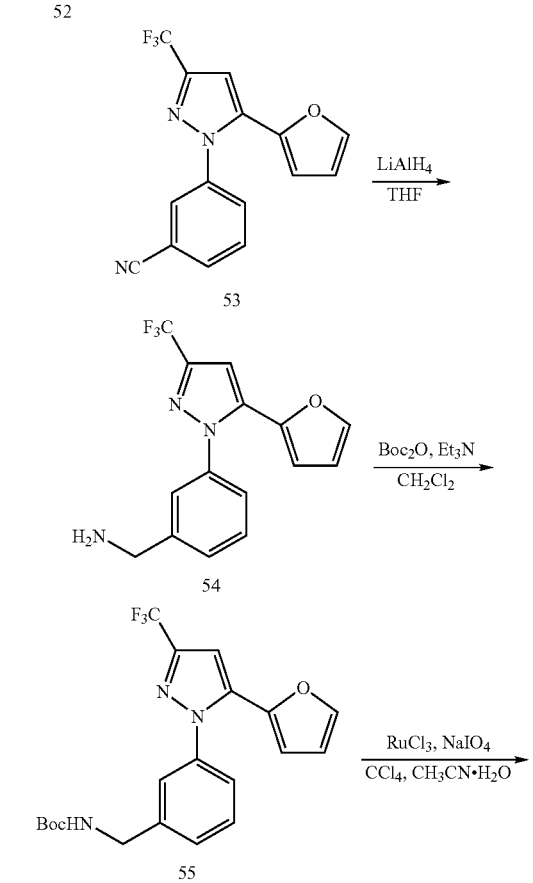

-continued

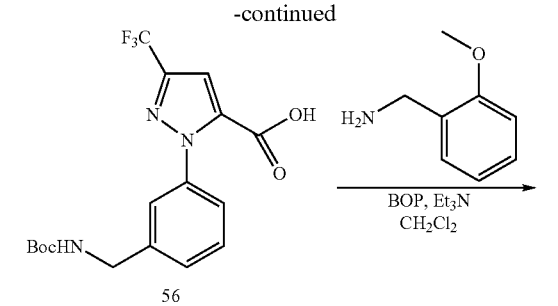

56

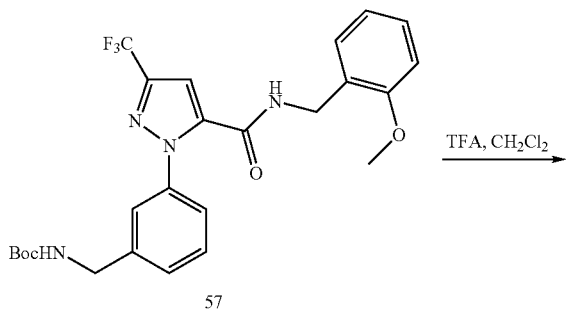

57

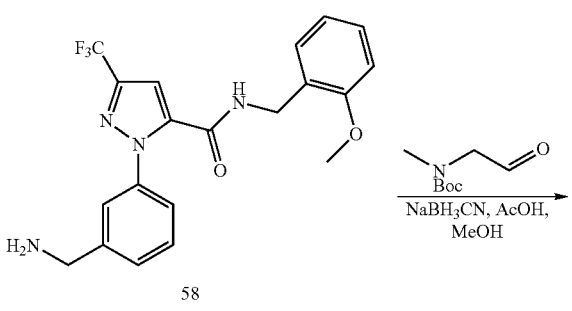

58

59

60: Example 6

Example 6

N-(2-methoxybenzyl)-1-(3-((2-(methylamino)ethylamino)methyl)phenyl)-3-(trifluoromethyl)-1H-pyrazole-5-carboxamide (60)

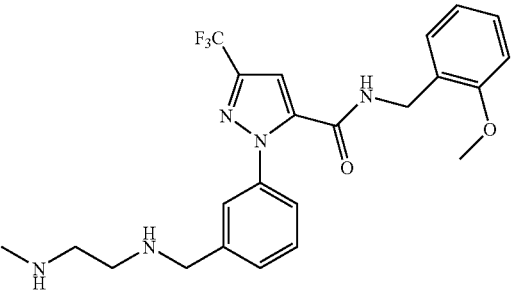

Step 1. 3-(5-(furan-2-yl)-3-(trifluoromethyl)-1H-pyrazol-1-yl)benzonitrile (53)

To a stirred suspension of 52 (J. Med. Chem. 2001, 44, 566-578) (4.73 g, 14.65 mmol) in acetic acid (60 mL) was added 4,4,4-trifluoro-1-(2-furyl)-1,3-butanedione (2.2 mL, 14.65 mmol). The resulting suspension was allowed to stir at 120° C. for 2 h. The acetic acid was removed under vacuum and the residue was partitioned between water and EtOAc. The organic phase was washed with 10% HCl solution, water and brine. It was then dried over $Na_2SO_4$ and evaporated. The residue was purified via silica gel flash chromatography (5% to 50% EtOAc/hexanes). The title product 53 (3 g, 67% yield) was isolated as a red solid. LRMS (ESI): calc. 303.2; found 304.1 $(MH)^+$ (compound 53 was prepared by a different method as described in Tetrahedron Letters 2002, 41, 3271-3273).

Step 2. (3-(5-(furan-2-yl)-3-(trifluoromethyl)-1H-pyrazol-1-yl)phenyl)methanamine (54)

To a stirred solution of 53 (3 g, 9.89 mmol) in THF (50 mL) at 0° C. was added lithium aluminium hydride (0.939 g, 24.73 mmol). The resulting suspension was allowed to stir for 0.5 h. The reaction mixture was then warmed to room temperature and stirred for another 1 h. The following was added sequentially: 0.9 mL of water, 0.9 mL of 15% NaOH and 1.8 mL of water. The white solid was removed by filtration and the filtrate evaporated under vacuum. The title product 54 (3.04 g, 100% yield) was isolated as a pale yellow oil. Crude was used without any further purification. LRMS (ESI): calc. 307.3; found 308.4 $(MH)^+$.

Step 3. tert-butyl 3-(5-(furan-2-yl)-3-(trifluoromethyl)-1H-pyrazol-1-yl)benzylcarbamate (55)

To a stirred solution of 54 (3.04 g, 9.89 mmol) in $CH_2Cl_2$ (49.5 mL) at 21° C. was added triethylamine (3.03 mL, 21.77 mmol) followed by di-tert-butyl dicarbonate (2.5 mL, 10.88 mmol). The resulting solution was allowed to stir overnight. The solution was evaporated to dryness and the residue was crystallized from EtOAc/hexanes. The title product 55 (2.98 g, 74% yield) was isolated as a pale yellow solid. LRMS (ESI): calc. 407.4; found 430.2 $(MNa)^+$.

Step 4. 1-(3-((tert-butoxycarbonylamino)methyl) phenyl)-3-(trifluoromethyl)-1H-pyrazole-5-carboxylic acid (56)

The title compound 56 (2.82 g, 100% yield) was obtained as a crude pale brown semi-solid using the same procedure described for compound 49 (scheme 7, example 5, step 5) except using 55 (2.98 g, 7.31 mmol) in place of 48. LRMS (ESI): calc. 385.3; found 408.3 (MNa)⁺.

Step 5. tert-butyl 3-(5-(2-methoxybenzylcarbamoyl)-3-(trifluoromethyl)-1H-pyrazol-1-yl)benzylcarbamate (57)

The title compound 57 (1.82 g, 49% yield) was obtained as a greenish solid using the same procedure described for compound 50 (scheme 7, example 5, step 6) except using 56 (2.8 g, 7.31 mmol) in place of 49. LRMS (ESI): calc. 504.5; found 505.6 (MH)⁺.

Step 6. 1-(3-(aminomethyl)phenyl)-N-(2-methoxybenzyl)-3-(trifluoromethyl)-1H-pyrazole-5-carboxamide (58)

To a stirred solution of 57 (900 mg, 1.784 mmol) in CH$_2$Cl$_2$ (3.4 mL) was added TFA (2.8 mL, 35.7 mmol). The mixture was allowed to stir at 21° C. for 2 h. A saturated NaHCO$_3$ aqueous solution was added and followed by extractions with CH$_2$Cl$_2$. It was then dried over Na$_2$SO$_4$ and evaporated. The crude was used without any further purification. The title product 58 (925 mg, 100% yield) was isolated as a beige powder. LRMS (ESI): calc. 404.4; found 405.6 (MH)⁺.

Step 7. tert-butyl 2-(3-(5-(2-methoxybenzylcarbamoyl)-3-(trifluoromethyl)-1H-pyrazol-1-yl)benzylamino)ethyl(methyl)carbamate (59)

To a stirred solution of 58 (200 mg, 0.386 mmol) in MeOH (2.0 mL) was added tert-butyl methyl(2-oxoethyl)carbamate (100 mg, 0.579 mmol) followed by acetic acid (44.2 μl, 0.772 mmol). After stirring for 30 min, sodium cyanoborohydride (61 mg, 0.964 mmol) was added and the resulting solution was allowed to stir at 21° C. for 16 h. The solvent was removed by evaporation and the residue taken in saturated NaHCO$_3$. It was then extracted three times with CH$_2$Cl$_2$, dried over Na$_2$SO$_4$ and evaporated. The residue was purified via silica gel flash chromatography (40% to 100% EtOAc/hexanes). The title product 59 (81 mg, 37% yield) was isolated as a yellow solid. LRMS (ESI): calc. 561.6; found 562.7 (MH)⁺.

Step 8. N-(2-methoxybenzyl)-1-(3-((2-(methylamino) ethylamino)methyl)phenyl)-3-(trifluoromethyl)-1H-pyrazole-5-carboxamide (60)

To a stirred solution of 59 (80 mg, 0.142 mmol) in CH$_2$Cl$_2$ (1.4 mL) was added TFA (0.3 mL, 4.27 mmol). The resulting solution was allowed to stir at 21° C. for 1.5 h. A saturated NaHCO$_3$ aqueous solution was added and followed by extractions with CH$_2$Cl$_2$. It was then dried over Na$_2$SO$_4$ and evaporated. The residue was purified by preparative HPLC. The title product 60 (18 mg, 22% yield) was lyophilized and obtained as a white solid. $^1$H NMR (CD$_3$OD) δ(ppm): 9.17 (br s, 0.5H), 7.69 (s, 1H), 7.62 (d, 1H, J=7.6 Hz), 7.56 (d, 1H, J=7.6 Hz), 7.50 (d, 1H, J=8.0 HZ), 7.28 (t, 1H, J=7.6 Hz), 7.24 (s, 1H), 7.21 (d, 1H, J=7.2 Hz), 6.97 (d, 1H, J=8.4 Hz), 6.91 (t, 1H, J=7.2 Hz), 4.67 (s, 2H), 4.31 (s, 2H), 3.83 (s, 3H), 3.37 (d, 2H, J=5.6 Hz), 3.34 (d, 2H, J=5.2 Hz), 2.74 (s, 3H). LRMS (ESI): calc. 461.5; found 462.6 (MH)⁺.

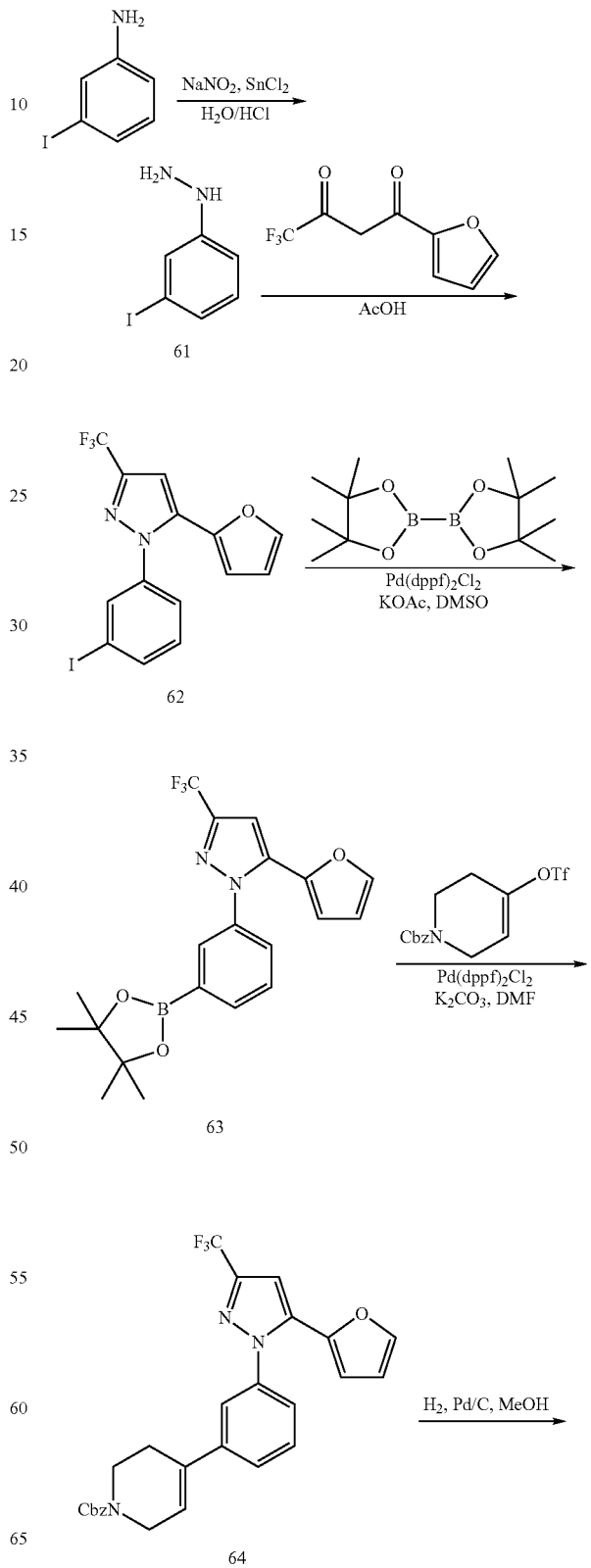

Scheme 9

-continued
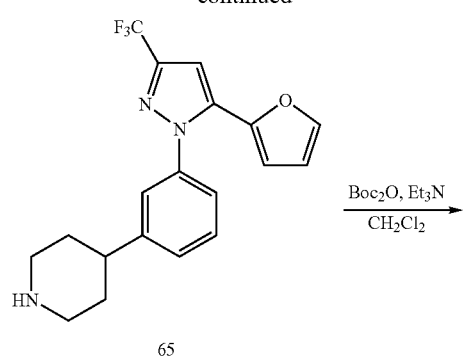
65
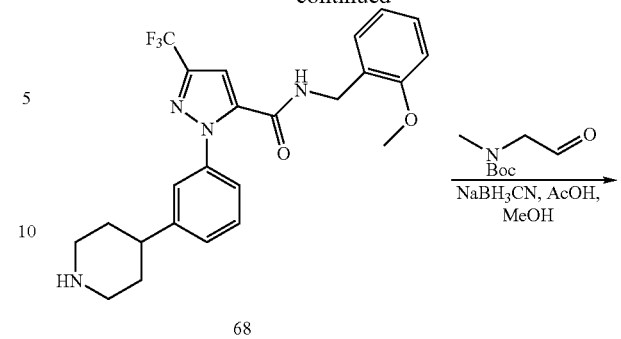
68
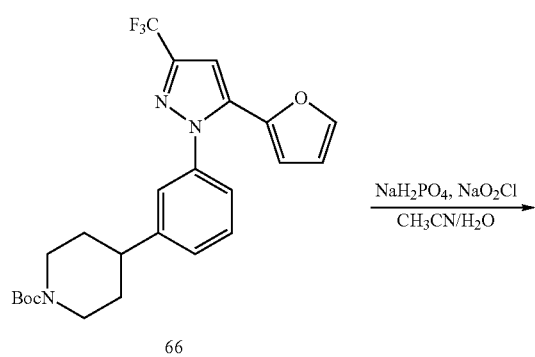
66
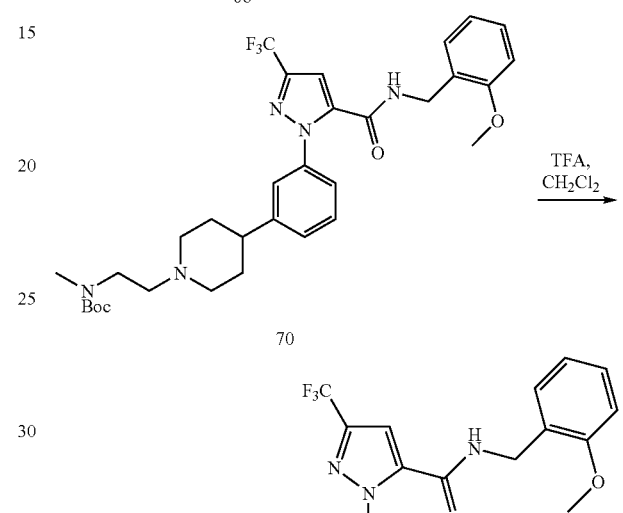
70
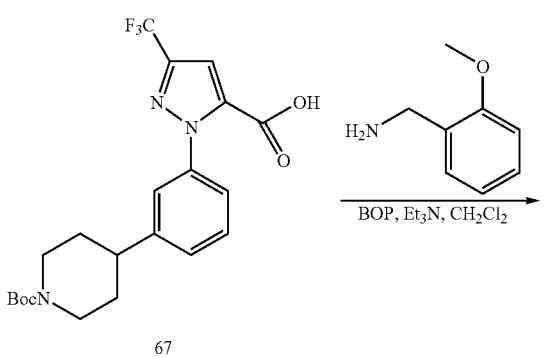
67
71: Example 7
Example 7
N-(2-methoxybenzyl)-1-(3-(1-(2-(methylamino)ethyl)piperidin-4-yl)phenyl)-3-(trifluoromethyl)-1H-pyrazole-5-carboxamide (71)
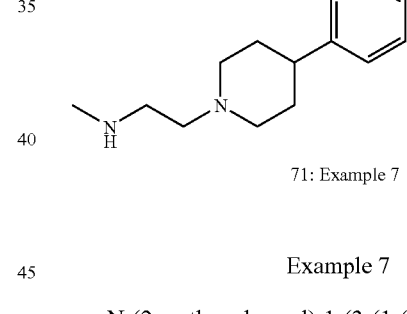
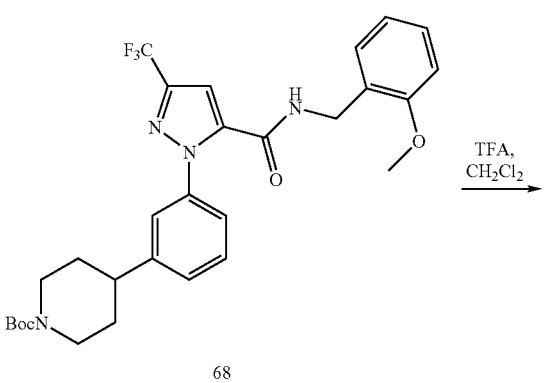
68
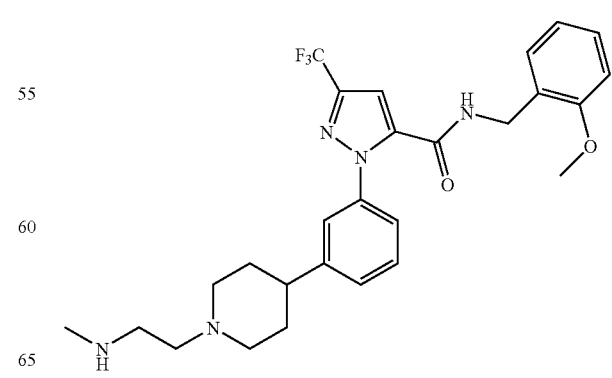

Step 1. (3-iodophenyl)hydrazine (61)

To a stirred suspension of 3-iodoaniline (2 g, 9.13 mmol) in 37% hydrochloric acid (11 mL) at 0° C. was added a cold solution of sodium nitrite (0.66 g, 9.59 mmol) in water (3.2 mL). The resulting suspension was allowed to stir for 40 min. Then, a cold solution of tin(II) chloride dihydrate (6.18 g, 27.4 mmol) in 37% hydrochloric acid (4.3 mL) was added to the reaction mixture and stirred for another 40 min. The flask was then placed in the refrigerator for 12 h. The precipitate was isolated by filtration and washed with ice-cold brine (25 mL) followed by 2:1 petroleum ether/ether (25 mL) solution. The light pink solid was dried under vacuum for 2 h to give the title compound 61 (3.63 g, 94% yield) as the $SnCl_2$ complex. LRMS (ESI): calc. 234.0; found 235.0 $(MH)^+$ (compound 61 as the free hydrazine was previously reported in Recueil des Travaux Chimiques des Pays-Bas (1961), 80 1348-56).

Step 2. 5-(furan-2-yl)-1-(3-iodophenyl)-3-(trifluoromethyl)-1H-pyrazole (62)

To a stirred suspension of 61 (3.63 g, 8.57 mmol) in acetic acid (34 mL) was added 4,4,4-trifluoro-1-(2-furyl)-1,3-butanedione (1.3 mL, 8.57 mmol). The resulting suspension was allowed to stir at 120° C. overnight turning clear upon heating. The mixture was then evaporated to dryness. The crude product was added to a silica gel column and eluted with 5% to 10% EtOAc/hexanes. The title product 62 (3.00 g, 87% yield) was isolated as a colorless oil that solidified upon standings. LRMS (ESI): calc. 404.1; found 405.2 $(MH)^+$.

Step 3. 5-(furan-2-yl)-1-(3-(4,4,5,5-tetramethyl-1,3,2-dioxaborolan-2-yl)phenyl)-3-(trifluoromethyl)-1H-pyrazole (63)

To a stirred solution of 62 (685 mg, 1.695 mmol) in DMSO (8.5 mL) were added bis(pinacolato)diboron (473 mg, 1.865 mmol) and potassium acetate (499 mg, 5.09 mmol) followed by 1,1'-bis(diphenylphosphino)ferrocenedichloro palladium (II) dichloromethane complex (37 mg, 0.051 mmol). The resulting black solution was allowed to stir at 70° C. for 12 h. It was then cooled to room temperature and the mixture was filtered through celite, diluted with EtOAc and washed with saturated $NaHCO_3$ solution and brine. It was then dried over $Na_2SO_4$ and evaporated. The residue was purified via silica gel flash chromatography (5% to 20% EtOAc/hexanes). The title product 63 (533 mg, 78% yield) was isolated as a tan oil that solidified upon standing. LRMS (ESI): calc. 404.2; found 405.2 $(MH)^+$.

Step 4. benzyl 4-(3-(5-(furan-2-yl)-3-(trifluoromethyl)-1H-pyrazol-1-yl)phenyl)-5,6-dihydropyridine-1 (2H)-carboxylate (64)

To a stirred solution of 63 (533 mg, 1.319 mmol) in DMF (6.6 mL) were added potassium carbonate (419 mg, 3.03 mmol) and benzyl 4-(trifluoromethylsulfonyloxy)-5,6-dihydropyridine-1 (2H)-carboxylate (578 mg, 1.582 mmol) followed by 1,1'-bis(diphenylphosphino)ferrocenedichloro palladium(II) dichloromethane complex (58 mg, 0.079 mmol). The resulting suspension was allowed to stir at 75° C. for 4 h. The mixture then was filtered through celite and washed with EtOAc. The organic phase was washed with brine and dried over $Na_2SO_4$. The solution was then evaporated to dryness. The residue was purified via silica gel flash chromatography (5% to 40% EtOAc/hexanes). The title product 64 (430 mg, 66% yield) was isolated as a colorless oil. LRMS (ESI): calc. 493.5; found 494.5 $(MH)^+$.

Step 5. 4-(3-(5-(furan-2-yl)-3-(trifluoromethyl)-1H-pyrazol-1-yl)phenyl)piperidine (65)

To a stirred solution of 64 (430 mg, 0.871 mmol) in MeOH (4.4 mL) was added palladium on carbon (9.27 mg, 0.087 mmol). Under a balloon of hydrogen the suspension was allowed to stir for 2 h. It was then filtered and filtrate evaporated. The crude was used without any further purification. The title product 65 (315 mg, 100% yield) was isolated as a colorless oil. LRMS (ESI): calc. 361.4; found 362.5 $(MH)^+$.

Step 6. tert-butyl 4-(3-(5-(furan-2-yl)-3-(trifluoromethyl)-1H-pyrazol-1-yl)phenyl)piperidine-1-carboxylate (66)

To a stirred solution of 65 (315 mg, 0.871 mmol) in $CH_2Cl_2$ (4.4 mL) was added $Et_3N$ (0.27 mL, 1.916 mmol) followed by $Boc_2O$ (0.2 mL, 0.915 mmol). The resulting solution was allowed to stir at 21° C. overnight. The mixture was evaporated to dryness. The residue was purified via silica gel flash chromatography (5% to 40% EtOAc/Hexane). The title product 66 (205 mg, 51% yield) was isolated as colorless crystals. LRMS (ESI): calc. 461.5; found 462.5 $(MH)^+$.

Step 7. 1-(3-(1-(tert-butoxycarbonyl)piperidin-4-yl)phenyl)-3-(trifluoromethyl)-1H-pyrazole-5-carboxylic acid (67)

The title compound 67 (100 mg, 51% yield) was obtained as a crude white foam following the procedure described above for the synthesis of compound 25 (scheme 4, example 2a, step 7), except using 66 (205 mg, 0.444 mmol) as the starting material.

Step 8. tert-butyl 4-(3-(5-(2-methoxybenzylcarbamoyl)-3-(trifluoromethyl)-1H-pyrazol-1-yl)phenyl)piperidine-1-carboxylate (68)

The title compound 68 (58 mg, 46% yield) was obtained as a colorless oil following the procedure described above for the synthesis of compound 50 (scheme 7, example 5, step 6), except using 67 (100 mg, 0.228 mmol) as the starting material.

Step 9. N-(2-methoxybenzyl)-1-(3-(piperidin-4-yl)phenyl)-3-(trifluoromethyl)-1H-pyrazole-5-carboxamide (69)

The title compound 69 (47 mg, 80% yield) was obtained as a beige powder by following the procedure described above for the synthesis of compound 58 (scheme 8, example 6, step 6), except using 68 (58 mg, 0.104 mmol) in place of 55. LRMS (ESI): calc. 458.5; found 459.5 $(MH)^+$.

Step 10. tert-butyl 2-(4-(3-(5-(2-methoxybenzylcarbamoyl)-3-(trifluoromethyl)-1H-pyrazol-1-yl)phenyl)piperidin-1-yl)ethyl(methyl)carbamate (70)

The title compound 70 (23 mg, 46% yield) was obtained as a colorless oil by following the procedure described above for the synthesis of compound 59 (scheme 8, example 6, step 7), except using 69 (47 mg, 0.082 mmol) in place of 58. LRMS (ESI): calc. 615.7; found 616.8 (MH)+.

Step 11. N-(2-methoxybenzyl)-1-(3-(1-(2-(methylamino)ethyl)piperidin-4-yl)phenyl)-3-(trifluoromethyl)-1H-pyrazole-5-carboxamide (71)

To a stirred solution of 70 (20 mg, 0.032 mmol) in CH$_2$Cl$_2$ (650 μl) was added TFA (50 μl, 0.650 mmol). The resulting solution was allowed to stir at 21° C. for 1.5 h. After the usual work-up, the residue was purified by preparative TLC using 10% MeOH/CH$_2$Cl$_2$. The title product 71 (16 mg, 79% yield) was isolated as a white solid. $^1$H NMR (CD$_3$OD) δ(ppm): 7.38-7.36 (m, 3H), 7.27-7.24 (m, 2H), 7.14 (s, 1H), 7.12 (s, 1H), 6.94 (d, 1H, J=8.0 Hz), 6.87 (t, 1H, J=7.2 HZ), 4.44 (s, 2H), 3.81 (s, 3H), 3.13 (t, 2H, J=5.6 Hz), 3.05 (d, 2H, J=11.6 Hz), 2.72 (s, 3H), 2.67 (t, 2H, J=6.0 Hz), 2.61-2.59 (m, 1H), 2.22 (td, 2H, J=2.8, 12.0 Hz), 1.83-1.77 (m, 4H). LRMS (ESI): calc. 515.6; found 516.8 (MH)+.

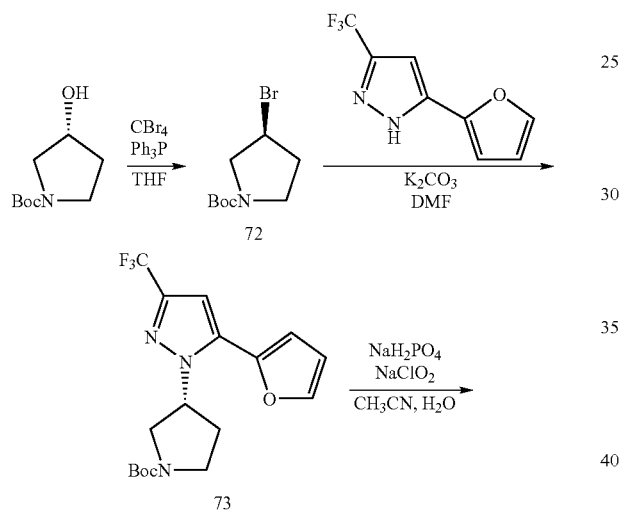

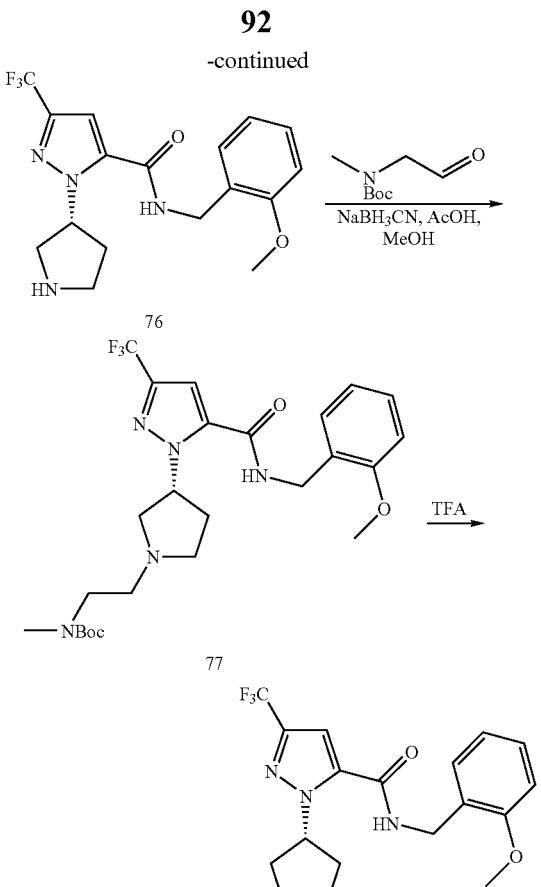

Example 8

(R)—N-(2-methoxybenzyl)-1-(1-(2-(methylamino)ethyl)pyrrolidin-3-yl)-3-(trifluoromethyl)-1H-pyrazole-5-carboxamide (78)

Step 1. (S)-tert-butyl 3-bromopyrrolidine-1-carboxylate (72)

To a stirred solution of N-Boc-(R)-3-hydroxypyrrolidine (0.936 g, 5 mmol) in THF (25 mL) was added carbon tetrabromide (2.487 g, 7.50 mmol) followed by triphenylphosphine (1.967 g, 7.50 mmol). The resulting suspension was allowed to stir at 60° C. for 1 h. Insoluble material was filtered, and concentrated. The residue was purified by silica gel column chromatography with a gradient of EtOAc (5-30%) in hexanes to afford 72 (1.12 g, 90%) as a colorless oil. LRMS (ESI): calc. 249.0; found 271.9 (MNa)+.

Step 2. (R)-tert-butyl 3-(5-(furan-2-yl)-3-(trifluoromethyl)-1H-pyrazol-1-yl)pyrrolidine-1-carboxylate (73)

To a stirred solution of 72 (681 mg, 2.72 mmol) in DMF (9.894 mL) was added potassium carbonate (855 mg, 6.18 mmol), and then 5-(furan-2-yl)-3-(trifluoromethyl)-1H-pyrazole (500 mg, 2.474 mmol) [made by following the procedure described above for the synthesis of compound 14 (scheme 2, example 1c, step 4), except using hydrazine hydrate instead of 13 as the starting material]. The resulting solution was allowed to stir at 100° C. for 1 h. The mixture was quenched with water and extracted with ethyl acetate, washed with brine, dried (MgSO$_4$) filtered and concentrated. The residue was purified by silica gel column chromatography with gradient of EtOAc (10-20%) in hexanes to afford 73 (340 mg, 37%) as a colorless oil. LRMS (ESI): calc. 371.1; found 394.0 (MNa)+.

Step 3. (R)-1-(1-(tert-butoxycarbonyl)pyrrolidin-3-yl)-3-(trifluoromethyl)-1H-pyrazole-5-carboxylic acid (74)

Title compound 74 (310 mg, 97%) was obtained as a white solid by following the procedure described above for the synthesis of compound 25 (scheme 4, example 2a, step 7), except using 73 (340 mg, 0.916 mmol) in place of 24. LRMS (ESI): calc. 349.1; found 348.0 (M-H)−.

Step 4. (R)-tert-butyl 3-(5-(2-methoxybenzylcarbamoyl)-3-(trifluoromethyl)-1H-pyrazol-1-yl)pyrrolidine-1-carboxylate (75)

Title compound 75 (225 mg, 54%) was obtained by following the procedure described above for the synthesis of compound 26a (scheme 4, example 2a, step 8), except using 74 (310 mg, 0.887 mmol) and (2-methoxyphenyl)methanamine in place of 25. LRMS (ESI): calc. 468.2; found 491.1 (MNa)+.

Step 5. (R)—N-(2-methoxybenzyl)-1-(pyrrolidin-3-yl)-3-(trifluoromethyl)-1H-pyrazole-5-carboxamide (76)

The title compound 76 was obtained by following the procedure described above for the synthesis of compound 58 (scheme 8, example 6, step 6), except using 75 (153 mg, 0.327 mmol) in place of 57. LRMS (ESI): calc. 368.1; found 369.1 (MH)+.

Step 6. (R)-tert-butyl 2-(3-(5-(2-methoxybenzylcarbamoyl)-3-(trifluoromethyl)-1H-pyrazol-1-yl)pyrrolidin-1-yl)ethyl(methyl)carbamate (77)

The title compound 77 (10 mg, 12% yield) was obtained as a colorless oil by following the procedure described above for the synthesis of compound 59 (scheme 8, example 6, step 7), except using 76 (79 mg, 0.164 mmol) in place of 58. LRMS (ESI): calc. 525.3; found 526.2 (MH)+.

Step 7. (R)—N-(2-methoxybenzyl)-1-(1-(2-(methylamino)ethyl)pyrrolidin-3-yl)-3-(trifluoromethyl)-1H-pyrazole-5-carboxamide (78)

To a stirred solution of 77 (10 mg, 0.019 mmol) in CH$_2$Cl$_2$ (0.38 mL) was added TFA (0.073 mL, 0.951 mmol). The resulting solution was allowed to stir at room temperature for 2 h. The mixture was concentrated and the residue was purified by silica gel column chromatography with gradient of methanol (5-30%) in dichloromethane to afford 78 (10 mg, 80%) as a white solid. $^1$H NMR (DMSO-d6) δ(ppm): 9.11 (t, J=5.1 Hz, 1H), 7.38 (s, 1H), 7.27-7.19 (m, 2H), 7.00 (d, J=7.8 Hz, 1H), 6.91 (t, J=7.4 Hz, 1H), 5.83 (qi, J=9.0 Hz, 1H), 4.41 (q, J=6.1 Hz, 2H), 3.81 (s, 3H), 3.20-3.16 (m, 1H), 2.96-2.92 (m, 2H), 2.80-2.68 (m, 4H), 2.53 (d, J=2.2 Hz, 3H), 2.32-2.17 (m, 3H). LRMS (ESI): calc. 425.2; found 426.1 (MH)+.

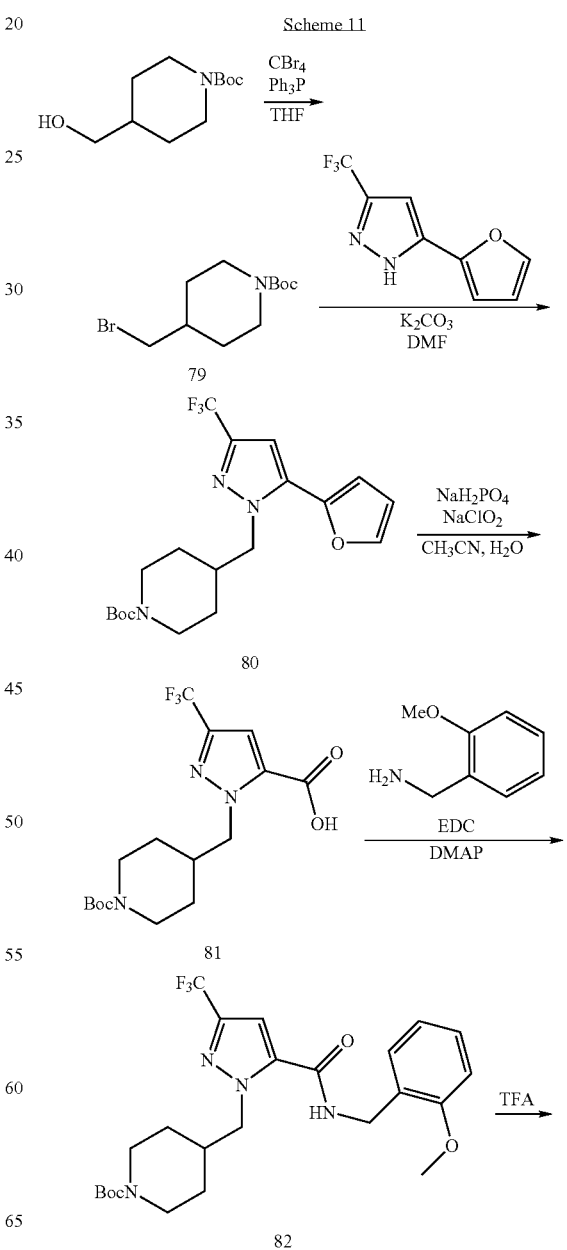

Scheme 11

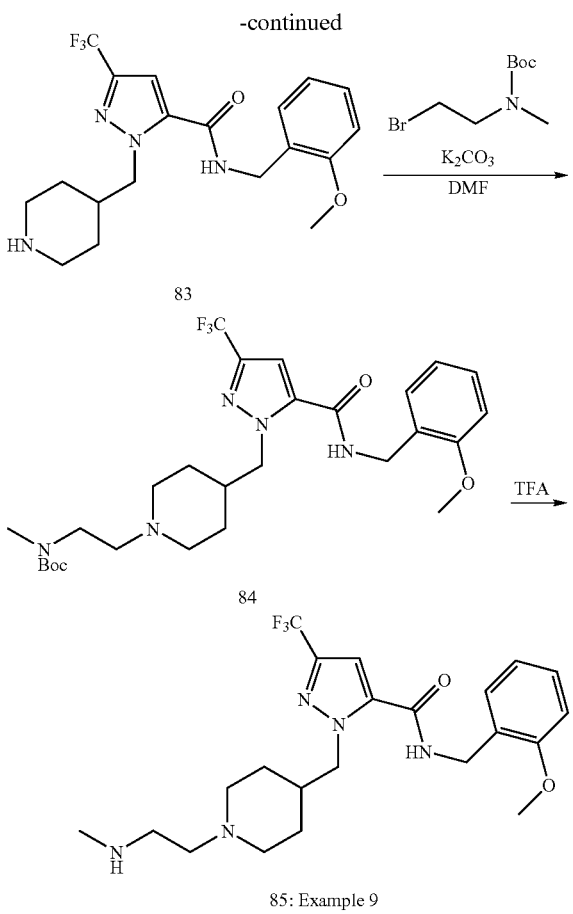

83

84

85: Example 9

Example 8a (S)—N-(2-methoxybenzyl)-1-(1-(2-(methylamino)ethyl)pyrrolidin-3-yl)-3-(trifluoromethyl)-1H-pyrazole-5-carboxamide (78a)

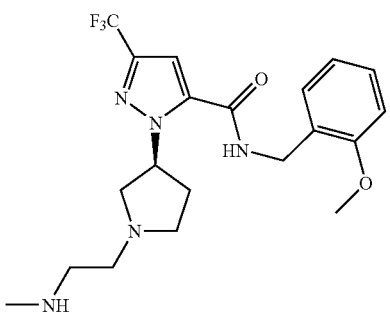

Compound 78a, white solid, was prepared following the procedure for compound 78 (scheme 10, Example 8, steps 1-7) except in step one use N-Boc-(R)-3-hydroxypyrrolidine was replaced with N-Boc-(S)-3-hydroxypyrrolidine. $^1$H NMR (DMSO-d6) δ(ppm): 9.11 (t, J=5.1 Hz, 1H), 7.38 (s, 1H), 7.27-7.19 (m, 2H), 7.00 (d, J=7.8 Hz, 1H), 6.91 (t, J=7.4 Hz, 1H), 5.83 (qi, J=9.0 Hz, 1H), 4.41 (q, J=6.1 Hz, 2H), 3.81 (s, 3H), 3.20-3.16 (m, 1H), 2.96-2.92 (m, 2H), 2.80-2.68 (m, 4H), 2.53 (d, J=2.2 Hz, 3H), 2.32-2.17 (m, 3H). LRMS (ESI): calc. 425.2; found 426.1 (MH)$^+$.

Example 9

N-(2-methoxybenzyl)-1-((1-(2-(methylamino)ethyl)piperidin-4-yl)methyl)-3-(trifluoromethyl)-1H-pyrazole-5-carboxamide (85)

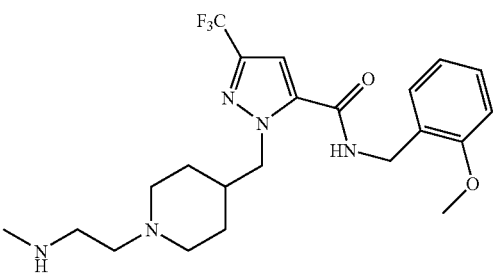

Step 1. tert-butyl 4-(bromomethyl)piperidine-1-carboxylate (79)

The title compound 79 (1.251 g, 90%) was obtained as colourless oil by following the procedure described above for the synthesis of compound 72 (scheme 10, example 8, step 1), except using tert-butyl 4-(hydroxymethyl)piperidine-1-carboxylate (1.076 g, 5 mmol) in place of N-Boc-(R)-3-hydroxypyrrolidine. LRMS (ESI): calc. 277.1; found 299.9 (MNa)$^+$.

Step 2. tert-butyl 4-((5-(furan-2-yl)-3-(trifluoromethyl)-1H-pyrazol-1-yl)methyl) piperidine-1-carboxylate (80)

The title compound 80 (819 mg, 60%) was obtained as colourless oil by following the procedure described above for the synthesis of compound 73 (scheme 10, example 8, step 2), except using 79 (1.141 g, 4.10 mmol) in place of 72. LRMS (ESI): calc. 399.2; found 422.0 (MNa)$^+$.

Step 3. 1-((1-(tert-butoxycarbonyl)piperidin-4-yl)methyl)-3-(trifluoromethyl)-1H-pyrazole-5-carboxylic acid (81)

Title compound 81 (489 mg, 63%) was obtained as a white solid by following the procedure described above for the synthesis of compound 25 (scheme 4, example 2a, step 7), except using 80 (819 mg, 2.051 mmol) in place of 24. LRMS (ESI): calc. 377.2; found 400.2 (MNa)$^+$.

Step 4. tert-butyl 4-((5-(2-methoxybenzylcarbamoyl)-3-(trifluoromethyl)-1H-pyrazol-1-yl)methyl) piperidine-1-carboxylate (82)

Title compound 82 (339 mg, 53%) was obtained by following the procedure described above for the synthesis of compound 26a (scheme 4, example 2a, step 8), except using 81 (489 mg, 1.30 mmol) and (2-methoxyphenyl)methanamine in place of 25. LRMS (ESI): calc. 496.2; found 519.1 (MNa)$^+$.

Step 5. N-(2-methoxybenzyl)-1-(piperidin-4-ylmethyl)-3-(trifluoromethyl)-1H-pyrazole-5-carboxamide (83)

The title compound 83 was obtained by following the procedure described above for the synthesis of compound 58 (scheme 8, example 6, step 6), except using 82 (339 mg, 0.683 mmol) in place of 57. LRMS (ESI): calc. 396.2; found 397.1 (MH)$^+$.

Step 6. tert-butyl 2-(4-((5-(2-methoxybenzylcarbamoyl)-3-(trifluoromethyl)-1H-pyrazol-1-yl)methyl)piperidin-1-yl)ethyl(methyl)carbamate (84)

To a stirred solution of 83 (87 mg, 0.171 mmol) in DMF (855 μl) was added potassium carbonate (59.1 mg, 0.428 mmol). The mixture was cooled to 0° C., then followed by the addition of tert-butyl 2-bromoethyl(methyl)carbamate (44.8 mg, 0.188 mmol) [made by following the procedure described above for the synthesis of 72 (scheme 10, example 8, step 1), except using tert-butyl 2-hydroxyethyl(methyl)carbamate in place of N-Boc-(R)-3-hydroxypyrrolidine]. The mixture was stirred at room temperature for 16 h, and then more tert-butyl 2-bromoethyl(methyl)carbamate (44.8 mg, 0.188 mmol) was added. The mixture was stirred at room temperature for 30 min, then at 80° C. for 1 hour. The mixture was quenched with water and extracted with ethyl acetate, washed with brine, dried (MgSO$_4$) filtered and concentrated. The residue was purified by silica gel column chromatography with gradient of methanol (0-10%) in dichloromethane to afford 84 (11 mg, 12%) as a white solid. LRMS (ESI): calc. 553.3; found 554.2 (MNa)$^+$.

Step 7. N-(2-methoxybenzyl)-1-((1-(2-(methylamino)ethyl)piperidin-4-yl)methyl)-3-(trifluoromethyl)-1H-pyrazole-5-carboxamide (85)

The title compound 85 (7 mg, 52%) was obtained as a white solid by following the procedure described above for the synthesis of compound 78 (scheme 10, example 8, step 7), except using 84 (11 mg, 0.02 mmol) in place of 77. $^1$H NMR (DMSO-d6) δ(ppm): 9.09 (t, J=5.7 Hz, 1H), 7.39 (s, 1H), 7.29-7.23 (m, 1H), 7.18 (d, J=5.9 Hz, 1H), 7.00 (d, J=8.0 Hz, 1H), 6.90 (t, J=7.4 Hz, 1H), 4.49 (d, J=7.0 Hz, 2H), 4.40 (d, J=5.7 Hz, 2H), 3.81 (s, 3H), 2.92 (t, J=5.5 Hz, 2H), 2.81-2.77 (m, 2H), 2.50 (s, 3H), 2.44 (t, J=5.5 Hz, 2H), 1.88-1.83 (m, 3H), 1.38-1.36 (m, 2H), 1.28-1.19 (m, 2H). LRMS (ESI): calc. 453.2; found 454.1 (MH)$^+$.

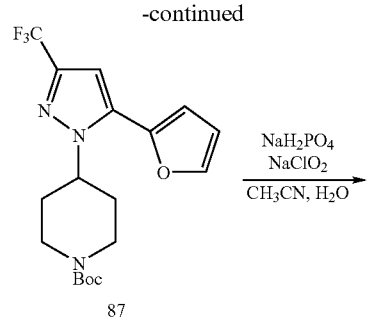

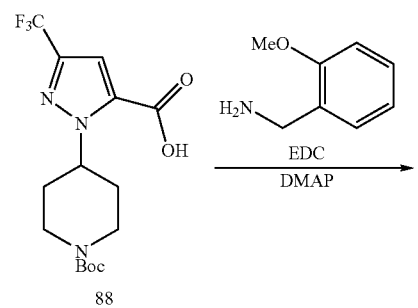

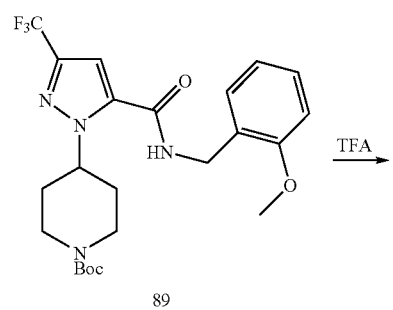

Scheme 12

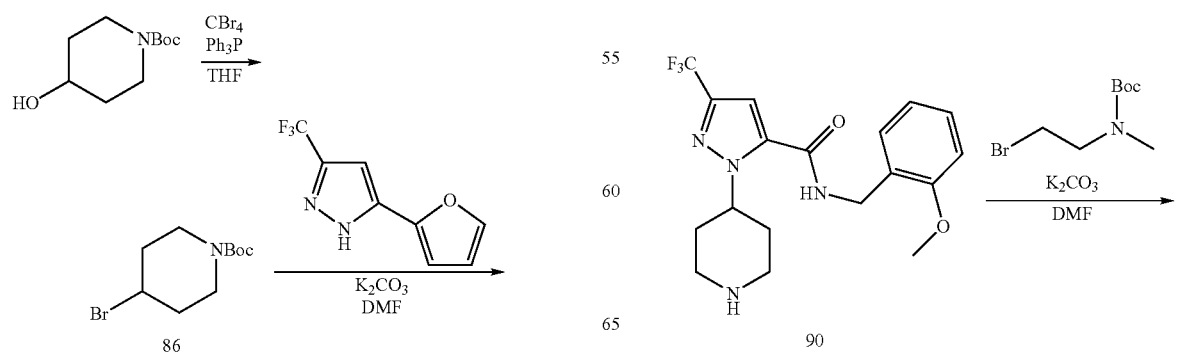

99
-continued

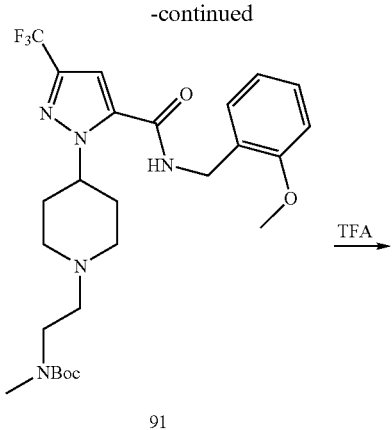

91

100
Example 10

N-(2-methoxybenzyl)-1-(1-(2-(methylamino)ethyl) piperidin-4-yl)-3-(trifluoromethyl)-1H-pyrazole-5-carboxamide (92)

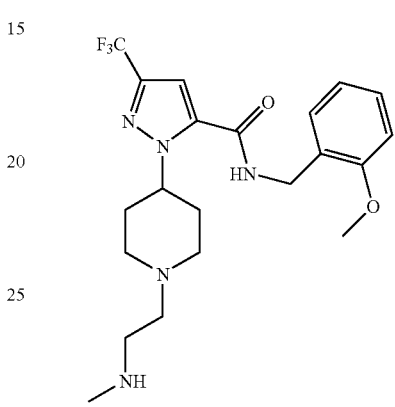

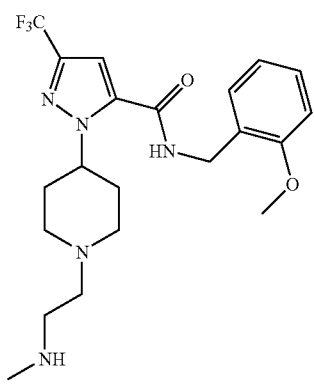

92: Example 10

The title compound 92 (7 mg, 22% for last step) was obtained as a white solid by following the procedures described above for the synthesis of compound 85 (scheme 11, example 9, steps 1-7), except that in step 1, tert-butyl 4-hydroxypiperidine-1-carboxylate in place of tert-butyl 4-(hydroxypimethyl)piperidine-1-carboxylate. $^1$H NMR (DMSO-d6) δ(ppm): 9.11 (bs, 1H), 7.39 (s, 1H), 7.28-7.20 (m, 2H), 7.00 (d, J=7.4 Hz, 1H), 6.91 (t, J=7.4 Hz, 1H), 5.31-5.12 (m, 1H), 4.41 (d, J=5.9 Hz, 2H), 3.81 (s, 3H), 3.70-2.89 (m, 7H), 2.58 (s, 3H), 2.30-1.85 (m, 5H). LRMS (ESI): calc. 439.2; found 440.1 (MH)$^+$.

Scheme 13

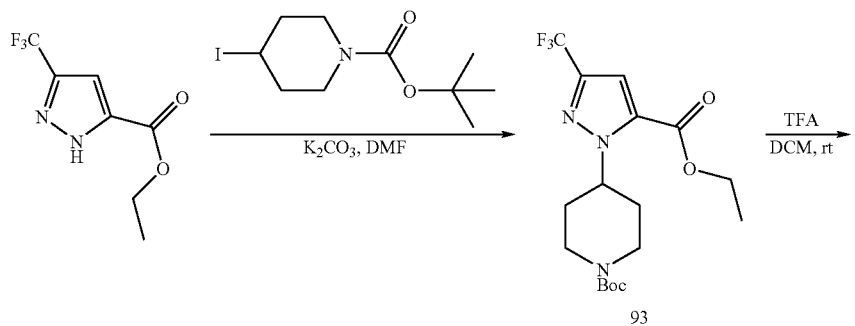

93

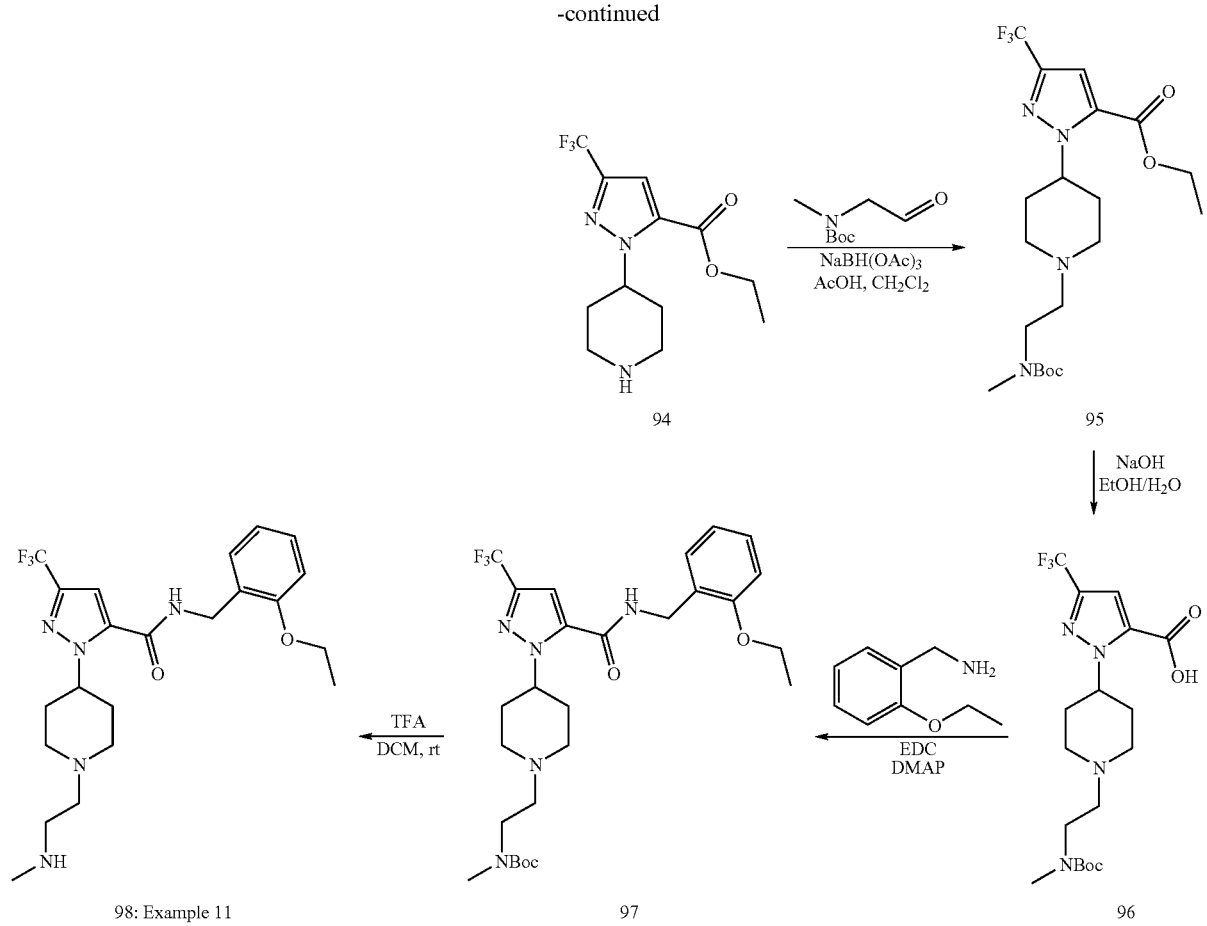

Example 11

N-(2-ethoxybenzyl)-1-(1-(2-(methylamino)ethyl) piperidin-4-yl)-3-(trifluoromethyl)-1H-pyrazole-5-carboxamide (98)

Step 1: tert-butyl 4-(5-(ethoxycarbonyl)-3-(trifluoromethyl)-1H-pyrazol-1-yl)piperidine-1-carboxylate (93)

tert-Butyl 4-iodopiperidine-1-carboxylate (5.683, 18.26 mmol, E.G. Corley et al, JOC, 2004, 69, 5120-5123) in DMF (30.7 ml) was added to a mixture of ethyl 3-(trifluoromethyl)-1H-pyrazole-5-carboxylate (3.2 g, 15.37 mmol, M.-A. Plancquaert et al, Tetrahedron, 52, 4383-4396) and potassium carbonate 95.31 g, 38.4 mmol) and the mixture was stirred at 80° C. for 16 h. After cooling, water was added and the mixture was extracted with EtOAc, and the organic extraxts were dried, filtered and concentrated. Chromatographic purification of the residue by Biotage (5-20% EtOAc in Hexanes, 25M column) gave compound 93 as colorless oil (2.4 g, 39.9% yield). LRMS (ESI): calc. 391.4; found 414.1 (M+Na)⁺.

Step 2: ethyl 1-(piperidin-4-yl)-3-(trifluoromethyl)-1H-pyrazole-5-carboxylate (94)

To a stirred solution of 93 (1.014, 2.59 mmol) in CH$_2$Cl$_2$ (13 ml) was added TFA (3 ml, 38.9 mmol). The resulting solution was allowed to stir at 21° C. for 2 h. After the usual work-up, crude 94 was obtained as colorless oil. LRMS (ESI): calc. 291.3; found 292.2 (MH)⁺.

Step 3: ethyl 1-(1-(2-(tert-butoxycarbonyl(methyl) amino)ethyl)piperidin-4-yl)-3-(trifluoromethyl)-1H-pyrazole-5-carboxylate (95)

The title compound 95 (1.092 g, 94% yield) was obtained as a colorless oil by following the procedure described above for the synthesis of compound 59 (scheme 8, example 6, step 7), except using 94 (0.754 g, 2.59 mmol) in place of 58. LRMS (ESI): calc. 448.5; found 449.3 (MH)⁺.

Step 4: 1-(1-(2-(tert-butoxycarbonyl(methyl)amino) ethyl)piperidin-4-yl)-3-(trifluoromethyl)-1H-pyrazole-5-carboxylic acid (96)

To a stirred suspension of 95 (1.09 g, 2.43 mmol) in ethanol (8.1 ml) was added a solution of NaOH (2.43 ml, 2N, 4.86 mmol) followed by THF (1.6 ml). After stirring at room temperature for 1 h, the mixture was taken to dryness and crude 96 was used as is for the next step. LRMS (ESI): calc. 420.4; found 421.3 (MH)⁺.

Step 5: tert-butyl 2-(4-(5-(2-ethoxybenzylcarbamoyl)-3-(trifluoromethyl)-1H-pyrazol-1-yl)piperidin-1-yl)ethyl(methyl)carbamate (97)

The title compound 97 (25.m g, 19% yield) was obtained as a colorless oil following the procedure described for the synthesis of compound 15a (scheme 2, example 1c, step 8) except using 96 (100 mg, 0.24 mmol) in place of 7. LRMS (ESI): calc.553.6; found 554.7 (MH)+.

Step 6: N-(2-ethoxybenzyl)-1-(1-(2-(methylamino)ethyl)piperidin-4-yl)-3-(trifluoromethyl)-1H-pyrazole-5-carboxamide (98)

The title compound 98 (8 m g, 39% yield) was obtained as white solid following the procedure described for the synthesis of compound 9a (scheme 2, example 1c, step 9), except using 97 (25 mg, 0.045 mmol) in place of 15a. LRMS (ESI): calc.453.5; found 454.4 (MH)+. $^1$H NMR: (CD$_3$OD) δ(ppm): 7.26-7.22 (m, 2H), 7.05 (s, 1H), 6.95 (d, J=7.6 Hz, 1H), 6.90 (t, J=7.4 Hz, 1H), 5.18-5.15 (m, 1H), 4.54 (s, 2H), 4.10 (q, J=6.8 Hz, 2H), 3.06 (bd, J=8.4 Hz, 2H), 2.76 (t, 6.8 Hz, 2H), 2.56 (t, 6.5 Hz, 2H), 2.46 (s, 3H), 2.26-2.16 (m, 4H), 2.02-1.97 (m, 2H), 1.41 (t, J=7.0 Hz, 3H).

Scheme 14

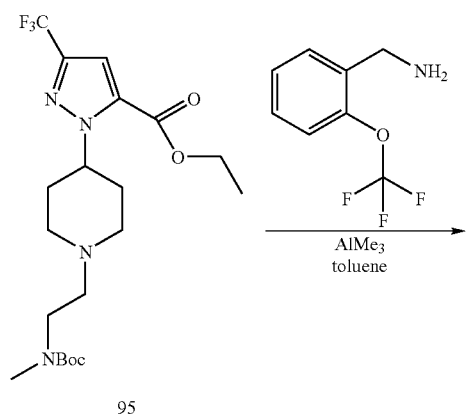

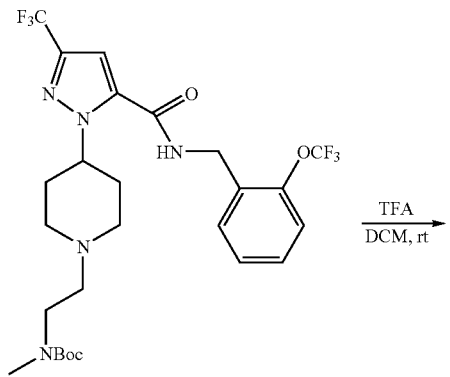

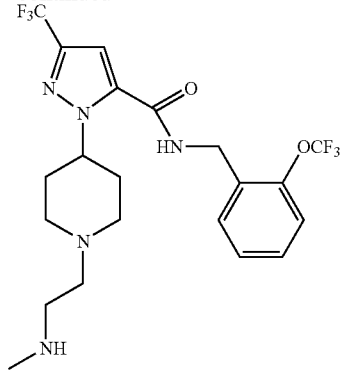

100: Example 12

Example 12

1-(1-(2-(methylamino)ethyl)piperidin-4-yl)-N-(2-(trifluoromethoxy)benzyl)-3-(trifluoromethyl)-1H-pyrazole-5-carboxamide (100)

Step 1: tert-butyl methyl(2-(4-(5-(2-(trifluoromethoxy)benzylcarbamoyl)-3-(trifluoromethyl)-1H-pyrazol-1-yl)piperidin-1-yl)ethyl)carbamate (99)

To a stirred solution of 2-(Trifluoromethoxy)benzylamine (58.6 mg, 0.307 mmol) in toluene (1.239 mL) at 0° C. was added trimethylaluminium (2M in toluene, 0.557 mL, 1.115 mmol) dropwise. The mixture was stirred for 5 min at 0° C., then a solution of 95 (125 mg, 0.279 mmol) in toluene (0.620 mL) was added dropwise. The mixture was stirred at room temperature for 1 h, then at 55° C. for 1 h, and at 95° C. for 1.5 h till the reaction was complete. Saturated NaHCO3 was added to the reaction mixture followed by extraction with EtOAc. The organic extracts were dried over MgSO4, filtrated and concentrated and the residue was purified via Biotage (5% to 20% MeOH/CH2Cl2; 12M column) to give 99 as yellow oil. LRMS (ESI): calc.593.6; found 594.3 (MH)+.

Step 2:1-(1-(2-(methylamino)ethyl)piperidin-4-yl)-N-(2-(trifluoromethoxy)benzyl)-3-(trifluoromethyl)-1H-pyrazole-5-carboxamide (100)

The title compound 100 (47 m g, 33% yield) was obtained as white solid following the procedure described for the synthesis of compound 9a (scheme 2, example 1c, step 9), except using 99 (116 mg, 0.195 mmol) in place of 15a. $^1$H NMR: (CD$_3$OD) δ(ppm): 9.14 (bs, 1H), 7.47 (d, J=7.4 Hz, 1H), 7.42-7.31 (m, 3H), 7.15 (d, J=3.5 Hz, 1H), 5.51-5.36 (m, 1H), 4.63 (d, J=5.7 Hz, 2H), 3.60-2.80 (m, 8H), 2.78 (d, J=3.1 Hz, 3H), 2.48-2.32 (m, 2H), 2.30-2.19 (m, 2H). LRMS(ESI): (calc.) 493.2 (found) 494.3 (MH)+

Examples 11a-e describe the preparation of compounds 98a-e using the same procedures as described for the synthesis of compound 98 in Example 11. Also, Examples 12a-e describes the preparation of compounds 100a-e using the same procedures as described for the synthesis of compound 100 in Example 12. Characterization data are presented in Table 3.

TABLE 3

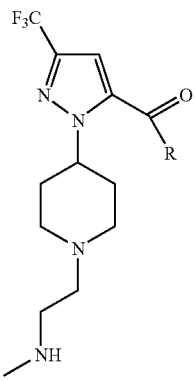

| Ex | Cpd | R | Name | Characterization | Scheme |
|---|---|---|---|---|---|
| 11a | 98a | ~NH—CH2—(2-OCHF2-C6H4) | N-(2-(difluoromethoxy)benzyl)-1-(1-(2-(methylamino)ethyl)piperidin-4-yl)-3-(trifluoromethyl)-1H-pyrazole-5-carboxamide | $^1$H NMR (CD$_3$OD) δ (ppm): 7.41 (dd, J = 7.6, 1.8 Hz, 1 H), 7.34 (td, J = 7.8, 1.8 Hz, 1 H), 7.23 (td, J = 7.6, 1.2 Hz, 1 H), 7.19 (d, J = 8.2 Hz, 1 H), 7.06 (s, 1 H), 6.88 (t, J = 74 Hz, 1 H), 5.18-5.14 (m, 1 H), 4.59 (s, 3 H), 3.06 (bd, J = 9.2 Hz, 2 H), 2.70 (t, J = 6.7 Hz, 2 H), 2.55 (t, J = 6.9 Hz, 2 H), 2.41 (s, 3 H), 2.25-2.15 (m, 4 H), 2.01-1.87 (m, 2 H). LRMS (ESI): (calc.) 475.2 (found) 476.3 (MH)+ | 13 |
| 11b | 98b | ~NH—CH2—(2-NHMe-C6H4) | N-(2-(methylamino)benzyl)-1-(1-(2-(methylamino)ethyl)piperidin-4-yl)-3-(trifluoromethyl)-1H-pyrazole-5-carboxamide | $^1$H NMR (CD$_3$OD) δ (ppm): 7.17 (td, J = 7.6, 2.0 Hz, 1 H), 7.11 (dd, J = 7.8, 1.6 Hz, 1 H), 7.02 (s, 1 H), 6.64 (d, J = 7.8 Hz, 2 H), 5.19 (qi, J = 4.3 Hz, 1 H), 4.43 (s, 2 H), 3.14 (t, J = 5.5 Hz, 2 H), 3.08-3.03 (m, 2 H), 2.83 (s, 3 H), 2.73 (s, 3 H), 2.68 (t, J = 5.9 Hz, 2 H), 2.32-2.21 (m, 4 H), 2.02-1.97 (m, 2 H). LRMS (ESI): (calc.) 438.2 (found) 439.2 (MH)+ | 13 |
| 11c | 98c | ~NH—CH2—(2-OPh-C6H4) | 1-(1-(2-(methylamino)ethyl)piperidin-4-yl)-N-(2-phenoxybenzyl)-3-(trifluoromethyl)-1H-pyrazole-5-carboxamide | $^1$H NMR (CD$_3$OD) δ (ppm): 7.43 (dd, J = 7.6, 1.6 Hz, 1 H), 7.34-7.24 (m, 3 H), 7.17-7.03 (m, 2 H), 6.97-6.92 (m, 2 H), 6.88 (dd, J = 8.0, 1.0 Hz, 1 H), 6.85 (s, 1 H), 5.12-5.03 (m, 1 H), 4.58 (s, 2 H), 3.12-2.97 (m, 2 H), 2.71 (t, J = 6.7 Hz, 2 H), 2.60-2.51 (m, 2 H), 2.42 (s, 3 H), 2.33-2.12 (m, 4 H), 2.00-1.87 (m, 2 H). LRMS (ESI): (calc.) 501.3 (found) 502.4 (MH)+ | 13 |

TABLE 3-continued

[Structure: 3-(trifluoromethyl)-1H-pyrazole-5-carboxamide with 1-(1-(2-(methylamino)ethyl)piperidin-4-yl) substituent, C(=O)-R group]

| Ex | Cpd | R | Name | Characterization | Scheme |
|---|---|---|---|---|---|
| 11d | 98d | [5-fluoro-2-methoxybenzyl-NH-] | N-(5-fluoro-2-methoxybenzyl)-1-(1-(2-(methylamino)ethyl)piperidin-4-yl)-3-(trifluoromethyl)-1H-pyrazole-5-carboxamide | $^1$H NMR (CD$_3$OD) δ (ppm): 7.10 (s, 1 H), 7.01-6.94 (m, 3 H), 5.22-5.17 (m, 1 H), 4.50 (s, 2 H), 3.86 (s, 3 H), 3.13 (t, J = 5.3 Hz, 2 H), 3.06 (bd, J = 7.6 Hz, 2 H), 2.72 (s, 3 H), 2.68 (t, J = 5.9 Hz, 2 H), 2.35-2.23 (m, 4 H), 2.06-1.98 (m, 2 H). LRMS (ESI): (calc.) 457.2 (found) 458.3 (MH)+ | 13 |
| 11e | 98e | [(2-methoxynaphthalen-1-yl)methyl-NH-] | N-((2-methoxynaphthalen-1-yl)methyl)-1-(1-(2-(methylamino)ethyl)piperidin-4-yl)-3-(trifluoromethyl)-1H-pyrazole-5-carboxamide | $^1$H NMR (CD$_3$OD) δ (ppm): 8.06 (d, J = 8.8 Hz, 1 H), 7.91 (d, J = 9.2 Hz, 1 H), 7.83 (d, J = 8.2 Hz, 1 H), 7.50 (td, J = 6.7, 1.2 Hz, 1 H), 7.44 (d, J = 9.2 Hz, 1 H), 7.35 (t, J = 6.8 Hz, 1 H), 6.90 (s, 1 H), 5.19-5.10 (m, 1 H), 5.04 (s, 2 H), 4.01 (s, 3 H), 3.14 (t, J = 5.5 Hz, 2 H), 3.06 (bd, J = 5.7 Hz, 2 H), 2.73 (s, 3 H), 2.69 (t, J = 5.9 Hz, 2 H), 2.28-2.21 (m, 4 H), 2.03-1.97 (m, 2 H). LRMS (ESI): (calc.) 489.2 (found) 490.3 (MH)+ | 13 |
| 12a | 100a | [2-methylbenzyl-NH-] | 1-(1-(2-(methylamino)ethyl)piperidin-4-yl)-N-(2-methylbenzyl)-3-(trifluoromethyl)-1H-pyrazole-5-carboxamide | $^1$H NMR (CD$_3$OD) δ (ppm): 9.01 (m, 1 H), 7.27 (t, J = 4.7 Hz, 1 H), 7.19-7.14 (m, 3 H), 7.13 (s, 1 H), 5.49-5.36 (m, 1 H), 4.54 (d, J = 5.5 Hz, 2 H), 3.43 (bd, J = 11 Hz, 2 H), 3.34 (t, J = 6.7 Hz, 2 H), 3.19-3.12 (m, 2 H), 2.88-2.78 (m, 2 H), 2.77 (s, 3 H), 2.44-2.35 (m, 2 H), 2.36 (s, 3 H), 2.20 (bd, J = 12 Hz, 2 H). LRMS (ESI): (calc.) 423.2 (found) 424.4 (MH)+ | 14 |

TABLE 3-continued

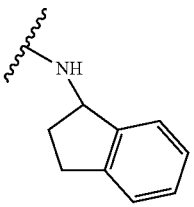

| Ex | Cpd | R | Name | Characterization | Scheme |
|---|---|---|---|---|---|
| 12b | 100b | 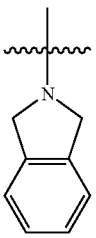 | N-(2,3-dihydro-1H-inden-1-yl)-1-(1-(2-(methylamino)ethyl)piperidin-4-yl)-3-(trifluoromethyl)-1H-pyrazole-5-carboxamide | $^1$H NMR (CD$_3$OD) δ (ppm): 8.93 (d, J = 8.4 Hz, 1 H), 7.29-7.19 (m, 4 H), 7.13 (s, 1 H), 5.59 (q, J = 8.0 Hz, 1 H), 5.50-5.46 (m, 1 H), 3.52 (bd, J = 11 Hz, 2 H), 3.39 (t, J = 6.7 Hz, 2 H), 3.28-3.23 (m, 2 H), 3.10-3.02 (m, 1 H), 3.01-2.82 (m, 3 H), 2.78 (s, 3 H), 2.60-2.52 (m, 1 H), 2.43 (bq, J = 12 Hz, 2 H), 2.27 (bt, J = 12 Hz, 2 H), 2.04-1.95 (m, 1 H). LRMS (ESI): (calc.) 435.2 (found) 436.4 (MH)+ | 14 |
| 12c | 100c | 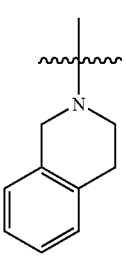 | isoindolin-2-yl(1-(1-(2-(methylamino)ethyl)piperidin-4-yl)-3-(trifluoromethyl)-1H-pyrazol-5-yl)methanone | $^1$H NMR (CD$_3$OD) δ (ppm): 7.40-7.38 (m, 1 H), 7.35-7.30 (m, 3 H), 7.19 (s, 1 H), 5.01 (s, 2 H), 4.98 (s, 2 H), 4.92-4.82 (m, 1 H), 3.46 (bd, J = 12 Hz, 2 H), 3.34 (t, J = 6.1 Hz, 2 H), 3.21-3.12 (m, 2 H), 2.92-2.81 (m, 2 H), 2.77 (s, 3 H), 2.42 (bq, J = 11 Hz, 2 H), 2.25 (bd, J = 11 Hz, 2 H). LRMS (ESI): (calc.) 421.2 (found) 422.3 (MH)+ | 14 |
| 12d | 100d | | (3,4-dihydroisoquinolin-2(1H)-yl)(1-(1-(2-(methylamino)ethyl)piperidin-4-yl)-3-(trifluoromethyl)-1H-pyrazol-5-yl)methanone | $^1$H NMR (CD$_3$OD) δ (ppm): 7.22-7.04 (m, 4 H), 6.87 (s, 1 H), 4.87 (s, 1 H), 4.67 (m, 1 H), 4.51-4.40 (m, 0.5 H), 4.36-4.23 (m, 0.5 H), 3.98 (t, J = 5.9 Hz, 1 H), 3.76 (t, J = 5.5 Hz, 1 H), 3.14-2.86 (m, 6 H), 2.73 (s, 1.5 H), 2.70 (s, 1.5 H), 2.66 (t, J = 6.1 Hz, 1 H), 2.61 (t, J = 4.9 Hz, 1 H), 2.37-2.17 (m, 3 H), 2.15-2.00 (m, 2 H), 1.92-1.83 (m, 1 H). LRMS (ESI): (calc.) 435.2 (found) 436.4 (MH)+ | 14 |

TABLE 3-continued
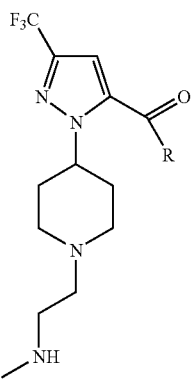
| Ex | Cpd | R | Name | Characterization | Scheme |
|---|---|---|---|---|---|
| 12e | 100e | ![R group with NH linked to 4-methoxybenzo[d]isoxazol-3-yl] | N-(4-methoxybenzo[d]isoxazol-3-yl)-1-(1-(2-(methylamino)ethyl)piperidin-4-yl)-3-(trifluoromethyl)-1H-pyrazole-5-carboxamide | $^1$H NMR (CD$_3$OD) δ (ppm): 8.45 (s, 1 H), 7.60 (t, J = 8.4 Hz, 1 H), 7.33 (s, 1 H), 7.20 (d, J = 8.4 Hz, 1 H), 5.25-5.20 (m, 1 H), 3.97 (s, 3 H), 3.14 (t, J = 5.7 Hz, 2 H), 3.09 (bd, J = 8.6 Hz, 2 H), 2.73 (s, 3 H), 2.69 (t, J = 5.9 Hz, 2 H), 2.35-2.26 (m, 4 H), 2.09 (bd, J = 8.8 Hz, 2 H). LRMS (ESI): (calc.) 466.2 (found) 467.3 (MH)+ | 14 |
Scheme 15
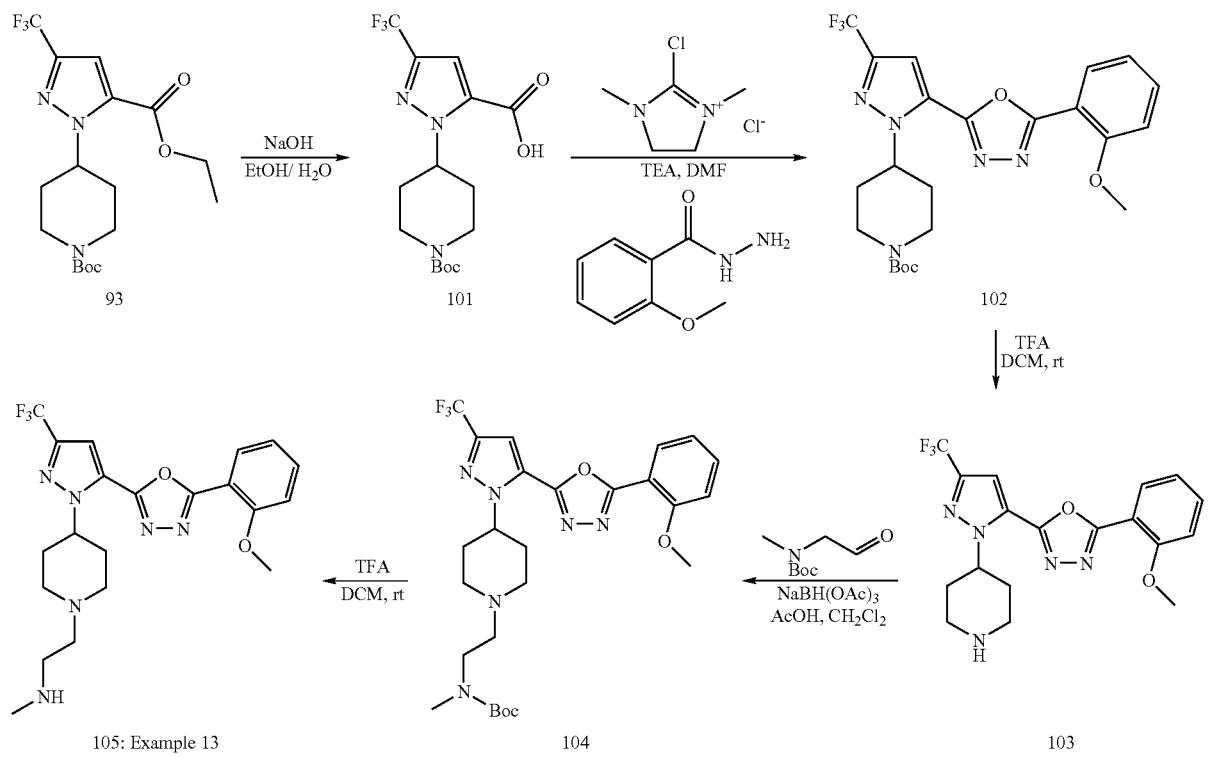

Example 13

2-(4-(5-(5-(2-methoxyphenyl)-1,3,4-oxadiazol-2-yl)-3-(trifluoromethyl)-1H-pyrazol-1-yl)piperidin-1-yl)-N-methylethanamine (105)

Step 1: 1-(1-(tert-butoxycarbonyl)piperidin-4-yl)-3-(trifluoromethyl)-1H-pyrazole-5-carboxylic acid (101)

To a stirred suspension of 93 (500 mg, 1.278 mmol) in ethanol (4.3 mL) was added a solution of NaOH (1.916 mL, 2N, 3.83 mmol) and the mixture was stirred at room temperature for 1 h, then it was concentrated and 1N HCl was added till the solution reached PH-1. Extraction with EtOAc and normal work-up gave crude 101 as colorless oil. LRMS (ESI): calc. 363.3; found 386.2 (MNa)$^+$.

Step 2: tert-butyl 4-(5-(5-(2-methoxyphenyl)-1,3,4-oxadiazol-2-yl)-3-(trifluoromethyl)-1H-pyrazol-1-yl)piperidine-1-carboxylate (102)

Triethylamine (0.46 mL, 3.3 mmol) was added to a solution of 101 (300 mg, 0.826 mmol), 2-methoxybenzhydride (137 mg, 0.826 mmol) and 2-Chloro-1,3-dimethylimidazolinium chloride (279 mg, 1.651 mmol) in DMF (4.13 mL). The mixture was stirred for 16 h at room temperature, then saturated NaHCO3 was added and the mixture was extracted with EtOAc. After work-up the residue was purified via Biotage (5% to 40% EtOAc/Hexane; 25M column) to give 102 (152 mg, 37.3% yield) as white solid. LRMS (ESI): calc. 493.5; found 494.4 (MH)$^+$.

Step 3: 2-(2-methoxyphenyl)-5-(1-(piperidin-4-yl)-3-(trifluoromethyl)-1H-pyrazol-5-yl)-1,3,4-oxadiazole (103)

The title compound 103 (108 m g, 89% yield) was obtained as beige solid following the procedure described for the synthesis of compound 9a (scheme 2, example 1c, step 9), except using 102 (152 mg, 0.31 mmol) in place of 15a. LRMS (ESI): calc. 393.4; found 394.2 (MH)$^+$.

Step 4: tert-butyl 2-(4-(5-(5-(2-methoxyphenyl)-1,3,4-oxadiazol-2-yl)-3-(trifluoromethyl)-1H-pyrazol-1-yl)piperidin-1-yl)ethyl(methyl)carbamate (104)

The title compound 104 (165 mg, quantitative yield) was obtained as a colorless oil following the procedure described above for the synthesis of compound 59 (scheme 8, example 6, step 7), except using 103 (108 mg, 0.275 mmol) in place of 58. LRMS (ESI): calc. 550.6; found 551.4 (MH)$^+$.

Step 5: 2-(4-(5-(5-(2-methoxyphenyl)-1,3,4-oxadiazol-2-yl)-3-(trifluoromethyl)-1H-pyrazol-1-yl)piperidin-1-yl)-N-methylethanamine (105)

The title compound 105 (133 m g, 71.5% yield) was obtained as beige solid following the procedure described for the synthesis of compound 9a (scheme 2, example 1c, step 9), except using 102 (165 mg, 0.275 mmol) in place of 15a. $^1$H NMR: (CD$_3$OD) δ(ppm): 8.02 (dd, J=1.6, 7.6 Hz, 1H), 7.65 (dt, J=1.6, 7.8 Hz, 1H), 7.44 (s, 1H), 7.28 (d, J=8.4 Hz, 1H), 7.17 (dt, J=0.8, 7.6 Hz, 1H), 5.68 (m, 1H), 4.01 (s, 3H), 3.90 (m, 2H), 3.59 (m, 4H), 3.40 (m, 2H), 2.83 (s, 3H), 2.70-2.65 (m, 2H), 2.55 (m, 2H). LRMS(ESI): (calc.) 450.2 (found) 451.3 (MH)+

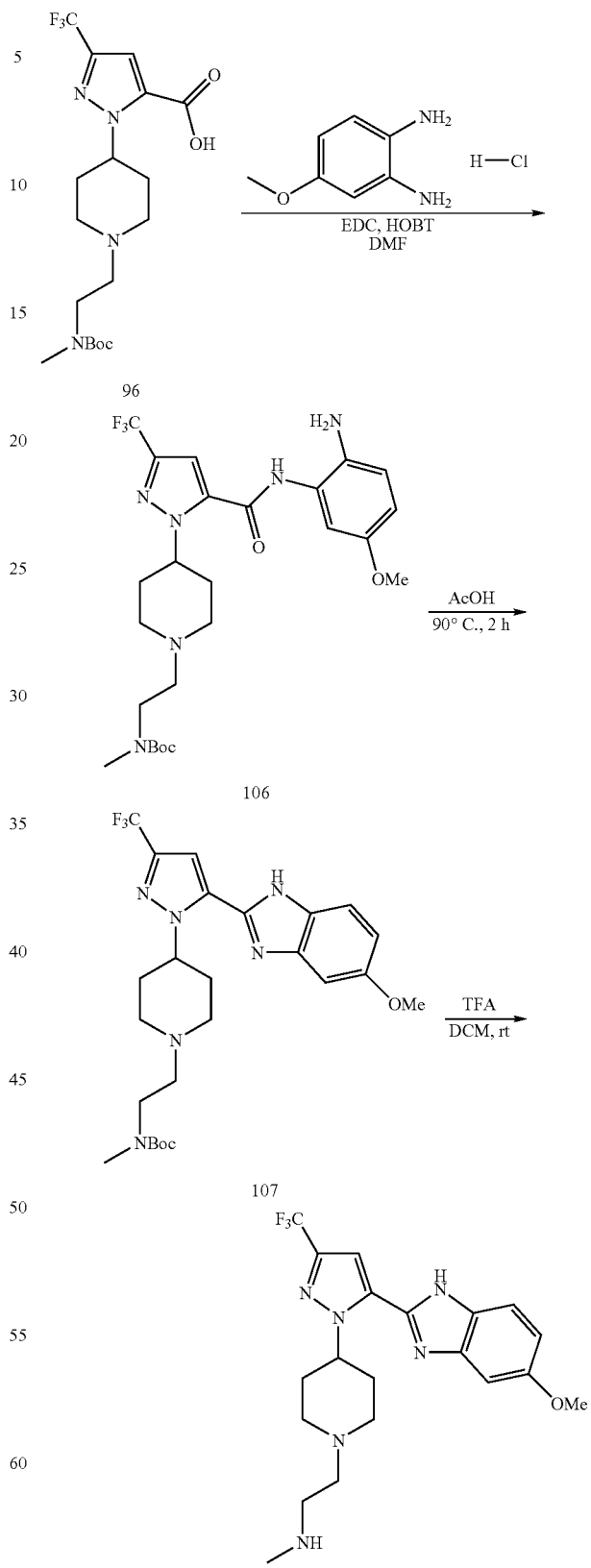

Scheme 16

108: Example 14

Example 14

2-(4-(5-(5-methoxy-1H-benzo[d]imidazol-2-yl)-3-(trifluoromethyl)-1H-pyrazol-1-yl)piperidin-1-yl)-N-methylethanamine (108)

Step 1: tert-butyl 2-(4-(5-(2-amino-5-methoxyphenylcarbamoyl)-3-(trifluoromethyl)-1H-pyrazol-1-yl)piperidin-1-yl)ethyl(methyl)carbamate (106)

To a stirred solution of 96 (160 mg, 0.381 mmol) in DMF (1.903 mL) was added EDC (88 mg, 0.457 mmol), HOBT (69.9 mg, 0.457 mmol) followed by 4-Methoxy-o-phenylenediamine dihydrochloride (73.1 mg, 0.419 mmol). The mixture was stirred for 16 h at room temperature. After the usual work-up, the residue was purified via Biotage (5% to 15% MeOH/CH2Cl2; 12M column) to afford 106 (172 mg, 84% yield) as yellow oil. LRMS (ESI): calc. 540.6; found 541.4 (MH)$^+$.

Step 2: tert-butyl 2-(4-(5-(5-methoxy-1H-benzo[d]imidazol-2-yl)-3-(trifluoromethyl)-1H-pyrazol-1-yl)piperidin-1-yl)ethyl(methyl)carbamate (107)

Acetic acid (1.591 mL) was added to compound 106 (86 mg, 0.159 mmol) and the solution was allowed to stir for 2 h at 90° C. The reaction was cooled and neutralized with a solution of saturated Na$_2$CO$_3$ and extract with AcOEt. After the usual work-up crude 106 was obtained as a light yellow solid. LRMS (ESI): calc. 522.7; found 523.4 (MH)$^+$.

Step 3: 2-(4-(5-(5-methoxy-1H-benzo[d]imidazol-2-yl)-3-(trifluoromethyl)-1H-pyrazol-1-yl)piperidin-1-yl)-N-methylethanamine (108)

The title compound 108 (15 m g, 28% yield) was obtained as white solid following the procedure described for the synthesis of compound 9a (scheme 2, example 1c, step 9), except using 102 (66 mg, 0.126 mmol) in place of 15a. $^1$H NMR: (CD$_3$OD) δ(ppm): 7.54 (bd, J=8.8 Hz, 1H), 7.10 (s, 2H), 6.96 (dd, J=9.0, 2.4 Hz, 1H), 5.65-5.54 (m, 1H), 3.87 (s, 3H), 3.15 (t, J=5.5 Hz, 2H), 3.09 (bd, J=6.1 Hz, 2H), 2.74 (s, 3H), 2.71 (t, J=5.9 Hz, 2H), 2.42-2.29 (m, 4H), 2.13-2.06 (m, 2H). LRMS(ESI): (calc.) 422.2 (found) 423.3 (MH)+

Scheme 17

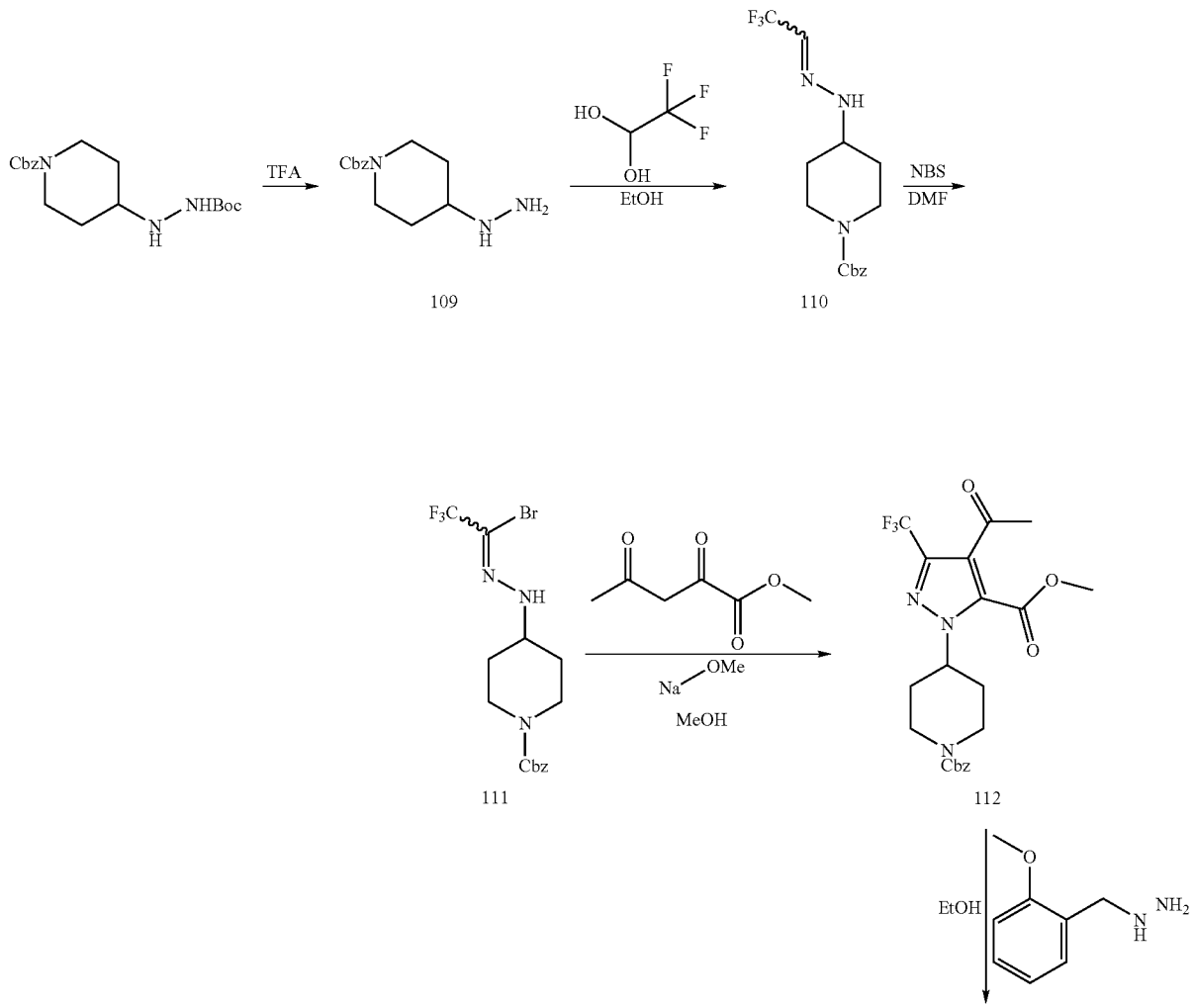

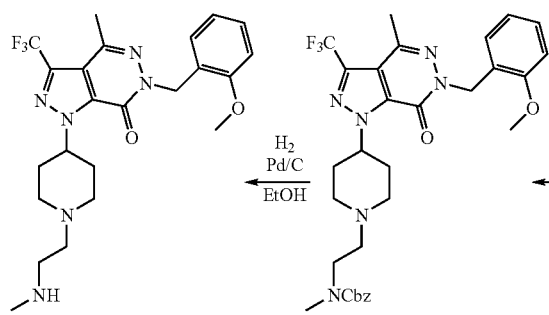
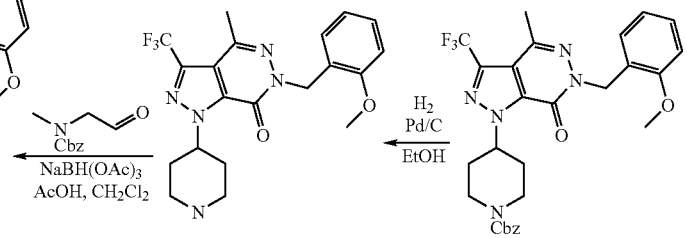

Example 15

6-(2-methoxybenzyl)-4-methyl-1-(1-(2-(methylamino)ethyl)piperidin-4-yl)-3-(trifluoromethyl)-1H-pyrazolo[3,4-d]pyridazin-7(6H)-one (116)

Step 1: benzyl 4-hydrazinylpiperidine-1-carboxylate (109)

The title compound 109 (12.7 g, crude yield) was obtained as colorless oil following the procedure described for the synthesis of compound 9a (scheme 2, example 1c, step 9), except using benzyl 4-(2-(2,2,2-trifluoroethylidene)hydrazinyl)piperidine-1-carboxylate (8.1 g, 23.1 mmol, J. Z. Deng et al, Tet. Lett., 2005, 46, 7993-7996) in place of 15a. LRMS (ESI): calc. 249.3; found 250.2 (MH)$^+$.

Step 2: benzyl 4-(2-(2,2,2-trifluoroethylidene)hydrazinyl)piperidine-1-carboxylate (110)

To a stirred solution of 109 (4 g, 8.38 mmol) in EtOH (42 ml) was added trifluoroacetaldehyde hydrate (0.648 ml, 8.38 mmol) and the resulting solution was allowed to stir for 3 h at 70° C. The solvent was evaporated and AcOEt was added to the residue and the organic layer was washed with 1N HCl then with brine, dried over MgSO4, filtrated and concentrated. Crude 110 was obtained as yellow oil and was used as is for the next step. LRMS (ESI): calc. 329.3; found 330.2 (MH)$^+$.

Step 3: benzyl 4-(2-(1-bromo-2,2,2-trifluoroethylidene)hydrazinyl)piperidine-1-carboxylate (111)

To a stirred solution of 110 (2.881 g, 8.75 mmol) in DMF (29.2 ml) was added NBS (1.713 g, 9.62 mmol) and the resulting solution was allowed to stir for 1 h at room temperature. Ethyl acetate was added followed by brine and water (50/50), and the AcOEt extracts were washed with water and brine, dried over MgSO4, filtrated and concentrated. The residue was purified via Biotage (5% to 20% EtOAc/Hexane; 25M column) to afford 111 (1.685 g, 47.2% yield) as yellow oil. LRMS (ESI): calc. 407.05 and 409.04; found 408.2 and 410.2 (MH)$^+$.

Step 4: benzyl 4-(4-acetyl-5-(methoxycarbonyl)-3-(trifluoromethyl)-1H-pyrazol-1-yl)piperidine-1-carboxylate (112)

To a stirred solution of Methyl 2,4-dioxopentanoate (892 mg, 6.19 mmol) in MeOH (11.5 mL) at room temperature was added Sodium methoxide (25% in MeOH, 0.891 mL, 4.13 mmol). Then a solution of 111 (842 mg, 2.063 mmol) in MeOH (2.3 mL) was added drop-wise and the suspension was stirred for 10 min at room temperature, then for 2 h at 65° C. After cooling, the mixture was taken to dryness and AcOEt and saturated NaHCO$_3$ were added, the organic layer was separated, dried over MgSO4, filtrated and evaporated and the residue was purified via Biotage (10% to 40% EtOAc/Hexane; 25S column) to afford 112 (361 mg, 38.6% yield) as red oil. LRMS (ESI): calc. 453.4; found 454.2 (MH)$^+$.

Step 5: benzyl 4-(6-(2-methoxybenzyl)-4-methyl-7-oxo-3-(trifluoromethyl)-6,7-dihydro-1H-pyrazolo[3,4-d]pyridazin-1-yl)piperidine-1-carboxylate (113)

To a stirred solution of 112 (361 mg, 0.796 mmol) in EtOH (3.2 mL) was added (2-Methoxy-benzyl)-hydrazine (242 mg, 1.592 mmol) and the resulting solution was allowed to stir for 1 h at room temperature, and for 2 h at 75° C. The solvent was evaporated, saturated NaHCO3 was added and the mixture extracted with EtOAc. After the usual work-up the residue was purified via Biotage (10% to 60% EtOAc/Hexane; 12M column) to afford 113 (81 mg, 18.3% yield) as white solid. LRMS (ESI): calc. 555.6; found 556.3 (MH)$^+$.

Step 6: 6-(2-methoxybenzyl)-4-methyl-1-(piperidin-4-yl)-3-(trifluoromethyl)-1H-pyrazolo[3,4-d]pyridazin-7(6H)-one (114)

To a stirred solution of 113 (81 mg, 0.146 mmol) in EtOH (1.5 mL) was added Pd/C (10% Degussa type, 15.5 mg, 0.015 mmol). The resulting suspension was allowed to stir for 30 min at room temperature under 1atm of H$_2$ gas. The catalyst was filtrate over Celite and the solvent was evaporated to give crude 114. LRMS (ESI): calc. 421.4; found 422.3 (MH)$^+$.

Step 7: benzyl 2-(4-(6-(2-methoxybenzyl)-4-methyl-7-oxo-3-(trifluoromethyl)-6,7-dihydro-1H-pyrazolo[3,4-d]pyridazin-1-yl)piperidin-1-yl)ethyl(methyl)carbamate (115)

The title compound 115 (102 mg, quantitative yield) was obtained as a colorless oil following the procedure described for the synthesis of compound 59 (scheme 8, example 6, step 7), except using 103 (62 mg, 0.146 mmol) in place of 58 and benzyl methyl(2-oxoethyl)carbamate in place of tert-butyl methyl(2-oxoethyl)carbamate (45 mg, 0.219 mmol). LRMS (ESI): calc. 612.6; found 613.4 (MH)$^+$.

Step 8: 6-(2-methoxybenzyl)-4-methyl-1-(1-(2-(methylamino)ethyl)piperidin-4-yl)-3-(trifluoromethyl)-1H-pyrazolo[3,4-d]pyridazin-7(6H)-one (116)

The title compound 116 (17 mg, 24.3% yield) was obtained as a colorless oil following the procedure described for the synthesis of compound 114 (scheme 17, example 15, step 6), except using 115 (89 mg, 0.146 mmol) in place of 113. $^1$H NMR: (CD$_3$OD) δ(ppm):7.27-7.22 (m, 1H), 6.98 (d, J=7.4 Hz, 1H), 6.90-6.88 (m, 1H), 6.86-6.82 (m, 1H), 5.52-5.43 (M, 1H), 5.38 (s, 2H), 3.86 (s, 3H), 3.14-3.09 (m, 2H), 2.72 (t, J=6.8 Hz, 2H), 2.57 (t, J=6.3 Hz, 2H), 2.54 (s, 3H), 2.42 (s, 3H), 2.34-2.23 (m, 4H), 2.14-2.06 (m, 2H). LRMS(ESI): (calc.) 478.2 (found) 479.3 (MH)+

Step 2: benzyl 4-(6-(2-methoxybenzyl)-4-oxo-3-(trifluoromethyl)-4,5-dihydro-1H-pyrazolo[3,4-d]pyrimidin-1-yl)piperidine-1-carboxylate (118)

To a stirred solution of 117 (327 mg, 0.795 mmol) in EtOH (3.2 mL) was added 2-Methoxyphenylacetic acid methyl ester (0.26 mL, 1.59 mmol), and then Sodium ethoxide (21% in EtOH, 0.6 mL, 1.59 mmol) and the resulting solution was

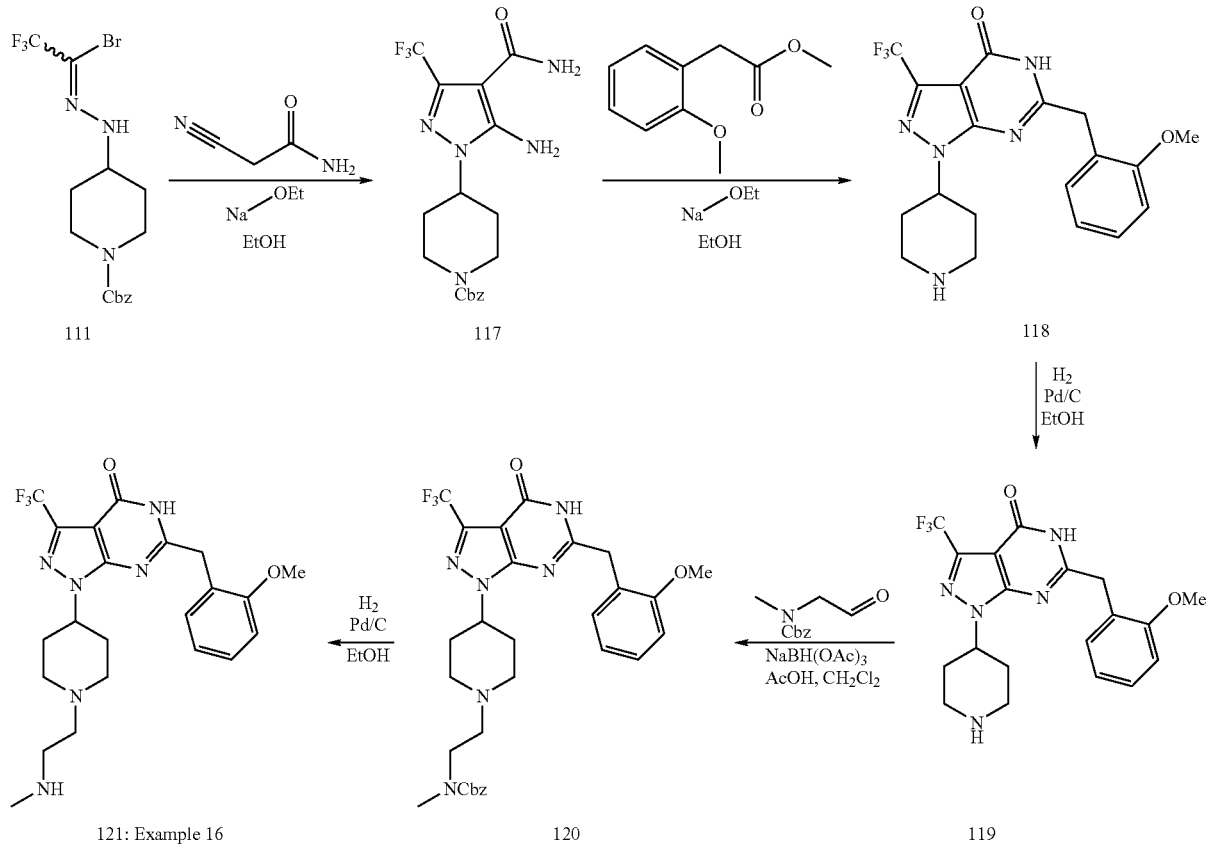

Scheme 18

Example 16

6-(2-methoxybenzyl)-1-(1-(2-(methylamino)ethyl)piperidin-4-yl)-3-(trifluoromethyl)-1H-pyrazolo[3,4-d]pyrimidin-4(5H)-one (121)

Step 1: benzyl 4-(5-amino-4-carbamoyl-3-(trifluoromethyl)-1H-pyrazol-1-yl)piperidine-1-carboxylate (117)

To a stirred solution of 2-Cyanoacetamide (520 mg, 6.19 mmol) in EtOH (8.6 mL) at room temperature was added Sodium ethoxide (21% in EtOH, 1.6 mL, 4.13 mmol). A solution of 111 (842 mg, 2.063 mmol) in EtOH (1.7 mL) was added dropwise and the resulting suspension was allowed to stir for 10 min at room temperature, then for 2 h at 80° C. The solvent was removed and after the usual work-up the crude material was purified via Biotage (10% to 40% EtOAc/Hexane; 25S column) to give 117 (327 mg, 38.5% yield) as an orange solid. LRMS (ESI): calc.411.4; found 412.1 (MH)+.

allowed to stir for 1 h at room temperature, then for 3 h at 75° C. After the usual work-up the crude material was purified via Biotage (10% to 60% EtOAc/Hexane; 12M column) to afford 118 (98 mg, 22.8% yield) as white solid, LRMS (ESI): calc. 541.5; found 542.3 (MH)+.

Step 3: 6-(2-methoxybenzyl)-1-(piperidin-4-yl)-3-(trifluoromethyl)-1H-pyrazolo[3,4-d]pyrimidin-4(5H)-one (119)

The title compound 119 was obtained as a colorless oil following the procedure described for the synthesis of compound 114 (scheme 17, example 15, step 6), except using 118 (98 mg, 0.181 mmol) in place of 113. LRMS (ESI): calc. 407.4; found 408.3 (MH)+.

Step 4: benzyl 2-(4-(6-(2-methoxybenzyl)-4-oxo-3-(trifluoromethyl)-4,5-dihydro-1H-pyrazolo[3,4-d]pyrimidin-1-yl)piperidin-1-yl)ethyl(methyl)carbamate (120)

The title compound 120 (119 mg, crude) was obtained as white solid following the procedure described for the synthesis of compound 59 (scheme 8, example 6, step 7), except using 119 (74 mg, 0.181 mmol) in place of 58 and benzyl methyl(2-oxoethyl)carbamate in place of tert-butyl methyl(2-oxoethyl)carbamate (56 mg, 0.272 mmol). LRMS (ESI): calc. 612.6; found 613.4 (MH)+.

Step 5; 6-(2-methoxybenzyl)-1-(1-(2-(methylamino) ethyl)piperidin-4-yl)-3-(trifluoromethyl)-1H-pyrazolo[3,4-d]pyrimidin-4(5H)-one (121)

The title compound 121 (23 mg, 27.4% yield) was obtained as a colorless oil following the procedure described for the synthesis of compound 114 (scheme 17, example 15, step 6), except using 120 (108 mg, 0.181 mmol) in place of 113. $^1$H NMR: (CD$_3$OD) δ(ppm): 7.28 (t, J=7.6 Hz, 1H), 7.20 (dd, J=7.4, 1.6 Hz, 1H), 6.98 (d, J=8.2 Hz, 1H), 6.92 (td, J=7.4, 1.0 Hz, 1H), 4.67-4.62 (m, 1H), 4.02 (s, 2H), 3.82 (s, 3H), 3.04 (bd, J=9.0 Hz, 2H), 2.71 (t, J=6.7 Hz, 2H), 2.55 (t, J=6.5 Hz, 2H), 2.42 (s, 3H), 2.30-2.17 (m, 4H), 1.92 (bd, J=10 Hz, 2H). LRMS(ESI): (calc.) 464.2 (found) 465.3 (MH)+

Example 17

N1-(3-(5-(5-(2-methoxyphenyl)-1,3,4-oxadiazol-2-yl)-3-(trifluoromethyl)-1H-pyrazol-1-yl)benzyl)-N2-methylethane-1,2-diamine (127)

Step 1: 3-(5-(furan-2-yl)-3-(trifluoromethyl)-1H-pyrazol-1-yl)benzaldehyde (122)

A solution of DIBAL (5.4 mL, 5.4 mmol, 1M in toluene) was added drop-wise to 53 (1.50 g, 4.95 mmol) in DCM (30 mL) under nitrogen at 0° C. The reaction was warmed to room temperature over 2 hours, then it was cooled in an ice bath and quenched with HCl (15 mL, 6N) and the mixture was stirred vigorously for 1 hour at room temperature. The mixture was then diluted with DCM and HCl (1N) was added and the organic layer was separated, dried over Na$_2$SO$_4$, filtered and

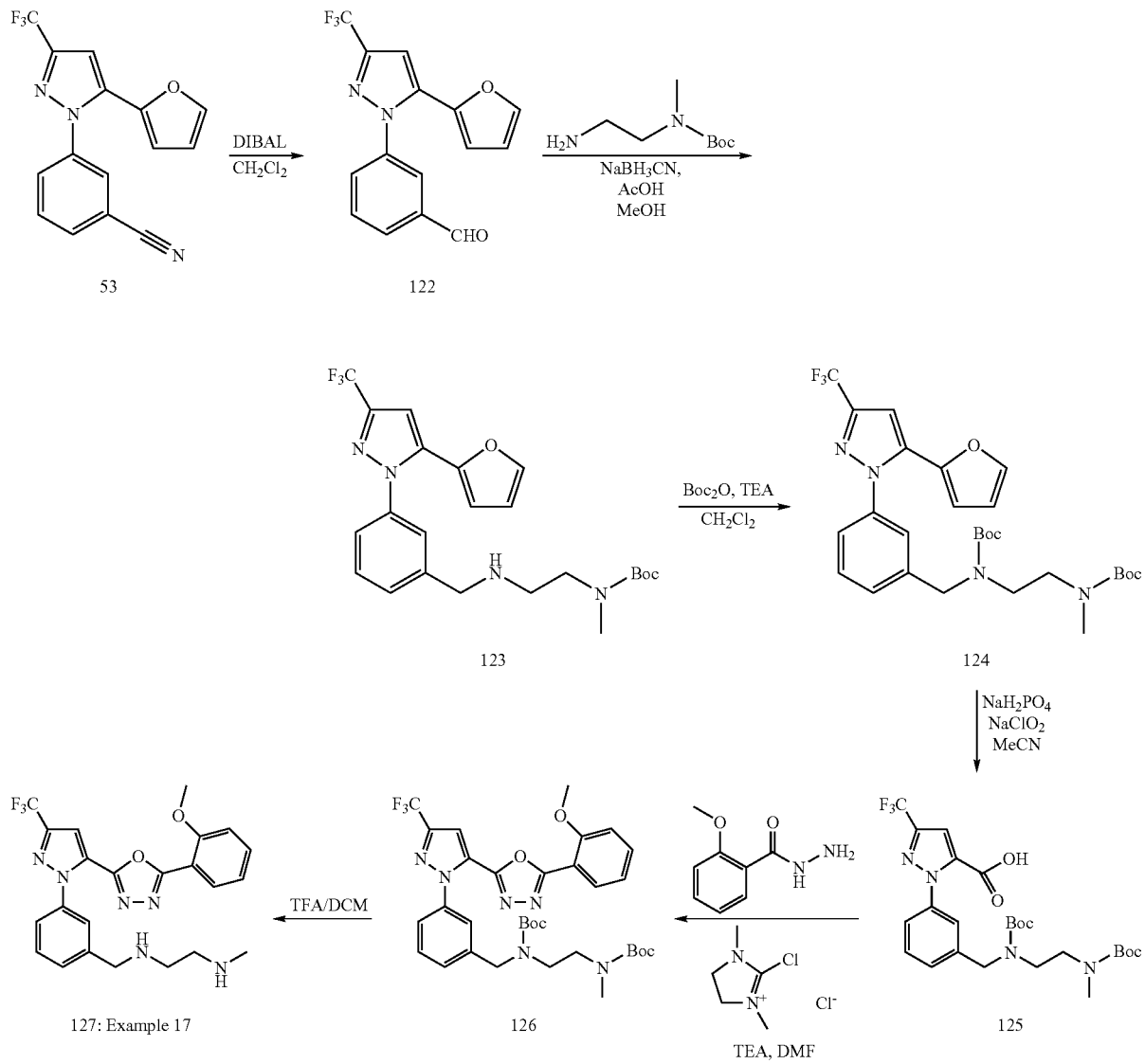

Scheme 19

Step 2: tert-butyl 2-(3-(5-(furan-2-yl)-3-(trifluoromethyl)-1H-pyrazol-1-yl)benzylamino)-ethyl(methyl)carbamate (123)

To a solution of crude 122 (1.522 g, 4.97 mmol) in MeOH (20 mL) was added a solution of tert-butyl 2-aminoethyl (methyl)carbamate (1.732 g, 9.94 mmol, E. Atherton et al, J. Chem. Soc. C, 1971, 3393-3396) in MeOH (5 mL) followed by acetic acid (1.1 mL, 20 mmol). The reaction was stirred at room temperature for 1 hour then sodium cyanoborohydride (0.625 g, 9.94 mmol) was added and the resulting mixture was stirred for 16 hours. After the usual work-up crude 123 (2.30 g, 4.95 mmol, 100% yield) was obtained as yellow oil. LRMS (ESI): (calc.) 464.5 (found) 465.2 (MH)$^+$, 487.2 (MNa)$^+$.

Step 3: 2-{1-(3-((tert-butoxycarbonyl(2-(tert-butoxycarbonyl(methyl)amino)ethyl)amino)methyl)-phenyl)-3-(trifluoromethyl)-1H-pyrazole-5-yl}furan (124)

The title compound 124 (2.76 g, 99% yield) was obtained as clear oil following the procedure described for the synthesis of compound 55 (scheme 8, example 6, step 3), except using 123 (2.30 g, 4.95 mmol) in place of 54. LRMS(ESI): (calc.) 564.6 (found) 565.3 (MH)$^+$, 587.2 (Mna)$^+$.

Step 4: 1-(3-((tert-butoxycarbonyl(2-(tert-butoxycarbonyl(methyl)amino)ethyl)amino)methyl)-phenyl)-3-(trifluoromethyl)-1H-pyrazole-5-carboxylic acid (125)

The title compound 125 (2.304 g, 4.25 mmol, 87% yield) was obtained as a brown solid following the procedure described for the synthesis of 25 (scheme 4, example 2a, step 7) replacing 24 with 124 (2.75 g, 4.87 mmol). LRMS(ESI): (calc.) 542.55 (found) 565.4 (Mna)$^+$.

Step 5: tert-butyl 3-(5-(5-(2-methoxyphenyl)-1,3,4-oxadiazol-2-yl)-3-(trifluoromethyl)-1H-pyrazol-1-yl)benzyl(2-((tert-butoxycarbonyl)methylamino)ethyl)carbamate (126)

The title compound 126 (27 mg, 0.040 mmol, 15.12% yield) was obtained following the procedure described for 102 (scheme 15, example 13, step 2) replacing 101 with 125 (0.144 g, 0.265 mmol), LRMS (ESI): (calc.) 672.2 (found) 673.4 (MH)$^+$; 573.4 (MH-Boc); 695.4 (Mna).

Step 6: N1-(3-(5-(5-(2-methoxyphenyl)-1,3,4-oxadiazol-2-yl)-3-(trifluoromethyl)-1H-pyrazol-1-yl)benzyl)-N2-methylethane-1,2-diamine (127)

The title compound 127 (27 mg, as the bis-TFA salt) was obtained as white powder following the procedure described for the synthesis of compound 9a (scheme 2, example 1c, step 9), except using 126 (27 mg, 0.039 mmol) in place of 15a $^1$H NMR: (CD$_3$OD) δ(ppm): 7.90-7.87 (m, 2H), 7.76-7.68 (m, 3H), 7.67 (s, 1H), 7.63 (dt, J=1.6, 7.6 Hz, 1H), 7.26 (d, J=8.0 Hz, 1H), 7.14 (dt, J=1.2, 8.0 Hz, 1H), 4.38 (s, 2H), 3.96 (s, 3H), 3.90-3.53 (m, 4H), 2.78 (s, 3H). LRMS (ESI): (calc.) 472.2 (found) 473.3 (MH)$^+$.

Examples 17a-c describe the preparation of compounds 127a-c using the same procedures as described for compound 127 in Example 17. Characterization data are presented in Table 4.

TABLE 4

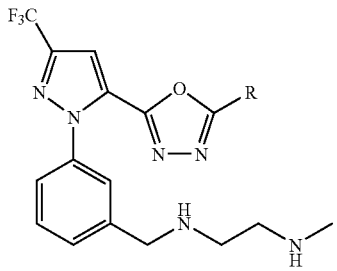

| Ex | Cpd | R | Name | Characterization | Scheme |
|---|---|---|---|---|---|
| 17a | 127a | 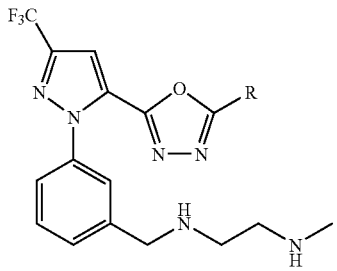 | N1-methyl-N2-(3-(5-(5-o-tolyl-1,3,4-oxadiazol-2-yl)-3-(trifluoromethyl)-1H-pyrazol-1-yl)benzyl)ethane-1,2-diamine | $^1$H NMR: (CD$_3$OD) δ (ppm): 7.89-7.87 (m, 2 H), 7.77-7.71 (m, 3 H), 7.68 (s, 1 H), 7.50 (dt, J = 1.2, 7.6 Hz, 1 H), 7.41 (d, J = 7.6 Hz, 1 H), 7.37 (t, J = 7.2 Hz, 2 H), 4.38 (s, 2 H), 3.44-3.38 (m, 4 H), 2.77 (s, 3 H), 2.62 (s, 3 H). LRMS (ESI): (calc.) 456.19 (found) 457.1 (MH)$^+$. | 19 |

TABLE 4-continued

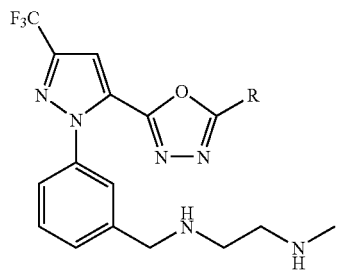

| Ex | Cpd | R | Name | Characterization | Scheme |
|----|-----|---|------|------------------|--------|
| 17b | 127b | ![methoxypyridine] | N1-(3-(5-(5-(2-methoxypyridin-3-yl)-1,3,4-oxadiazol-2-yl)-3-(trifluoromethyl)-1H-pyrazol-1-yl)benzyl)-N2-methylethane-1,2-diamine | $^1$H NMR: (DMSO-$d_6$) δ (ppm): 8.43 (dd, J = 2.0, 5.2 Hz, 1 H), 8.19 (dd, J = 2.0, 8.0 Hz, 1 H), 7.87 (s, 1 H), 7.59 (m, 1 H), 7.59-7.50 (m, 3 H), 7.21 (dd, J = 4.8, 7.6 Hz, 1 H), 3.91 (s, 3 H), 3.75 (s, 2 H), 2.50-2.42 (m, 4 H), 2.19 (s, 3 H). LRMS (ESI): (calc.) 473.2 (found) 474.5 (MH)$^+$. | 19 |
| 17c | 127c | ![bromophenyl] | N1-(3-(5-(5-(2-bromophenyl)-1,3,4-oxadiazol-2-yl)-3-(trifluoromethyl)-1H-pyrazol-1-yl)benzyl)-N2-methylethane-1,2-diamine | $^1$H NMR: (CD$_3$OD) δ (ppm): 7.86-7.80 (m, 2 H), 7.63-7.61 (m, 2 H), 7.57-7.50 (m, 5 H), 3.86 (s, 2 H), 2.72-2.70 (m, 4 H), 2.39-2.37 (m, 3 H). LRMS (ESI): (calc.) 520.8 (found) 521.2 (MH)$^+$. | 19 |

Scheme 20

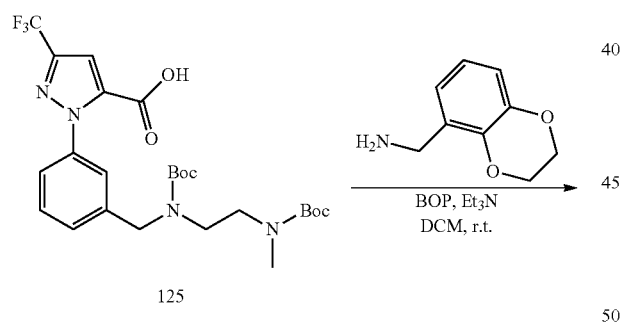

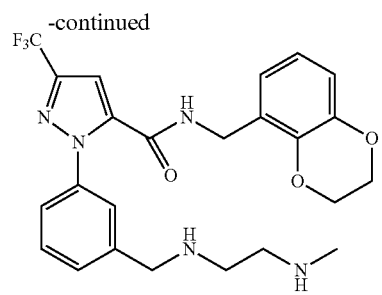

129: Example 18

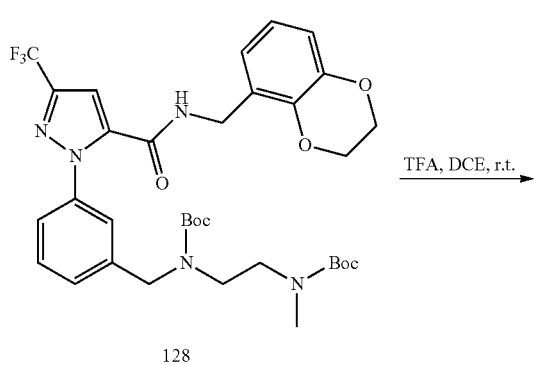

128

Example 18

N-((2,3-dihydrobenzo[b][1,4]dioxin-5-yl)methyl)-1-(3-((2-(methylamino)ethylamino)methyl)phenyl)-3-(trifluoromethyl)-1H-pyrazole-5-carboxamide (129)

Step 1: tert-butyl 2-((tert-butoxycarbonyl)(methyl)amino)ethyl(3-(5-((2,3-dihydrobenzo[b][1,4]dioxin-5-yl-methyl)carbamoyl)-3-(trifluoromethyl)-1H-pyrazol-1-yl)benzyl)carbamate (128)

The title compound 128 (153 mg, 0.222 mmol, 80%) was obtained as clear oil following the procedure for the synthesis of 57 (scheme 8, example 6, step 5) replacing 56 with 125 (150 mg, 0.276 mmol). LRMS (ESI): (calc.) 689.7 (found) 712.5 (MNa)$^+$.

Step 2: N-((2,3-dihydrobenzo[b][1,4]dioxin-5-yl)methyl)-1-(3-((2-(methylamino)ethylamino)methyl)phenyl)-3-(trifluoromethyl)-1H-pyrazole-5-carboxamide (129)

The title compound 129 (104 mg, 0.145, 65% yield, as the bis-TFA salt) was obtained as beige powder following the procedure described for the synthesis of compound 9a (scheme 2, example 1c, step 9), except using 128 (153, 0.222 mmol) in place of 15a. $^1$H NMR: (DMSO-d$_6$) δ(ppm): 9.29 (t, J=5.9 Hz, 1H); 9.11 (br, 2H); 8.64 (br, 2H); 7.71 (s, 1H); 7.61-7.46 (m, 4H); 6.79-6.74 (m, 3H); 4.34-4.23 (m, 8H); 3.27-3.22 (m, 4H); 2.63 (s, 3H). LRMS(ESI): (calc.) 489.2 (found) 490.3 (MH)$^+$.

Examples 18a-i describe the preparation of compounds 129a-i using the same procedures as described for the synthesis of compound 129 in Example 18, scheme 20. Characterization data are presented in Table 5.

TABLE 5

| Ex | Cpd | R | Name | Characterization | Scheme |
|---|---|---|---|---|---|
| 18a | 129a | 5-fluoro-2-methoxybenzyl | N-(5-fluoro-2-methoxybenzyl)-1-(3-((2-(methylamino)ethylamino)methyl)phenyl)-3-(trifluoromethyl)-1H-pyrazole-5-carboxamide | $^1$H NMR: (CD$_3$OD) δ (ppm): 7.68 (s, 1 H); 7.60 (d, J = 7.8 Hz, 1 H); 7.55 (t, J = 7.8 Hz, 1 H); 7.48 (d, J = 8.0 Hz, 1 H); 7.26 (s, 1 H); 7.00-6.93 (m, 3 H); 4.45 (s, 2 H); 4.25 (s, 2 H); 3.83 (s, 3 H); 3.30-3.26 (m, 4 H); 2.74 (s, 3 H). LRMS (ESI): (calc.) 479.2 (found) 480.3 (MH)+ | 20 |
| 18b | 129b | 2-ethoxybenzyl | N-(2-ethoxybenzyl)-1-(3-((2-(methylamino)ethylamino)methyl)phenyl)-3-(trifluoromethyl)-1H-pyrazole-5-carboxamide | $^1$H NMR: (CD$_3$OD) δ (ppm): 7.54 (s, 1 H); 7.48-7.42 (m, 2 H); 7.37-7.34 (m, 1 H); 7.25 (t, J = 8.2 Hz, 1 H); 7.18-7.16 (m, 2 H); 6.94 (d, J = 8.2 Hz, 1 H); 6.89 (t, J = 7.4 Hz, 1 H); 4.48 (s, 2 H); 4.06 (q, J = 6.8 Hz, 2 H); 3.83 (s, 2 H); 2.98-2.95 (m, 2 H); 2.82-2.79. LRMS (ESI): (calc.) 475.2 (found) 476.3 (MH)+ (m, 2 H); 2.60 (s, 3 H); 1.38 (t, J = 7.0 Hz, 3 H). | 20 |
| 18c | 129c | 2-(trifluoromethoxy)benzyl | 1-(3-((2-(methylamino)ethylamino)methyl)phenyl)-N-(2-(trifluoromethoxy)benzyl)-3-(trifluoromethyl)-1H-pyrazole-5-carboxamide | $^1$H NMR: (CD$_3$OD) δ (ppm): 7.67 (s, 1 H); 7.61-7.52 (m, 2 H); 7.48-7.31 (m, 5 H); 7.27 (s, 1 H); 4.57 (s, 2 H); 4.20 (s, 2 H); 3.24 (br, 4 H); 2.72 (s, 3 H). LRMS (ESI): (calc.) 515.2 (found) 516.3 (MH)+ | 20 |
| 18d | 129d | 2-(difluoromethoxy)benzyl | N-(2-(difluoromethoxy)benzyl)-1-(3-((2-(methylamino)ethylamino)methyl)phenyl)-3-(trifluoromethyl)-1H-pyrazole-5-carboxamide | $^1$H NMR: (CD$_3$OD) δ (ppm): 7.55 (s, 1 H); 7.47-7.42 (m, 2 H); 7.36-7.33 (m, 3 H); 7.24-7.17 (m, 3 H); 6.86 (t, J = 73.9 Hz, 1 H); 4.53 (s, 2 H); 3.85 (s, 2 H); 3.00-2.97 (m, 2 H); 2.84-2.81 (m, 2 H); 2.61 (s, 3 H). | 20 |

TABLE 5-continued

| Ex | Cpd | R | Name | Characterization | Scheme |
|---|---|---|---|---|---|
| 18e | 129e | | N-(2-ethylbenzyl)-1-(3-((2-(methylamino)ethyl amino)methyl) phenyl)-3-(trifluoromethyl)-1H-pyrazole-5-carboxamide | $^1$H NMR: (CD$_3$OD) δ (ppm): 7.54 (s, 1 H); 7.53-7.43 (m, 2 H); 7.35 (dt, J = 7.6, 2.2 Hz, 1 H); 7.24-7.16 (m, 5 H); 4.51 (s, 2 H); 3.84 (s, 2 H); 2.96-2.93 (m, 2 H); 2.82-2.79 (m, 2 H); 2.67 (q, J = 7.6 Hz, 2 H); 2.58 (s, 3 H); 1.20 (t, J = 7.6 Hz, 3 H). LRMS (ESI): (calc.) 459.2 (found) 460.3 (MH)+ | 20 |
| 18f | 129f | | N-(cyclohexylmethyl)-1-(3-((2-(methylamino)ethyl amino)methyl) phenyl)-3-(trifluoromethyl)-1H-pyrazole-5-carboxamide | $^1$H NMR: (CD$_3$OD) δ (ppm): 8.89-8.85 (m, 1 H); 7.73 (s, 1 H); 7.67-7.60 (m, 2 H); 7.56-7.53 (m, 1 H); 7.23 (s, 1 H); 4.39 (s, 2 H); 3.49-3.34 (m, 4 H); 3.13 (dd, J = 6.61, 6.1 Hz, 2 H); 2.79 (s, 3 H); 1.75-1.67 (m, 5 H); 1.58-1.52 (m, 1 H); 1.28-1.18 (m, 3 H); 1.00-0.91 (m, 2 H). | 20 |
| 18g | 129g | | 1-(3-((2-(methylamino)ethyl amino)methyl) phenyl)-N-(naphthalen-1-ylmethyl)-3-(trifluoromethyl)-1H-pyrazole-5-carboxamide | $^1$H NMR: (DMSO-d$_6$) δ (ppm): 9.52 (t, J = 5.9 Hz, 1 H); 9.11 (br, 2 H); 8.64 (br, 2 H); 8.09-8.06 (m, 1 H); 7.99-7.96 (m, 1 H); 7.89 (dd, J = 4.9, 4.9 Hz, 1 H); 7.72 (s, 1 H); 7.61-7.47 (m, 8 H); 4.87 (d, J = 5.9 Hz, 2 H); 4.29 (br, 2 H); 3.26-3.23 (m, 4 H); 2.67-2.59 (m, 3 H). LRMS (ESI): (calc.) 481.2 (found) 482.3 (MH)+ | 20 |
| 18h | 129h | | N-((1H-benzo[d]imidazol-2-yl)methyl)-1-(3-((2-(methylamino)ethyl amino)methyl) phenyl)-3-(trifluoromethyl)-1H-pyrazole-5-carboxamide | $^1$H NMR: (DMSO-d$_6$) δ (ppm): 9.90 (t, J = 5.5 Hz, 1 H); 7.74-7.71 (m, 3 H); 7.63-7.49 (m, 4 H); 7.43-7.41 (m, 2 H); 4.83 (d, J = 5.5 Hz, 2 H); 4.28 (s, 2 H); 3.26-3.22 (m, 4 H); 2.62 (s, 3 H). LRMS (ESI): (calc.) 471.2 (found) 472.3 (MH)+ | 20 |

TABLE 5-continued

| Ex | Cpd | R | Name | Characterization | Scheme |
|---|---|---|---|---|---|
| 18i | 129i | | N-((1-methyl-1H-benzo[d]imidazol-2-yl)methyl)-1-(3-((2-(methylamino)ethyl amino)methyl)phenyl)-3-(trifluoromethyl)-1H-pyrazole-5-carboxamide | $^1$H NMR: (DMSO-$d_6$) δ (ppm): 9.80 (br, 1 H); 7.77-7.63 (m, 3 H); 7.61-7.56 (m, 3 H); 7.52-7.39 (m, 3 H); 4.86 (d, J = 5.5 Hz, 2 H); 4.28 (s, 2 H); 3.89 (s, 3 H); 3.27-3.24 (m, 4 H); 2.63 (s, 3 H). | 20 |
| 18j | 129j | | N-(2-(1H-indol-3-yl)ethyl)-1-(3-((2-(methylamino)ethyl amino)methyl)phenyl)-3-(trifluoromethyl)-1H-pyrazole-5-carboxamide | $^1$H NMR: (CD$_3$OD) δ (ppm): 7.56 (ddd, J = 7.8, 1.0, 1.0 Hz, 1 H); 7.51 (dd, J = 1.6, 1.6 Hz, 1 H); 7.45 (d, J = 7.8 Hz, 1 H); 7.39 (dd, J = 7.8, 7.8 Hz, 1 H); 7.36 (ddd, J = 8.0, 0.8, 0.8 Hz, 1 H); 7.19 (ddd, J = 7.8, 2.2, 1.2 Hz, 1 H); 7.10 (ddd, J = 8.2, 7.0, 1.2 Hz, 1 H); 7.06 (s, 1 H); 7.04 (s, 1 H); 6.99 (ddd, J = 8.0, 7.0, 1.0 Hz, 1 H); 3.86 (s, 2 H); 3.60 (t, J = 7.0 Hz, 2 H); 3.03-2.98 (m, 4 H); 2.86-2.83 (m, 2 H); 2.61 (s, 3 H). LRMS (ESI): (calc.) 484.2 (found) 485.3 (MH)+ | 20 |
| 18k | 129k | | N-(biphenyl-3-ylmethyl)-1-(3-((2-(methylamino)ethyl amino)methyl)phenyl)-3-(trifluoromethyl)-1H-pyrazole-5-carboxamide | $^1$H NMR: (DMSO-$d_6$) δ (ppm): 9.51 (t, J = 6.1 Hz, 1 H); 9.10 (br, 2 H); 8.63 (br, 2 H); 7.71 (s, 1 H); 7.64 (d, J = 7.0 Hz, 2 H); 7.59-7.37 (m, 10 H); 7.29 (d, J = 7.4 Hz, 1 H); 4.47 (d, J = 5.9 Hz, 2 H); 4.28 (s, 2 H); 3.25-3.22 (m, 4 H); 2.62 (s, 3 H). LRMS (ESI): (calc.) 507.2 (found) 508.4 (MH)+ | 20 |
| 18l | 129l | | N-benzyl-1-(3-((2-(methylamino)ethyl amino)methyl)phenyl)-3-(trifluoromethyl)-1H-pyrazole-5-carboxamide | $^1$H NMR: (DMSO-$d_6$) δ (ppm): 9.46 (t, J = 6.1 Hz, 1 H); 9.12 (br, 2 H); 8.65 (br, 2 H); 7.70 (s, 1 H); 7.61-7.46 (m, 4 H); 7.36-7.25 (m, 5 H); 4.40 (d, J = 5.9 Hz, 2 H); 4.30 (s, 2 H); 3.27-3.23 (m, 4 H); 2.63 (s, 3 H). LRMS (ESI): (calc.) 431.2 (found) 432.3 (MH)+ | 20 |

TABLE 5-continued
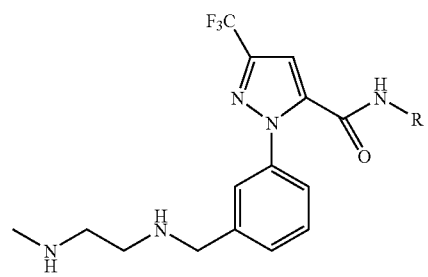
| Ex | Cpd | R | Name | Characterization | Scheme |
|----|-----|---|------|------------------|--------|
|    |     | [2-aminobenzyl group] | N-(2-aminobenzyl)-1-(3-((2-(methylamino)ethyl amino)methyl)phenyl)-3-(trifluoromethyl)-1H-pyrazole-5-carboxamide | $^1$H NMR: (DMSO-$d_6$) δ (ppm): 9.36 (t, J = 5.9 Hz, 1 H); 7.71 (s, 1 H); 7.62-7.49 (m, 4 H); 7.06-7.02 (m, 2 H); 6.74 (d, J = 7.6 Hz, 1 H); 6.63 (t, J = 7.0 Hz, 1 H); 4.30 (s, 2 H); 4.27 (d, J = 5.9 Hz, 2 H); 3.28-3.23 (m, 4 H); 2.63 (s, 3 H). | 20 |
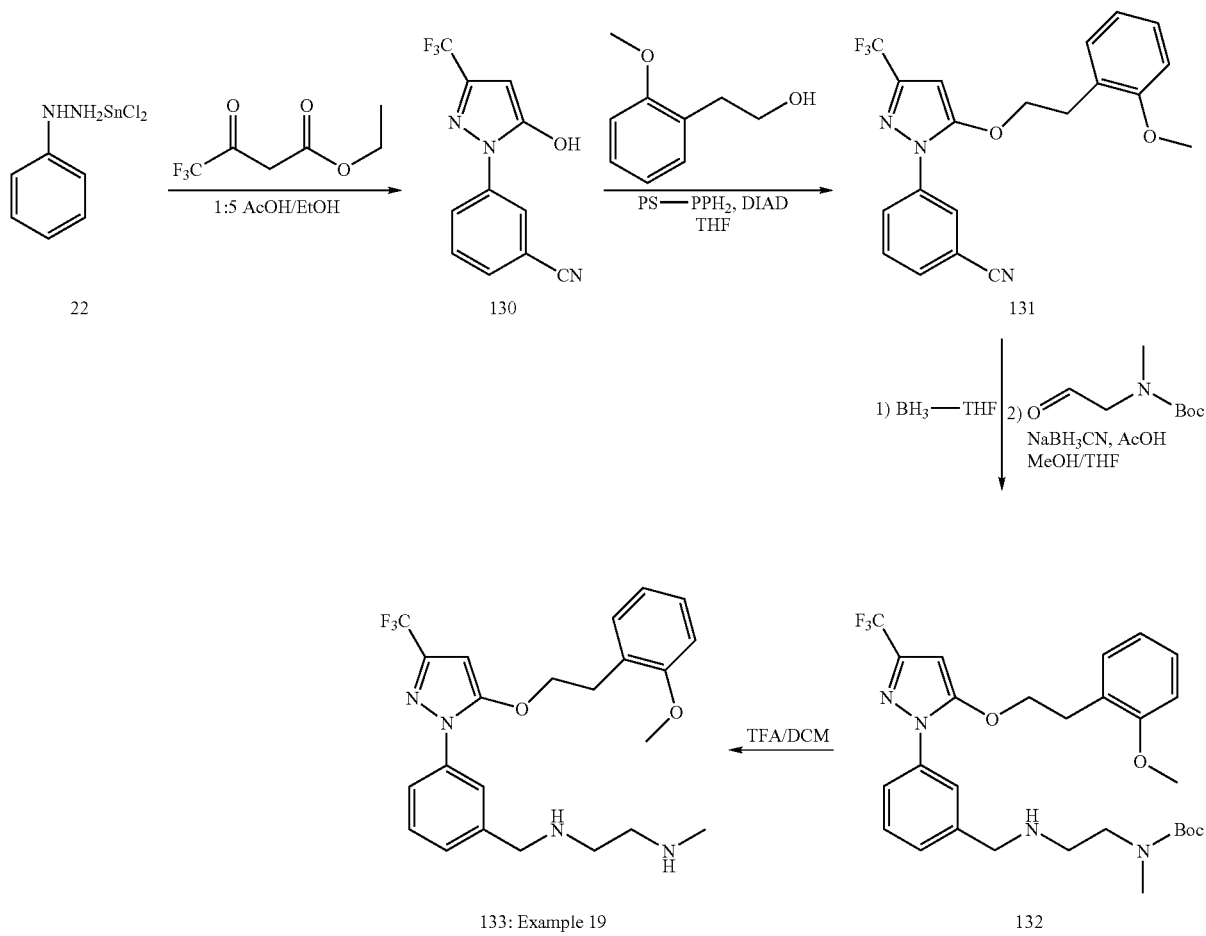

Example 19

N1-(3-(5-(2-methoxyphenethoxy)-3-(trifluoromethyl)-1H-pyrazol-1-yl)benzyl)-N2-methylethane-1,2-diamine (133)

Step 1: 3-(5-hydroxy-3-(trifluoromethyl)-1H-pyrazol-1-yl)benzonitrile (130)

A mixture of 22 (0.5 g, 1.549 mmol) and ethyl 4,4,4-trifluoroacetoacetate (0.23 mL, 1.549 mmol) was heated in EtOH (5 mL) and acetic Acid (1 mL) for 5 hours at 90° C. It was cooled to room temperature and poured over NaHCO₃ (satd) and the product was extracted with ethyl acetate, washed with water, brine, dried over Na₂SO₄, filtered and concentrated. The residue was purified by silica gel chromatography (Biotage 25M, 0 to 20% ethyl acetate in DCM) to give 130 (162 mg, 0.640 mmol, 41.3% yield) as yellow solid. LRMS(ESI): (calc.) 253.2 (found) 254.0 (MH)+

Step 2: 3-(5-(2-methoxyphenethoxy)-3-(trifluoromethyl)-1H-pyrazol-1-yl)benzonitrile (131)

A suspension of 130 (200 mg, 0.790 mmol) and PS-PPh₂ (2.15 mmol/g, 0.522 g, 1.5 eq, polymer supported triphenylphosphine) in THF (7 mL) under a nitrogen atmosphere was stirred for 10 minutes. DIAD (0.154 mL, 0.790 mmol) was added and after 1 hour of stirring at room temperature 2-methoxy-phenethyl alcohol (0.112 mL, 0.790 mmol) was added and the suspension was stirred for 48 h. The reaction mixture was filtered and the resin washed with DCM, the filtrate was concentrated and the residue purified by silica gel chromatography (Biotage 25M, 5-20% ethyl acetate in hexanes) to give 131 (86 mg, 0.222 mmol, 28.1% yield) as white solid. LRMS(ESI): (calc.) 387.4 (found) 388.1 (MH)+, 410.0 (MNa)+.

Step 3: tert-butyl 2-(3-(5-(2-methoxyphenethoxy)-3-(trifluoromethyl)-1H-pyrazol-1-yl)benzylamino)ethyl(methyl)carbamate (132)

To a solution of 131 (85 mg, 0.219 mmol) in THF (0.4 mL) at 0° C. under nitrogen was added BH₃ in THF (1.114 mL, 1.0M solution, 1.114 mmol). The reaction was stirred at room temperature for 1 hour then it was cooled to at 0° C. and quenched carefully with methanol. The mixture was concentrated, MeOH (1.5 mL), tert-butyl methyl(2-oxoethyl)carbamate (38.0 mg, 0.219 mmol) and acetic acid (25.1 µL, 0.439 mmol) were added and the mixture was stirred at room temperature for 1 h after which sodium cyanoborohydride (34.5 mg, 0.549 mmol) was added. After 16 h, the reaction was worked-up as usual and the residue was purified by silica gel chromatography (Biotage 12M, 0-5% MeOH/DCM) to give 132 (29.3 mg, 0.053 mmol, 24.34% yield) as clear oil. LRMS(ESI): (calc.) 548.6 (found) 549.2 (MH)+.

Step 4: N1-(3-(5-(2-methoxyphenethoxy)-3-(trifluoromethyl)-1H-pyrazol-1-yl)benzyl)-N2-methylethane-1,2-diamine (133)

The title compound 133 (15.8 mg, 0.035 mmol, 66.6% yield, bis-TFA salt) was obtained as white fluffy solid following the procedure described for the synthesis of compound 9a (scheme 2, example 1c, step 9), except using 132 (29 mg, 0.053 mmol) in place of 15a.

¹H NMR (of the mono-TFA salt): (CD₃OD) δ(ppm): 7.61 (s, 1H), 7.42-7.37 (m, 3H), 7.23 (dt, J=2.0, 8.4 Hz, 1H), 7.14 (dd, J=1.6, 7.2 Hz, 1H), 6.95 (d, J=8.0 Hz, 1H), 6.86 (dt, J=0.8, 7.6 Hz, 1H), 6.21 (s, 1H), 4.42 (t, J=6.4 Hz, 2H), 3.84 (s, 2H), 3.81 (s, 3H), 3.12 (t, J=6.4 Hz, 2H), 3.03 (t, J=6.0 Hz, 2H), 2.84 (t, J=5.8 Hz, 2H), 2.65 (s, 3H). LRMS (ESI): (calc.) 448.2; (found) 449.2 (MH)+.

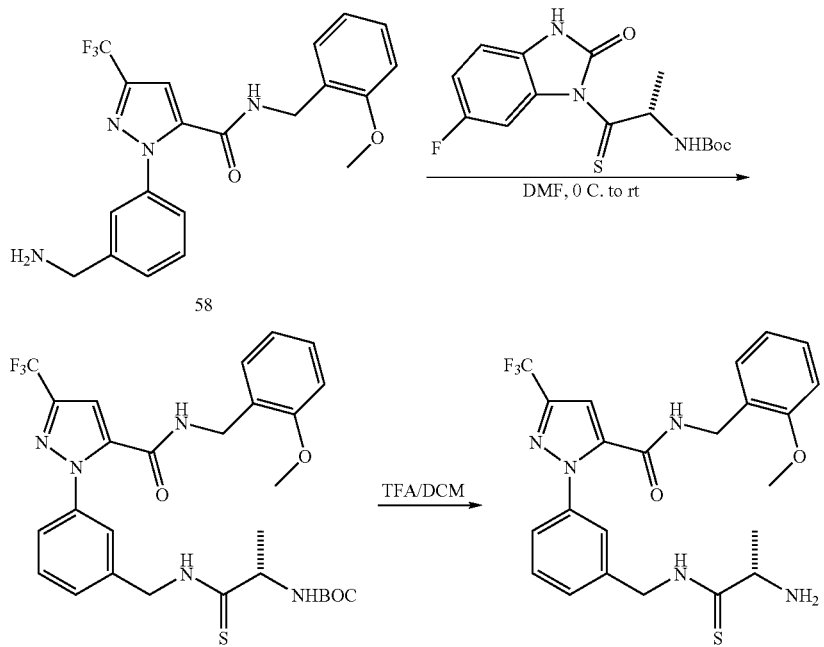

Scheme 22

Example 20

(S)-1-(3-((2-aminopropanethioamido)methyl)phenyl)-N-(2-methoxybenzyl)-3-(trifluoromethyl)-1H-pyrazole-5-carboxamide (135)

Step 1: (S)-tert-butyl 1-(3-(5-(2-methoxybenzylcarbamoyl)-3-(trifluoromethyl)-1H-pyrazol-1-yl)benzylamino)-1-thioxopropan-2-ylcarbamate (134)

To a solution of 58 (62 mg, 0.153 mmol) in dry DMF (0.3 mL) at 0° C. was added (R)-tert-butyl 1-(6-fluoro-2-oxo-2,3-dihydro-1H-benzo[d]imidazol-1-yl)-1-thioxopropan-2-ylcarbamate (57.2 mg, 0.169 mmol; J. Med. Chem.1999, 42, 2046-2052) in two equal portions over 10 minutes and the reaction was stirred at 0° C. for 2 hours and then at room temperature for 16 h. It was then diluted with water (~15 mL) and extracted into dichloromethane using an "IST phase-separator." The DCM extracts were combined and concentrated and the crude material purified by silica gel chromatography (Biotage 12M, 20% to 30% to 40% ethyl acetate in hexanes) to give 134 (35 mg, 0.059 mmol, 38.6% yield) as white solid. LRMS(ESI): (calc.) 529.3 (found) 614.3 (MNa)+.

Step 2: (S)-1-(3-((2-aminopropanethioamido)methyl)phenyl)-N-(2-methoxybenzyl)-3-(trifluoromethyl)-1H-pyrazole-5-carboxamide (135)

The title compound 135 (34.7 mg, 0.057 mmol, 96% yield, bis-TFA salt) was obtained as a white solid following the procedure described for the synthesis of compound 9a (scheme 2, example 1c, step 9), except using 134 (35.5 mg, 0.060 mmol) in place of 15a.

$^1$H NMR: (CD$_3$OD) δ(ppm): 9.08 (t, 1H), 7.48-7.42 (m, 3H), 7.37 (td, J=2.0, 7.2 Hz, 1H), 7.27 (dt, J=1.6, 8.0 Hz, 1H), 7.19 (dd, J=1.6, 7.2 Hz, 1H), 7.15 (s, 1H), 6.95 (d, J=7.6 Hz, 1H), 6.89 (dt, J=1.2, 7.6 Hz, 1H), 4.89 (d, J=14.8 Hz, 1H), 4.82 (d, J=14.8 Hz, 1H), 4.47-4.45 (m, 2H), 4.15 (q, J=6.8 Hz, 1H), 3.82 (s, 3H), 1.52 (d, J=6.8 Hz, 3H). LRMS(ESI): (calc.) 491.2 (found) 492.3 (MH)+.

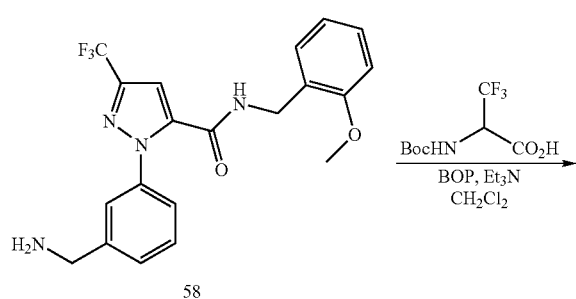

Scheme 23

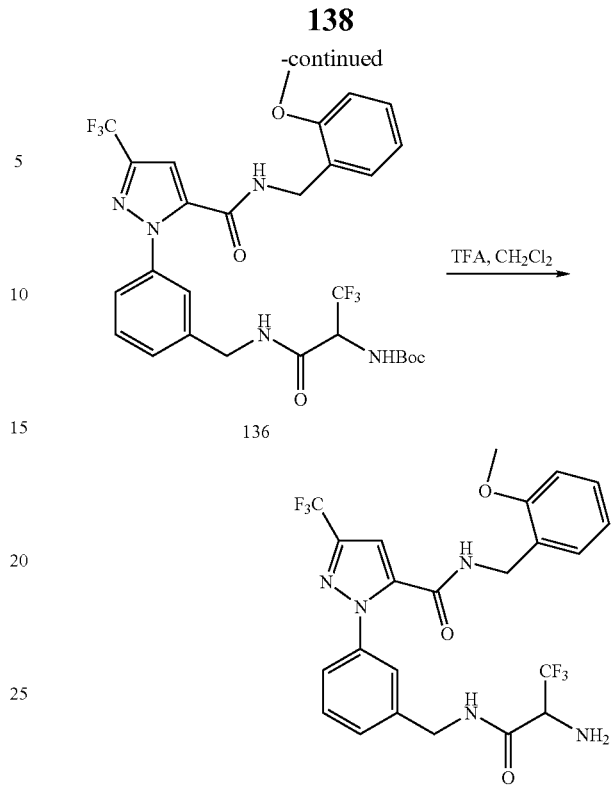

136

137: Example 21

Example 21

1-(3-((2-amino-3,3,3-trifluoropropanamido)methyl)phenyl)-N-(2-methoxybenzyl)-3-(trifluoromethyl)-1H-pyrazole-5-carboxamide (137)

Step 1: Tert-butyl 1,1,1-trifluoro-3-(3-(5-(2-methoxybenzylcarbamoyl)-3-(trifluoromethyl)-1H-pyrazol-1-yl)benzylamino)-3-oxopropan-2-ylcarbamate (136)

The title compound 136 (55 mg, 0.087 mmol, 29% yield) was obtained as a pale yellow solid following the procedure for the synthesis of 57 (scheme 8, example 6, step 5) replacing 56 with 2-(tert-butoxycarbonylamino)-3,3,3-trifluoropropanoic acid (72.7 mg, 0.299 mmol) and (2-methoxyphenyl)methanamine with 58 (155 mg, 0.299 mmol). LRMS (ESI): (calc.) 629.6; (found) 652.3 (MNa)+.

Step 2:1-(3-((2-Amino-3,3,3-trifluoropropanamido)methyl)phenyl)-N-(2-methoxybenzyl)-3-(trifluoromethyl)-1H-pyrazole-5-carboxamide (137)

The title compound 137 (16 mg, 0.025 mmol, 29% yield) was obtained as white solid following the procedure described for the synthesis of compound 9a (scheme 2, example 1c, step 9), except using 136 (55 mg, 0.087 mmol) in place of 15a.

$^1$H NMR: (CD$_3$OD) □ (ppm) 1H: 7.41-7.39 (m, 3H), 7.34-7.32 (m, 1H), 7.27 (t, 1H, J=7.6 Hz), 7.19 (d, 1H, J=7.2 Hz), 7.13 (s, 1H), 6.95 (d, 1H, J=8.0 Hz), 6.90 (t, 1H, J=7.2 Hz), 4.45-4.43 (m, 4H), 3.97 (q, 1H, J=7.6 Hz), 3.81 (s, 3H). LRMS (ESI): (calc.) 529.4; (found) 530.3 (MH)+.

139

Scheme 24

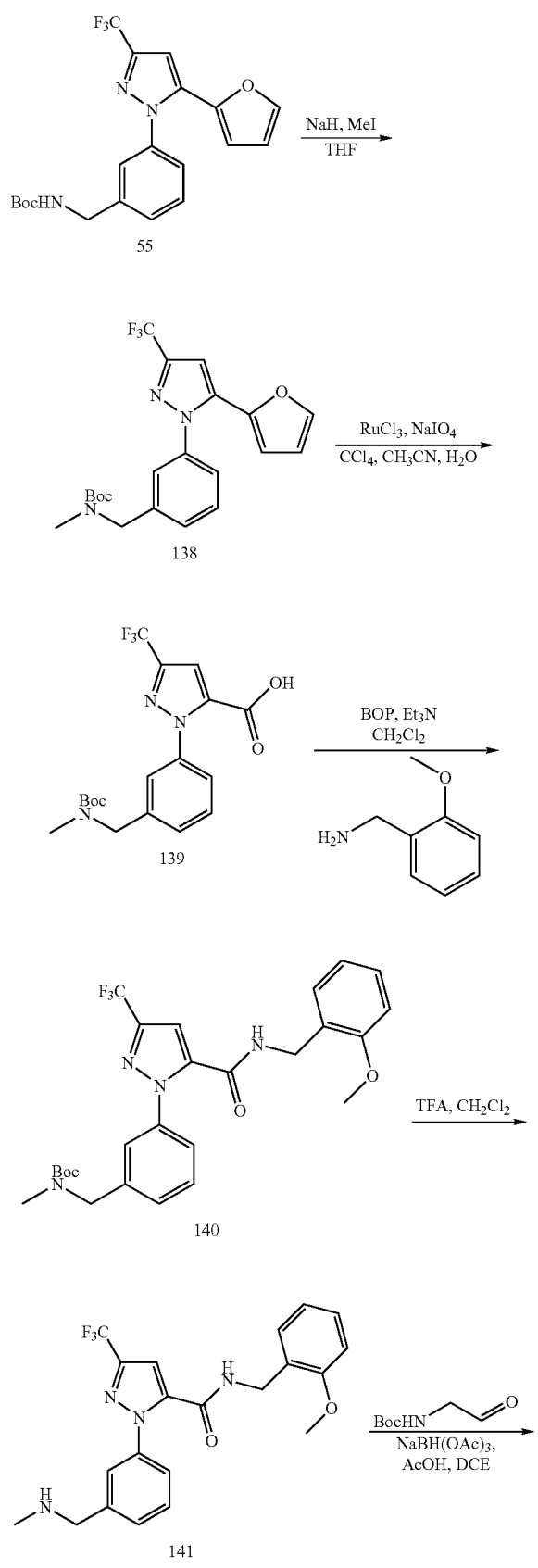

140

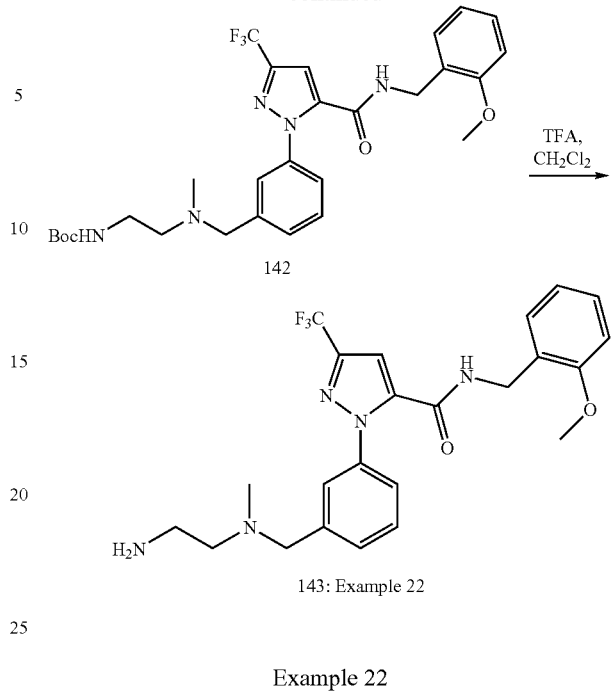

143: Example 22

Example 22

1-(3-(((2-Aminoethyl)(methyl)amino)methyl)phenyl)-N-(2-methoxybenzyl)-3-(trifluoromethyl)-1H-pyrazole-5-carboxamide (143)

Step 1: Tert-butyl 3-(5-(furan-2-yl)-3-(trifluoromethyl)-1H-pyrazol-1-yl)benzyl(methyl)carbamate (138)

To a stirred solution of 55 (3.51 g, 8.62 mmol) in THF (43 ml) was added NaH (0.689 g, 17.23 mmol). After 15 minutes MeI (2.69 ml, 43.1 mmol) was added and the resulting suspension was allowed to stir at 0° C. for 1 h and at 21° C. for 16 h. Water was added the product was extracted with EtOAc. After the usual work-up the residue was purified via Biotage (5% to 45% EtOAc/Hexane; 40+M column) to afford 138 (3.2 g, 7.59 mmol, 88% yield) as colorless oil. LRMS (ESI): (calc.) 421.4; (found) 444.2 (MNa)⁺.

Step 2: 1-(3-((Tert-butoxycarbonyl(methyl)amino)methyl)phenyl)-3-(trifluoromethyl)-1H-pyrazole-5-carboxylic acid (139)

The title compound 139 (3.03 g, 7.59 mmol, 100% yield) was obtained as pale brown semi-solid following the procedure described for the synthesis of compound 49 (scheme 7, example 5, step 5), except using 138 (3.2 g, 7.59 mmol) in place of 48.

Step 3: Tert-butyl 3-(5-(2-methoxybenzylcarbamoyl)-3-(trifluoromethyl)-1H-pyrazol-1-yl)benzyl (methyl)carbamate (140)

The title compound 140 (2.25 g, 4.34 mmol, 57% yield) was obtained as a green foam following the procedure described for the synthesis of compound 50 (scheme 7, example 5, step 6), except using 138 (3.03 g, 7.59 mmol) in place of 49. LRMS (ESI): (calc.) 518.5; (found) 541.5 (MNa)⁺.

Step 4:N-(2-Methoxybenzyl)-1-(3-((methylamino)methyl)phenyl)-3-(trifluoromethyl)-1H-pyrazole-5-carboxamide (141)

The title compound 141 (411 mg, 0.771 mmol, 100% yield) was obtained as brown oil following the procedure described for the synthesis of compound 9a (scheme 2, example 1c, step 9), except using 140 (400 mg, 0.771 mmol) in place of 15a. LRMS (ESI): (calc.) 418.4; (found) 419.1 (MH)+.

Step 5: Tert-butyl 2-((3-(5-(2-methoxybenzylcarbamoyl)-3-(trifluoromethyl)-1H-pyrazol-1-yl)benzyl)(methyl)amino)ethylcarbamate (142)

The title compound 142 (58 mg, 0.103 mmol, 27% yield) was obtained as colorless oil following the procedure described for the synthesis of compound 59 (scheme 8, example 6, step 7), except using 141 (205 mg, 0.3855 mmol) in place of 58, and tert-butyl 2-oxoethylcarbamate (61.4 mg, 0.386 mmol) in place of tert-butyl methyl(2-oxoethyl)carbamate. LRMS (ESI): (calc.) 561.6; (found) 562.4 (MH)+.

Step 6:1-(3-(((2-Aminoethyl)(methyl)amino)methyl)phenyl)-N-(2-methoxybenzyl)-3-(trifluoromethyl)-1H-pyrazole-5-carboxamide (143)

The title compound 143 (66.9 mg, 0.097 mmol, 99% yield, bis-TFA salt) was obtained as a white solid following the procedure described for the synthesis of compound 9a (scheme 2, example 1c, step 9), except using 142 (55 mg, 0.098 mmol) in place of 15a. $^1$H NMR: (CD$_3$OD) □ (ppm) 1H: 9.18 (br s, 0.5H), 7.64 (s, 1H), 7.58-7.46 (m, 3H), 7.28 (t, 1H, J=7.8 Hz), 7.23 (s, 1H), 7.20 (d, 1H, J=7.6 Hz), 6.97 (d, 1H, J=8.0 Hz), 6.91 (t, 1H, J=7.6 Hz), 4.46 (s, 2H), 4.11 (s, 2H), 3.84 (s, 3H), 3.20 (t, 2H, J=6.8 Hz), 3.07 (br s, 2H), 2.64 (s, 3H). LRMS (ESI): (calc.) 461.5; (found) 462.3 (MH)+.

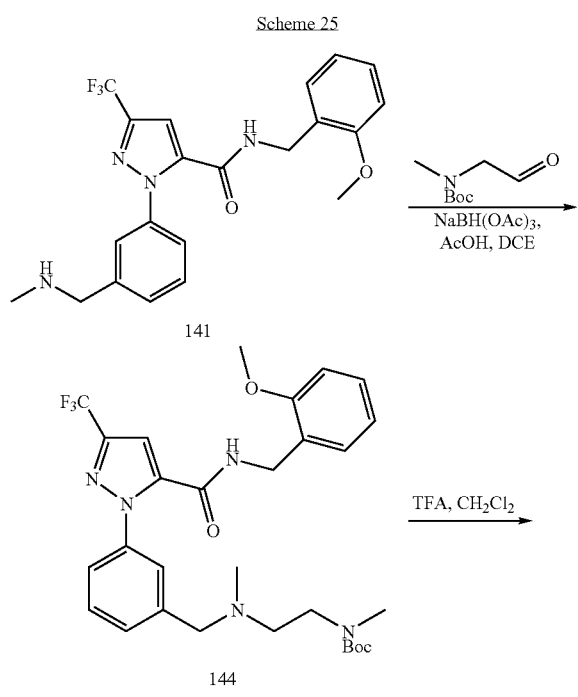

Scheme 25

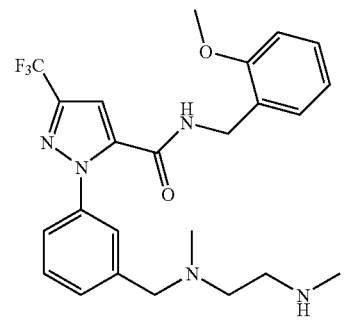

145: Example 23

Example 23

N-(2-Methoxybenzyl)-1-(3-((methyl(2-(methylamino)ethyl)amino)methyl)phenyl)-3-(trifluoromethyl)-1H-pyrazole-5-carboxamide (145)

Step 1: Tert-butyl 2-((3-(5-(2-methoxybenzylcarbamoyl)-3-(trifluoromethyl)-1H-pyrazol-1-yl)benzyl)(methyl)amino)ethyl(methyl)carbamate (144)

The title compound 142 (103 mg, 0.179 mmol, 46% yield) was isolated as white foam following the procedure described for the synthesis of compound 59 (scheme 8, example 6, step 7), except using 141 (205 mg, 0.3855 mmol) in place of 58. LRMS (ESI): (calc.) 575.6; (found) 576.5 (MH)+.

Step 2:N-(2-Methoxybenzyl)-1-(3-((methyl(2-(methylamino)ethyl)amino)methyl)phenyl)-3-(trifluoromethyl)-1H-pyrazole-5-carboxamide (145)

The title compound 145 (55.3 mg, 0.079 mmol, 45% yield) was isolated as a white solid following the procedure described for the synthesis of compound 9a (scheme 2, example 1c, step 9), except using 144 (100 mg, 0.174 mmol) in place of 15a. $^1$H NMR: (CD$_3$OD) δ (ppm) 1H: 9.22 (t, 1H, J=5.6 Hz), 8.2 (br, 2H), 7.48-7.41 (m, 4H), 7.34 (d, 1H, J=7.2 Hz), 7.25 (t, 1H, J=7.8 Hz), 7.15 (d, 1H, J=7.2 Hz), 6.98 (d, 1H, J=8.0 Hz), 6.90 (t, 1H, J=7.2 Hz), 4.34 (d, 2H, J=6.0 Hz), 3.78 (s, 3H), 3.56 (s, 3H), 3.03 (t, 2H, J=6.0 Hz), 2.59 (t, 2H, J=6.0 Hz), 2.52 (s, 3H), 2.12 (s, 3H). LRMS (ESI): (calc.) 475.5; (found) 476.3 (MH)+.

Scheme 26
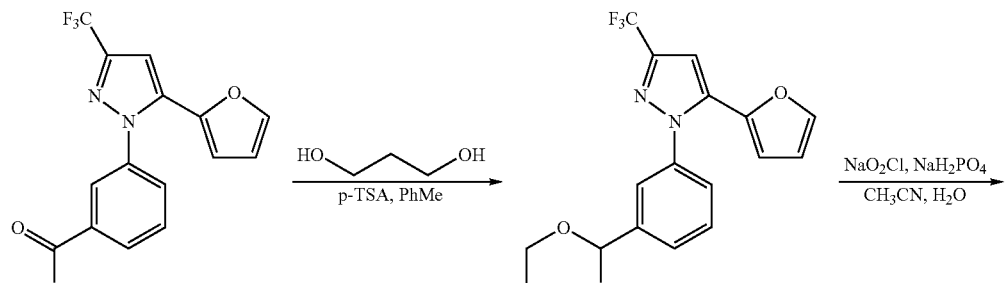
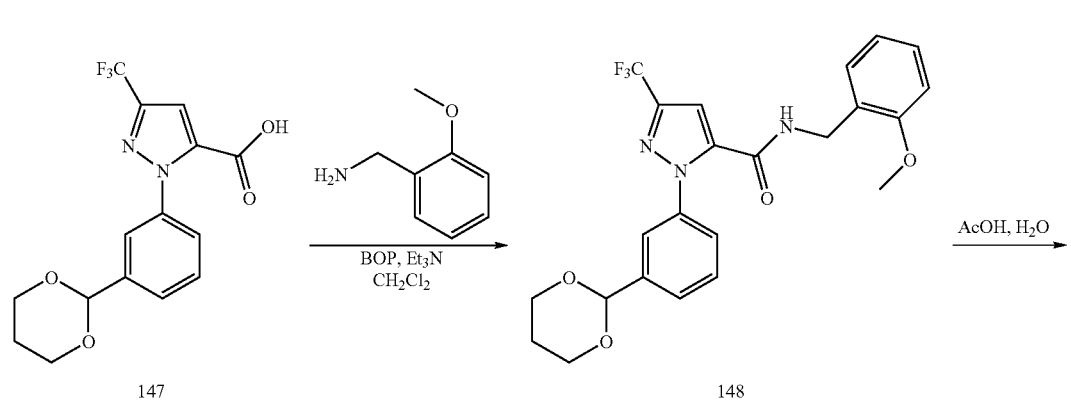
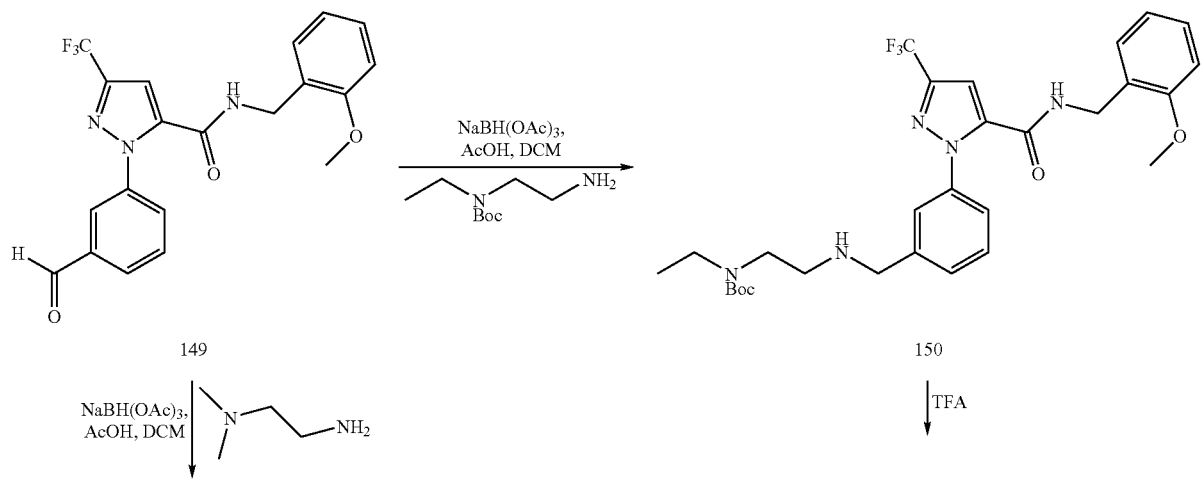

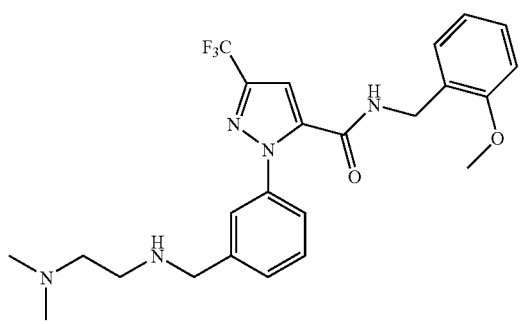

152: Example 25

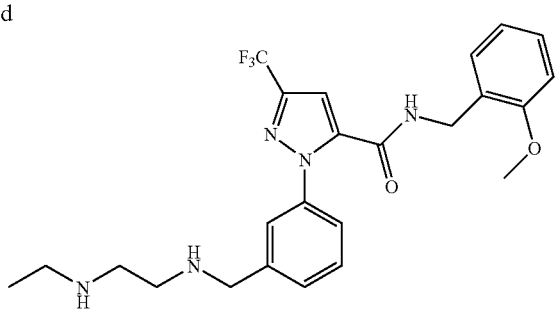

151: Example 24

Example 24

1-(3-((2-(ethylamino)ethylamino)methyl)phenyl)-N-(2-methoxybenzyl)-3-(trifluoromethyl)-1H-pyrazole-5-carboxamide (150)

Step 1: 1-(3-(1,3-Dioxan-2-yl)phenyl)-5-(furan-2-yl)-3-(trifluoromethyl)-1H-pyrazole (146)

To a stirred solution of 122 (3.25 g, 10.62 mmol) in PhMe (53 ml) was added 1,3-propanediol (1.616 g, 21.24 mmol) followed by p-toluenesulfonic acid monohydrate (0.202 g, 1.062 mmol) and the resulting solution was allowed to stir at reflux with a Dean-Stark trap for 16 h. The solution was evaporated to dryness, and saturated $NaHCO_3$ aqueous solution was added and the mixture was extracted with EtOAc and the extracts were dried over $Na_2SO_4$ and evaporated. The residue was purified via Biotage (5% to 40% EtOAc/Hexane; 40+M column). The title product 146 (3.04 g, 8.34 mmol, 79% yield) was obtained as an off-white solid. LRMS (ESI): (calc.) 364.3; (found) 365.2 $(MH)^+$.

Step 2: 1-(3-(1,3-Dioxan-2-yl)phenyl)-3-(trifluoromethyl)-1H-pyrazole-5-carboxylic acid (147)

The title compound 147 (1.93 g, 5.64 mmol, 68% yield) was obtained as white foam following the procedure described for the synthesis of compound 25 (scheme 4, example 2a, step 7), except using 146 (3.04 g, 8.34 mmol) in place of 24. LRMS (ESI): (calc.) 342.3; (found) 343.1 $(MH)^+$.

Step 3: 1-(3-(1,3-Dioxan-2-yl)phenyl)-N-(2-methoxybenzyl)-3-(trifluoromethyl)-1H-pyrazole-5-carboxamide (148)

The title compound 148 (1.26 g, 2.73 mmol, 48% yield) was obtained as a pale yellow solid following the procedure described for the synthesis of compound 57 (scheme 8, example 6, step 5), except using 147 (1.93 g, 5.64 mmol) in place of 56. LRMS (ESI): (calc.) 461.4; (found) 462.3 $(MH)^+$.

Step 4: 1-(3-Formylphenyl)-N-(2-methoxybenzyl)-3-(trifluoromethyl)-1H-pyrazole-5-carboxamide (149)

A stirred solution of 148 (105 mg, 0.228 mmol) in AcOH (1.8 mL) and water (0.5 mL) was allowed to stir at 90° C. for 2 h. After cooling to room temperature, water was added and the mixture was extracted with EtOAc and the extractis were dried over $Na_2SO_4$ and concentrated to give crude 149 (92 mg, 0.228 mmol, 100% yield) as a pale yellow solid. The material was used as is for the next step.

Step 5: Tert-butyl ethyl(2-(3-(5-(2-methoxybenzyl-carbamoyl)-3-(trifluoromethyl)-1H-pyrazol-1-yl)benzylamino)ethyl)carbamate (150)

Compound 150 (106 mg, 0.184 mmol, 81% yield) was obtained as a white foam following the procedure described for the synthesis of compound 123 (scheme 19, example 17, step 2), except using 149 (92 mg, 0.228 mmol) in place of 122 and tert-butyl 2-aminoethyl(ethyl)carbamate (42.9 mg, 0.228 mmol) in place of tert-butyl 2-aminoethyl(methyl)carbamate. LRMS (ESI): (calc.) 575.6; (found) 576.4 $(MH)^+$.

Step 6: 1-(3-((2-(Ethylamino)ethylamino)methyl)phenyl)-N-(2-methoxybenzyl)-3-(trifluoromethyl)-1H-pyrazole-5-carboxamide (151)

The title compound 151 (36 mg, 0.061 mmol, 33% yield) was obtained as a white solid following the procedure described for the synthesis of compound 9a (scheme 2, example 1c, step 9) except using 150 (106 mg, 0.184 mmol) in place of 15a. $^1$H NMR: ($CD_3OD$) δ (ppm) 1H: 7.53 (s, 1H), 7.47-7.41 (m, 2H), 7.33 (d, 1H, J=7.6 Hz), 7.27 (t, 1H, J=7.6 Hz), 7.19-7.16 (m, 2H), 6.96 (d, 1H, J=8.4 Hz), 6.90 (t, 1H, J=7.2 Hz), 4.46 (s, 2H), 3.83 (s, 2H), 3.82 (s, 3H), 3.01-2.95 (m, 4H), 2.82 (t, 2H, J=6.0 Hz), 1.25 (t, 3H, J=7.2 Hz). LRMS (ESI): (calc.) 475.5; (found) 476.3 $(MH)^+$.

Examples 24a-b and 25 describe the preparation of compounds 151a-b, and 152 using the same procedures described for the synthesis of compound 151 (scheme 26, Example 24). Characterization data are presented in Table 6.

TABLE 6

| Ex | Cpd | R | Name | Characterization | Scheme |
|---|---|---|---|---|---|
| 24a | 151a | (isopropylamino)- | 1-(3-((2-(Isopropylamino)ethylamino)methyl)phenyl)-N-(2-methoxybenzyl)-3-(trifluoromethyl)-1H-pyrazole-5-carboxamide | ¹H NMR: (CD₃OD) δ (ppm) 1 H: 9.18 (br s, 1 H), 7.70 (s, 1 H), 7.64 (d, 1 H, J = 7.2 Hz), 7.58-7.51 (m, 2 H), 7.30-7.21 (m, 3 H), 6.97 (d, 1 H, J = 8.0 Hz), 6.92 (t, 1 H, J = 7.2 Hz), 4.47 (s, 2 H), 4.34 (s, 2 H), 3.83 (s, 3 H), 3.31 (s, 2 H), 1.34 (s, 3 H), 1.33 (s, 3 H), 0.91-0.87 (m, 1 H). LRMS (ESI): (calc.) 489.5; (found) 490.4 (MH)+. | 26 |
| 24b | 151b | NH₂ | 1-(3-((2-Aminoethylamino)methyl)phenyl)-N-(2-methoxybenzyl)-3-(trifluoromethyl)-1H-pyrazole-5-carboxamide | ¹H NMR: (CD₃OD) δ (ppm) 1 H: 9.28 (t, 1 H, J = 6.0 Hz), 9.09 (br s, 1 H), 7.94 (br s, 2 H), 7.71 (s, 1 H), 7.60-7.48 (m, 4 H), 7.26 (t, 1 H, J = 7.6 Hz), 7.19 (d, 1 H, J = 6.0 Hz), 6.99 (d, 1 H, J = 8.0 Hz), 6.91 (t, 1 H, J = 7.6 Hz), 4.35 (d, 2 H, J = 6.0 Hz), 4.29 (s, 2 H), 3.79 (s, 3 H), 3.19 (s, 2 H), 3.12 (s, 2 H). LRMS (ESI): (calc.) 447.5; (found) 448.3 (MH)+. | 26 |
| 25 | 152 | N(CH₃)₂ | 1-(3-((2-(Dimethylamino)ethylamino)methyl)phenyl)-N-(2-methoxybenzyl)-3-(trifluoromethyl)-1H-pyrazole-5-carboxamide | ¹H NMR: (CD₃OD) δ (ppm) 1 H: 7.47-7.39 (m, 3 H), 7.34 (d, 1 H, J = 7.6 Hz), 7.27 (td, 1 H, J = 1.6, 7.8 Hz), 7.18 (d, 1 H, J = 7.2 Hz), 7.14 (s, 1 H), 6.95 (d, 1 H, J = 8.0 Hz), 6.90 (t, 1 H, J = 7.6 Hz), 4.45 (s, 2 H), 3.81 (s, 3 H), 3.79 (s, 2 H), 2.70 (t, 2 H, J = 6.8 Hz), 2.51 (t, 2 H, J = 6.4 Hz), 2.26 (s, 6 H). LRMS (ESI): (calc.) 475.5; (found) 476.4 (MH)+. | 26 |

Scheme 27

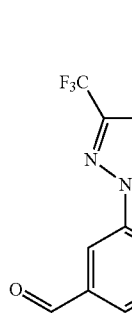

149

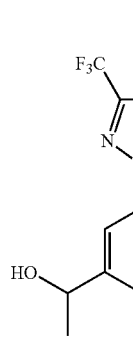

153

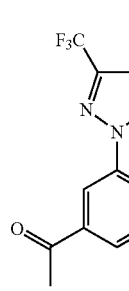

154

155

156: Example 26

Example 26

N-(2-methoxybenzyl)-1-(3-(1-(2-(methylamino)ethylamino)ethyl)phenyl)-3-(trifluoromethyl)-1H-pyrazole-5-carboxamide (156)

Step 1: 1-(3-(1-hydroxyethyl)phenyl)-N-(2-methoxybenzyl)-3-(trifluoromethyl)-1H-pyrazole-5-carboxamide (153)

To a solution of 149 (764.1 mg, 1.894 mmol) in THF (18.9 ml) 78° C. was added drop-wise a solution of methyl magnesium bromide (1.579 ml, 4.74 mmol). The temperature was allowed to slowly warm to 0° C. and the reaction was stirred an additional hour at 0° C., then it was quenched with water and extracted with EtOAc. The organic layer was dried over $Na_2SO_4$ and concentrated and the residue was purified by chromatography (Biotage, 20 to 70% EtOAc in hexane) to afford 153 (646 mg, 1.54 mmol, 87%) as peach oil. LRMS (ESI): (calc.) 419.2 (found) 442.2 $(MNa)^+$.

Step 2: 1-(3-acetylphenyl)-N-(2-methoxybenzyl)-3-(trifluoromethyl)-1H-pyrazole-5-carboxamide (154)

To a stirred solution of 153 (650 mg, 1.550 mmol) in DCM (7.75 ml) under $N_2$ was added Dess-Martin periodinane (0.50 ml, 1.627 mmol) and the mixture was stirred at room temperature for 3 h. The reaction mixture was taken to dryness and the residue was purified by chromatography (Biotage 15 to 65% EtOAc in hexane) to afford 154 (565 mg, 1.35 mmol, 88%). LRMS (ESI): (calc.) 417.1 (found) 440.2 $(MNa)^+$.

Step 3: tert-butyl 2-(1-(3-(5-(2-methoxybenzylcarbamoyl)-3-(trifluoromethyl)-1H-pyrazol-1-yl)phenyl)ethylamino)ethyl(methyl)carbamate (155)

The title compound 155 (233 mg, 0.404 mmol, 30% yield) was obtained as a white solid following the procedure described for the synthesis of compound 123 (scheme 19, example 17, step 2), except using 154 (565 mg, 1.35 mmol) in place of 122. LRMS (ESI): (calc.) 575.3 (found) 576.4 $(MH)^+$.

Step 4: N-(2-methoxybenzyl)-1-(3-(1-(2-(methylamino)ethylamino)ethyl)phenyl)-3-(trifluoromethyl)-1H-pyrazole-5-carboxamide (156)

The title compound 156 (226 mg, 0.321 mmol, 80%) was obtained as white solid. following the procedure described for the synthesis of compound 9a (scheme 2, example 1c, step 9), except using 155 (233 mg, 0.404 mmol) in place of 15a. $^1$H NMR: $(CD_3OD)$ δ (ppm) 1H: 7.71 (dd, J=1.8, 1.8 Hz, 1H); 7.65-7.58 (m, 2H); 7.53 (ddd, J=7.6, 1.6, 1.6 Hz, 1H); 7.30-7.26 (m, 2H); 7.21 (dd, J=7.4, 1.6 Hz, 1H); 6.99 (d, J=8.2 Hz, 1H); 6.92 (ddd, J=7.4, 7.4, 0.8 Hz, 1H); 4.52-4.47 (m, 3H); 3.85 (s, 3H); 3.30-3.24 (m, 3H); 3.12-3.10 (m, 1H); 2.69 (s, 3H); 1.73 (d, J=6.8 Hz, 3H). LRMS(ESI): (calc.) 475.2 (found) 476.3 $(MH)^+$.

Scheme 28

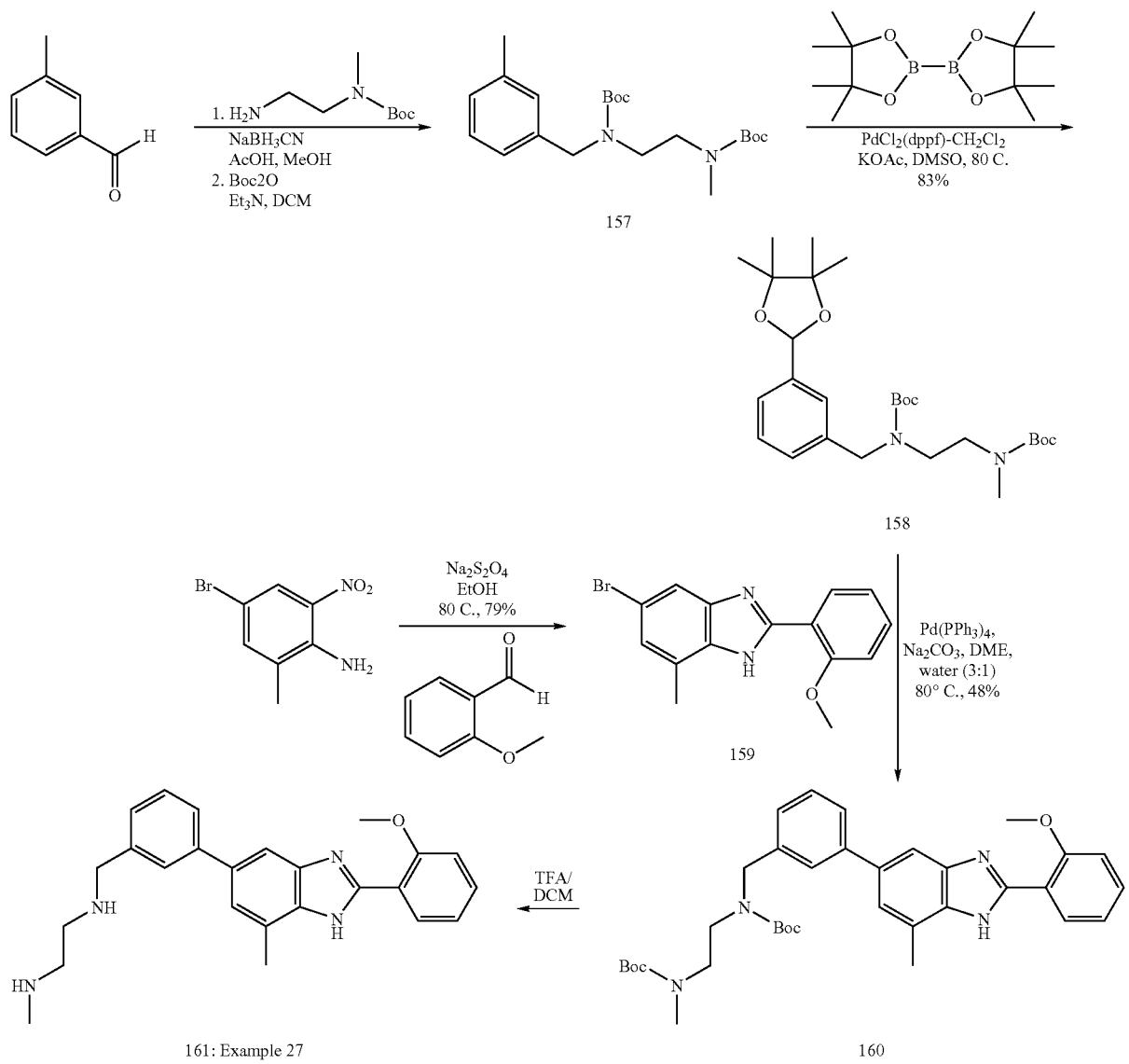

Example 27

N1-(3-(2-(2-methoxyphenyl)-7-methyl-1H-benzo[d]imidazol-5-yl)benzyl)-N2-methylethane-1,2-diamine (161)

Steps 1: tert-butyl 2-[(3-iodobenzyl)-(tert-butoxycarbonyl)amino]ethyl(methyl)carbamate (157)

The titled compound 157 (0.565 g, 89%) was obtained as a clear oil using the same procedure as described for the synthesis of compound 124 (scheme 19, example 17, steps 2 and 3) except using 3-iodobenzaldehyde (0.300 g, 1.29 mmol) in place of 122. LRMS (ESI): (calc.) 490.2 (found) 513.1 (MNa).

Step 2: tert-butyl 2-[((3-(4,4,5,5-tetramethyl-1,3,2-dioxaborolan-2-yl)benzyl)-(tert-butoxycarbonyl)amino)]ethyl(methyl)carbamate (158)

To a solution of 157 (0.200 g, 0.408 mmol) in DMSO (2 ml) under nitrogen was added bis(pinacolato)diboron (0.114 g, 0.449 mmol), potassium acetate (0.120 g, 1.22 mmol) and then $PdCl_2(dppf)$-$CH_2Cl_2$ (10 mg, 0.012 mmol). After degassing with nitrogen the mixture was heated to 80° C. for 16 hours. After the usual work-up the crude material was purified by silica gel chromatography (Biotage 25S, 15% -30% ethyl acetate in hexanes) to give 158 as clear oil (0.165 g, 0.336 mmol, 82% yield). LRMS (ESI): (calc.) 490.4 (found) 491.4 $(MH)^+$, 513.3 $(MNa)^+$.

Step 3: 5-bromo-2-(2-methoxyphenyl)-7-methyl-1H-benzo[d]imidazole (159)

o-Anisaldehyde (0.105 ml, 0.866 mmol) and 4-bromo-2-methyl-6-nitroaniline (0.2 g, 0.866 mmol) in EtOH (3.46 ml)

were treated with solid sodium dithionite (0.535 g, 2.60 mmol) and the mixture was heated to 80° C. for 16 hours following the procedure of D. Yang et. al. (Synthesis 2005, 47-56). The reaction mixture was taken to dryness and partitioned between ethyl acetate and 2N $NH_4OH(aq)$. After the usual work-up the crude material was purified by silica gel chromatography (Biotage 25S, 20% -40% ethyl acetate in hexanes) to obtained 159 (0.217 g, 0.684 mmol, 79% yield) as yellow solid. LRMS (ESI): (calc.) 316.0 and 318.0 (found) 317.1 and 319.1 $(MH)^+$.

Step 4: tert-butyl 3-(2-(2-methoxyphenyl)-7-methyl-1H-benzo[d]imidazol-5-yl)benzyl(2-((tert-butoxycarbonyl)methylamino)ethyl)carbamate (160)

To a solution of 158 (0.165 g, 0.336 mmol) in DME (1.5 mL) and water (0.5 mL) was added 159 (0.107 g, 0.336 mmol), sodium carbonate (0.107 g, 1.009 mmol) followed by $Pd(Ph_3P)_4$ (0.025 g, 0.022 mmol). The reaction mixture was degassed with nitrogen and heated to 80° C. for 16 hours. After the usual work-up the crude material was purified by silica gel chromatography (Biotage 25M, 20 to 30 to 50% ethyl acetate in hexanes) to give 160 (97.7 mg, 0.163 mmol, 48.3% yield) as yellow crusty solid. LRMS (ESI): (calc.) 600.7 (found) 601.5 $(MH)^+$.

Step 5: N1-(3-(2-(2-methoxyphenyl)-7-methyl-1H-benzo[d]imidazol-5-yl)benzyl)-N2-methylethane-1,2-diamine (161)

The title compound 161 (79 mg, as the tris-TFA salt) was obtained as white sticky solid following the procedure described for the synthesis of compound 9a (scheme 2, example 1c, step 9), except using 160 (72.4 mg, 0.121 mmol) in place of 15a. $^1$H NMR: ($CD_3OD$) δ(ppm): 8.12 (dd, J=1.2, 7.6 Hz, 1H), 7.92-7.90 (m, 2H), 7.81 (td, J=1.2, 7.2 Hz, 1H), 7.77 (dt, J=2.0, 7.6 Hz, 1H), 7.71 (m, 1H), 7.61 (t, J=7.6 Hz, 1H), 7.56 (td, J=1.6, 7.6 Hz, 1H), 7.41 (d, J=8.0 Hz, 1H), 7.30 (dt, J=0.8, 8.0 Hz, 1H), 4.40 (s, 2H), 4.13 (s, 3H), 3.54-3.50 (m, 2H), 3.46-3.42 (m, 2H), 2.79 (s, 3H), 2.78 (s, 3H). LRMS (ESI): (calc.) 400.2 (found) 401.3 $(MH)^+$.

Example 28, compound 162 (83 mg, tris-TFA salt) was obtained as white solid following the procedures described for the synthesis of compound 161 (scheme 28, example 27, steps 1-5) except using 4-iodobenzaldehyde in step 1 in place of 3-iodobezaldehyde. Characterization is presented in Table 7.

TABLE 7

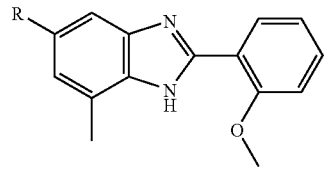

| Ex | Cpd | R | Name | Characterization | Scheme |
|---|---|---|---|---|---|
| 28 | 162 | | N1-(4-(2-(2-methoxyphenyl)-7-methyl-1H-benzo[d]imidazol-5-yl)benzyl)-N2-methylethane-1,2-diamine | $^1$H NMR: ($CD_3OD$) δ (ppm): 8.13 (dd, J = 1.6, 8.0 Hz, 1 H), 7.88 (m, 1 H), 7.82 (d, J = 8.4 Hz, 2 H), 7.78 (dt, J = 1.6, 7.6 Hz, 1 H), 7.71 (m, 1 H), 7.66 (d, J = 8.4 Hz, 2 H), 7.42 (d, J = 8.0 Hz, 1 H), 7.31 (dt, J = 0.8, 7.6 Hz, 1 H), 4.37 (s, 2 H), 4.13 (s, 3 H), 3.52-3.48 (m, 2 H), 3.45-3.42 (m, 2 H), 2.80 (s, 3 H), 2.78 (s, 3 H). LRMS (ESI): (calc.) 400.2 (found) 401.3 (MH)+ | 28 |

Scheme 29

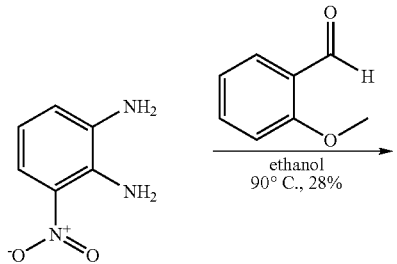

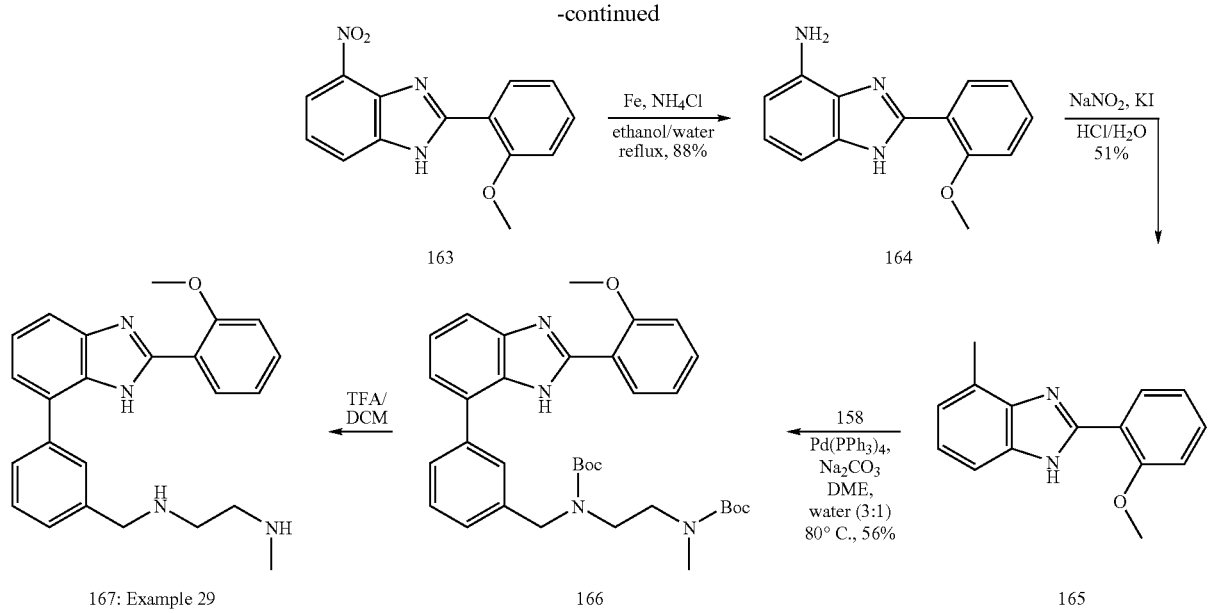

Example 29

N1-(3-(2-(2-methoxyphenyl)-1H-benzo[d]imidazol-7-yl)benzyl)-N2-methylethane-1,2-diamine (167)

Step 1:
2-(2-methoxyphenyl)-4-nitro-1H-benzo[d]imidazole (163)

A solution of o-anisaldehyde (0.789 ml, 6.53 mmol) and 3-nitro-o-phenylenediamine (1 g, 6.53 mmol) in ethanol (30 ml) was heated to 90° C. for 20 hours in a sealed tube. The red reaction mixture was taken to dryness and purified by silica gel chromatography (Biotage 40M, 75% DCM in hexanes to 100% DCM) to give 163 (0.62 g, 2.303 mmol, 35.3% yield) as yellow solid. LRMS (ESI): (calc.) 269.3 (found) 270.1 (MH)$^+$.

Step 2:
2-(2-methoxyphenyl)-1H-benzo[d]imidazol-4-amine (164)

A suspension of 163 (0.620 g, 2.303 mmol), ammonium chloride (0.105 g, 1.957 mmol) and iron (0.643 g, 11.51 mmol) in ethanol (20 ml) and water (4.00 ml) was heated at reflux for 2 hours. The reaction mixture was cooled and filtered through Celite and the filtrate was taken to dryness, H2O was added and the material extracted with ethyl acetate. The EtOAc extracts were washed with brine, dried over Na$_2$SO$_4$, filtered and concentrated to give crude 164 (0.5245 g, 2.192 mmol, 95% yield) as brown solid. LRMS (ESI): (calc.) 239.3 (found) 240.2 (MH)$^+$.

Step 3:
4-iodo-2-(2-methoxyphenyl)-1H-benzo[d]imidazole (165)

A solution of sodium nitrite (0.165 g, 2.391 mmol) in water (4.25 mL) was added drop-wise to a suspension of 164 (0.52 g, 2.173 mmol) in concentrated hydrochloric acid (8.5 mL) at 0° C. The resulting orange solution was stirred for 30 minutes at 0° C. then it was added drop-wise via a pipette to a solution of KI (3.61 g, 21.73 mmol) in water (8.50 mL) at 0° C. The resulting dark suspension was kept at 0° C. for 72 hours. EtoAc was added and the organic extracts were washed with NaHCO$_3$ (satd) (3×), water, brine, dried over Na$_2$SO$_4$, filtered and concentrated. The crude material was purified by silica gel chromatography (Biotage 25M, 15 to 30% ethyl acetate in hexanes) to give 165 (0.446 g, 1.274 mmol, 58.6% yield) as a rusty-colored solid. LRMS (ESI): (calc.) 250.2 (found) 351.0 (MH)$^+$.

Step 4: tert-butyl 3-(2-(2-methoxyphenyl)-1H-benzo[d]imidazol-4-yl)benzyl (2-((tert-butoxycarbonyl)methylamino)ethyl)carbamate (166)

The title compound 166 (53 mg, 58%) was obtained as a yellow solid following the procedure described for the synthesis of 160 (scheme 28, example 27, step 4) except using 165 in place of 159. LRMS (ESI): (calc.) 586.7 (found) 587.5 (MH)$^+$.

Step 5: N1-(3-(2-(2-methoxyphenyl)-1H-benzo[d]imidazol-7-yl)benzyl)-N2-methylethane-1,2-diamine (167)

The title compound 167 (52 mg, as tris-TFA salt) was obtained as a sticky white solid following the same procedure as described for the synthesis of compound 9a (scheme 2, example 1c, step 9), except using 166 (53 mg) in place of 15a. $^1$H NMR: (CD$_3$OD) δ(ppm): 8.06 (dd, J=1.2, 8.0 Hz, 1H), 7.94 (m, 1H), 7.87-7.85 (m, 2H), 7.76-7.62 (m, 5H), 7.37 (d, J=7.6 Hz, 1H), 7.23 (dt, J=1.2, 7.6 Hz, 1H), 4.43 (s, 2H), 4.09 (s, 3H), 3.56-3.52 (m, 2H), 3.47-3.43 (m, 2H), 2.78 (s, 3H). LRMS (ESI): (calc.) 386.2 (found) 387.3 (MH)$^+$.

Example 30, compound 168 (44 mg) was obtained as an off-white solid using the sequence described for the synthesis of compound 167 (scheme 29, example 29, steps 4-5) using 165 (45 mg, 0.129 mmol) and tert-butyl 2-[((4-(4,4,5,5-tetramethyl-1,3,2-dioxaborolan-2-yl)benzyl)-(tert-butoxycarbonyl)amino)]ethyl(methyl)carbamate in place of 158 (63 mg, 0.129 mmol, prepared according to the procedure described for the synthesis of 158 [scheme 28, example 27, steps 1 and 2 except using 4-iodobenzaldehyde in place of 3-iodobenzaldehyde in step 1]). Characterization is presented in Table 8.

TABLE 8

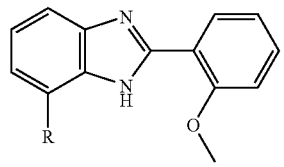

| Ex | Cpd | R | Name | Characterization | Scheme |
|---|---|---|---|---|---|
| 30 | 168 | (structure with benzyl-NH-CH2CH2-NH-CH3) | N1-(4-(2-(2-methoxyphenyl)-1H-benzo[d]imidazol-7-yl)benzyl)-N2-methylethane-1,2-diamine | $^1$H NMR: (CD$_3$OD) δ (ppm): 8.06 (dd, J = 1.6, 8.0 Hz, 1 H), 7.87-7.84 (m, 3 H), 7.76-7.71 (m, 3 H), 7.69 (t, J = 8.0 Hz, 1 H), 7.59 (dd, J = 1.2, 7.6 Hz, 1 H), 7.37 (d, J = 8.0 Hz, 1 H), 7.24 (dt, J = 1.2, 8.0 Hz, 1 H), 4.42 (s, 2 H), 4.09 (s, 3 H), 3.56-3.52 (m, 2 H), 3.48-3.45 (m, 2 H), 2.81 (s, 3 H). LRMS (ESI): (calc.) 386.2 (found) 387.3 (MH)+. (found) 401.3 (MH)+ | 29 |

Scheme 30

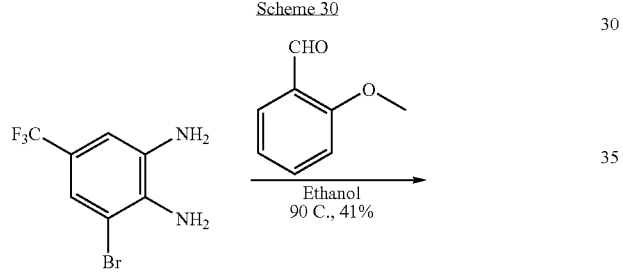

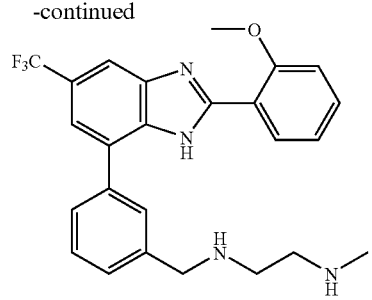

171: Example 31

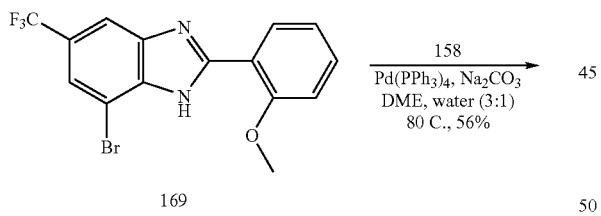

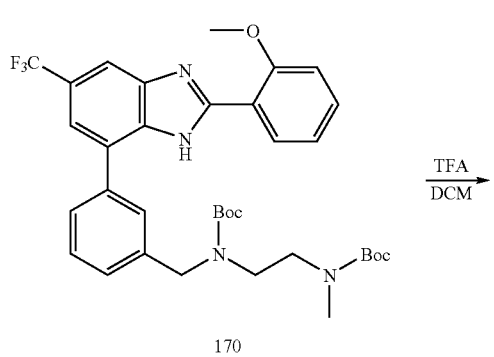

170

Example 31

N1-(3-(2-(2-methoxyphenyl)-5-(trifluoromethyl)-1H-benzo[d]imidazol-7-yl)benzyl)-N2-methyl-ethane-1,2-diamine (171)

Step 1: 7-bromo-2-(2-methoxyphenyl)-5-(trifluoromethyl)-1H-benzo[d]imidazole (169)

The titled compound 169 (0.210 g, 41.2%) was obtained as a white solid following the procedure described for the synthesis of 163 (scheme 29, example 29, step 1) except using 3-bromo-4,5-diaminobenzotrifluoride (0.350 g, 1.37 mmol) in place of 3-nitro-o-phenylenediamine. LRMS (ESI): (calc.) 369.99 (found) 371.1 (MH)$^+$.

Steps 2: tert-butyl 3-(2-(2-methoxyphenyl)-6-(trifluoromethyl)-1H-benzo[d]imidazol-4-yl)benzyl(2-((tert-butoxycarbonyl)methylamino)ethyl)carbamate (170)

The title compound 170 (40 mg, 0.061 mmol, 45.4% yield) was obtained as a white crusty solid following the procedure described for the synthesis of 160 (scheme 28, example 27, step 3) replacing 159 with 169 (50 mg, 0.135 mmol). LRMS (ESI): (calc.) 654.7 (found) 655.5 (MH)$^+$.

Step 3: N1-(3-(2-(2-methoxyphenyl)-5-(trifluoromethyl)-1H-benzo[d]imidazol-7-yl)benzyl)-N2-methylethane-1,2-diamine (171)

The title compound 171 (38 mg) was obtained as a sticky white solid following the same procedure as described for the synthesis of compound 9a (scheme 2, example 1c, step 9), except using 170 (53 mg) in place of 15a. $^1$H NMR: (CD$_3$OD) δ(ppm): 8.23 (dd, J=1.6, 7.6 Hz, 1H), 8.09-8.04 (m, 2H), 7.42-7.40 (m, 1H), 7.70 (t, J=7.6 Hz, 1H), 7.66-7.62 (m, 2H), 7.32 (d, J=8.0 Hz, 1H), 7.18 (dt, J=0.8, 7.6 Hz, 1H), 4.44 (s, 2H), 4.10 (s, 3H), 3.54-3.51 (m, 2H), 3.45-3.42 (m, 2H), 2.78 (s, 3H). LRMS(ESI): (calc.) 454.2 (found) 455.3 (MH)+

Scheme 31

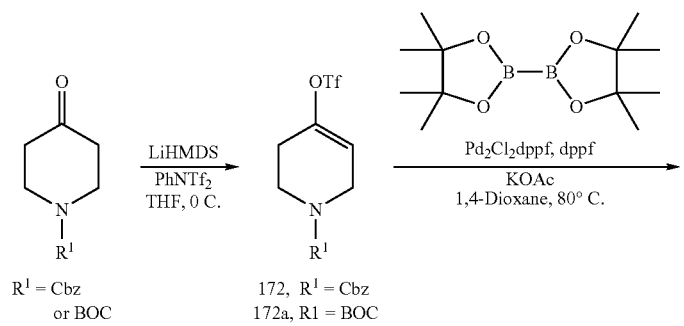

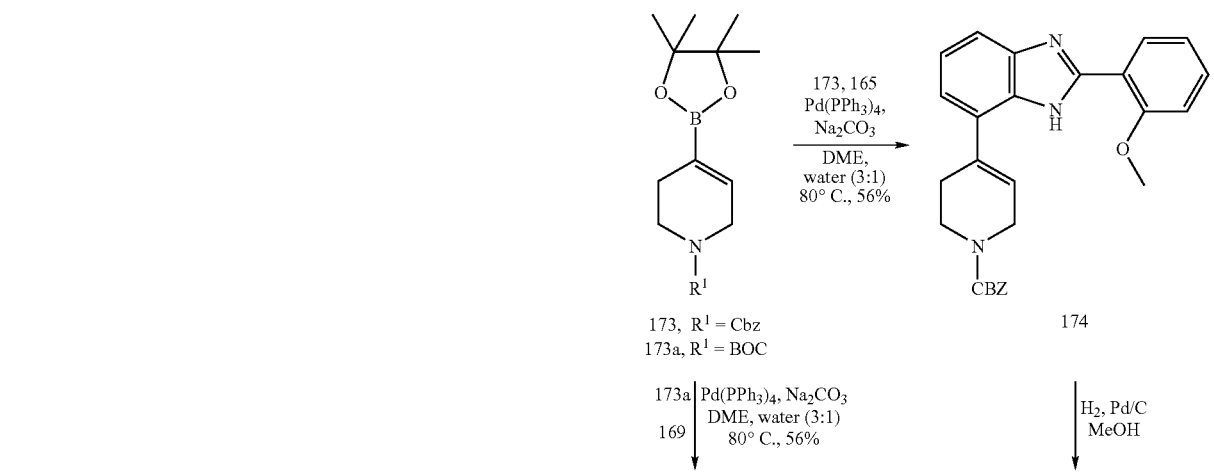

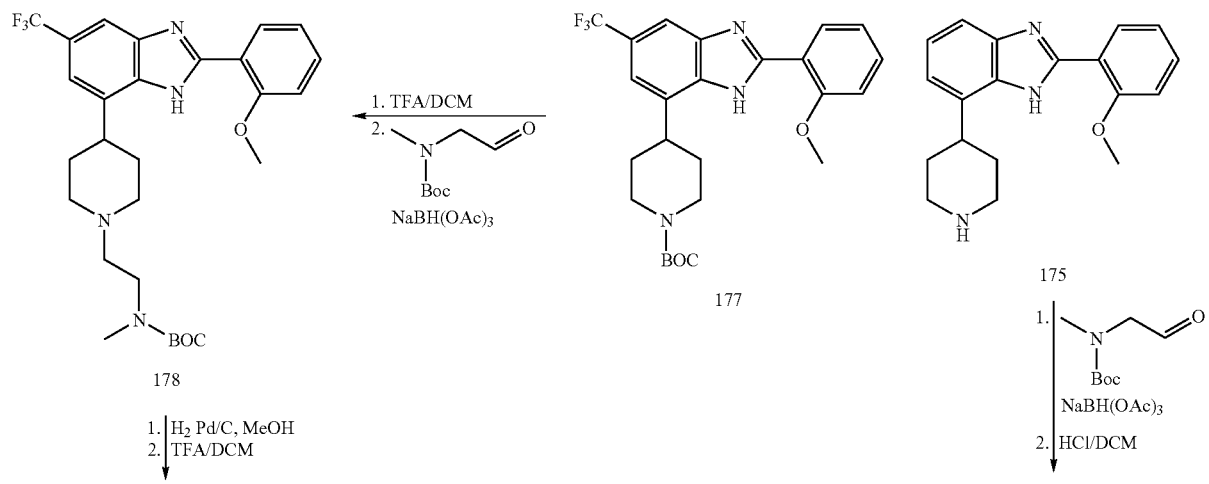

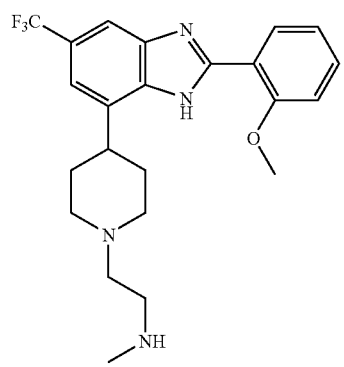

179: Example 33

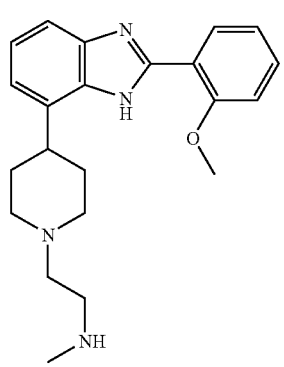

176: Example 32

Example 32

2-(4-(2-(2-methoxyphenyl)-1H-benzo[d]imidazol-7-yl)piperidin-1-yl)-N-methylethanamine (176)

Step 1: Benzyl 4-(trifluoromethylsulfonyloxy)-5,6-dihydropyridine-1(2H)-carboxylate (172)

A solution of LHMDS (22.51 ml, 1.0M solution, 22.51 mmol) in THF was slowly added to a solution of benzyl 4-oxopiperidine-1-carboxylate (5 g, 21.44 mmol) in THF (22.5 ml) at −78° C. After 60 minutes at −78° C. a solution of N-phenyltrifluoromethanesulfonimide (8.04 g, 22.51 mmol) in THF (22.50 ml) was added over 30 minutes and the reaction was stirred for 1 hour at −78° C. and then was allowed to come to room temperature and stirred for an additional 3 hours. The reaction was quenched with $NaHCO_3$ (satd) (15 mL) and extracted with ethyl acetate, and the extracts washed with 15% $KHSO_4$ (2×), $NaHCO_3$ (satd), 1N NaOH, brine, dried over $Na_2SO_4$, filtered and concentrated. The crude material was purified by silica gel chromatography (10 to 20% ethyl acetate in hexanes) to give 172 (5.26 g, 12.96 mmol, 60.5% yield) as a clear oil.

Step 2: benzyl 4-(4,4,5,5-tetramethyl-1,3,2-dioxaborolan-2-yl)-5,6-dihydropyridine-1(2H)-carboxylate (173)

A mixture of bis(pinacolato)diboron (3.14 g, 12.38 mmol), 172 (5.26 g, 12.38 mmol), DPPF (0.206 g, 0.371 mmol), $PdCl_2$(dppf)-$CH_2Cl_2$ adduct (0.303 g, 0.371 mmol) and potassium acetate (2.430 g, 24.76 mmol) was heated at 90° C. in 1,4-dioxane (60 mL) for 16 hours. It was then diluted with water (200 ml) and extracted with ethyl acetate (3×), dried over $Na_2SO_4$, filtered and then purified by silica gel chromatography (Flash, 200 g silica and 10 to 20% ethyl acetate in hexanes) to give 173 (1.86 g, 5.42 mmol, 43.8% yield). LRMS (ESI): (calc.) 343.2 (found) 344.3 (MH)+

Step 3: benzyl 4-(2-(2-methoxyphenyl)-1H-benzo[d]imidazol-7-yl)-5,6-dihydropyridine-1(2H)-carboxylate (174)

The titled compound 174 (0.418 g, 74.8%) was obtained as a yellow crust following the procedure described for compound 160 (scheme 28, example 27, step 5) replacing 158 with the vinyl boronate 173 (490 mg, 1.27 mmol) and 159 with iodobenzimidazole 165 (445 mg, 1.27 mmol). LRMS (ESI): (calc.) 439.2 (found) 440.2 (MH)+

Step 4: 2-(2-methoxyphenyl)-7-(piperidin-4-yl)-1H-benzo[d]imidazole (175)

The title compound 175 (220 mg, 0.716 mmol, 75% yield) was obtained as yellow gum following the procedure described for 65 (scheme 9, example 7, step 5) replacing 64 with 174 (418 mg, 0.951 mmol). LRMS (ESI): (calc.) 307.2 (found) 308.3 (MH)+

Step 5: 2-(4-(2-(2-methoxyphenyl)-1H-benzo[d]imidazol-7-yl)piperidin-1-yl)-N-methylethanamine (176)

To a solution of tert-butyl methyl(2-oxoethyl)carbamate (0.165 g, 0.950 mmol) in DCM (3 ml) was added a solution of 175 (0.292 g, 0.950 mmol) in MeOH (3.00 ml) followed by acetic acid (0.082 ml, 1.425 mmol) and after 1 hour of stirring at room temperature, sodium triacetoxyborohydride (0.242 g, 1.140 mmol) was added according to the procedure described for 59 (scheme 8, example 6, step 7) to give tert-butyl 2-(4-(2-(2-methoxyphenyl)-1H-benzo[d]imidazol-7-yl)piperidin-1-yl)ethyl(methyl)-carbamate (0.114 g, 0.245 mmol, 25.8% yield) as a white crusty solid. LRMS (ESI): (calc.) 464.6 (found) 465.5 (MH)+

The material from above (113 mg, 0.243 mmol) was stirred in a saturated solution of HCl in DCM (5 mL) for 3 hours after which the reaction was taken to dryness and the residue was triturated with methanol and ether, filtered and dried under vacuum to give 176 (94 mg, tri-HCl salt) as a white solid. $^1$H NMR: ($CD_3OD$) δ(ppm): 8.27 (d, J=7.6 Hz, 1H), 7.81-7.76 (m, 2H), 7.63 (t, J=8.0 Hz, 1H), 7.56 (d, J=7.6 Hz, 1H), 7.41 (d, J=8.0 Hz, 1H), 7.31 (t, J=8.0 Hz, 1H), 4.13 (s, 3H), 3.89-3.79 (m, 3H), 3.79 (s, 4H), 3.49-3.42 (m, 2H), 2.84 (s, 3H), 2.41-2.28 (m, 4H). LRMS (ESI): (calc.) 364.2 (found) 365.4 (MH)+.

Example 33

2-(4-(2-(2-methoxyphenyl)-5-(trifluoromethyl)-1H-benzo[d]imidazol-7-yl)piperidin-1-yl)-N-methylethanamine (179)

Step 1: tert-butyl 4-(trifluoromethylsulfonyloxy)-5,6-dihydropyridine-1(2H)-carboxylate (172a).

The titled compound 172a (0.50 g, 30%) was obtained as a clear oil after following the procedure described for 172 (scheme 31, example 32, step 1) whereby N-(tert-butoxycarbonyl)-4-piperidone (1.00 g, 5.02 mmol) was used instead of benzyl 4-oxo-1-piperidinecarboxylate. LRMS (ESI): (calc.) 331.1 (found) 354.1 (MNa).

Step 2: tert-butyl 4-(4,4,5,5-tetramethyl-1,3,2-dioxaborolan-2-yl)-5,6-dihydropyridine-1 (2H)-carboxylate (173a)

The titled compound 173a (53.2 mg, 40%) was obtained as a clear oil after following the procedure described for the synthesis of 173 (scheme 31, example 32, step 2) except using 172a (0.15 g, 0.453 mmol) in place of 172. LRMS (ESI): (calc.) 309.2 (found) 332.3 (MNa)+.

Step 3: tert-butyl 4-(2-(2-methoxyphenyl)-5-(trifluoromethyl)-1H-benzo[d]imidazol-7-yl)-5,6-dihydropyridine-1(2H)-carboxylate (177)

The titled compound 177 (47.3 mg, 75.0%) was obtained as a white crusty solid following the procedure described for compound 160 (scheme 28, example 27, step 5) replacing 158 with vinyl boronate 173a (49.3 mg, 0.159 mmol) and 159 with bromobenzimidazole 169 (49.3 mg, 0.159 mmol). LRMS (ESI): (calc.) 473.2 (found) 473.3 (MH)+

Step 4: tert-butyl 2-(4-(2-(2-methoxyphenyl)-5-(trifluoromethyl)-1H-benzo[d]imidazol-7-yl)-5,6-dihydropyridin-1(2H)-yl)ethyl(methyl)carbamate (178)

Compound 177 (47 mg, 0.099 mmol) was stirred in a solution of DCM (0.8 mL) and TFA (0.200 mL) for 1 hour. After the usual work-up 2-(2-methoxyphenyl)-7-(1,2,3,6-tetrahydropyridin-4-yl)-5-(trifluoromethyl)-1H-benzo[d]imidazole was obtained (34 mg, 0.091 mmol, 92% yield). LRMS (ESI): (calc.) 373.4 (found) 374.1 (MH)+

The material from above (34 mg, 0.091 mmol) was reacted according to the method described for 70 (scheme 9, example 7, step 10) to give the title compound 178 (14.7 mg, 30.4%) as a yellow film. LRMS (ESI): (calc.) 530.2 (found) 553.4 (Mna)+.

Step 5: 2-(4-(2-(2-methoxyphenyl)-5-(trifluoromethyl)-1H-benzo[d]imidazol-7-yl)piperidin-1-yl)-N-methylethanamine (179)

Compound 177 (14.7 mg, 0.028 mmol) was reduced with hydrogen gas according to the procedure described for 64 (Example 7, scheme 9, step 5) to give tert-butyl 2-(4-(2-(2-methoxyphenyl)-5-(trifluoromethyl)-1H-benzo[d]imidazol-7-yl)piperidin-1-yl)ethyl(methyl)carbamate (4.3 mg, 29%). LRMS (ESI): (calc.) 532.2 (found) 533.4 (MH)+.

The material from above (4 mg, 7.51 μmol) was reacted with TFA (0.04 mL) in DCM (0.2 mL) following the procedure described for the synthesis of compound 9a (scheme 2, example 1c, step 9) to give the title compound 179 (3.4 mg, tris-TFA salt) as a white sticky solid. $^1$H NMR: (CD$_3$OD) δ(ppm): 8.39 (dd, J=1.6, 8.4 Hz, 1H), 7.95 (s, 1H), 7.66 (dt, J=1.6, 7.6 Hz, 1H), 7.33 (d, J=8.0 Hz, 1H), 7.22 (dt, J=1.2, 8.0 Hz, 1H), 4.11 (s, 3H), 3.82-3.71 (m, 3H), 3.57 (s, 4H), 3.38-3.26 (m 2H), 2.83 (s, 3H), 2.37-2.31 (m, 4H). LRMS(ESI): (calc.) 432.2 (found) 433.3 (MH)+.

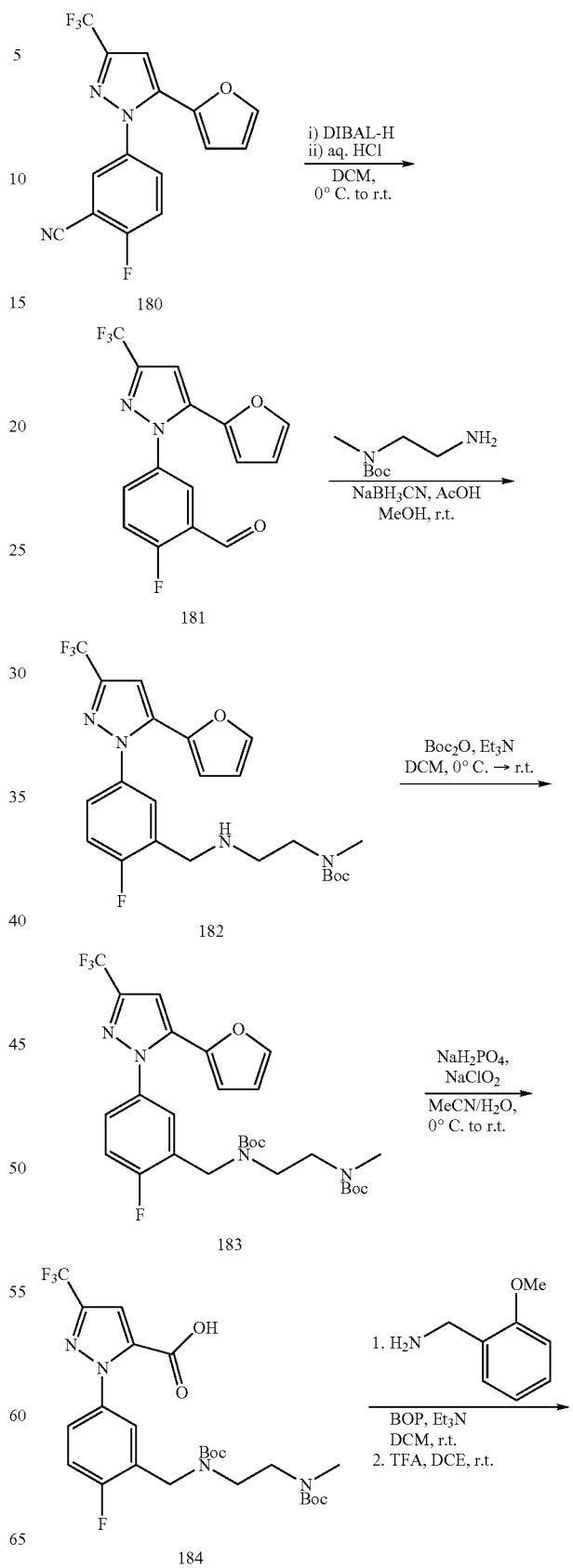

Scheme 32

-continued

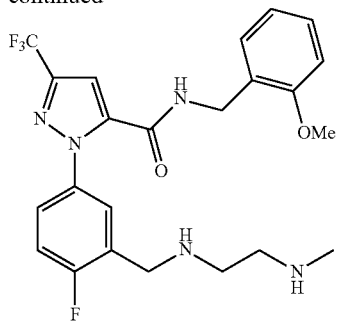

185: Example 34

Example 34

1-(4-fluoro-3-((2-(methylamino)ethylamino)methyl)
phenyl)-N-(2-methoxybenzyl)-3-(trifluoromethyl)-
1H-pyrazole-5-carboxamide (185)

Step 1: 2-fluoro-5-(5-(furan-2-yl)-3-(trifluoromethyl)-1H-pyrazol-1-yl)benzaldehyde (181)

Aldehyde 181 (3.57 g, 11.0 mmol, 95%) was obtained as a beige solid following the procedure described for the synthesis of 122 (Scheme 19, Example 17, step 1) using 180 (3.74 g, 11.1 mmol, prepared according to the procedure of F. Jin and P. N. Confalone, Tet. Lett. 2000, 41, 3271-3274) in place of 53. $^1$H NMR: (CDCl$_3$) δ (ppm) 10.37 (s, 1H); 7.95 (dd, J=5.9, 2.7 Hz, 1H); 7-74-7.70 (m, 1H); 7.42 (dd, J=2.0, 0.9 Hz, 1H); 7.33 (t, J=9.2 Hz, 1H); 6.90 (s, 1H); 6.41 (dd, J=3.5, 2.0 Hz, 1H); 6.21 (dd, J=3.5, 0.6 Hz, 1H).

Step 2: tert-butyl 2-(2-fluoro-5-(5-(furan-2-yl)-3-(trifluoromethyl)-1H-pyrazol-1-yl)benzylamino)
ethyl(methyl)carbamate (182)

Compound 182 (3.72 g, 7.71 mmol, 100%) was obtained as a yellow oil following the procedure described for the synthesis of 123 (Scheme 19, Example 17, step 2) replacing 122 with 181 (2.50 g, 7.71 mmol). LRMS (ESI): calc. 482.2, found 483.3 (MH)$^+$.

Step 3: tert-butyl 2-((tert-butoxycarbonyl)(methyl)
amino)ethyl(2-fluoro-5-(5-(furan-2-yl)-3-(trifluoromethyl)-1H-pyrazol-1-yl)benzyl)carbamate (183)

The title compound 183 (3.69 g, 6.33 mmol, 82%) was obtained as clear oil following the procedure described for the synthesis of 124 (Scheme 19, Example 17, step 3) replacing 123 with 182 (3.72 g, 7.71 mmol). LRMS (ESI): calc. 582.3, found 605.4 (Mna)$^+$.

Step 4: 1-(3-((tert-butoxycarbonyl(2-(tert-butoxycarbonyl(methyl)amino)ethyl)amino)methyl)-4-fluorophenyl)-3-(trifluoromethyl)-1H-pyrazole-5-carboxylic acid (184)

The title compound 184 (3.55 g, 6.33 mmol, 100%) was obtained as dark brown sticky solid following the procedure described for the synthesis of 125 (Scheme 19, Example 17, step 4) replacing 124 with 183 (3.69 g, 6.33 mmol). LRMS (ESI): calc. 560.2, found 558.9 (M-1)$^+$.

Step 5: 1-(4-fluoro-3-((2-(methylamino)ethylamino)
methyl)phenyl)-N-(2-methoxybenzyl)-3-(trifluoromethyl)-1H-pyrazole-5-carboxam ide (185)

The title compound 185 (32 mg, 0.045 mmol, 20%) was obtained as a white solid following the procedure described for the synthesis of 129 (scheme 20, Example 18, steps 1 and 2) replacing 125 with 184 (126 mg, 0.225 mmol)
$^1$H NMR: (CD$_3$OD) δ(ppm): 7.60 (dd, J=6.5, 2.7 Hz, 1H); 7.38-7.34 (m, 1H); 7.28 (ddd, J=8.2, 8.2, 1.8 Hz, 1H); 7.21-7.17 (m, 3H); 6.96 (d, J=8.2 Hz, 1H); 6.90 (ddd, J=7.4, 7.4, 1.2 Hz, 1H); 4.45 (s, 2H); 3.85 (s, 2H); 3.83 (s, 3H); 2.99-2.96 (m, 2H); 2.83-2.80 (m, 2H); 2.61 (s, 3H). LRMS (ESI): calc. 479.2, found 480.3 (MH)$^+$.

Example 35, compound 186 (40 mg) was obtained as yellow solid using the sequence described for the synthesis of compound 185 (scheme 32, example 34, steps 1-5) using naphthalen-1-ylmethanamine in place of (2-methoxyphenyl)methanamine. Characterization is presented in Table 9.

TABLE 9

| Ex | Cpd | R | Name | Characterization | Scheme |
|----|-----|---|------|------------------|--------|
| 35 | 186 | naphthalen-1-ylmethyl | 1-(4-fluoro-3-((2-(methylamino)ethylamino)methyl)phenyl)-N-(aphthalene-1-ylmethyl)-3-(trifluoromethyl)-1H-pyrazole-5-carboxamide | $^1$H NMR: (CD$_3$OD) δ (ppm): 8.05-8.03 (m, 1 H); 7.94-7.91 (m, 1 H); 7.85 (dd, J = 5.7, 1.8 Hz, 1 H); 7.72 (dd, J = 6.3, 2.5 Hz, 1 H); 7.56-7.44 (m, 5 H); 7.29-7.24 (m, 2 H); 4.96-4.95 (m, 2 H); 4.22 (s, 2 H); 3.24 (s, 4 H); 2.70 (s, 3 H LRMS (ESI): (calc.) 499.2 (found) 500.3 (MH)+ | 32 |

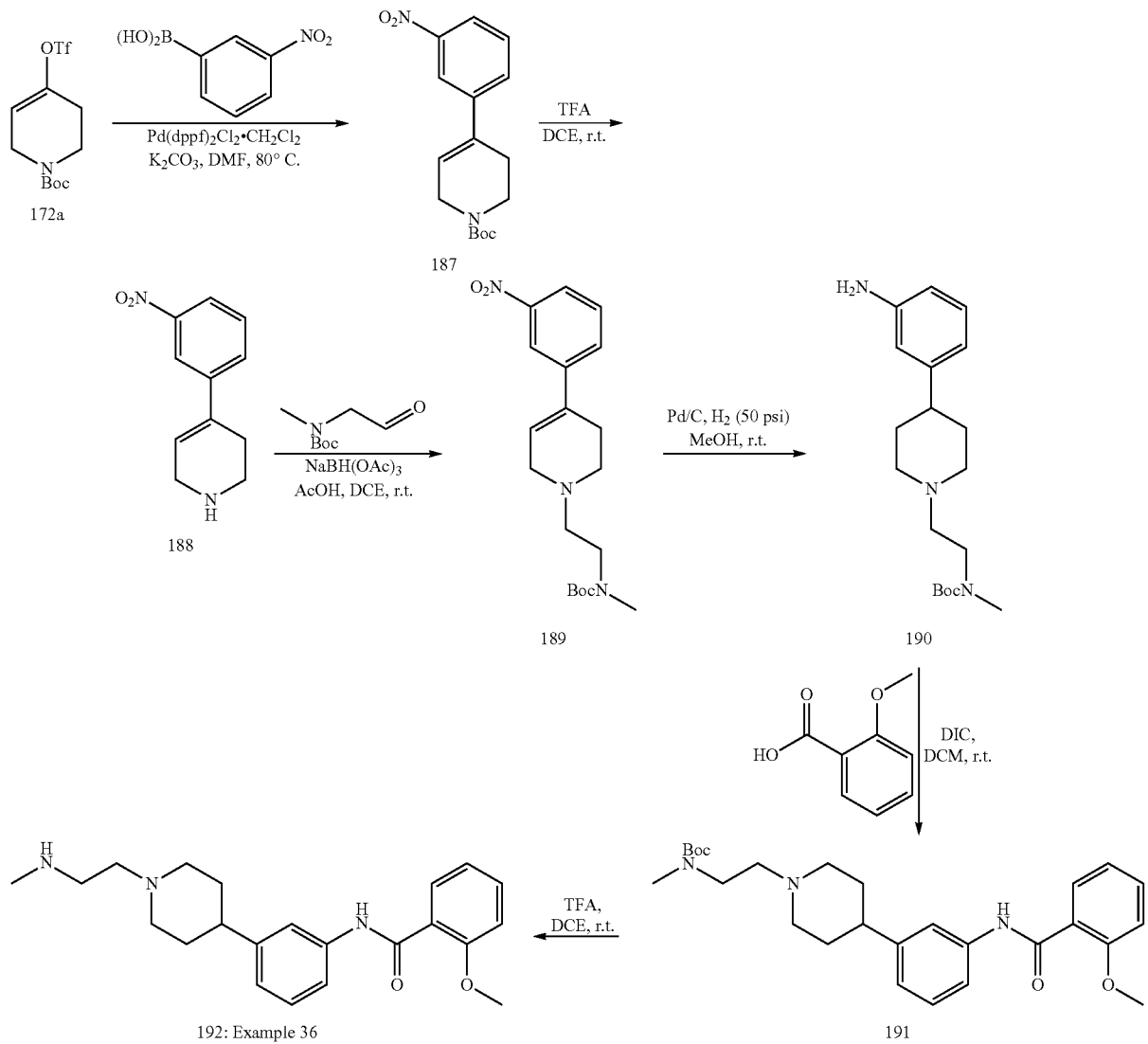

Example 36

2-methoxy-N-(3-(1-(2-(methylamino)ethyl)piperidin-4-yl)phenyl)benzamide (192)

Step 1: tert-butyl 4-(3-nitrophenyl)-5,6-dihydropyridine-1 (2H)-carboxylate (187)

A mixture of 3-Nitrophenylboronic acid (1.00 g, 5.99 mmol), 172a (2.183 g, 6.59 mmol), Pd(dppf)$_2$Cl$_2$·CH$_2$Cl$_2$ (200 mg, 0.273 mmol) and K$_2$CO$_3$ (1.90 g, 13.8 mmol) was stirred under N$_2$ and heated at 80° C. for 16 h. After the usual work-up the crude material was purified by flash chromatography using 15 to 20% EtOAc in hexane to afford 187 (1.31 g, 4.30 mmol, 72%). LRMS (ESI): calc. 304.1, found 327.2 (MNa)$^+$.

Step 2: 4-(3-nitrophenyl)-1,2,3,6-tetrahydropyridine (188)

Crude 188 (1.37 g, 4.30 mmol, 100%) was obtained following the procedure described for the synthesis of compound 9a (scheme 2, example 1c, step 9) except using 187 (1.31 g, 4.3 mmol) in place of 15a. LRMS (ESI): calc. 204.1, found 205.1 (MH)$^+$.

Step 3: tert-butyl methyl(2-(4-(3-nitrophenyl)-5,6-dihydropyridin-1 (2H)-yl)ethyl)carbamate (189)

The title compound 189 (416 m g, 1.15 mmol, 27%) was obtained following the procedure described for the synthesis of 70 (scheme 9, example 7, step 10) using 188 (878 mg, 4.26 mmol) in place of 69. LRMS (ESI): calc. 361.2, found 362.2 (MH)$^+$.

Step 4: tert-butyl 2-(4-(3-aminophenyl)-5,6-dihydropyridin-1 (2H)-yl)ethyl(methyl)carbamate (190)

A mixture of 189 (416.2 mg, 1.152 mmol) and 10% Pd/C (300 mg) in Methanol (25 mL) was shaken under H$_2$ (50 psi) for 18 h at room temperature. The catalyst was filtered through Celite and the filtrate was taken to dryness to give 190

Step 5: tert-butyl 2-(4-(3-(2-methoxybenzamido) phenyl)piperidin-1-yl)ethyl(methyl)carbamate (191)

To a solution of 190 (177 mg, 0.530 mmol) and o-Anisic acid (97 mg, 0.636 mmol) in DCM (5 mL) was added dropwise a solution of 1,3-Diisopropylcarbodiimide (0.100 mL, 0.636 mmol) in 2 mL of DCM and the resulting mixture was stirred at room temperature for 3 hours. After the usual workup the residue was purified by flash chromatography using 4 to 6% MeOH in DCM to afford 191 (84.7 mg, 0.181 mmol, 34% yield) as a yellow oil. LRMS (ESI): calc. 467.3, found 468.2 (MH)$^+$.

Step 6: 2-methoxy-N-(3-(1-(2-(methylamino)ethyl) piperidin-4-yl)phenyl)benzamide (192)

The title compound 192 (23 m g, 0.039 mmol, 21%) was obtained as a beige gum following the procedure described for the synthesis of 9a (scheme 2, example 1c, step 9) except using 191 (85 mg, 0.144 mmol) in place of 15a. $^1$H NMR (CD$_3$OD) δ(ppm): 7.89 (dd, J=1.6, 7.6 Hz, 1H), 7.72 (s, 1H), 7.56-7.50 (m, 2H), 7.34 (t, J=8.0 Hz, 1H), 7.20 (d, J=8.4 Hz, 1H), 7.10 (dt, J=1.2, 7.6 Hz, 1H), 4.03 (s, 3H), 3.82-3.78 (m, 2H), 3.58-3.54 (m, 4H), 3.28-3.20 (m, 2H), 3.00-2.91 (m, 1H), 2.82 (s, 3H), 2.28-2.12 (m, 4H).LRMS (ESI): calc. 367.2, found 368.2 (MH)$^+$.

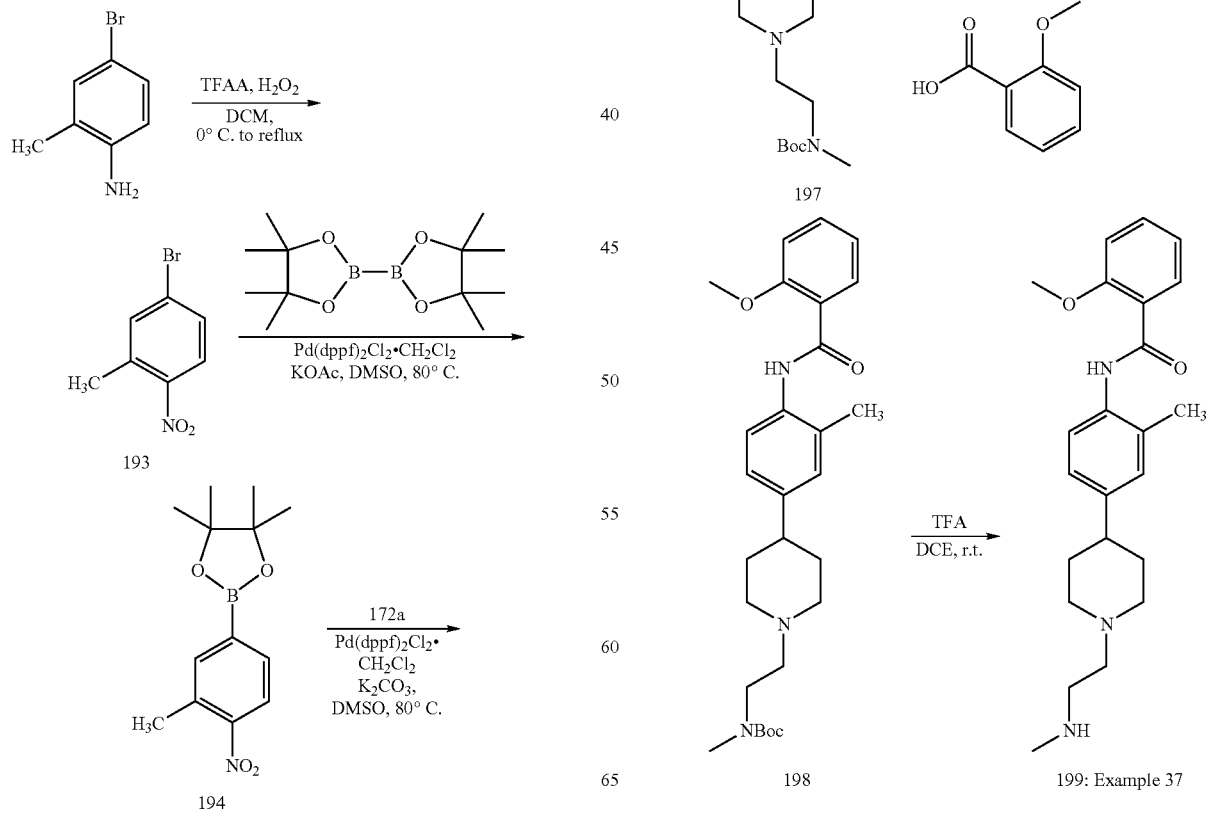

Example 37

2-methoxy-N-(2-methyl-4-(1-(2-(methylamino)ethyl)piperidin-4-yl)phenyl)benzamide (199)

Step 1: 4-bromo-2-methyl-1-nitrobenzene (193)

To a mixture of $H_2O_2$ (3.95 ml, 64.5 mmol) in DCM (32.0 ml) cooled at 0° C. was added TFAA (10.93 ml, 77 mmol) and the mixture was stirred for 5 minutes at that temperature then the ice bath was removed and a reflux condenser was installed and a solution of 4-bromo-2-methylaniline (3 g, 16.12 mmol) in DCM (6.4 ml) was added drop-wise over approx. 30 minutes. The reaction was heated at reflux for an additional hour then it it was cooled, washed with 30 mL of water then 30 mL of sat. $NaHCO_3$ and the organic layer was dried over $MgSO_4$ and concentrated under vacuum. The crude material was purified by flash to afford 193 (2.57 g, 11.9 mmol, 74%). $^1$H NMR ($CDCl_3$) δ (ppm): 7.88 (d, J=8.6 Hz, 1H); 7.53 (d, J=2.2 Hz, 1H); 7.49 (dd, J=8.6, 2.2 Hz, 1H); 2.60 (s, 3H).

Step 2: 4,4,5,5-tetramethyl-2-(3-methyl-4-nitrophenyl)-1,3,2-dioxaborolane (194)

The title compound 194 (2.63 g, 9.98 mmol, 84%) was obtained as a beige solid following the procedure described for the synthesis of 63 (scheme 9, Example 7, step 3) using 193 in (2.57 g, 11.88 mmol) in place of 62. $^1$H NMR ($CDCl_3$) δ (ppm): 7.92 (d, J=8.0 Hz, 1H); 7.77 (s, 1H); 7.75 (d, J=8.2 Hz, 1H); 2.59 (s, 3H); 1.36 (s, 12H).

Step 3: tert-butyl 4-(3-methyl-4-nitrophenyl)-5,6-dihydropyridine-1(2H)-carboxylate (195)

The title compound 195 (2.10 g, 6.60 mmol, 100%) was obtained following the procedure described for the synthesis of 177 (scheme 31, Example 33, step 4) using 194 (1.74 g, 6.6 mmol) in place of 169. LRMS (ESI): calc. 318.2, found 341.2 (MNa)$^+$.

Step 4: 4-(3-methyl-4-nitrophenyl)-1,2,3,6-tetrahydropyridine (196)

The title compound 196 (2.10 g, 6.32 mmol, 96%) was obtained following the procedure described for the synthesis of 9a (scheme 2, example 1c, step 9) except using 195 (2.10 g, 6.58) in place of 15a. LRMS (ESI): calc. 218.1, found 219.2 (MH)$^+$.

Step 5: tert-butyl 2-(4-(4-amino-3-methylphenyl)piperidin-1-yl)ethyl(methyl)carbamate (197)

The title compound 197 (1.93 g, 5.55 mmol, 88% for the 2 step sequence) was obtained following the procedure described for the synthesis of 70 (Scheme 9, Example 7, step 10) using 196 (2.10 g, 6.3 mmol) in place of 69 followed by catalytic hydrogenation as described for the synthesis of 65 (scheme 9, Example 7, step 5). LRMS (ESI): calc. 347.3, found 348.3 (MH)$^+$.

Step 6: 2-methoxy-N-(2-methyl-4-(1-(2-(methylamino)ethyl)piperidin-4-yl)phenyl)benzamide (199)

O-Anisic acid (0.930 g, 6.11 mmol) in Pyridine (18.51 ml) was cooled to 0° C., 197 (1.93 g, 5.55 mmol) was added followed by drop-wise addition of $POCl_3$ (0.569 ml, 6.11 mmol). The reaction mixture was stirred at 0° C. for 30 min and then slowly warmed to room temperature and stirred for an additional 1 h. After the usual work-up the crude material was purified by chromatography to give 198. The material was treated with TFA 25% in DCE (10 mL) for 1 hour then it was concentrated and purified by prep-HPLC followed by trituration from $Et_2O$/hexane to give 199 (2 mg, 0.00524 mmol, 0.1% yield for the 2 step sequence) as a white solid. LRMS (ESI): calc. 381.2, found 382.3 (MH)$^+$.

$^1$H NMR: ($CD_3OD$) δ(ppm): 8.54 (br, 2H); 8.05 (dd, J=7.6, 1.6 Hz, 1H); 7.80 (d, J=8.4 Hz, 1H); 7.57 (ddd, J=9.2, 7.2, 1.8 Hz, 1H); 7.24 (d, J=8.4 Hz, 1H); 7.15-7.11 (m, 3H); 4.08 (s, 3H); 3.13-3.06 (m, 4H); 2.71 (s, 3H); 2.67 (t, J=6.1 Hz, 2H); 2.55-2.54 (m, 1H); 2.36 (s, 3H); 2.23 (td, J=10.8, 3.5 Hz, 2H); 1.91-1.80 (m, 4H).

Examples 37a and 37b, compounds 199a-b were obtained using the same sequence described for the synthesis of compound 199 (scheme 34, example 37, steps 1-5). Characterization is presented in Table 10.

TABLE 10

| Ex | Cpd | R | Name | Characterization | Scheme |
|---|---|---|---|---|---|
| 37a | 199a | | 2-methoxy-N-(4-(1-(2-(methylamino)ethyl)piperidin-4-yl)phenyl)benzamide | $^1$H NMR (pyridine d-5) δ (ppm): 10.50 (s, 1 H); 8.35 (dd, J = 7.6, 1.8 Hz, 1 H); 8.07 (d, J = 8.5 Hz, 2 H); 7.42 (ddd, J = 8.2, 7.3, 1.8 Hz, 1 H); 7.16 (d, J = 8.5 Hz, 2 H); 7.09 (ddd, J = 7.6, 7.6, 1.2 Hz, 1 H); 6.97 (d, J = 8.5 Hz, 1 H); 3.75 (s, 3 H); 3.28 (t, J = 5.6 Hz, 2 H); 2.96 (d, J = 11.5 Hz, 2 H); 2.86 (s, 3 H); 2.75 (t, J = 5.9 Hz, 2 H); 2.39-2.33 (m, 1 H); 1.96 (t, J = 10.0 Hz, 2 H); 1.61 (d, J = 10.9 Hz, 2 H); 1.51-1.41 (m, 2 H). LRMS (ESI): (calc.) 367.2 found) 368.3 (MH)+ | 34 |

TABLE 10-continued
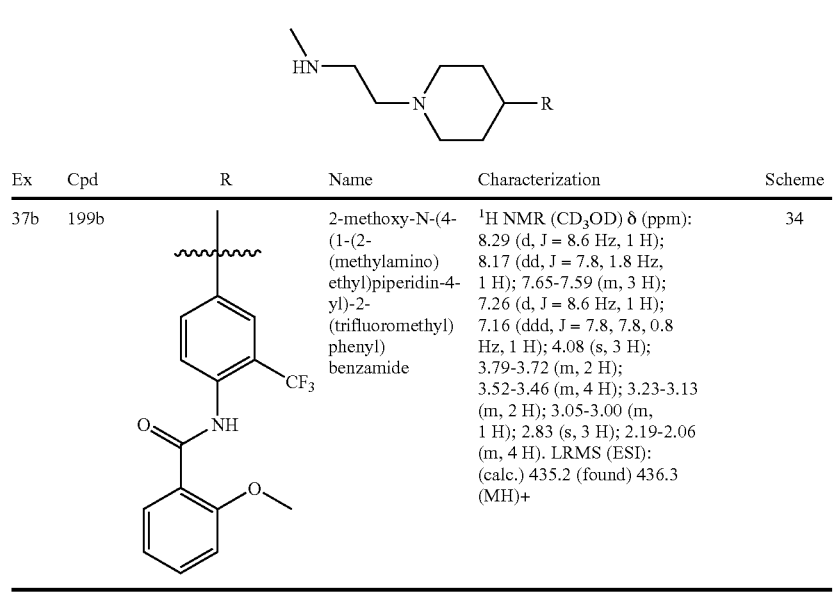
| Ex | Cpd | R | Name | Characterization | Scheme |
|----|-----|---|------|------------------|--------|
| 37b | 199b | (structure shown) | 2-methoxy-N-(4-(1-(2-(methylamino)ethyl)piperidin-4-yl)-2-(trifluoromethyl)phenyl)benzamide | $^1$H NMR (CD$_3$OD) δ (ppm): 8.29 (d, J = 8.6 Hz, 1 H); 8.17 (dd, J = 7.8, 1.8 Hz, 1 H); 7.65-7.59 (m, 3 H); 7.26 (d, J = 8.6 Hz, 1 H); 7.16 (ddd, J = 7.8, 7.8, 0.8 Hz, 1 H); 4.08 (s, 3 H); 3.79-3.72 (m, 2 H); 3.52-3.46 (m, 4 H); 3.23-3.13 (m, 2 H); 3.05-3.00 (m, 1 H); 2.83 (s, 3 H); 2.19-2.06 (m, 4 H). LRMS (ESI): (calc.) 435.2 (found) 436.3 (MH)+ | 34 |
Scheme 35
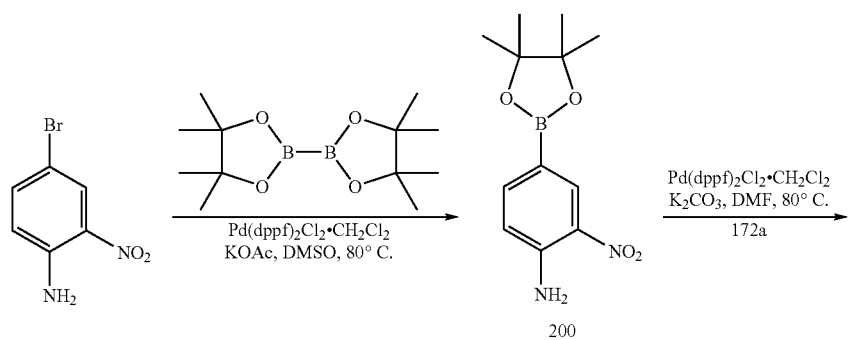
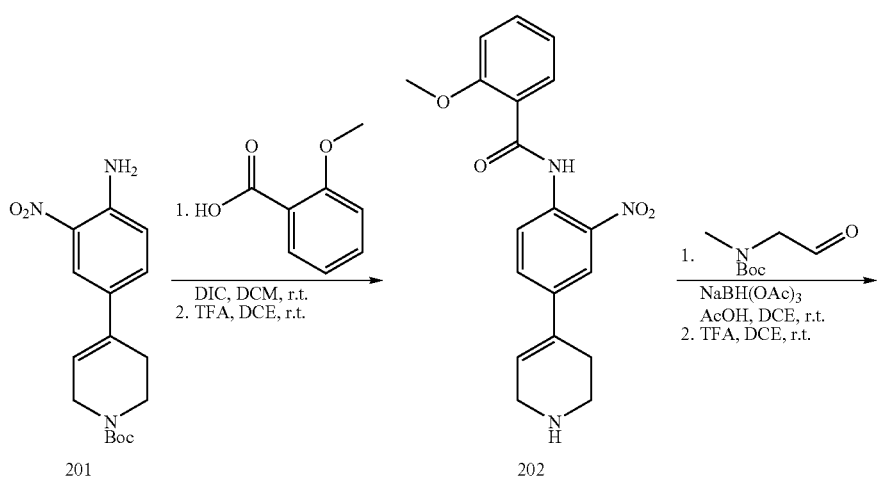

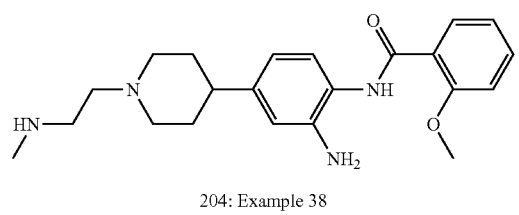
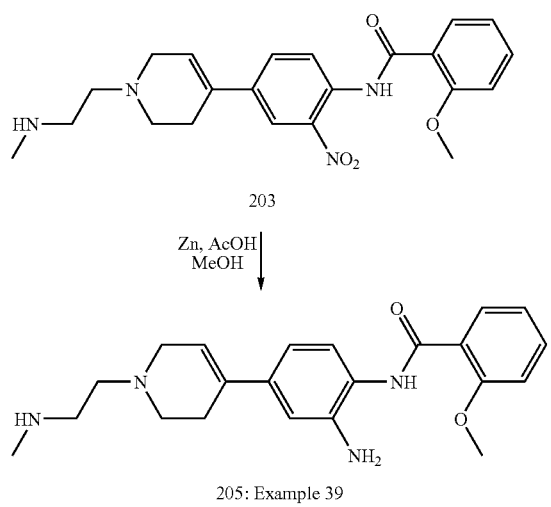

205: Example 39

Example 38

N-(2-amino-4-(1-(2-(methylamino)ethyl)piperidin-4-yl)phenyl)-2-methoxybenzamide (204)

Step 1: 2-nitro-4-(4,4,5,5-tetramethyl-1,3,2-dioxaborolan-2-yl)aniline (200)

The title compound 200 (4.86 g, 18.4 mmol, 80%) was obtained following the procedure for the synthesis of 63 (scheme 9, Example 7, step 3) using 4-Bromo-2-nitroaniline (5.00 g, 23 mmol) in place of 62. LRMS (ESI): calc. 264.1, found 287.2 (MNa)⁺.

Step 2: tert-butyl 4-(4-amino-3-nitrophenyl)-5,6-dihydropyridine-1 (2H)-carboxylate (201)

The title compound 201 (1.82 g, 5.70 mmol, 45%) was obtained as a bright orange solid following the procedure described for the synthesis of 195 (scheme 34, Example 37, step 3) using 200 (3.37 g, mmol) in place of 194. LRMS (ESI): calc. 319.2, found 342.2 (MNa)⁺.

Step 3: 2-methoxy-N-(2-nitro-4-(1,2,3,6-tetrahydropyridin-4-yl)phenyl)benzamide (202)

The title compound 202 (1.04 g, 2.22 mmol, 71%) was prepared following the procedures described for the synthesis of 192 (scheme 33, Example 36, steps 5 and 6) using 201 (1.00 g, 3.13 mmol) in place of 190. LRMS (ESI): calc. 353.1, found 411.3 (MH)⁺.

Step 4: 2-methoxy-N-(4-(1-(2-(methylamino)ethyl)-1,2,3,6-tetrahydropyridin-4-yl)-2-nitrophenyl)benzamide (203)

Crude 203 was obtained as a yellow solid following the procedures described for the synthesis of 105 (scheme 15, Example 13, steps 4 and 5) using 202 (1.04 g, mmol) in place of 103. LRMS (ESI): calc. 410.2, found 354.3 (MH)⁺.

Step 5: N-(2-amino-4-(1-(2-(methylamino)ethyl)piperidin-4-yl)phenyl)-2-methoxybenzamide (204)

Palladium over charcoal (10%, 300 mg) was added to crude 203 in MeOH (30 ml) and the suspension was shaken under H₂ gas (50 psi) at room temperature for 16 h. The catalyst was filtered and the filtrate was concentrated and purified by chromatography (30% MeOH/DCM) to give the title compound 204 (290 mg, 0.475 mmol, 21%) as beige solid. LRMS (ESI): calc. 382.2, found 383.4 (MH)⁺. ¹H-NMR (CDCl3) □ (ppm): 9.54 (s, 1H), 8.28 (dd, J=7.6, 1.8 Hz, 1H), 7.51 (ddd, J=8.8, 8.8, 1.8 Hz, 1H), 7.31 (d, J=8.2 Hz, 1H), 7.13 (dd, J=7.4, 7.4 Hz, 1H), 7.04 (d, J=8.0 Hz, 1H), 6.69-6.66 (m, 2H), 4.30 (s, 3H), 3.25-3.21 (m, 4H), 3.14-3.06 (m, 2H), 2.75 (s, 3H), 2.60-2.46 (m, 3H), 1.96-1.88 (m, 4H).

Example 39

N-(2-amino-4-(1-(2-(methylamino)ethyl)-1,2,3,6-tetrahydropyridin-4-yl)phenyl)-2-methoxybenzamide (205)

To a solution of 203 (143.9 mg, 0.225 mmol) in MeOH (4.5 mL) and Acetic Acid (1.1 mL) at room temperature was added Zinc dust (85 mg, 1.307 mmol). The solution was stirred 1 h and then filtered and concentrated and the crude residue was purified by flash chromatography (10 to 30% MeOH in DCM) and the material was further triturated with hexane to afford 205 (30 mg, 0.060 mmol, 27%) as a yellow solid. LRMS (ESI): calc. 380.2, found 381.2 (MH)⁺. ¹H-NMR (CDCl₃+CD₃OD) δ(ppm): 8.15 (dd, J=8.0, 2.2 Hz, 1H), 7.46 (ddd, J=8.8, 8.8, 2.3 Hz, 1H), 7.31 (d, J=8.6 Hz, 1H), 7.07 (dd, 7.4, 7.4 Hz, 1H), 7.00 (d, J=8.2 Hz, 1H), 6.82-6.79 (m, 2H), 3.98 (s, 3H), 3.19-3.16 (m, 2H), 3.08-3.04 (m, 2H), 2.79-2.71 (m, 4H), 2.64 (s, 3H), 2.52-2.47 (m, 2H).

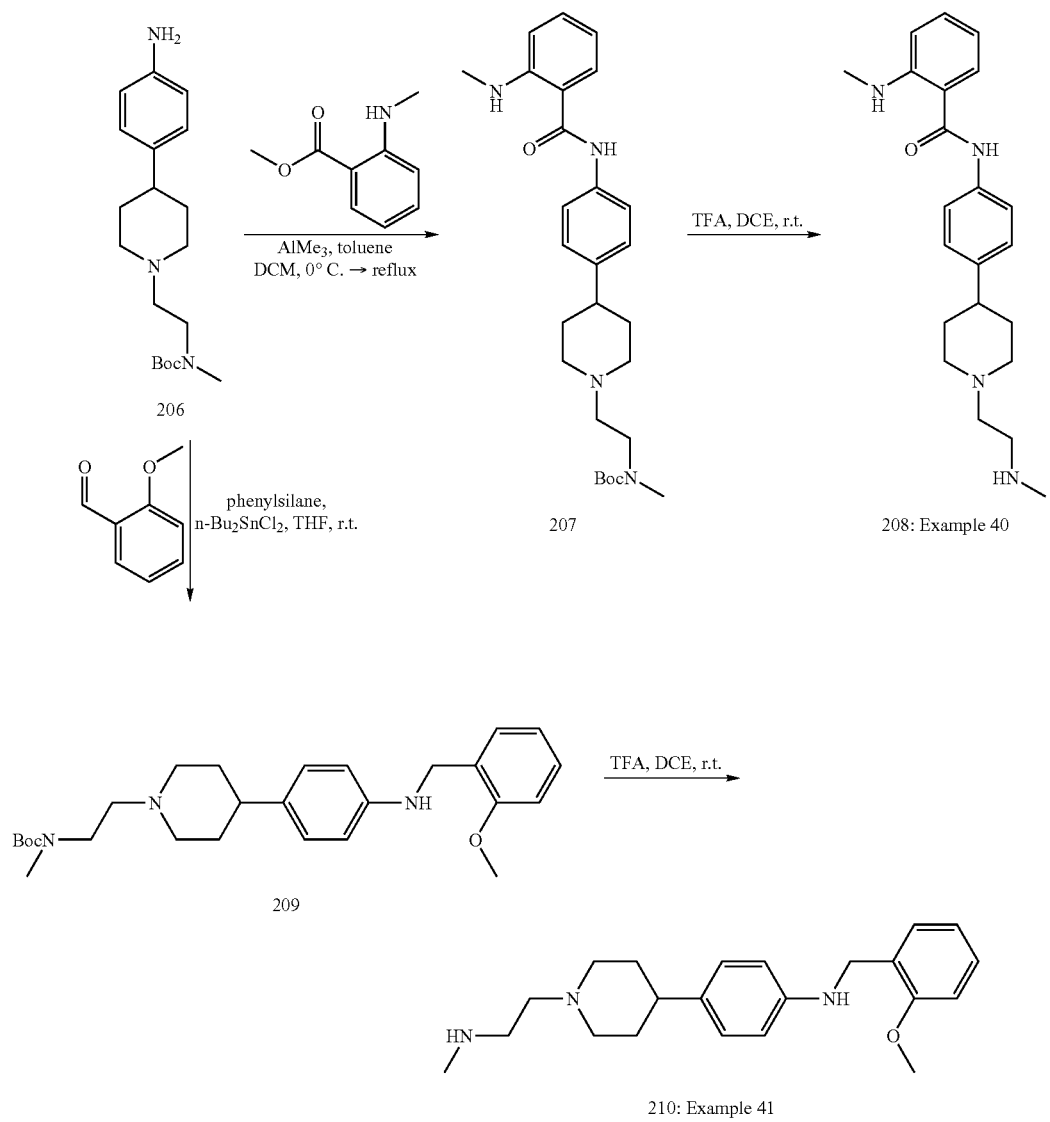

Example 40

2-(methylamino)-N-(4-(1-(2-(methylamino)ethyl) piperidin-4-yl)phenyl)benzamide (208)

Step 1: tert-butyl methyl(2-(4-(4-(2-(methylamino) benzamido)phenyl)piperidin-1-yl)ethyl)carbamate (207)

To a solution of 206 (200 mg, 0.600 mmol, prepared according to the method described for 90, scheme 33, example 36, steps 1-4 using 4-nitrophenylboronic acid in step 1 in place of 3-nitrophenylboronic acid) in DCM at 0° C. was added Trimethylaluminum (1.20 ml, 2M in toluene, 2.40 mmol). The mixture was stirred 5 min at that temperature then a solution of Methyl N-methylanthranilate (0.096 ml, 0.660 mmol) in DCM was added drop-wise at 0° C. The temperature was then allowed to warm up to room temperature and the solution was stirred for an additional 2 h, then toluene was added and the solution was heated to reflux for 16 h. After cooling, Sat. NaHCO$_3$ was added, and the mixture was extracted with EtOAc and the extracts were dried over Na$_2$SO$_4$ and concentrated. The residue was purified by flash chromatography (5% MeOH in DCM) to afford 207 (34.8 mg, 0.075 mmol, 12%). LRMS (ESI): calc. 466.3, found 467.4 (MH)$^+$.

Step 2: 2-(methylamino)-N-(4-(1-(2-(methylamino) ethyl)piperidin-4-yl)phenyl)benzamide (208)

The title compound 208 (10 mg, 0.017 mmol, 22%) was obtained as a yellowish semi-solid following the procedure described for the synthesis of 9a (scheme 2, example 1c, step 9) using 207 (34.8 mg, 0.075 mmol) in place of 15a. LRMS (ESI): calc. 366.2, found 367.2 (MH)$^+$. $^1$H-NMR (CD$_3$OD) δ(ppm): 7.61 (dd, J=7.8, 1.6 Hz, 1H), 7.54 (d, J=8.4 Hz, 2H), 7.35 (ddd, J=8.8, 7.2, 1.6 Hz, 1H), 7.22 (d, J=8.8 Hz, 2H), 6.73 (d, J=8.2 Hz, 1H), 6.66 (dd, J=7.4, 7.4 Hz, 1H), 3.13 (t, J=5.9 Hz, 2H), 3.10-3.04 (m, 2H), 2.86 (s, 3H), 2.72 (s, 3H), 2.68 (t, J=6.3 Hz, 2H), 2.60-2.51 (m, 1H), 2.27-2.19 (m, 2H), 1.88-1.79 (m, 4H).

Example 41

N-(2-methoxybenzyl)-4-(1-(2-(methylamino)ethyl)piperidin-4-yl)aniline (210)

Step 1: tert-butyl 2-(4-(4-(2-methoxybenzylamino)phenyl)piperidin-1-yl)ethyl(methyl)carbamate (209)

To a solution of 206 (198 mg, 0.594 mmol) in THF (1 mL) was added o-Anisaldehyde (0.072 mL, 0.594 mmol) and dibutyltin dichloride (3.61 mg, 0.012 mmol). After stirring for 2 minutes at room temperature, phenylsilane (0.081 mL, 0.653 mmol) was added and the mixture was stirred for 2 hours, then it was taken to dryness and purified by flash chromatography (2 to 5% MeOH in DCM). The title compound 209 (252 mg, 0.556 mmol, 94% yield) was obtained as clear oil. LRMS (ESI): calc. 453.3, found 454.4 (MH)+.

Step 2: N-(2-methoxybenzyl)-4-(1-(2-(methylamino)ethyl)piperidin-4-yl)aniline (210)

The title compound 210 (16 mg, 0.028 mmol, 6%) was obtained as a pale yellow solid following the procedure described for the synthesis of 9a (scheme 2, example 1c, step 9) using 209 (252 mg, 0.556 mmol) in place of 15a. LRMS (ESI): calc. 353.3, found 354.2 (MH)+. 1H-NMR (CDCl3) δ(ppm): 7.27-7.21 (m, 2H); 6.99 (d, J=1.8 Hz, 2H); 6.90 (dd, J=7.9, 7.9 Hz, 2H); 6.74 (d, J=8.5 Hz, 2H); 4.34 (s, 2H); 3.86 (s, 3H); 3.65-3.60 (m, 4H); 3.47-3.43 (m, 2H); 2.90-2.86 (m, 2H); 2.72 (s, 3H); 2.62-2.59 (m, 1H); 2.09-2.03 (m, 2H); 1.96-1.92 (m, 2H).

Scheme 37

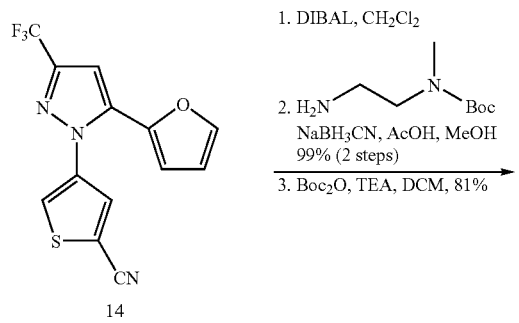

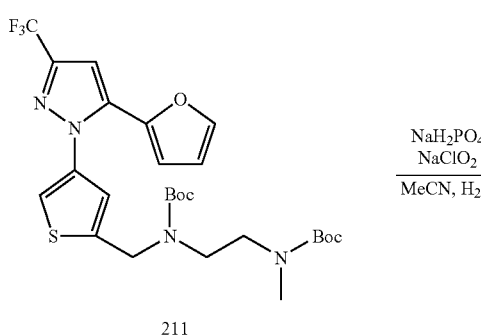

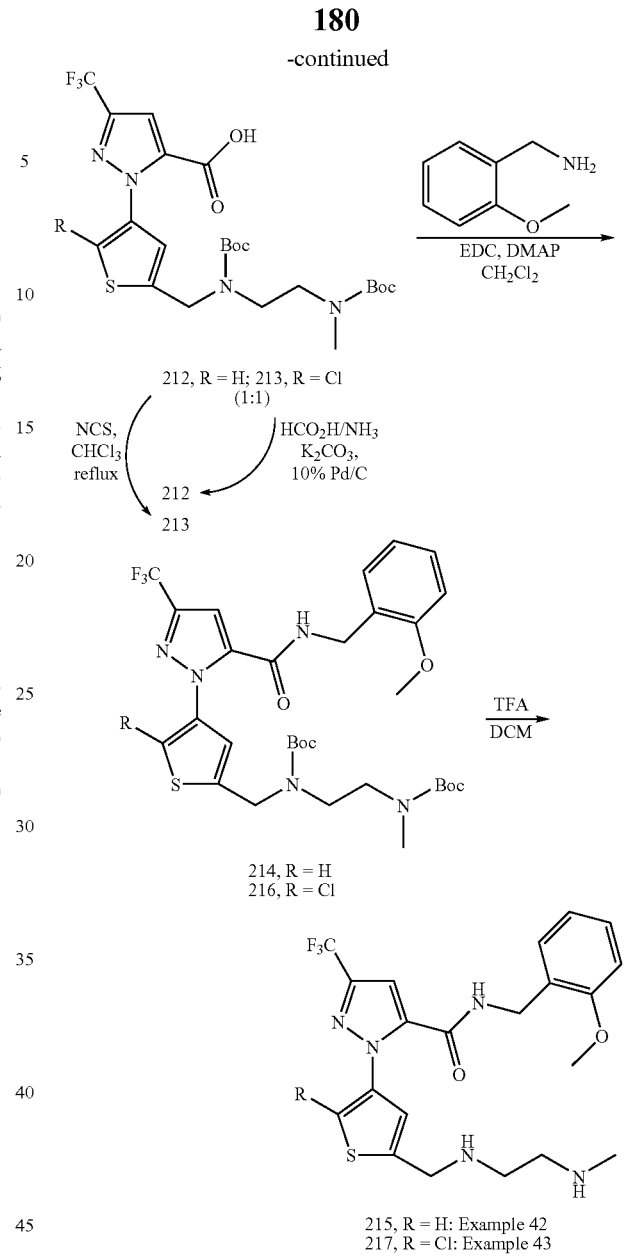

215, R = H: Example 42
217, R = Cl: Example 43

Example 42

N-(2-methoxybenzyl)-1-(5-((2-(methylamino)ethylamino)methyl)thiophen-3-yl)-3-(trifluoromethyl)-1H-pyrazole-5-carboxamide (217)

Steps 1: 2-{1-(5-(((tert-butoxycarbonyl(2-(tert-butoxycarbonyl(methyl)amino)ethyl)amino)methyl)-thiophen-3-yl)-3-(trifluoromethyl)-1H-pyrazole-5-yl}furan (211)

The titled compound 211 (2.94 g, 80% over all yield) was obtained as a clear oil after following the procedures described for the synthesis of 124 (Scheme 19, example 17, steps 1-3) using 14 (2 g, 6.47 mmol) in place of 53 in step 1. LRMS(ESI): (calc.) 570.2 (found) 593.3 (MNa)+.

Step 2: 1-(5-(((tert-butoxycarbonyl(2-(tert-butoxycarbonyl(methyl)amino)ethyl)amino)methyl)thiophen-3-yl)-3-(trifluoromethyl)-1H-pyrazole-5-carboxylic acid (212) and 1-(5-(((tert-butoxycarbonyl(2-(tert-butoxycarbonyl(methyl)amino)ethyl)amino)methyl)-2-chlorothiophen-3-yl)-3-(trifluoromethyl)-1H-pyrazole-5-carboxylic acid (213)

To a solution of 211 (2.95 g, 5.17 mmol) in acetonitrile (12.31 ml) at 0° C. was added sodium dihydrogen phosphate (3.10 g, 25.8 mmol) in water (4.92 ml) followed by sodium chlorite (4.68 g, 51.7 mmol) in Water (17.23 ml). The ice-bath was removed and the reaction was stirred quickly at room temperature for a total of one hour. The orange reaction mixture was quenched with 15% NaOH(aq) (50 mL) and DCM was added followed by slow addition of concentrated HCl (75 mL) till the mixture reached pH=2. The product was extracted with DCM (3×) and the extracts were combined, washed with brine, dried over $Na_2SO_4$, filtered and concentrated. The residue was purified by silica gel chromatography using (5% methanol: 1% AcOH: DCM) to give 212 and 213 (1.81 g) as a yellow solid. The mixture was 1:1 by HPLC.

Step 3: 1-(5-(((tert-butoxycarbonyl(2-(tert-butoxycarbonyl(methyl)amino)ethyl)amino)methyl)thiophen-3-yl)-3-(trifluoromethyl)-1H-pyrazole-5-carboxylic acid (212)

The title compound 212 (1.64 g, 2.99 mmol) was obtained as a light brown solid following the procedure described for the synthesis of compound 7 (scheme 2, example 1c, step 7) using the mixture of 212 and 213 from above (1.81 g). LRMS (ESI): (calc.) 548.2 (found) 571.3 (MNa)+.

Step 4: tert-butyl 2-((tert-butoxycarbonyl)(methyl)amino)ethyl((4-(5-(2-methoxybenzylcarbamoyl)-3-(trifluoromethyl)-1H-pyrazol-1-yl)thiophen-2-yl)methyl)carbamate (214)

The titled compound 214 (140 mg, 38%) was obtained as a white crusty solid after following the method described to obtain compound 15a (scheme 2, example 1c, step 8) by using 212 (0.300 g, 0.547 mmol) and 2-methoxybenzylamine (75 mg, 0.547 mmol). LRMS(ESI): (calc.) 667.2 (found) 690.4 (MNa)+.

Step 5: N-(2-methoxybenzyl)-1-(5-((2-(methylamino)ethylamino)methyl)thiophen-3-yl)-3-(trifluoromethyl)-1H-pyrazole-5-carboxamide (215)

The title compound 214 (133 mg, bis-TFA salt) was obtained as a white fluffy solid following the procedure described for the synthesis of 9a (scheme 2, example 1c, step 9) using 214 (135 mg, 0.202 mmol) in place of 15a $^1$H NMR: ($CD_3OD$) δ(ppm): 9.16 (t, J=5.6 Hz, 1H), 7.72 (d, J=1.6 Hz, 1H), 7.49 (d, J=1.6 Hz, 1H), 7.28 (dt, J=2.0, 8.4 Hz, 1H), 7.23 (dd, J=1.6, 7.6 Hz, 1H), 7.19 (s, 1H), 6.98 (d, J=8.4 Hz, 1H), 6.91 (dt, J=1.2, 7.2 Hz, 1H), 4.50-4.49 (m, 4H), 3.45 (s, 3H), 3.40-3.33 (m, 4H), 2.75 (s, 3H). LRMS (ESI): (calc.) 467.2 (found) 468.3 (MH)+.

Example 43

1-(2-chloro-5-((2-(methylamino)ethylamino)methyl)thiophen-3-yl)-N-(2-methoxybenzyl)-3-(trifluoromethyl)-1H-pyrazole-5-carboxamide (217)

Step 1: 1-(5-(((tert-butoxycarbonyl(2-(tert-butoxycarbonyl(methyl)amino)ethyl)amino)methyl)-2-chlorothiophen-3-yl)-3-(trifluoromethyl)-1H-pyrazole-5-carboxylic acid (213)

A solution of a mixture of 212 and 213 (0.265 g, 0.483 mmol) and NCS (0.065 g, 0.483 mmol) in $CHCl_3$ (4 mL) was heated to reflux. After about 5 hours of heating another 15 mg of NCS was added and the reaction continued for another 2 hours. The reaction was concentrated to dryness and used as is in the next reaction. LRMS (ESI): (calc.) 582.12 (found) 605.3 (MNa)+.

Step 2: tert-butyl 2-((tert-butoxycarbonyl)(methyl)amino)ethyl((5-chloro-4-(5-(2-methoxybenzylcarbamoyl)-3-(trifluoromethyl)-1H-pyrazol-1-yl)thiophen-2-yl)methyl)carbamate (216)

The titled compound 216 (83.8 mg, 26.7%) was obtained as a white crusty solid following the procedure described for the synthesis of compound 15a (scheme 2, example 1c, step 8) and using 213 (0.282 g, 0.484 mmol) and 2-methoxybenzylamine (66.4 mg, 0.484 mmol). LRMS(ESI): (calc.) 701.23 (found) 724.4 (MNa)+.

Step 3: 1-(2-chloro-5-((2-(methylamino)ethylamino)methyl)thiophen-3-yl)-N-(2-methoxybenzyl)-3-(trifluoromethyl)-1H-pyrazole-5-carboxamide (217)

The title compound 217 (73 mg, 0.145 mmol, 128% yield, bis-TFA salt) was obtained as a white solid following the procedure described for the synthesis of 9a (scheme 2, example 1c, step 9) using 216 (80 mg, 0.114 mmol) in place of 15a.

$^1$H NMR: ($CD_3OD$) δ(ppm): 9.16 (t, J=5.6 Hz, 1H), 7.38 (s, 1H), 7.32 (s, 1H), 7.26 (dt, J=1.6, 8.0 Hz, 1H), 7.20 (dd, J=1.2, 7.6 Hz, 1H), 6.89 (dt, J=1.2, 7.2 Hz, 1H), 4.78-4.46 (m, 4H), 3.84 (s, 3H), 3.41-3.30 (m, 4H), 2.75 (s, 3H). LRMS (ESI): (calc.) 501.1 (found) 502.3 (MH)+

Scheme 38

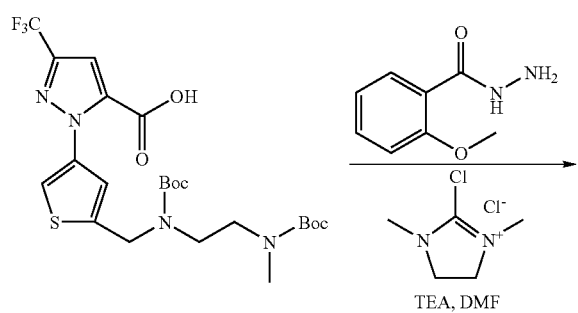

N1-((4-(5-(5-(2-methoxyphenyl)-1,3,4-oxadiazol-2-yl)-3-(trifluoromethyl)-1H-pyrazol-1-yl)thiophen-2-yl)methyl)-N2-methylethane-1,2-diamine (219)

Step 1: tert-butyl (4-(5-(5-(2-methoxyphenyl)-1,3,4-oxadiazol-2-yl)-3-(trifluoromethyl)-1H-pyrazol-1-yl)thiophen-2-yl-methyl)(2-((tert-butoxycarbonyl)(methyl)amino)ethyl)carbamate (218)

The titled compound 218 (23. mg, 12%) was obtained as a clear film following the procedure described for the synthesis of compound 126 (scheme 19, example 17, step 5) using 212 (0.150 g, 0.273 mmol) in place of 125 and 2-methoxybenzoic hydrazide (0.045 g, 0.273 mmol). LRMS (ESI): (calc.) 678.2 (found) 701.4 (MNa)+.

Step 2: N1-((4-(5-(5-(2-methoxyphenyl)-1,3,4-oxadiazol-2-yl)-3-(trifluoromethyl)-1H-pyrazol-1-yl)thiophen-2-yl)methyl)-N2-methylethane-1,2-diamine (219)

The title compound 219 (25 mg, bis-TFA salt) was obtained as yellow fluffy material following the procedure described for the synthesis of 9a (scheme 2, example 1c, step 9) using 218 (23 mg, 0.034 mmol) in place of 15a.

$^1$H NMR: (CD$_3$OD) δ(ppm): 8.06 (d, J=1.6 Hz, 1H), 7.92 (dd, J=1.6, 7.6 Hz, 1H), 7.65-7.63 (m, 2H), 7.62 (s, 1H), 7.27 (d, J=8.4 Hz, 1H), 7.15 (dt, J=1.2, 7.6 Hz, 1H), 4.57 (s, 2H), 3.98 (s, 3H), 3.48-3.38 (m, 4H), 2.80 (s, 3H). LRMS (ESI): (calc.) 478.2 (found) 479.3 (MH)+.

Scheme 39
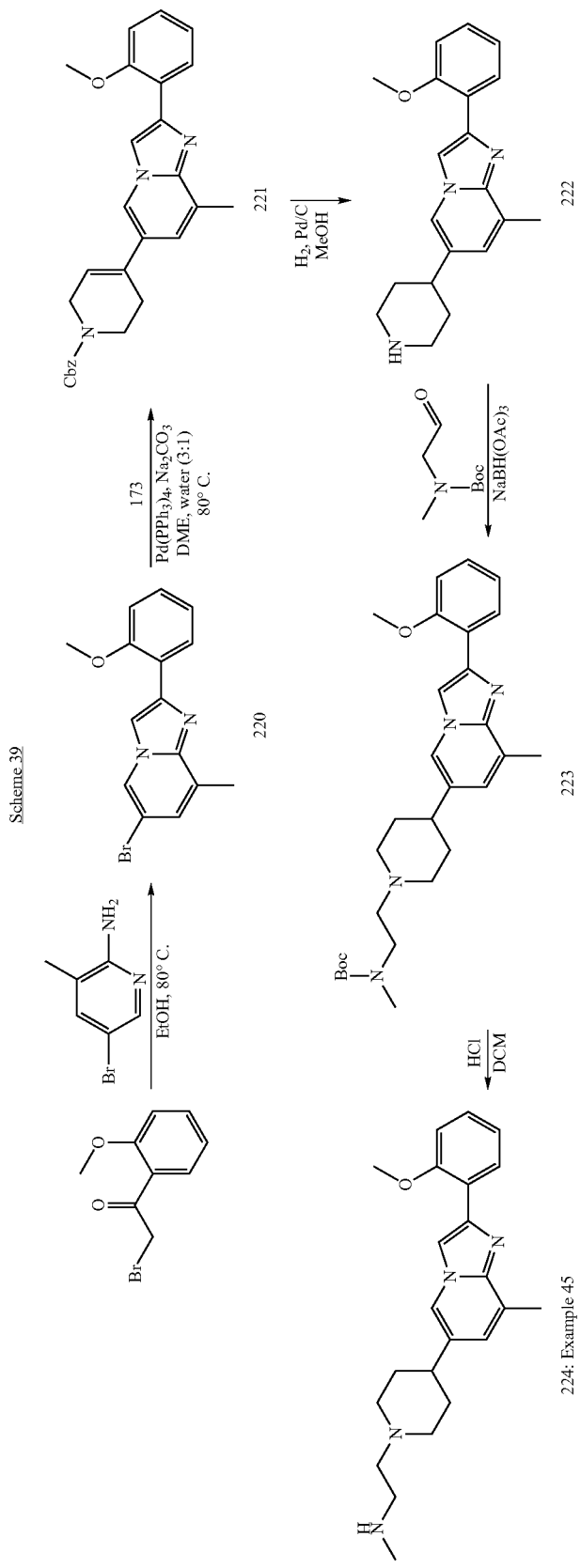

Example 45

2-(4-(2-(2-methoxyphenyl)-8-methylimidazo[1,2-a]pyridin-6-yl)piperidin-1-yl)-N-methylethanamine (224)

Step 1: 6-bromo-2-(2-methoxyphenyl)-8-methylimidazo[1,2-a]pyridine (220)

A mixture of 2-bromo-2'-methoxyacetophenone (0.500 g, 2.183 mmol) and 2-amino-5-bromo-3-methylpyridine (0.408 g, 2.183 mmol) in ethanol (8 mL) was heated to 80° C. for 16 hours in a pressure vessel. A yellow thick precipitate formed. Water was added and the solid was extracted with ethyl acetate (some DCM and MeOH were added to help in the dissolution). The organic extracts were then washed with brine, dried over $Na_2SO_4$, filtered and concentrated and the residue was purified by silica gel chromatography (Biotage SNAP 100 g, 10 to 20% ethyl acetate in hexanes) to give 220 (0.375 g, 1.182 mmol, 54.2% yield) as a white solid. LRMS (ESI): calc. 316.02 found 317.1 $(MH)^+$.

Step 2: benzyl 4-(2-(2-methoxyphenyl)-8-methylimidazo[1,2-a]pyridin-6-yl)-5,6-dihydropyridine-1(2H)-carboxylate (221)

The titled compound 221 (0.141 g, 63.5%) was obtained as a white crust following the procedure described for the synthesis of 160 (scheme 28, example 27, step 5) replacing 158 with the vinyl boronate 173 (490 mg, 1.27 mmol) and 159 with 220 (155 mg, 0.489 mmol). LRMS (ESI): (calc.) 453.2 (found) 454.4 $(MH)^+$.

Step 3: 2-(2-methoxyphenyl)-8-methyl-6-(piperidin-4-yl)imidazo[1,2-a]pyridine (222)

The titled compound 222 (75 mg, 76%) was obtained as a yellow gum following the procedure described for the synthesis of 65 (scheme 9, example 7, step 5) except using 221 (140 mg, 0.309 mmol) in place of 64. LRMS (ESI): (calc.) 321.2 (found) 322.3 $(MH)^+$.

Step 4: tert-butyl 2-(4-(2-(2-methoxyphenyl)-8-methylimidazo[1,2-a]pyridin-6-yl)piperidin-1-yl)ethyl(methyl)carbamate (223)

The titled compound 223 (50 mg, 43%) was obtained as an off-white crusty solid following the procedure described for the synthesis of 70 (scheme 9, example 7, step 10) using 222 (75 mg, 0.233 mmol) in place of 69. LRMS (ESI): (calc.) 478.29 (found) 479.5 $(MH)^+$.

Step 5: 2-(4-(2-(2-methoxyphenyl)-8-methylimidazo[1,2-a]pyridin-6-yl)piperidin-1-yl)-N-methylethanamine (224)

Compound 223 (45 mg, 0.094 mmol) was stirred in a saturated solution of HCl in DCM (1 mL) for 1.5 hours. The reaction was taken to dryness under high vacuum to give 224 (45.5 mg, tris-HCl salt) as a white solid. $^1H$ NMR: (DMSO-$d_6$) δ(ppm): 11.23 (br s, 1H), 9.51 (br s, 2H), 8.74 (s, 1H), 8.69 (s, 1H), 8.22 (d, J=8.0 Hz, 1H), 7.71 (s, 1H), 7.52 (dt, J=1.6, 8.8 Hz, 1H), 7.27 (d, J=7.6 Hz, 1H), 7.17 (t, J=7.2 Hz, 1H), 3.98 (s, 3H), 3.75-3.72 (m, 2H), 3.54 (m, 4H), 3.24-3.16 (m, 2H), 3.05-2.99 (m, 1H), 2.69 (s, 3H), 2.60 (t, J=5.2 Hz, 3H), 2.19-2.05 (m, 4H). LRMS (ESI): (calc.) 378.2 (found) 379.4 $(MH)^+$.

Scheme 40

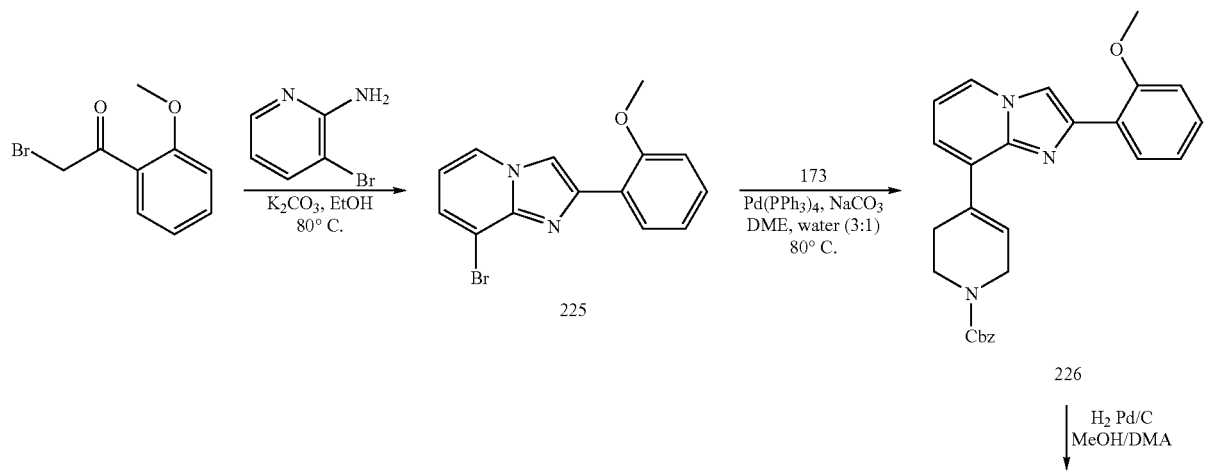

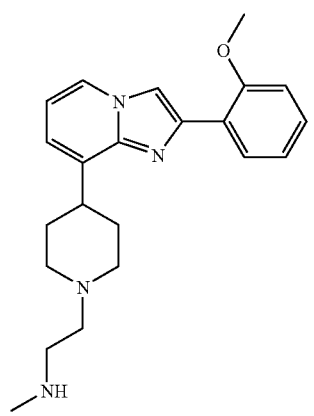

229: Example 46

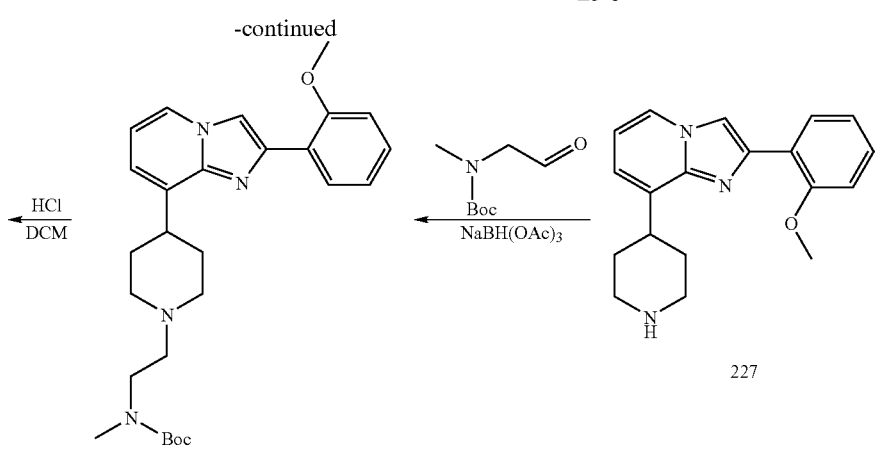

228

Example 46

2-(4-(2-(2-methoxyphenyl)imidazo[1,2-a]pyridin-8-yl)piperidin-1-yl)-N-methylethanamine (229)

Step 1: 8-bromo-2-(2-methoxyphenyl)imidazo[1,2-a]pyridine (225)

Compound 225 (0.326 g, 61.6% yield) was obtained as a yellow solid following the procedure described for the synthesis of 220 (scheme 39, Example 45, step 1) replacing 2-amino-5-bromo-3-methylpyridine with 2-amino-3-bromopyridine (0.302 g, 1.746 mmol). LRMS (ESI): (calc.) 302.01 (found) 303.1 (MH)+.

Step 2: benzyl 4-(2-(2-methoxyphenyl)imidazo[1,2-a]pyridin-8-yl)-5,6-dihydropyridine-1 (2H)-carboxylate (226)

The titled compound 226 (0.182 g, 84.0%) was obtained as a white solid following the procedure described for the synthesis of 160 (scheme 28, example 27, step 5) replacing 158 with the vinyl boronate 173 (0.170 g, 0.495 mmol) and 159 with 225 (0.150 g, 0.495 mmol). LRMS (ESI): (calc.) 439.19 (found) 440.3 (MH)+.

Step 3: 2-(2-methoxyphenyl)-8-(piperidin-4-yl)imidazo[1,2-a]pyridine (227)

The titled compound 227 (127 mg, 100%) was obtained as a yellow gum following the procedure described for the synthesis of 65 (scheme 9, example 7, step 5) except using 226 (182 mg, 0.414 mmol) in place of 64. LRMS (ESI): (calc.) 307.12 (found) 308.3 (MH)+.

Step 4: tert-butyl 2-(4-(2-(2-methoxyphenyl)imidazo[1,2-a]pyridin-8-yl)piperidin-1-yl)ethyl(methyl)carbamate (228)

The titled compound 228 (31.7 mg, 16.4%) was obtained as an off-white crusty solid following the procedure described for the synthesis of 70 (scheme 9, example 7, step 10) using 227 (128 mg, 0.415 mmol) in place of 69. LRMS (ESI): (calc.) 464.28 (found) 465.5 (MH)+.

Step 5: 2-(4-(2-(2-methoxyphenyl)imidazo[1,2-a]pyridin-8-yl)piperidin-1-yl)-N-methylethanamine (229)

The title compound 229 (28.5 mg, tris-HCl salt) was obtained as a white solid using the procedure described for the synthesis of 224 (scheme 39, Example 45, step 5) using 228 (31 mg, 0.067 mmol) in place of 223. $^1$H NMR: (CD$_3$OD) δ(ppm): 8.74 (dd, J=0.8, 6.8 Hz, 1H), 8.63 (s, 1H), 8.07 (d, J=7.6 Hz, 1H), 7.91 (d, J=7.6 Hz, 1H), 7.56 (dt, J=1.2, 7.8 Hz, 1H), 7.51 (t, J=7.2 Hz, 1H), 7.27 (d, J=8.4 Hz, 1H), 7.20 (dt, J=1.2, 7.6 Hz, 1H), 4.04 (3H), 3.90-3.81 (m, 3H), 3.62 (br s, 4H), 3.50-3.40 (m, 2H), 2.84 (s, 3H), 2.39-2.33 (m, 4H). LRMS (ESI): (calc.) 364.2 (found) 365.3 (MH)+.

Compositions

In a second aspect, the invention provides compositions comprising a compound according to the invention and a pharmaceutically acceptable carrier, excipient, or diluent. Compounds of the invention may be formulated by any method known in the art and may be prepared for administration by any route, including, without limitation, parenteral, oral, sublingual, transdermal, topical, intranasal, intratracheal, or intrarectal. In certain preferred embodiments, compounds of the invention are administered intravenously in a hospital setting. In certain other preferred embodiments, administration may preferably be by the oral route. The compositions may be in any form, including but not limited to, liquid solutions or suspensions; for oral administration, formulations may be in the form of tablets or capsules; and for intranasal formulations, in the form of powders, nasal drops or aerosols. The compositions of the invention may be administered systemically or locally.

The characteristics of the carrier, excipient or diluent will depend on the route of administration. As used herein, the term "pharmaceutically acceptable" means a non-toxic material that is compatible with a biological system such as a cell, cell culture, tissue, or organism, and that does not adversely interfere with the effectiveness of the biological activity of the active ingredient(s). Thus, compositions according to the invention may contain, in addition to the compound, diluents, fillers, salts, buffers, stabilizers, solubilizers, or other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

The active compound is included in the pharmaceutically acceptable carrier or diluent in an amount sufficient to deliver an inhibition effective amount without causing serious toxic effects. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

Depending on the particular condition, or disease, to be treated, additional therapeutic agents, that could be normally administered to treat that condition, or disease, may also be present in the compositions of this invention. In other words, compounds of this invention can be administered as the sole pharmaceutical agent or in combination with one or more other additional therapeutic (pharmaceutical) agents where the combination causes no unacceptable adverse effects. This may be of particular relevance for the treatment of hyperproliferative diseases such as cancer. In this instance, the compound of this invention can be combined with a known anti-cancer agent(s), as well as with admixtures and combinations thereof. As used herein, additional therapeutic agents that are normally administered to treat a particular disease, or condition, are known as "appropriate for the disease, or condition, being treated". As used herein, "additional therapeutic agents" is meant to include, for example, chemotherapeutic agents and other anti-proliferative agents. Administration of such agents may be done sequentially or concurrently. In certain preferred embodiments of the present invention the composition comprises a compound according to the present invention and a PRMT and/or CARM-I inhibitor known in the art or which will be discovered. The active ingredients of such compositions preferably act synergistically to produce a therapeutic effect.

Inhibition of Protein Methyltransferase

In a third aspect, the present invention provides a method of inhibiting PRMT and/or CARM-I, comprising contacting the PRMT and/or CARM-I with an inhibition effective amount of a compound according to the present invention.

In another embodiment of the third aspect, the invention provides a method of inhibiting PRMT and/or CARM-I in a cell, comprising contacting the cell in which inhibition of PRMT and/or CARM-I is desired with an inhibition effective amount of an inhibitor of PRMT and/or CARM-I, or composition thereof, according to the present invention.

Because compounds of the invention inhibit PRMT and/or CARM-I, they are useful research tools for in vitro study of PRMTs and/or CARM-I and their role in biological processes.

Measurement of the enzymatic activity of a PRMT and/or CARM-I can be achieved using known methodologies. For example, WO 2006/069155, describes the assessment of CARM-I enzymatic activity by the detection of methylated Histone H3.

In some preferred embodiments, the PRMT and/or CARM-I inhibitor interacts with and reduces the activity of all protein arginine methyltransferases in a cell. In some other preferred embodiments according to this aspect of the invention, the PRMT and/or CARM-I inhibitor interacts with and reduces the activity of fewer than all protein arginine methyltransferases in the cell. In certain preferred embodiments, the inhibitor interacts with and reduces the activity of CARM-I but, does not interact with or reduce the activities of other protein arginine methyltransferases.

The term "inhibition effective amount" is meant to denote a dosage sufficient to cause inhibition of PRMT and/or CARM-I activity in a cell, which cell can be in a multicellular organism. The multicellular organism can be a plant or an animal, preferably a mammal, more preferably a human. If in a multicellular organism, the method according to this aspect of the invention comprises administering to the organism a compound or composition according to the present invention. Administration may be by any route, including, without limitation, parenteral, oral, sublingual, transdermal, topical, intranasal, intratracheal, or intrarectal. In certain particularly preferred embodiments, compounds of the invention are administered intravenously in a hospital setting. In certain other preferred embodiments, administration may preferably be by the oral route.

In certain preferred embodiments of the third aspect of the invention, the method further comprises contacting a PRMT and/or CARM-I enzyme or a cell expressing PRMT and/or CARM-I activity with an additional inhibitory agent. The combined use of separate agents results in an improved inhibitory effect, thereby reducing the amounts of individual inhibitors required to obtain a given inhibitory effect as compared to the amounts necessary when either is used alone. Administration of such separate agents may be done sequentially or concurrently. When co-administered, the separate agents preferably act synergistically to produce a therapeutic effect.

The present invention will be more readily understood by referring to the following examples, which are given to illustrate the invention rather than to limit its scope.

ASSAY EXAMPLES

Assay Example I

Inhibition of Enzymatic Activity

The following protocol is used to assay the compounds of the invention for inhibition of CARM-1 methylation activity.

Histone H3 (Sigma-Aldrich) is used as the substrate for CARM-1 enzyme (Millipore), and the methylation is monitored using tritiated S-Adenosyl-Methionine (SAM) (Amersham Pharmacia Biotech) as a methyl donor. The reactions are performed at room temperature for a total of 30-35 minutes, using enzyme (CARM-1), substrate (histone H3), and co-factor (SAM) in the absence and presence of compound.

I. Reaction Mixtures and Solutions:
5× Histone Methyltransferase Buffer (HMTB; Millipore):
  250 mM Tris-HCl, pH 9.0
  2.5 mM dithiothreitol
10× Compound Solution (2 µL per well):
  Test compounds are diluted in 100% DMSO
CARM-1 Enzyme Mixture (8 µL per well):
  0.75 µL of 1 µg/µL CARM-1 enzyme
  4 µL HMTB
  3.25 µL $H_2O$
Histone H3/[$^3$H] SAM Mixture (10 µL per well):
  2 µL of 1 mg/mL histone H3
  1 µL 0.55 mCi/mL [$^3$H]-SAM
  7 µL $H_2O$
Wash Buffer (WB):
  10% trichloroacetic acid
II. Reaction Steps:
The reaction mixtures and solutions are added in the following order:
  2 µL Compound Solution
  8 µL CARM-1 Enzyme Mixture The mixture is left to pre-incubate for 10 minutes at room temperature (20-23° C.), followed by the addition of 10 µL Histone H3/[$^3$H] SAM Mixture. This is left to incubate for an additional 20 minutes at room temperature, and then 5 μL of the mixture is spotted onto P30 Filtermat paper. The Filtermat is washed twice for 15 minutes each with WB, and then washed once for 5 minutes with 95% ethanol. The Filtermat is allowed to dry and is placed on a heating plate pre-warmed at 70-75° C. A sheet of melt-on scintillant is placed on top and allowed to melt. The Filtermat is then removed from the heating plate and the wax allowed to solidify. The Filtermat is then placed in a sample bag, heat sealed, and read using a Wallac Microbeta counter. The data is analyzed to generate $IC_{50}$ values.

Compounds of the present invention have activity in the above described assay. Compounds of the present invention described herein have an $IC_{50}$ of less than 10 μM.

The pharmacological properties of the compounds of the present invention may be confirmed by a number of pharmacological assays. Inhibition of tumor cell proliferation upon treatment with compounds of the invention, for example, can be monitored using known methodologies. For example, WO 2006/069155, describes the use of a 3H thymidine incorporation assay.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A compound of Formula (I),

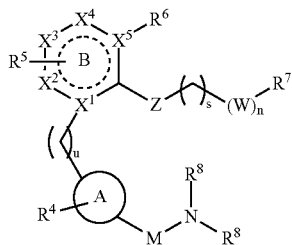

(I)

or a pharmaceutically acceptable salt thereof, wherein

A is phenyl or piperidinyl;

B together with $R^6$ and Z is

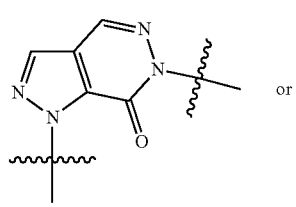 or

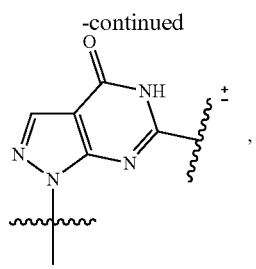

M is selected from the group consisting of

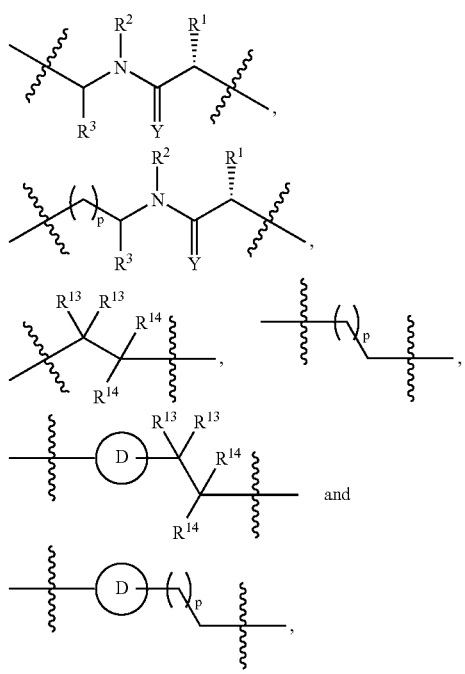

or

M is selected from the group consisting of

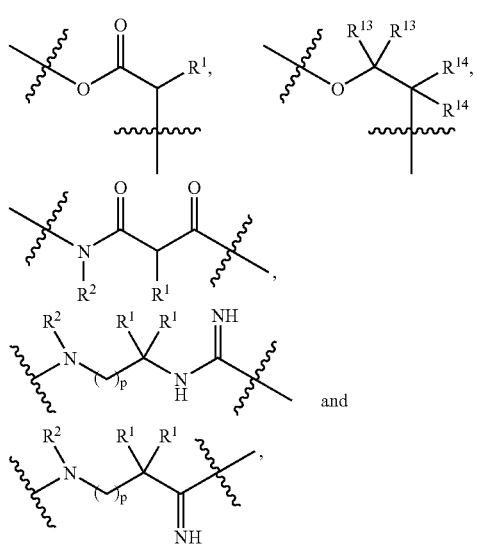

or

M is selected from the group consisting of

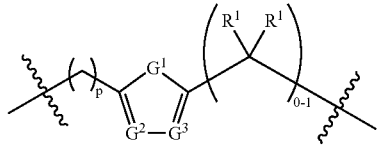

and

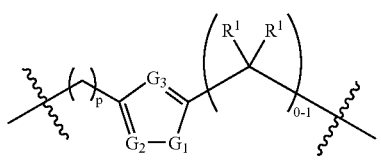

or

M is selected from the group consisting of

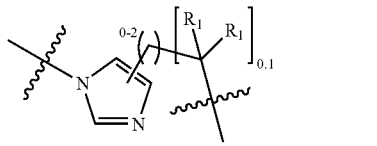

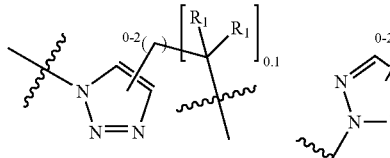

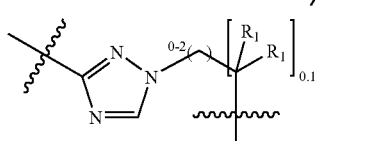

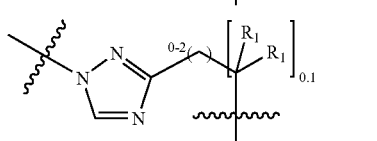

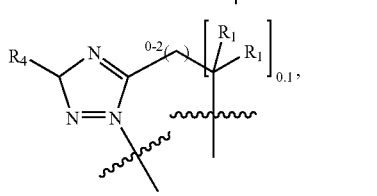

wherein p is 1, 2 or 3;

each $R^{13}$ is independently selected from the group consisting of H and $C_1$-$C_4$alkyl;

each $R^{14}$ is independently selected from the group consisting of H and $C_1$-$C_4$alkyl; or alternatively, $R^8$ and $R^{14}$ may join to form a 4-, 5- or 6-membered saturated ring containing one N atom; and ring D is a heterocycle, preferably selected from the group consisting of

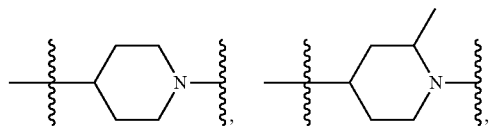

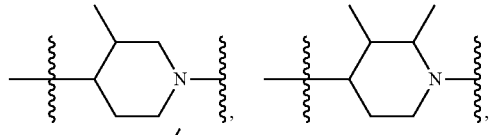

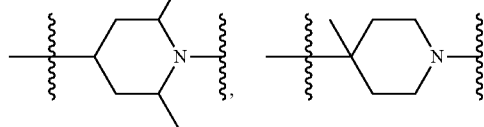

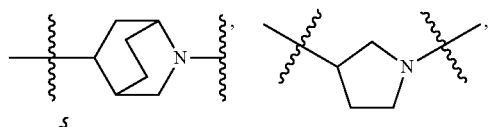

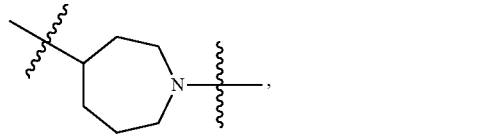

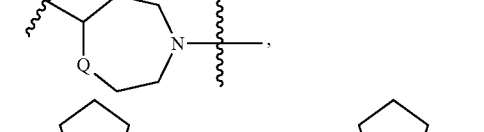

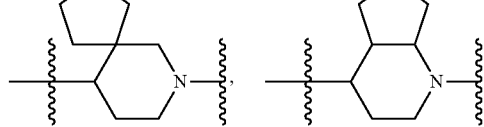

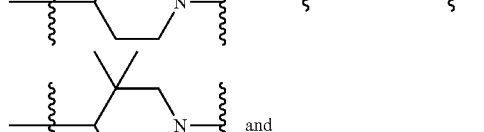

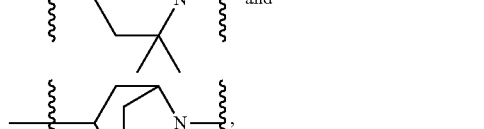

wherein the left side of ring D as shown is attached to ring A; and wherein Q is selected from the group consisting of —N($R^{15}$)—, O and S; and $R^{15}$ is $C_1$-$C_6$alkyl; and each $R^1$ is independently selected from the group consisting of H, —OH, —$CF_3$, —$CHF_2$, —$CH_2F$, halo, —CN, alkyl, alkenyl, alkynyl, aryl, heteroaryl, alkoxy, cycloalkyl, heterocyclyl, —O-alkyl, —S(O)$_{0-1}$-alkyl, —O-cycloalkyl, —S(O)$_{0-1}$-cycloalkyl, —O-heterocyclyl, —S(O)$_{0-1}$-heterocyclyl, —O-aryl, —S(O)$_{0-1}$aryl, —O-heteroaryl, —S(O)$_{0-1}$-heteroaryl, -alkyl-cycloalkyl, -alkyl-heterocyclyl, -alkyl-aryl, -alkyl-heteroaryl and =O;

$R^2$ is selected from the group consisting of H, alkyl, aryl, heteroaryl, cycloalkyl, heterocyclyl, -alkyl-aryl, -alkyl-heteroaryl, -alkyl-cycloalkyl and -alkyl-heterocycle, each of which is optionally substituted; or $R^1$ and $R^2$ together form a 5-, 6- or 7-membered heterocycle, each of which is optionally substituted; or $R^2$ optionally bonds with Ring A to form a 5 or 6 membered heterocycle fused to ring A;

$R^3$ is selected from the group consisting of H, —OH, —CF$_3$, —CHF$_2$, —CH$_2$F, halo, —CN, alkyl, alkenyl, alkynyl, aryl, heteroaryl, alkoxy, cycloalkyl, heterocyclyl, —O-alkyl, —S(O)$_{0-1}$-alkyl, —O-cycloalkyl, —S(O)$_{0-1}$-cycloalkyl, —O-heterocyclyl, —S(O)$_{0-1}$-heterocyclyl, —O-aryl, —S(O)$_{0-1}$aryl, —O-heteroaryl, —S(O)$_{0-1}$-heteroaryl, -alkyl-cycloalkyl, -alkyl-heterocyclyl, -alkyl-aryl, -alkyl-heteroaryl and =O; or $R^2$ together with $R^3$ optionally form a 4-, 5-, 6- or 7-membered heterocycle, each of which is optionally substituted;

$R^4$ is selected from the group consisting of H, —OH, halo, —CN, alkyl, alkenyl, alkynyl, aryl, heteroaryl, alkoxy, cycloalkyl, heterocyclyl, —O-alkyl, —S(O)$_{0-1}$-alkyl, —O-cycloalkyl, —S(O)$_{0-1}$-cycloalkyl, —O-heterocyclyl, —S(O)$_{0-1}$-heterocyclyl, —O-aryl, —S(O)$_{0-1}$aryl, —O-heteroaryl, —S(O)$_{0-1}$-heteroaryl, -alkyl-cycloalkyl, -alkyl-heterocyclyl, -alkyl-aryl, -alkyl-heteroaryl and =O, each of which is optionally substituted;

$R^5$ is selected from the group consisting of H, —NO$_2$, halo, —CN, —CF$_3$, —CHF$_2$, —CH$_2$F, —OH, —SH, C$_1$-C$_6$alkyl, C$_2$-C$_6$alkenyl, C$_2$-C$_6$alkynyl, alkoxy, cycloalkyl, heterocyclyl, aryl, heteroaryl, —O-alkyl, —S(O)$_{0-1}$-alkyl, —O-cycloalkyl, —S(O)$_{01}$-cycloalkyl, —O-heterocyclyl, —S(O)$_{0-1}$-heterocyclyl, =O, —O-aryl, —S(O)$_{0-1}$-aryl, —O-heteroaryl, —S(O)$_{0-1}$-heteroaryl, —O—C(O)—N(R$^2$)$_2$, —N(R$^2$)—C(O)—O—R$^2$, —C(O)—NH2, —C(O)—O—R$^2$, —C(O)—N(R$^2$)$_2$;

$R^7$ is selected from the group consisting of cycloalkyl, substituted cycloalkyl, heterocycle, substituted heterocycle, aryl, substituted aryl, heteroaryl and substituted heteroaryl, alkyl, optionally substituted alkyl;

each $R^8$ is independently selected from the group consisting of H and C$_1$-C$_4$alkyl;

Y is —H, O, S or —N(R$^8$);

G$^1$ is O, S or NR$^8$;

G$^2$ is N or CH;

G$^3$ is N or CH;

wherein $R^{10}$ is selected from the group consisting of H, alkyl, aryl, heteroaryl, cycloalkyl, heterocyclyl, -alkyl-aryl, -alkyl-heteroaryl, -alkyl-cycloalkyl and -alkyl-heterocycle, each of which is optionally substituted;

W is selected from the group consisting of a bond, an optionally substituted C$_1$-C$_4$alkyl, —O—, —S(O)$_{0-2}$—, —N(R$^{10}$)—, —O—C(O)—N(R$^{10}$)—, —N(R$^{10}$)—C(O)—O—, —O—C(S)—N(R$^{10}$)—, —N(R$^{10}$)—C(S)—O—, —N(R$^{10}$)—S(O)$_2$—, —S(O)$_2$—N(R$^{10}$)—, —C(O)—, —C(S)—, —O—C(O)— and —C(O)—O—; or u is 0 or 1;

s is 0, 1, 2 or 3; and n is 0 or 1.

2. The compound according to claim 1, wherein ring A is selected from the group consisting of

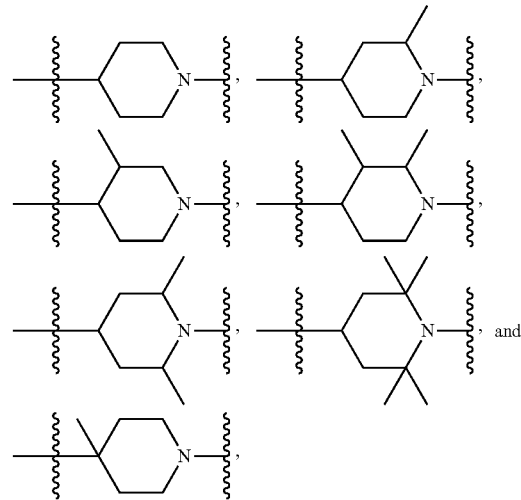

wherein group M is attached via the N atom of ring A;

Q is selected from the group consisting of —N(R$^{15}$)—, O and S; and

R$^{15}$ is C$_1$-C$_6$alkyl.

3. The compound according to claim 1, wherein ring A is phenyl.

4. The compound according to claim 1, wherein ring A is

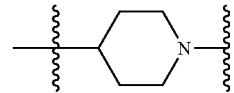

wherein group M is attached via the N atom of ring A.

5. The compound according to claim 1, wherein $R^7$ is aryl, heteroaryl, substituted aryl or substituted heteroaryl.

6. The compound according to claim 1, wherein $R^7$ is selected from the group consisting of phenyl, pyridine, napthylene and cyclohexyl, each of is optionally substituted.

7. The compound according to claim 1, wherein $R^7$ is an optionally substituted heterocycle.

8. The compound according to claim 1, wherein $R^7$ is selected from the group consisting of

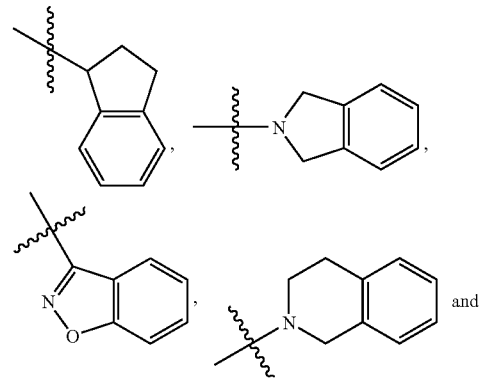

-continued

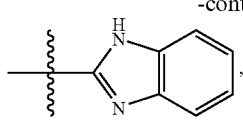

each of which is optionally substituted.

9. The compound according to claim 1, wherein M is

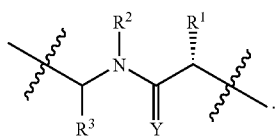

10. The compound according to claim 1, wherein M is

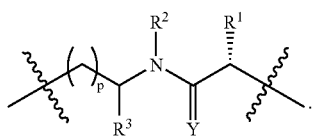

11. The compound according to claim 1, wherein M is

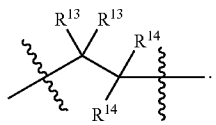

12. The compound according to claim 1, wherein M is

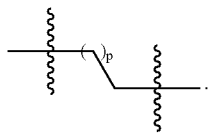

13. The compound according to claim 1, wherein M is

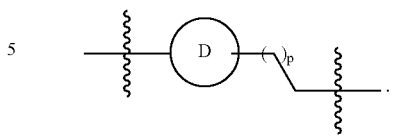

14. The compound according to claim 1, wherein W is —O—.

15. The compound according to claim 1, wherein $R^4$ is halo or alkyl.

16. The compound according to claim 1, wherein $X^4$ is a bond, $X^1$ and $X^2$ are each N, and $X^3$ and $X^5$ are each C, wherein $X^3$ is substituted with —$CF_3$.

17. The compound according to claim 1, wherein $R^7$ is substituted with a substituent selected from the group consisting of alkoxy, alkyl, halo, —$CO_2$-alkyl, —$CF_3$, —C(O)—O-alkyl, fused heterocycle, —O—$CF_3$, —O—$CHF_2$, —$NH_2$, —NH-alkyl, —N(alkyl)$_2$ and —O-phenyl.

18. The compound according to claim 1, wherein each $R^8$ is independently selected from the group consisting of H, methyl, ethyl and isopropyl.

19. The compound according to claim 1, wherein D is

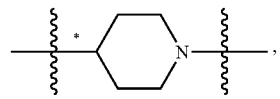

wherein * represents the point of attachment to ring A.

20. The compound according to claim 1, wherein M and ring B are in a meta or para position on ring A.

21. A composition comprising a compound according to claim 1 and a pharmaceutically acceptable carrier or diluent.

22. The composition according to claim 21, further comprising an additional therapeutic agent.

23. An N-oxide, prodrug or complex of the compound according to claim 1 and racemic mixtures, diastereomers, enantiomers and tautomers thereof.

24. A prodrug of the compound of claim 1.

25. A racemic mixture, diastereomer, enantiomer or tautomer of the compound according to claim 1.

* * * * *